US012492407B2

(12) United States Patent
Mathew

(10) Patent No.: US 12,492,407 B2
(45) Date of Patent: Dec. 9, 2025

(54) METHODS AND COMPOSITIONS FOR IMPROVING PLANT ARCHITECTURE AND YIELD TRAITS

(71) Applicant: Pairwise Plants Services, Inc., Durham, NC (US)

(72) Inventor: Lolita George Mathew, Cary, NC (US)

(73) Assignee: Pairwise Plants Services, Inc., Durham, NC (US)

( * ) Notice: Subject to any disclaimer, the term of this patent is extended or adjusted under 35 U.S.C. 154(b) by 412 days.

(21) Appl. No.: 17/929,061

(22) Filed: Sep. 1, 2022

(65) Prior Publication Data

US 2023/0151379 A1 May 18, 2023

Related U.S. Application Data

(60) Provisional application No. 63/240,132, filed on Sep. 2, 2021.

(51) Int. Cl.
*C12N 15/82* (2006.01)
*A01H 6/54* (2018.01)
*C12N 9/22* (2006.01)

(52) U.S. Cl.
CPC ......... *C12N 15/8243* (2013.01); *A01H 6/542* (2018.05); *C12N 9/22* (2013.01); *C12N 2310/20* (2017.05)

(58) Field of Classification Search
None
See application file for complete search history.

(56) References Cited

PUBLICATIONS

Rehman, N. et al. Microbial Pathogenesis (2018) V. 114, pp. 420-430. (Year: 2018).*
Haq, B. et al. BMC Plant Biology (2017) 17:259; 20 pages. (Year: 2017).*
International Search Report and Written Opinion corresponding to International Application No. PCT/US2022/075806 dated Dec. 16, 2022 (14 pages).
Akiyama, Kohki, et al., "Plant sesquiterpenes induce hyphal branching in *Arbuscular mycorrhizal* fungi", Nature, 435 (7043), 2005, 824-827.
Bari, Vinay Kumar, et al., "CRISPR/Cas9 mediated mutagenesis of More Axillary Growth 1 in tomato confers resistance to root parasitic weed *Phelipanche aegyptiaca*", Scientific Reports, 11(1), 2021, 3905.
Beveridge, Christine A., et al., "Auxin inhibition of decapitation-induced branching is dependent on graft-transmissible signals regulated by genes Rms1 and Rms2", Plant Physiology, 123(2), 2000, 689-698.
Beveridge, Christine A., et al., "Axillary meristem development. Budding relationships between networks controlling flowering, branching, and photoperiod responsiveness", Plant Physiology, 131(3), 2003, 927-934.
Booker, Jonathan, et al., "MAX1 encodes a cytochrome P450 family member that acts downstream of MAX3/4 to produce a carotenoid-derived branch-inhibiting hormone", Developmental Cell, 8(3), 2005, 443-449.
Booker, Jonathan, et al., "MAX3/CCD7 is a carotenoid cleavage dioxygenase required for the synthesis of a novel plant signaling molecule", Current Biology, 14(14), 2004, 1232-1238.
Challis, Richard J., "A role for more axillary growth1 (MAX1) in evolutionary diversity in strigolactone signaling upstream of MAX2", Plant Physiology, 161(4), 2013, 1885-1902.
Kumar, Manu, et al., "Strigolactone signaling genes showing differential expression patterns in *Arabidopsis* max mutants", Plants, 8(9), 2019, 352.
Mori, Narumi, et al., "Chemical identification of 18-hydroxycarlactonoic acid as an LjMAX1 product and in planta conversion of its methyl ester to canonical and non-canonical strigolactones in Lotus japonicus", Phytochemistry, 174, 2020, 112349.
Sorefan, Karim, et al., "MAX4 and RMS1 are orthologous dioxygenase-like genes that regulate shoot branching in *Arabidopsis* and pea", Genes & Development, 17(12), 2003, 1469-1474.
Stirnberg, Petra, et al., "MAX1 and MAX2 control shoot lateral branching in *Arabidopsis*", Development, The Company of Biologists Ltd, GB vol. 129, No. 5, 2002, 1131-1141.
Wang, Yuexing, et al., "A strigolactone biosynthesis gene contributed to the green revolution in rice", Molecular Plant, 13(6), 2020, 923-932.
Wang, Lei, et al., "Transcriptional regulation of strigolactone signalling in *Arabidopsis*", Nature, 583(7815), 2020, 277-281.
Wani, Kaiser Iqbal, et al., "Mechanistic insights into strigolactone biosynthesis, signaling, and regulation during plant growth and development", Journal of Plant Growth Regulation, 2020, 1-17.
Zhang, Yanxia, et al., "Rice cytochrome P450 MAX1 homologs catalyze distinct steps in strigolactone biosynthesis", Nature Chemical Biology, 10(12), 2014, 1028-1033.
Zhang, Yanxia, et al., "The tomato MAX1 homolog, SlMAX1, is involved in the biosynthesis of tomato strigolactones from carlactone", New Phytologist, 219(1), 2018, 297-309.
Zheng, Ming, et al., "Knockout of two Bna MAX 1 homologs by CRISPR/Cas9-targeted mutagenesis improves plant architecture and increases yield in rapeseed (*Brassica napus* L.)", Plant Biotechnology Journal, 18(3), 2020, 644-654.

* cited by examiner

*Primary Examiner* — Russell Kallis
(74) *Attorney, Agent, or Firm* — Myers Bigel, P.A.

(57) ABSTRACT

This invention relates to compositions and methods for modifying More Axillary Growth 1 (MAX1) genes in plants, optionally to improve plant architecture and/or improved yield traits. The invention further relates to plants having improved plant architecture and/or improved yield traits produced using the methods and compositions of the invention.

20 Claims, No Drawings

Specification includes a Sequence Listing.

SEQUENCE LISTING

```
Sequence total quantity: 187
SEQ ID NO: 1            moltype = AA  length = 1228
FEATURE                 Location/Qualifiers
REGION                  1..1228
                        note = Lachnospiraceae bacterium
source                  1..1228
                        mol_type = protein
                        organism = unidentified
SEQUENCE: 1
MSKLEKFTNC YSLSKTLRFK AIPVGKTQEN IDNKRLLVED EKRAEDYKGV KKLLDRYYLS  60
FINDVLHSIK LKNLNNYISL FRKKTRTEKE NKELENLEIN LRKEIAKAFK GNEGYKSLFK  120
KDIIETILPE FLDDKDEIAL VNSFNGFTTA FTGFFDNREN MFSEEAKSTS IAFRCINENL  180
TRYISNMDIF EKVDAIFDKH EVQEIKEKIL NSDYDVEDFF EGEFFNFVLT QEGIDVYNAI  240
IGGFVTESGE KIKGLNEYIN LYNQKTKQKL PKFKPLYKQV LSDRESLSFY GEGYTSDEEV  300
LEVFRNTLNK NSEIFSSIKK LEKLFKNFDE YSSAGIFVKN GPAISTISKD IFGEWNVIRD  360
KWNAEYDDIH LKKKAVVTEK YEDDRRKSFK KIGSFSLEQL QEYADADLSV VEKLKEIIIQ  420
KVDEIYKVYG SSEKLFDADF VLEKSLKKND AVVAIMKDLL DSVKSFENYI KAFFGEGKET  480
NRDESFYGDF VLAYDILLKV DHIYDAIRNY VTQKPYSKDK FKLYFQNPQF MGGWDKDKET  540
DYRATILRYG SKYYLAIMDK KYAKCLQKID KDDVNGNYEK INYKLLPGPN KMLPKVFFSK  600
KWMAYYNPSE DIQKIYKNGT FKKGDMFNLN DCHKLIDFFK DSISRYPKWS NAYDFNFSET  660
EKYKDIAGFY REVEEQGYKV SFESASKKEV DKLVEEGKLY MFQIYNKDFS DKSHGTPNLH  720
TMYFKLLFDE NNHGQIRLSG GAELFMRRAS LKKEELVVHP ANSPIANKNP DNPKKTTTLS  780
YDVYKDKRFS EDQYELHIPI AINKCPKNIF KINTEVRVLL KHDDNPYVIG IDRGERNLLY  840
IVVVDGKGNI VEQYSLNEII NNFNGIRIKT DYHSLLDKKE KERFEARQNW TSIENIKELK  900
AGYISQVVHK ICELVEKYDA VIALEDLNSG FKNSRVKVEK QVYQKFEKML IDKLNYMVDK  960
KSNPCATGGA LKGYQITNKF ESFKSMSTQN GFIFYIPAWL TSKIDPSTGF VNLLKTKYTS  1020
IADSKKFISS FDRIMYVPEE DLFEFALDYK NFSRTDADYI KKWKLYSYGN RIRIFRNPKK  1080
NNVFDWEEVC LTSAYKELFN KYGINYQQGD IRALLCEQSD KAFYSSFMAL MSLMLQMRNS  1140
ITGRTDVDFL ISPVKNSDGI FYDSRNYEAQ ENAILPKNAD ANGAYNIARK VLWAIGQFKK  1200
AEDEKLDKVK IAISNKEWLE YAQTSVKH                                    1228

SEQ ID NO: 2            moltype = AA  length = 1307
FEATURE                 Location/Qualifiers
source                  1..1307
                        mol_type = protein
                        organism = Acidaminococcus sp.
SEQUENCE: 2
MTQFEGFTNL YQVSKTLRFE LIPQGKTLKH IQEQGFIEED KARNDHYKEL KPIIDRIYKT  60
YADQCLQLVQ LDWENLSAAI DSYRKEKTEE TRNALIEEQA TYRNAIHDYF IGRTDNLTDA  120
INKRHAEIYK GLFKAELFNG KVLKQLGTVT TTEHENALLR SFDKFTTYFS GFYENRKNVF  180
SAEDISTAIP HRIVQDNFPK FKENCHIFTR LITAVPSLRE HFENVKKAIG IFVSTSIEEV  240
FSFPFYNQLL TQTQIDLYNQ LLGGISREAG TEKIKGLNEV LNLAIQKNDE TAHIIASLPH  300
RFIPLFKQIL SDRNTLSFIL EEFKSDEEVI QSFCKYKTLL RNENVLETAE ALFNELNSID  360
LTHIFISHKK LETISSALCD HWDTLRNALY ERRISELTGK ITKSAKEKVQ RSLKHEDINL  420
QEIISAAGKE LSEAFKQKTS EILSHAHAAL DQPLPTTLKK QEEKEILKSQ LDSLLGLYHL  480
LDWFAVDESN EVDPEFSARL TGIKLEMEPS LSFYNKARNY ATKKPYSVEK FKLNFQMPTL  540
ASGWDVNKEK NNGAILFVKN GLYYLGIMPK QKGRYKALSF EPTEKTSEGF DKMYYDYFPD  600
AAKMIPKCST QLKAVTAHFQ THTTPILLSN NFIEPLEITK EIYDLNNPEK EPKKFQTAYA  660
KKTGDQKGYR EALCKWIDFT RDFLSKYTKT TSIDLSSLRP SSQYKDLGEY YAELNPLLYH  720
ISFQRIAEKE IMDAVETGKL YLFQIYNKDF AKGHHGKPNL HTLYWTGLFS PENLAKTSIK  780
LNGQAELFYR PKSRMKRMAH RLGEKMLNKK LKDQKTPIPD TLYQELYDYV NHRLSHDLSD  840
EARALLPNVI TKEVSHEIIK DRRFTSDKFF FHVPITLNYQ AANSPSKFNQ RVNAYLKEHP  900
ETPIIGIDRG ERNLIYITVI DSTGKILEQR SLNTIQQFDY QKKLDNREKE RVAARQAWSV  960
VGTIKDLKQG YLSQVIHEIV DLMIHYQAVV VLENLNFGFK SKRTGIAEKA VYQQFEKMLI  1020
DKLNCLVLKD YPAEKVGGVL NPYQLTDQFT SFAKMGTQSG FLFYVPAPYT SKIDPLTGFV  1080
DPFVWKTIKN HESRKHFLEG FDFLHYDVKT GDFILHFKMN RNLSFQRGLP GFMPAWDIVF  1140
EKNETQFDAK GTPFIAGKRI VPVIENHRFT GRYRDLYPAN ELIALLEEKG IVFRDGSNIL  1200
PKLLENDDSH AIDTMVALIR SVLQMRNSNA ATGEDYINSP VRDLNGVCFD SRFQNPEWPM  1260
DADANGAYHI ALKGQLLLNH LKESKDLKLQ NGISNQDWLA YIQELRN                1307

SEQ ID NO: 3            moltype = AA  length = 1241
FEATURE                 Location/Qualifiers
source                  1..1241
                        mol_type = protein
                        organism = Butyrivibrio proteoclasticus
SEQUENCE: 3
MLLYENYTKR NQITKSLRLE LRPQGKTLRN IKELNLLEQD KAIYALLERL KPVIDEGIKD  60
IARDTLKNCE LSFEKLYEHF LSGDKKAYAK ESERLKKEIV KTLIKNLPEG IGKISEINSA  120
KYLNGVLYDF IDKTHKDSEE KQNILSDILE TKGYLALFSK FLTSRITTLE QSMPKRVIEN  180
FEIYAANIPK MQDALERGAV SFAIEYESIC SVDYYNQILS QEDIDSYNRL ISGIMDEDGA  240
KEKGINQTIS EKNIKIKSEH LEEKPFRILK QLHKQILEER EKAFTIDHID SDEEVVQVTK  300
EAFEQTKEQW ENIKKINGFY AKDPGDITLF IVVGPNQTHV LSQLIYGEHD RIRLLLEEYE  360
KNTLEVLPRR TKSEDARYDK FVNAVPKKVA KESHTFDGLQ KMTGDDRLFI LYRDELARNY  420
MRIKEAYGTF ERDILKSRRG IKGNRDVQES LVSFYDELTK FRSALRIINS GNDEKADPIF  480
YNTFDGIFEK ANRTYKAENL CRNYVTKSPA DDARIMASCL GTPARLRTHW WNGEENFAIN  540
```

```
DVAMIRRGDE YYYFVLTPDV KPVDLKTKDE TDAQIFVQRK GAKSFLGLPK ALFKCILEPY  600
FESPEHKNDK NCVIEEYVSK PLTIDRRAYD IFKNGTFKKT NIGIDGLTEE KFKDDCRYLI  660
DVYKEFIAVY TRYSCFNMSG LKRADEYNDI GEFFSDVDTR LCTMEWIPVS FERINDMVDK  720
KEGLLFLVRS MFLYNRPRKP YERTFIQLFS DSNMEHTSML LNSRAMIQYR AASLPRRVTH  780
KKGSILVALR DSNGEHIPMH IREAIYKMKN NFDISSEDFI MAKAYLAEHD VAIKKANEDI  840
IRNRRYTEDK FFLSLSYTKN ADISARTLDY INDKVEEDTQ DSRMAVIVTR NLKDLTYVAV  900
VDEKNNVLEE KSLNEIDGVN YRELLKERTK IKYHDKTRLW QYDVSSKGLK EAYVELAVTQ  960
ISKLATKYNA VVVVESMSST FKDKFSFLDE QIFKAFEARL CARMSDLSFN TIKEGEAGSI  1020
SNPIQVSNNN GNSYQDGVIY FLNNAYTRTL CPDTGFVDVF DKTRLITMQS KRQFFAKMKD  1080
IRIDDGEMLF TFNLEEYPTK RLLDRKEWTV KIAGDGSYFD KDKGEYVYVN DIVREQIIPA  1140
LLEDKAVFDG NMAEKFLDKT AISGKSVELI YKWFANALYG IITKKDGEKI YRSPITGTEI  1200
DVSKNTTYNF GKKFMFKQEY RGDGDFLDAF LNYMQAQDIA V                     1241

SEQ ID NO: 4            moltype = AA  length = 1238
FEATURE                 Location/Qualifiers
source                  1..1238
                        mol_type = protein
                        organism = Candidatus Methanoplasma termitum
SEQUENCE: 4
MNNYDEFTKL YPIQKTIRFE LKPQGRTMEH LETFNFFEED RDRAEKYKIL KEAIDEYHKK  60
FIDEHLTNMS LDWNSLKQIS EKYYKSREEK DKKVFLSEQK RMRQEIVSEF KKDDRFKDLF  120
SKKLFSELLK EEIYKKGNHQ EIDALKSFDK FSGYFIGLHE NRKNMYSDGD EITAISNRIV  180
NENFPKFLDN LQKYQEARKK YPEWIIKAES ALVAHNIKMD IVFSLEYFNK VLNQEGIQRY  240
NLALGGYVTK SGEKMMGLND ALNLAHQSEK SSKGRIHMTP LFKQILSEKE SFSYIPDVFT  300
EDSQLLPSIG GFFAQIENDK DGNIFDRALE LISSYAEYDT ERIYIRQADI NRVSNVIFGE  360
WGTLGGLMRE YKADSINDIN LERTCKKVDK WLDSKEFALS DVLEAIDRTG NNDAFNEYIS  420
KMRTAREKID AARKEMKFIS EKISGDEESI HIIKTLLDSV QQFLHFFNLF KARQDIPLDG  480
AFYAEFDEVH SKLFAIVPLY NKVRNYLTKN NLNTKKIKLN FKNPTLANGW DQNKVYDYAS  540
LIFLRDGNYY LGIINPKRKK NIKFEQGSGN GPFYRKMVYK QIPGPNKNLR PVFLTSTKGK  600
KEYKPSKEII EGYEADKHIR GDKFDLDFCH KLIDFFKESI EKHKDWSKFN FYFSPTESYG  660
DISEFYLDVE KQGYRMHFEN ISAETIDEYV EKGDLFLFQI YNKDFVKAAT GKKDMHTIYW  720
NAAFSPENLQ DVVVKLNGEA ELFYRDKSDI KEIVHREGEI LVNRTYNGRT PVPDKIHKKL  780
TDYHNGRTKD LGEAKEYLDK VRYFKAHYDI TKDRRYLNDK IYFHVPLTLN FKANGKKNLN  840
KMVIEKFLSD EKAHIIGIDR GERNLLYYSI IDRSGKIIDQ QSLNVIDGFD YREKLNQREI  900
EMKDARQSWN AIGKIKDLKE GYLSKAVHEI TKMAIQYNAI VVMEELNYGF KRGRFKVEKQ  960
IYQKFENMLI DKMNYLVFKD APDESPGGVL NAYQLTNPLE SFAKLGKQTG ILFYVPAAYT  1020
SKIDPTTGFV NLFNTSSKTN AQERKEFLQK FESISYSAKD GGIFAFAFDY RKFGTSKTDH  1080
KNVWTAYTNG ERMRYIKEKK RNELFDPSKE IKEALTSSGI KYDGGQNILP DILRSNNNGL  1140
IYTMYSSFIA AIQMRVYDGK EDYIISPIKN SKGEFFRTDP KRRELPIDAD ANGAYNIALR  1200
GELTMRAIAE KFDPDSEKMA KLELKHKDWF EFMQTRGD                        1238

SEQ ID NO: 5            moltype = AA  length = 1281
FEATURE                 Location/Qualifiers
source                  1..1281
                        mol_type = protein
                        organism = Eubacterium eligens
SEQUENCE: 5
MNGNRSIVYR EFVGVIPVAK TLRNELRPVG HTQEHIIQNG LIQEDELRQE KSTELKNIMD  60
DYYREYIDKS LSGVTDLDFT LLFELMNLVQ SSPSKDNKKA LEKEQSKMRE QICTHLQSDS  120
NYKNIFNAKL LKEILPDFIK NYNQYDVKDK AGKLETLALF NGFSTYFTDF FEKRKNVFTK  180
EAVSTSIAYR IVHENSLIFL ANMTSYKKIS EKALDEIEVI EKNNQDKMGD WELNQIFNPD  240
FYNMVLIQSG IDFYNEICGV VNAHMNLYCQ QTKNNYNLFK MRKLHKQILA YTSTSFEVPK  300
MFEDDMSVYN AVNAFIDETE KGNIIGKLKD IVNKYDELDE KRIYISKDFY ETLSCFMSGN  360
WNLITGCVEN FYDENIHAKG KSKEEKVKKA VKEDKYKSIN DVNDLVEKYI DEKERNEFKN  420
SNAKQYIREI SNIITDTETA HLEYDDHISL IESEEKADEM KKRLDMYMNM YHWAKAFIVD  480
EVLDRDEMFY SDIDDIYNIL ENIVPLYNRV RNYVTQKPYN SKKIKLNFQS PTLANGWSQS  540
KEFDNNAIIL IRDNKYYLAI FNAKNKPDKK IIQGNSDKKN DNDYKKMVYN LLPGANKMLP  600
KVFLSKKGIE TFKPSDYIIS GYNAHKHIKT SENFDISFCR DLIDYFKNSI EKHAEWRKYE  660
FKFSATDSYS DISEFYREVE MQGYRIDWTY ISEADINKLD EEGKIYLFQI YNKDFAENST  720
GKENLHTMYF KNIFSEENLD KIIKLNGQAE LFYRRASVKN PVKHKKDSVL VNKTYKNQLD  780
NGDVVRIPIP DDIYNEIYKM YNGYIKESDL SEAAKEYLDK VEVRTAQKDI VKDYRYTVDK  840
YFIHTPITIN YKVTARNNVN DMVVKYIAQN DDIHVIGIDR GERNLIYISV IDSHGNIVKQ  900
KSYNILNNYD YKKKLVEKEK TREYARKNWK SIGNIKELKE GYISGVVHEI AMLIVEYNAI  960
IAMEDLNYGF KRGRFKVERQ VYQKFESMLI NKLNYFASKE KSVDEPGGLL KGYQLTYVPD  1020
NIKNLGKQCG VIFYVPAAFT SKIDPSTGFI SAFNFKSIST NASRKQFFMQ FDEIRYCAEK  1080
DMFSFGFDYN NFDTYNITMG KTQWTVYTNG ERLQSEFNNA RRTGKTKSIN LTETIKLLLE  1140
DNEINYADGH DIRIDMEKMD EDKKSEFFAQ LLSLYKLTVQ MRNSYTEAEE QENGISYDKI  1200
ISPVINDEGE FFDSDNYKES DDKECKMPKD ADANGAYCIA LKGLYEVLKI KSEWTEDGFD  1260
RNCLKLPHAE WLDFIQNKRY E                                          1281

SEQ ID NO: 6            moltype = AA  length = 1300
FEATURE                 Location/Qualifiers
source                  1..1300
                        mol_type = protein
                        organism = Francisella novicida
SEQUENCE: 6
MSIYQEFVNK YSLSKTLRFE LIPQGKTLEN IKARGLILDD EKRAKDYKKA KQIIDKYHQF  60
FIEEILSSVC ISEDLLQNYS DVYFKLKKSD DDNLQKDFKS AKDTIKKQIS EYIKDSEKFK  120
NLFNQNLIDA KKGQESDLIL WLKQSKDNGI ELFKANSDIT DIDEALEIIK SFKGWTTYFK  180
```

-continued

```
GFHENRKVNY SSNDIPTSII YRIVDDNLPK FLENKAKYES LKDKAPEAIN YEQIKKDLAE  240
ELTFDIDYKT SEVNQRVFSL DEVFEIANFN NYLNQSGITK FNTIIGGKFV NGENTKRKGI  300
NEYINLYSQQ INDKTLKKYK MSVLFKQILS DTESKSFVID KLEDDSDVVT TMQSFYEQIA  360
AFKTVEEKSI KETLSLLFDD LKAQKLDLSK IYFKNDKSLT DLSQQVFDDY SVIGTAVLEY  420
ITQQIAPKNL DNPSKKEQEL IAKKTEKAKY LSLETIKLAL EEFNKHRDID KQCRFEEILA  480
NFAAIPMIFD EIAQNKDNLA QISIKYQNQG KKDLLQASAE DDVKAIKDLL DQTNNLLHKL  540
KIFHISQSED KANILDKDEH FYLVFEECYF ELANIVPLYN KIRNYITQKP YSDEKFKLNF  600
ENSTLANGWD KNKEPDNTAI LFIKDDKYYL GVMNKKNNKI FDDKAIKENK GEGYKKIVYK  660
LLPGANKMLP KVFFSAKSIK FYNPSEDILR IRNHSTHTKN GSPQKGYEKF EFNIEDCRKF  720
IDFYKQSISK HPEWKDFGFR FSDTQRYNSI DEFYREVENQ GYKLTFENIS ESYIDSVVNQ  780
GKLYLFQIYN KDFSAYSKGR PNLHTLYWKA LFDERNLQDV VYKLNGEAEL FYRKQSIPKK  840
ITHPAKEAIA NKNKDNPKKE SVFEYDLIKD KRFTEDKFFF HCPITINFKS SGANKFNDEI  900
NLLLKEKAND VHILSIDRGE RHLAYYTLVD GKGNIIKQDT FNIIGNDRMK TNYHDKLAAI  960
EKDRDSARKD WKKINNIKEM KEGYLSQVVH EIAKLVIEYN AIVVFEDLNF GFKRGRFKVE  1020
KQVYQKLEKM LIEKLNYLVF KDNEFDKTGG VLRAYQLTAP FETFKKMGKQ TGIIYYVPAG  1080
FTSKICPVTG FVNQLYPKYE SVSKSQEFFS KFDKICYNLD KGYFEFSFDY KNFGDKAAKG  1140
KWTIASFGSR LINFRNSDKN HNWDTREVYP TKELEKLLKD YSIEYGHGEC IKAAICGESD  1200
KKFFAKLTSV LNTILQMRNS KTGTELDYLI SPVADVNGNF FDSRQAPKNM PQDADANGAY  1260
HIGLKGLMLL GRIKNNQEGK KLNLVIKNEE YFEFVQNRNN                        1300

SEQ ID NO: 7           moltype = AA  length = 1206
FEATURE                Location/Qualifiers
source                 1..1206
                       mol_type = protein
                       note = Lachnospiraceae sp.
                       organism = unidentified
SEQUENCE: 7
MYYESLTKQY PVSKTIRNEL IPIGKTLDNI RQNNILESDV KRKQNYEHVK GILDEYHKQL  60
INEALDNCTL PSLKIAAEIY LKNQKEVSDR EDFNKTQDLL RKEVVEKLKA HENFTKIGKK  120
DILDLLEKLP SISEDDYNAL ESFRNFYTYF TSYNKVRENL YSDKEKSSTV AYRLINENFP  180
KFLDNVKSYR FVKTAGILAD GLGEEEQDSL FIVETFNKTL TQDGIDTYNS QVGKINSSIN  240
LYNQKNQKAN GFRKIPKMKM LYKQILSDRE ESFIDEFQSD EVLIDNVESY GSVLIESLKS  300
SKVSAFFDAL RESKGKNVYV KNDLAKTAMS VIVFENWRTF DDLLNQEYDL ANENKKKDDK  360
YFEKRQKELK KNKSYSLEHL CNLSEDSCNL IENYIHQISD DIENIIINNE TFLRIVINEH  420
DRSRKLAKNR KAVKAIKDFL DSIKVLEREL KLINSSGQEL EKDLIVYSAH EELLVELKQV  480
DSLYNMTRNY LTKKPFSTEK VKLNFNRSTL LNGWDRNKET DNLGVLLLKD GKYYLGIMNT  540
SANKAFVNPP VAKTEKVFKK VDYKLLPVPN QMLPKVFFAK SNIDFYNPSS EIYSNYKKGT  600
HKKGNMFSLE DCHNLIDFFK ESISKHEDWS KFGFKFDTQA SYNDISEFYR EVEKQGYKLT  660
YTDIDETYIN DLIERNELYL FQIYNKDFSM YSKGKLNLHT LYFMMLFDQR NIDDVVYKLN  720
GEAEVFYRPA SISEDELIIH KAGEEIKNKN PNRARTKETS TFSYDIVKDK RYSKDKFTLH  780
IPITMNFGVD EVKRFNDAVN SAIRIDENVN VIGIDRGERN LLYVVVIDSK GNILEQISLN  840
SIINKEYDIE TDYHALLDER EGGRDKARKD WNTVENIRDL KAGLYLQVVN VVAKLVLKYN  900
AIICLEDLNF GFKRGRQKVE KQVYQKFEKM LIDKLNYLVI DKSREQTSPK ELGGALNALQ  960
LTSKFKSFKE LGKQSGVIYY VPAYLTSKID PTTGFANLFY MKCENVEKSK RFFDGFDFIR  1020
FNALENVFEF GFDYRSFTQR ACGINSKWTV CTNGERIIKY RNPDKNNMFD EKVVVVTDEM  1080
KNLFEQYKIP YEDGRNVKDM IISNEEAEFY RRLYRLLQQT LQMRNSTSDG TRDYIISPVK  1140
NKREAYFNSE LSDGSVPKDA DANGAYNIAR KGLWVLEQIR QKSEGEKINL AMTNAEWLEY  1200
AQTHLL                                                             1206

SEQ ID NO: 8           moltype = AA  length = 1233
FEATURE                Location/Qualifiers
source                 1..1233
                       mol_type = protein
                       note = Lachnospiraceae sp.
                       organism = unidentified
SEQUENCE: 8
MDYGNGQFER RAPLTKTITL RLKPIGETRE TIREQKLLEQ DAAFRKLVET VTPIVDDCIR  60
KIADNALCHF GTEYDFSCLG NAISKNDSKA IKKETEKVEK LLAKVLTENL PDGLRKVNDI  120
NSAAFIQDTL TSFVQDDADK RVLIQELKGK TVLMQRFLTT RITALTVWLP DRVFENFNIF  180
IENAEKMRIL LDSPLNEKIM KFDPDAEQYA SLEFYGQCLS QKDIDSYNLI ISGIYADDEV  240
KNPGINEIVK EYNQQIRGDK DESPLPKLKK LHKQILMPVE KAFFVRVLSN DSDARSILEK  300
ILKDTEMLPS KIIEAMKEAD AGDIAVYGSR LHELSHVIYG DHGKLSQIIY DKESKRISEL  360
METLSPKERK ESKKRLEGLE EHIRKSTYTF DELNRYAEKN VMAAYIAAVE ESCAEIMRKE  420
KDLRTLLSKE DVKIRGNRHN TLIVKNYFNA WTVFRNLIRI LRRKSEAEID SDFYDVLDDS  480
VEVLSLTYKG ENLCRSYITK KIGSDLKPEI ATYGSALRPN SRWWSPGEKF NVKFHTIVRR  540
DGRLYYFILP KGAKPVELED MDGDIECLQM RKIPNPTIFL PKLVFKDPEA FFRDNPEADE  600
FVFLSGMKAP VTITRETYEA YRYKLYTVGK LRDGEVSEEE YKRALLQVLT AYKEFLENRM  660
IYADLNFGFK DLEEYKDSSE FIKQVETHNT FMCWAKVSSS QLDDLVKSGN GLLFEIWSER  720
LESYYKYGNE KVLRGYEGVL LSILKDENLV SMRTLLNSRP MLVYRPKESS KPMVVHRDGS  780
RVVDRFDKDG KYIPPEVHDE LYRFFNNLLI KEKLGEKARK ILDNKKVKVK VLESERVKWS  840
KFYDEQFAVT FSVKKNADCL DTTKDLNAEV MEQYSESNRL ILIRNTTDIL YYLVLDKNGK  900
VLKQRSLNII NDGARDVDWK ERFRQVTKDR NEGYNEWDYS RTSNDLKEVY LNYALKEIAE  960
AVIEYNAILI IEKMSNAFKD KYSFLDDVTF KGFETKKLAK LSDLHFRGIK DGEPCSFTNP  1020
LQLCQNDSNK ILQDGVIFMV PNSMTRSLDP DTGFIFAIND HNIRTKKAKL NFLSKFDQLK  1080
VSSEGCLIMK YSGDSLPTHN TDNRVWNCCC NHPITNYDRE TKKVEFIEEP VEELSRVLEE  1140
NGIETDTELN KLNERENVPG KVVDAIYSLV LNYLRGTVSG VAGQRAVYYS PVTGKKYDIS  1200
FIQAMNLNRK CDYYRIGSKE RGEWTDFVAQ LIN                                1233

SEQ ID NO: 9           moltype = AA  length = 1227
```

```
FEATURE                 Location/Qualifiers
source                  1..1227
                        mol_type = protein
                        note = Lachnospiraceae sp.
                        organism = unidentified
SEQUENCE: 9
MSKLEKFTNC YSLSKTLRFK AIPVGKTQEN IDNKRLLVED EKRAEDYKGV KKLLDRYYLS  60
FINDVLHSIK LKNLNNYISL FRKKTRTEKE NKELENLEIN LRKEIAKAFK GNEGYKSLFK  120
KDIIETILPE FLDDKDEIAL VNSFNGFTTA FTGFFDNREN MFSEEAKSTS IAFRCINENL  180
TRYISNMDIF EKVDAIFDKH EVQEIKEKIL NSDYDVEDFF EGEFFNFVLT QEGIDVYNAI  240
IGGFVTESGE KIKGLNEYIN LYNQKTKQKL PKFKPLYKQV LSDRESLSFY GEGYTSDEEV  300
LEVFRNTLNK NSEIFSSIKK LEKLFKNFDE YSSAGIFVKN GPAISTISKD IFGEWNVIRD  360
KWNAEYDDIH LKKKAVVTEK YEDDRRKSFK KIGSFSLEQL QEYADADLSV VEKLKEIIIQ  420
KVDEIYKVYG SSEKLFDADF VLEKSLKKND AVVAIMKDLL DSVKSFENYI KAFFGEGKET  480
NRDESFYGDF VLAYDILLKV DHIYDAIRNY VTQKPYSKDK FKLYFQNPQF MGGWDKDKET  540
DYRATILRYG SKYYLAIMDK KYAKCLQKID KDDVNGNYEK INYKLLPGPN KMLPKVFFSK  600
KWMAYYNPSE DIQKIYKNGT FKKGDMFNLN DCHKLIDFFK DSISRYPKWS NAYDFNFSET  660
EKYKDIAGFY REVEEQGYKV SFESASKKEV DKLVEEGKLY MFQIYNKDFS DKSHGTPNLH  720
TMYFKLLFDE NNHGQIRLSG GAELFMRRAS LKKEELVVHP ANSPIANKNP DNPKKTTTLS  780
YDVYKDKRFS EDQYELHIPI ANINKCPKNI FKINTEVRVL LKHDDNPYVI GIDRGERNLL  840
YIVVVDGKGN IVEQYSLNEI INNFNGIRIK TDYHSLLDKK EKERFEARQN WTSIENIKEL  900
KAGYISQVVH KICELVEKYD AVIALEDLNS GFKNSRVKVE KQVYQKFEKM LIDKLNYMVD  960
KKSNPCATGG ALKGYQITNK FESFKSMSTQ NGFIFYIPAW LTSKIDPSTG FVNLLKTKYT  1020
SIADKKFISS FDRIMYVPEE DLFEFALDYK NFSRTDADYI KKWKLYSYGN RIRIFRNPKK  1080
NNVFDWEEVC LTSAYKELFN KYGINYQQGD IRALLCEQSD KAFYSSFMAL MSLMLQMRNS  1140
ITGRTDVDFL ISPVKNSDGI FYDSRNYEAQ ENAILPKNAD ANGAYNIARK VLWAIGQFKK  1200
AEDEKLDKVK IASNKEWLEY AQTSVKH                                    1227

SEQ ID NO: 10           moltype = AA  length = 1264
FEATURE                 Location/Qualifiers
source                  1..1264
                        mol_type = protein
                        organism = Leptospira inadai
SEQUENCE: 10
MEDYSGFVNI YSIQKTLRFE LKPVGKTLEH IEKKGFLKKD KIRAEDYKAV KKIIDKYHRA  60
YIEEVFDSVL HQKKKKDKTR FSTQFIKEIK EFSELYYKTE KNIPDKERLE ALSEKLRKML  120
VGAFKGEFSE EVAEKYNKNL FSKELIRNEI EKFCETDEER KQVSNFKSFT TYFTGFHSNR  180
QNIYSDEKKS TAIGYRIIHQ NLPKFLDNLK IIESIQRRFK DFPWSDLKKN LKKIDKNIKL  240
TEYFSIDGFV NVLNQKGIDA YNTILGGKSE ESGEKIQGLN EYINLYRQKN NIDRKNPLNV  300
KILFKQILGD RETKSFIPEA FPDDQSVLNS ITEFAKYLKL DKKKSIIAE LKKFLSSFNR  360
YELDGIYLAN DNSLASISTF LFDDWSFIKK SVSFKYDESV GDPKKKIKSP LKYEKEKEKW  420
LKQKYYTISF LNDAIESYSK SQDEKRVKIR LEAYFAEFKS KDDAKKQFDL LERIEEAYAI  480
VEPLLGAEYP RDRNLKADKK EVGKIKDFLD SIKSLQFFLK PLLSAEIFDE KDLGFYNQLE  540
GYYEEIDISG HLYNKVRNYL TGKIYSKEKF KLNFENSTLL KGWDENREVA NLCVIFREDQ  600
KYYLGVMDKE NNTILSDIPK VKPNELFYEK MVYKLIPTPH MQLPRIIFSS DNLSIYNPSK  660
SILKIREAKS FKEGKNFKLK DCHKFIDFYK ESISKNEDWS RFDFKFSKTS SYENISEFYR  720
EVERQGYNLD FKKVSKFYID SLVEDGKLYL FQIYNKDFSI FSKGKPNLHT IYFRSLFSKE  780
NLKDVCLKLN GEAEMFFRKK SINYDEKKKR EGHHPELFEK LKYPILKDKR YSEDKFQFHL  840
PISLNFKSKE RLNFNLKVNE FLKRNKDINI IGIDRGERNL LYLVMINQKG EILKQTLLDS  900
MQSGKGRPEI NYKEKLQEKE IERDKARKSW GTVENIKELK EGYLSIVIHQ ISKLMVENNA  960
IVVLEDLNIG FKRGRQKVER QVYQKFEKML IDKLNFLVFK ENKPTEPGGV LKAYQLTDEF  1020
QSFEKLSKQT GFLFYVPSWN TSKIDPRTGF IDFLHPAYEN IEKAKQWINK FDSIRFNSKM  1080
DWFEFTADTR KFSENLMLGK NRVWVICTTN VERYFTSKTA NSSIQYNSIQ ITEKLKELFV  1140
DIPFSNGQDL KPEILRKNDA VFFKSLLFYI KTTLSLRQNN GKKGEEEKDF ILSPVVDSKG  1200
RFFNSLEASD DEPKDADANG AYHIALKGLM NLLVLNETKE ENLSRPKWKI KNKDWLEFVW  1260
ERNR                                                             1264

SEQ ID NO: 11           moltype = AA  length = 1373
FEATURE                 Location/Qualifiers
source                  1..1373
                        mol_type = protein
                        organism = Moraxella bovoculi
SEQUENCE: 11
MLFQDFTHLY PLSKTVRFEL FIDRTLEHIH AKNFLSQDET MADMHQKVKV ILDDYHRDFI  60
ADMMGEVKLT KLAEFYDVYL KFRKNPKDDE LQKAQLKDLQ AVLRKEIVKP IGNGGKYKAG  120
YDRLFGAKLF KDGKELGDLA KFVIAQEGES SPKLAHLAHF EKFSTYFTGF HDNRKNMYSD  180
EDKHTAIAYR LIHENLPRFI DNLQILTTIK QKHSALYDQI INELTASGLD VSLASHLDGY  240
HKLLTQEGIT AYNTLLGGIS GEAGSPKIQG INELINSHHN QHCHKSERIA KLRPLHKQIL  300
SDGMSVSFLP SKFADDSEMC QAVNEFYRHY ADVFAKVQSL FDGFDDHQKD GIYVEHKNLN  360
ELSKQAFGDF ALLGRVLDGY YVDVVNPEFN ERFAKAKTDN AKAKLTKEKD KFIKGVHSLA  420
SLEQAIEHYT ARHDDESVQA GKLGQYFKHG LAGVDNPIQK IHNNHSTIKG FLERERPAGE  480
RALPKIKSGK NPEMTQLRQL KELLDNALNV AHFAKLLTTK TTLDNQDGNF YGEFGVLYDE  540
LAKIPTLYNK VRDYLSQKPF STEKYKLNFG NPTLLNGWDL NKEKDNFGVI LQKDGCYYLA  600
LLDKAHKKVF DNAPNTGKSI YQKMIYKYLE VRKQFPKVFF SKEAIAINYH PSKELVEIKD  660
KGRQRSDDER LKLYRFILEC LKIHPKYDKK FEGAIGDIQL FKKDKKGREV PISEKDLFKD  720
INGIFSSKPK LEMEDFFIGE FKRYNPSQDL VDQYNIYKKI DSNDNRKKEN FYNNHPKFKK  780
DLVRYYYESM CKHEEWEESF EFSKKLQDIG CYVDVNELFT EIETRRLNYK ISFCNINADY  840
IDELVEQGQL YLFQIYNKDF SPKAHGKPNL HTLYFKALFS EDNLADPIYK LNGEAQIFYR  900
KASLDMNETT IHRAGEVLEN KNPDNPKKRQ FVYDIIKDKR YTQKDFMLHV PITMNFGVQG  960
```

```
MTIKEFNKKV NQSIQQYDEV NVIGIDRGER HLLYLTVINS KGEILEQCSL NDITTASANG  1020
TQMTTPYHKI LDKREIERLN ARVGWGEIET IKELKSGYLS HVVHQISQLM LKYNAIVVLE  1080
DLNFGFKRGR FKVEKQIYQN FENALIKKLN HLVLKDKADD EIGSYKNALQ LTNNFTDLKS  1140
IGKQTGFLFY VPAWNTSKID PETGFVDLLK PRYENIQASQ AFFGKFDKIC YNADKDYFEF  1200
HIDYAKFTDK AKNSRQIWTI CSHGDKRYVY DKTANQNKGA AKGINVNDIL KSLFARHHIN  1260
EKQPNLVMDI CQNNDKEFHK SLMYLLKTLL ALRYSNASSD EDFILSPVAN DEGVFFNSAL  1320
ADDTQPQNAD ANGAYHIALK GLWLLNELKN SDDLNKVKLA IDNQTWLNFA QNR         1373

SEQ ID NO: 12          moltype = AA  length = 1352
FEATURE                Location/Qualifiers
source                 1..1352
                       mol_type = protein
                       note = Parcubacteria bacterium
                       organism = unidentified
SEQUENCE: 12
MENIFDQFIG KYSLSKTLRF ELKPVGKTED FLKINKVFEK DQTIDDSYNQ AKFYFDSLHQ  60
KFIDAALASD KTSELSFQNF ADVLEKQNKI ILDKKREMGA LRKRDKNAVG IDRLQKEIND  120
AEDIIQKEKE KIYKDVRTLF DNEAESWKTY YQEREVDGKK ITESKADLKQ KGADFLTAAG  180
ILKVLKYEFP EEKEKEFQAK NQPSLFVEEK ENPGQKRYIF DSFDKFAGYL TKFQQTKKNL  240
YAADGTSTAV ATRIADNFII FHQNTKVFRD KYKNNHTDLG FDEENIFEIE RYKNCLLQRE  300
IEHIKNENSY NKIIGRINKK IKEYRDQKAK DTKLTKSDFP FFKNLDKQIL GEVEKEKQLI  360
EKTREKTEED VLIERFKEFI ENNEERFTAA KKLMNAFCNG EFESEYEGIY LKNKAINTIS  420
RRWFVSDRDF ELKLPQQKSK NKSEKNEPKV KKFISIAEIK NAVEELDGDI FKAVFYDKKI  480
IAQGGSKLEQ FLVIWKYEFE YLFRDIEREN GEKLLGYDSC LKIAKQLGIF PQEKEAREKA  540
TAVIKNYADA GLGIFQMMKY FSLDDKDRKN TPGQLSTNFY AEYDGYYKDF EFIKYYNEFR  600
NFITKKPFDE DKIKLNFENG ALLKGWDENK EYDFMGVILK KEGRLYLGIM HKNHRKLFQS  660
MGNAKGDNAN RYQKMIYKQI ADASKDVPRL LLTSKKAMEK FKPSQEILRI KKEKTFKRES  720
KNFSLRDLHA LIEYYRNCIP QYSNWSFYDF QFQDTGKYQN IKEFTDDVQK YGYKISFRDI  780
DDEYINQALN EGKMYLFEVV NKDIYNTKNG SKNLHTLYFE HILSAENLND PVFKLSGMAE  840
IFQRQPSVNE REKITTQKNQ CILDKGDRAY KYRRYTEKKI MFHMSLVLNT GKGEIKQVQF  900
NKIINQRISS SDNEMRVNVI GIDRGEKNLL YYSVVKQNGE IIEQASLNEI NGVNYRDKLI  960
EREKERLKNR QSWKPVVKIK DLKKGYISHV IHKICQLIEK YSAIVVLEDL NMRFKQIRGG  1020
IERSVYQQFE KALIDKLGYL VFKDNRDLRA PGGVLNGYQL SAPFVSFEKM RKQTGILFYT  1080
QAEYTSKTDP ITGFRKNVYI SNSASLDKIK EAVKKFDAIG WDGKEQSYFF KYNPYNLADE  1140
KYKNSTVSKE WAIFASAPRI RRQKGEDGYW KYDRVKVNEE FEKLLKVWNF VNPKATDIKQ  1200
EIIKKIKAGD LQGEKELDGR LRNFWHSFIY LFNLVLELRN SFSLQIKIKA GEVIAVDEGV  1260
DFIASPVKPF FTTPNPYIPS NLCWLAVENA DANGAYNIAR KGVMILKKIR EHAKKDPEFK  1320
KLPNLFISNA EWDEAARDWG KYAGTTALNL DH                                1352

SEQ ID NO: 13          moltype = AA  length = 1260
FEATURE                Location/Qualifiers
source                 1..1260
                       mol_type = protein
                       organism = Porphyromonas crevioricanis
SEQUENCE: 13
MDSLKDFTNL YPVSKTLRFE LKPVGKTLEN IEKAGILKED EHRAESYRRV KKIIDTYHKV  60
FIDSSLENMA KMGIENEIKA MLQSFCELYK KDHRTEGEDK ALDKIRAVLR GLIVGAFTGV  120
CGRRENTVQN EKYESLFKEK LIKEILPDFV LSTEAESLPF SVEEATRSLK EFDSFTSYFA  180
GFYENRKNIY STKPQSTAIA YRLIHENLPK FIDNILVFQK IKEPIAKELE HIRADFSAGG  240
YIKKDERLED IFSLNYYIHV LSQAGIEKYN ALIGKIVTEG DGEMKGLNEH INLYNQQRGR  300
EDRLPLFRPL YKQILSDREQ LSYLPESFEK DEELLRALKE FYDHIAEDIL GRTQQLMTSI  360
SEYDLSRIYV RNDSQLTDIS KKMLGDWNAI YMARERAYDH EQAPKRITAK YERDRIKALK  420
GEESISLANL NSCIAFLDNV RDCRVDTYLS TLGQKEGPHG LSNLVENVFA SYHEAEQLLS  480
FPYPEENNLI QDKDNVVLIK NLLDNISDLQ RFLKPLWGMG DEPDKDERFY GEYNYIRGAL  540
DQVIPLYNKV RNYLTRKPYS TRKVKLNFGN SQLLSGWDRN KEKDNSCVIL RKGQNFYLAI  600
MNNRHKRSFE NKMLPEYKEG EPYFEKMDYK FLPDPNKMLP KVFLSKKGIE IYKPSPKLLE  660
QYGHGTHKKG DTFSMDDLHE LIDFFKHSIE AHEDWKQFGF KFSDTATYEN VSSFYREVED  720
QGYKLSFRKV SESYVYSLID QGKLYLFQIY NKDFSPCSKG TPNLHTLYWR MLFDERNLAD  780
VIYKLDGKAE IFFREKSLKN DHPTHPAGKP IKKKSRQKKG EESLFEYDLV KDRRYTMDKF  840
QFHVPITMNF KCSAGSKVND MVNAHIREAK DMHVIGIDRG ERNLLYICVI DSRGTILDQI  900
SLNTINDIDY HDLLESRDKD RQQEHRNWQT IEGIKELKQG YLSQAVHRIA ELMVAYKAVV  960
ALEDLNMGFK RGRQKVESSV YQQFEKQLID KLNYLVDKKK RPEDIGGLLR AYQFTAPFKS  1020
FKEMGKQNGF LFYIPAWNTS NIDPTTGFVN LFHVQYENVD KAKSFFQKFD SISYNPKKDW  1080
FEFAFDYKNF TKKAEGSRSM WILCTHGSRI KNFRNSQKNG QWDSEEFALT EAFKSLFVRY  1140
EIDYTADLKT AIVDEKQKDF FVDLLKLFKL TVQMRNSWKE KDLDYLISPV AGADGRFFDT  1200
REGNKSLPKD ADANGAYNIA LKGLWALRQI RQTSEGGKLK LAISNKEWLQ FVQERSYEKD  1260

SEQ ID NO: 14          moltype = AA  length = 664
FEATURE                Location/Qualifiers
source                 1..664
                       mol_type = protein
                       organism = Prevotella disiens
SEQUENCE: 14
NSYKEDKKRL NKVIIAYIEQ IKQTNIKKSI IESISKYPNI SDDDKVTPSS LLEKIKKVSI  60
DSYNGILSFK SFQSVNKEVI DNLLKTISPL KNKAEFLDLI NKDYQIFTEV QAVIDEICKQ  120
KTFIYFPISN VELEKEMGDK DKPLCLFQIS NKDLSFAKTF SANLRKKRGA ENLHTMLFKA  180
LMEGNQDNLD LGSGAIFYRA KSLDGNKPTH PANEAIKCRN VANKDKVSLF TYDIYKNRRY  240
MENKFLFHLS IVQNYKAAND SAQLNSSATE YIRKADDLHI IGIDRGERNL LYYSVIDMKG  300
NIVEQDSLNI IRNNDLETDY HDLLDKREKE RKANRQNWEA VEGIKDLKKG YLSQAVHQIA  360
```

```
QLMLKYNAII ALEDLGQMFV TRGQKIEKAV YQQFEKSLVD KLSYLVDKKR PYNELGGILK  420
AYQLASSITK NNSDKQNGFL FYVPAWNTSK IDPVTGFTDL LRPKAMTIKE AQDFFGAFDN  480
ISYNDKGYFE FETNYDKFKI RMKSAQTRWT ICTFGNRIKR KKDKNYWNYE EVELTEEFKK  540
LFKDSNIDYE NCNLKEEIQN KDNRKFFDDL IKLLQLTLQM RNSDDKGNDY IISPVANAEG  600
QFFDSRNGDK KLPLDADANG AYNIARKGLW NIRQIKQTKN KDDLNLSISS TEWLDFVREK  660
PYLK                                                              664

SEQ ID NO: 15          moltype = AA  length = 1484
FEATURE                Location/Qualifiers
SITE                   1073
                       note = misc_feature - Xaa can be any naturally occurring
                        amino acid
source                 1..1484
                       mol_type = protein
                       note = Peregrinibacteria bacterium
                       organism = unidentified
SEQUENCE: 15
MSNFFKNFTN LYELSKTLRF ELKPVGDTLT NMKDHLEYDE KLQTFLKDQN IDDAYQALKP  60
QFDEIHEEFI TDSLESKKAK EIDFSEYLDL FQEKKELNDS EKKLRNKIGE TFNKAGEKWK  120
KEKYPQYEWK KGSKIANGAD ILSCQDMLQF IKYKNPEDEK IKNYIDDTLK GFFTYFGGFN  180
QNRANYYETK KEASTAVATR IVHENLPKFC DNVIQFKHII KRKKDGTVEK TERKTEYLNA  240
YQYLKNNNKI TQIKDAETEK MIESTPIAEK IFDVYYFSSC LSQKQIEEYN RIIGHYNLLI  300
NLYNQAKRSE GKHLSANEKK YKDLPKFKTL YKQIGCGKKK DLFYTIKCDT EEEANKSRNE  360
GKESHSVEEI INKAQEAINK YFKSNNDCEN INTVPDFINY ILTKENYEGV YWSKAAMNTI  420
SDKYFANYHD LQDRLKEAKV FQKADKKSED DIKIPEAIEL SGLFGVLDSL ADWQTTLFKS  480
SILSNEKLKI ITDSQTPSEA LLKMIFNDIE KNMESFLKET NDIITLKKYK GNKEGTEKIK  540
QWFDYTLAIN RMLKYFLVKE NKIKGNSLDT NISEALKTLI YSDDAEWFKW YDALRNYLTQ  600
KPQDEAKENK LKLNFDNPSL AGGWDVNKEC SNFCVILKDK NEKKYLAMIK KGENTLFQKE  660
WTEGRGKNLT KKSNPLFEIN NCEILSKMEY DFWADVSKMI PKCSTQLKAV VNHFKQSDNE  720
FIFPIGYKVT SGEKFREECK ISKQDFELNN KVFNKNELSV TAMRYDLSST QEKQYIKAFQ  780
KEYWELLFKQ EKRDTKLTNN EIFNEWINFC NKKYSELLSW ERKYKDALTN WINFCKYFLS  840
KYPKTTLFNY SFKESENYNS LDEFYRDVDI CSYKLNINTT INKSILDRLV EEGKLYLFEI  900
KNQDSNDGKS IGHKNNLHTI YWNAIFENFD NRPKLNGEAE IFYRKAISKD KLGIVKGKKT  960
KNGTWIIKNY RFSKEKFILH VPITLNFCSN NEYVNDIVNT KFYNFSNLHF LGIDRGEKHL  1020
AYYSLVNKNG EIVDQGTLNL PFTDKDGNQR SIKKEKYFYN KQEDKWEAKE VDXWNYNDLL  1080
DAMASNRDMA RKNWQRIGTI KEAKNGYVSL VIRKIADLAV NNERPAFIVL EDLNTGFKRS  1140
RQKIDKSVYQ KFELALAKKL NFLVDKNAKR DEIGSPTKAL QLTPPVNNYG DIENKKQAGI  1200
MLYTRANYTS QTDPATGWRK TIYLKAGPEE TTYKKDGKIK NKSVKDQIIE TFTDIGFDGK  1260
DYYFEYDKGE FVDEKTGEIK PKKWRLYSGE NGKSLDRFRG EREKDKYEWK IDKIDIVKIL  1320
DDLFVNFDKN ISLLKQLKEG VELTRNNEHG TGESLRFAIN LIQQIRNTGN NERDNDFILS  1380
PVRDENGKHF DSREYWDKET KGEKISMPSS GDANGAFNIA RKGIIMNAHI LANSDSKDLS  1440
LFVSDEEWDL HLNNKTEWKK QLNIFSSRKA MAKRKKKRPA ATKK                  1484

SEQ ID NO: 16          moltype = AA  length = 1245
FEATURE                Location/Qualifiers
source                 1..1245
                       mol_type = protein
                       organism = Porphyromonas macacae
SEQUENCE: 16
MKTQHFFEDF TSLYSLSKTI RFELKPIGKT LENIKKNGLI RRDEQRLDDY EKLKKVIDEY  60
HEDFIANILS SFSFSEEILQ SYIQNLSISE ARAKIEKTMR DTLAKAFSED ERYKSIFKKE  120
LVKKDIPVWC PAYKSLCKKF DNFTTSLVPF HENRKNLYTS NEITASIPYR IVHVNLPKFI  180
QNIEALCELQ KKMGADLYLE MMENLRNVWP SFVKTPDDLC NLKTYNHLMV QSSISEYNRF  240
VGGYSTEDGT KHQGINEWIN IYRQRNKEMR LPGLVFLHKQ ILAKVDSSSF ISDTLENDDQ  300
VFCVLRQFRK LFWNTVSSKE DDAASLKDLF CGLSGYDPEA IYVSDAHLAT ISKNIFDRWN  360
YISDAIRRKT EVLMPRKKES VERYAEKISK QIKKRQSYSL AELDDLLAHY SEESLPAGFS  420
LLSYFTSLGG QKYLVSDGEV ILYEEGSNIW DEVLIAFRDL QVILDKDFTE KKLGKDEEAV  480
SVIKKALDSA LRLRKFFDLL SGTGAEIRRD SSFYALYTDR MDKLKGLLKM YDKVRNYLTK  540
KPYSIEKFKL HFDNPSLLSG WDKNKELNNL SVIFRQNGYY YLGIMTPKGK NLFKTLPKLG  600
AEEMFYEKME YKQIAEPMLM LPKVFFPKKT KPAFAPDQSV VDIYNKKTFK TGQKGFNKKD  660
LYRLIDFYKE ALTVHEWKLF NFSFSPTEQY RNIGEFFDEV REQAYKVSMV NVPASYIDEA  720
VENGKLYLFQ IYNKDFSPYS KGIPNLHTLY WKALFSEQNQ SRVYKLCGGG ELFYRKASLH  780
MQDTTVHPKG ISIHKKNLNK KGETSLFNYD LVKDKRFTED KFFFHVPISI NYKNKKITNV  840
NQMVRDYIAQ NDDLQHGIDR GERNLLYISR IDTRGNLLEQ FSLNVIESDK GDLRTDYQKI  900
LGDREQERLR RRQEWKSIES IKDLKDGYMS QVVHKICNMV VEHKAIVVLE NLNLSFMKGR  960
KKVEKSVYEK FERMLVDKLN YLVVDKKNLS NEPGGLYAAY QLTNPLFSFE ELHRYPQSGI  1020
LFFVDPWNTS LTDPSTGFVN LLGRINYTNV GDARKFFDRF NAIRYDGKGN ILFDLDLSRF  1080
DVRVETQRKL WTLTTFGSRI AKSKKSGKWM VERIENLSLC FLELFEQFNI GYRVEKDLKK  1140
AILSQDRKEF YVRLIYLFNL MMQIRNSDGE EDYILSPALN EKNLQFDSRL IEAKDLPVDA  1200
DANGAYNVAR KGLMVVQRIK RGDHESIHRI GRAQWLRYVQ EGIVE                 1245

SEQ ID NO: 17          moltype = AA  length = 1250
FEATURE                Location/Qualifiers
source                 1..1250
                       mol_type = protein
                       organism = Smithella sp.
SEQUENCE: 17
MQTLFENFTN QYPVSKTLRF ELIPQGKTKD FIEQKGLLKK DEDRAEKYKK VKNIIDEYHK  60
DFIEKSLNGL KLDGLEKYKT LYLKQEKDDK DKKAFDKEKE NLRKQIANAF RNNEKFKTLF  120
```

```
AKELIKNDLM SFACEEDKKN VKEFEAFTTY FTGFHQNRAN MYVADEKRTA IASRLIHENL  180
PKFIDNIKIF EKMKKEAPEL LSPFNQTLKD MKDVIKGTTL EEIFSLDYFN KTLTQSGIDI  240
YNSVIGGRTP EEGKTKIKGL NEYINTDFNQ KQTDKKKRQP KFKQLYKQIL SDRQSLSFIA  300
EAFKNDTEIL EAIEKFYVNE LLHFSNEGKS TNVLDAIKNA VSNLESFNLT KMYFRSGASL  360
TDVSRKVFGE WSIINRALDN YYATTYPIKP REKSEKYEER KEKWLKQDFN VSLIQTAIDE  420
YDNETVKGKN SGKVIADYFA KFCDDKETDL IQKVNEGYIA VKDLLNTPCP ENEKLGSNKD  480
QVKQIKAFMD SIMDIMHFVR PLSLKDTDKE KDETFYSLFT PLYDHLTQTI ALYNKVRNYL  540
TQKPYSTEKI KLNFENSTLL GGWDLNKETD NTAIILRKDN LYYLGIMDKR HNRIFRNVPK  600
ADKKDFCYEK MVYKLLPGAN KMLPKVFFSQ SRIQEFTPSA KLLENYANET HKKGDNFNLN  660
HCHKLIDFFK DSINKHEDWK NFDFRFSATS TYADLSGFYH EVEHQGYKIS FQSVADSFID  720
DLVNEGKLYL FQIYNKDFSP FSKGKPNLHT LYWKMLFDEN NLKDVVYKLN GEAEVFYRKK  780
SIAEKNTTIH KANESIINKN PDNPKATSTF NYDIVKDKRY TIDKFQFHIP ITMNFKAEGI  840
FNMNQRVNQF LKANPDINII GIDRGERHLL YYALINQKGK ILKQDTLNVI ANEKQKVDYH  900
NLLDKKEGDR ATARQEWGVI ETIKELKEGY LSQVIHKLTD LMIENNAIIV MEDLNFGFKR  960
GRQKVEKQVY QKFEKMLIDK LNYLVDKNKK ANELGGLLNA FQLANKFESF QKMGKQNGFI  1020
FYVPAWNTSK TDPATGFIDF LKPRYENLNQ AKDFFEKFDS IRLNSKADYF EFAFDFKNFT  1080
EKADGGRTKW TVCTTNEDRY QWNRALNNNR GSQEKYDITA ELKSLFDGKV DYKSGKDLKQ  1140
QIASQESADF FKALMKNLSI TLSLRHNNGE KGDNEQDYIL SPVADSKGRF FDSRKADDDM  1200
PKNADANGAY HIALKGLWCL EQISKTDDLK KVKLAISNKE WLEFVQTLKG             1250

SEQ ID NO: 18          moltype = DNA  length = 3987
FEATURE                Location/Qualifiers
source                 1..3987
                       mol_type = other DNA
                       organism = synthetic construct
SEQUENCE: 18
atggccggga gcaagaagcg ccggataaag caggacacgc agttcgaggg cttcaccaac  60
ctgtaccaag tctccaagac gctccggttc gagcttatcc cgcaagggaa gaccctgaaa  120
cacatccagg aacaaggttt catcgaggag gacaaggccc gcaacgacca ctacaaggag  180
ctcaagccca taatcgatcg gatctacaag acgtacgccg accagtgcct ccaactggtg  240
cagctcgact gggagaacct gagcgccgcc attgacagct accgcaagga aaagacggag  300
gagacgcgca acgcccttat tgaggagcaa gccacctacc gcaacgccat ccacgactac  360
ttcatcgggc gcaccgacaa cctgacggac gcgatcaaca agcgccacgc ggaaatctac  420
aagggccttt tcaaggccga gctcttcaac gggaaggtcc taaaacagct cgggactgtc  480
acgacaaccg agcatgagaa cgccctcctt cgcagcttcg acaagttcac cacatacttc  540
tcgggcttct accggaaccg caagaacgtt ttcagcgccg aggacatctc caccgccatc  600
ccgcacagga tcgtccagga caacttcccc aagttcaagg agaactgcca catcttcacg  660
cgcctgatta cagccgtacc ttcacttcgt gagcacttcg agaacgtcaa aaaggccatc  720
gggatcttcg tctccacgtc catcgaggag gtattctctt tcccgttcta taaccagctc  780
ctgacccaga cgcagatcga cctctacaac cagctactgg gcggcatcag ccgggaggcc  840
gggaccgaga aaataaaggg cctcaacgaa gttctcaacc tggccatcca gaagaacgac  900
gagaccgcgc atatcatcgc atccctgccg catcgcttca ttcctttgtt caagcagata  960
ttgagcgacc ggaacaccct ctcgttcatc ctcgaagaat tcaagagcga cgaggaggtc  1020
attcagtctt tctgcaagta caagacgctc ctacggaatg agaatgtgct ggagaccgcg  1080
gaggcactct tcaatgagct gaactccatt gacctgaccc acatcttcat tagccacaag  1140
aaactggaga cgatctccag cgccctgtgc gaccactggg acactctccg caacgccctc  1200
tacgaacgcc ggatctccga acttaccggc aagataacta agtcggctaa ggagaaggtg  1260
caacggagcc tcaagcacga ggacatcaac cttcaggaaa tcatctcagc cgcgggcaag  1320
gagctgagcg aggcgtttaa gcagaaaaca tcggagatac tgagccacgc gcacgcggcc  1380
ctggatcaac cgctgccgac gactctcaag aagcaagagg agaaggaaat ccttaagtcc  1440
cagctcgact cgctgctcgg cctctatcac ttgctcgact ggttcgcggt tgatgagtcc  1500
aacgaggtgg acccggagtt ctccgcgcgc ctcacgggta ttaagctgga gatggagcca  1560
agcttaagct tctacaacaa ggcccgcaac tacgcgacca aaaaaccgta ctcagtcgag  1620
aaattcaagc tgaatttcca gatgcctaca ttggcgaggg ggtgggacgt gaaccgcgag  1680
aagaacaatg gagccatcct gttcgtcaaa aatgggttgt actacctggg catcatgccc  1740
aagcagaagg gccgttacaa ggccctgtca ttcgagccta ccgagaagac ctcggagggc  1800
ttcgacaaga tgtactacga ctatttcccg gacgccgcca agatgatccc gaagtgctcc  1860
acgcagctca aagccgtcac ggcccacttc cagacgcata ccacgccgat acttctgagc  1920
aacaacttca ttgagccgct agagatcacg aaggagatat acgacctaaa caaccccgaa  1980
aaggagccca agaagttcca gacagcctac gctaagaaga caggtgatca gaagggatat  2040
agggaggcac tctgcaagtg gatcgacttc acgcgcgact tcctgtcgaa atatacaaag  2100
acgaccagca ttgacctaag ttctctccgc ccatcctccc agtacaagga tctgggcgag  2160
tattatgcgg agctgaaccc attgctgtac cacatcagct tccagaggat cgccgagaag  2220
gagattatgg acgcggtgga gacggggaaa ctatacctgt tccaaatata taacaaggac  2280
ttcgctaaag ggcaccacgg gaagcccaac ctgcacacac tctactggac gggcttgttt  2340
tcgccagaaa atttggccaa gacttcgatc aagctcaacg gccaggcgga gttgttttac  2400
cgtcccaagt ctcgcatgaa gcgcatggcg catcgcctcg gagagaaaat gcttaacaag  2460
aagctcaagg atcagaagac gcccatacct gatacgttgt accaggaatt gtacgactac  2520
gtgaaccacc gcctatcgca cgacctctca gacgaggccc gcgccctcct cccaaacgtg  2580
attactaagg aggtttccca tgaaataatc aaggaccgac ggttcaccag cgacaaattt  2640
tttttccacg tgcctatcac gctcaattac caggcggcca actccccatc gaagttcaac  2700
cagcgcgtga acgcctacct taaggagcac ccggagaccc caatcatcgg gatcgaccgt  2760
ggcgagcgga acctgatcta tattacggtg atcgatagca ccgggaagat cctggagcag  2820
cgctccctga acacaatcca gcagtttgac taccagaaga aactcgacaa ccgggagaag  2880
gagcgcgtcg cagcccggca agcatggagt gtggtcggca ccataaagga cctgaaacag  2940
ggttacctaa gtcaagttat ccacgagatc gttgacctga tgatacacta tcaagccgta  3000
gtcgtgctgg agaacctcaa cttcgggttt aagtccaagc gcaccggcat cgcggagaag  3060
gcggtgtacc agcagttcga gaagatgctg atcgacaagc tgaactgcct ggtgctcaag  3120
gactaccctg cggagaaggt cggcggggtc ttgaacccgt accagctaac cgaccagttc  3180
```

```
acgagcttcg ccaaaatggg cacgcagtcc ggattcttgt tttatgtccc ggctccatat  3240
acaagtaaga tcgacccgct gacagggttt gttgacccat tcgtgtggaa gaccatcaag  3300
aaccacgaga gcaggaaaca cttcttagag ggcttcgact tcctgcatta cgacgttaag  3360
acaggcgact tcatcctgca cttcaagatg aaccgcaacc tgtcgttcca gaggggcctg  3420
cccggcttca tgcccgcctg ggatatcgtc tttgagaaga atgagacgca gttcgacgcg  3480
aaggggacgc cgttcatcgc tggaaagcgg atcgtgccgg tcatcgagaa ccaccgcttc  3540
acgggtcgct accgagattt ataccccgcc aacgaactaa ttgcgctgct ggaggagaag  3600
gggatcgtgt tccgagatgg cagcaacatt ctcccgaagc tgctggagaa cgacgactcg  3660
cacgctattg acacgatggt cgccctcata cggagcgtgc ttcagatgcg gaacagtaac  3720
gctgccacgg gcgaggacta cattaactcc cccgtccgcg acctcaacgg ggtctgcttc  3780
gatagccgct tccagaaccc ggagtggcct atggatgcgg acgcgaacgg ggcctaccac  3840
atcgccctca agggccaact cctgctcaac cacttgaagg aaagcaaaga cctcaaattg  3900
cagaatggca tcagtaacca ggactggctc gcgtacatcc aggaactgag aaacgggtcc  3960
aagaagcggc gtatcaagca agattga                                      3987

SEQ ID NO: 19           moltype = DNA  length = 3987
FEATURE                 Location/Qualifiers
source                  1..3987
                        mol_type = other DNA
                        organism = synthetic construct
SEQUENCE: 19
atggcgggaa gcaaaaagcg ccggattaag caagacacgc agttcgaggg cttcacgaac  60
ctctaccaag tcagcaagac cctccggttc gagctgatac cacagggaaa gacgctcaag  120
cacatccagg aacagggctt catcgaggag gacaaggcgc gcaacgacca ctacaaggag  180
ttgaaaccga tcatcgaccg catctacaag acgtacgccg accagtgcct ccagctcgtg  240
cagctcgact gggagaacct ctccgccgcc attgactcgt accggaagga gaagactgag  300
gagacccgca acgccctgat cgaggagcaa gcaacctacc ggaacgccat ccacgactac  360
ttcatcggcc gcaccgacaa cctcaccgac gcgatcaaca agcggcacgc ggagatatac  420
aaagggctgt tcaaggcgga gctgttcaac ggcaaggtgc tcaagcagct agggacggtg  480
accacgaccg agcacgagaa cgcgctcctc cgcagcttcg acaagttcac cacctacttc  540
agcggcttct accggaaccg caagaatgtg ttcagcgcgg aggacatcag cacggccatc  600
ccgcaccgca tcgtccagga caacttcccg aagttcaagg agaactgcca catcttcacc  660
cgcctgataa ccgccgtccc ctccctgcgg gagcacttcg agaacgtcaa aaaggcaatt  720
gggatcttcg tctcgaccag cattgaggag gtgttcagct tcccctteta caaccagctc  780
ctcacccaga cgcagatcga cctgtacaat cagttgctcg gcgggataag ccgcgaggcg  840
ggaaccgaaa aaatcaaggg gctgaacgaa gtgttgaacc tcgccatcca gaagaacgac  900
gagaccgcgc acatcatcgc ctccctgccc caccggttca tcccgctgtt caagcagatc  960
ctctctgacc ggaacaccct gtccttcatt cttgaggagt tcaagtcgga cgaggaggtc  1020
atccagagct tctgcaagta caagacgctg ctacggaacg agaacgtgct ggagacggcg  1080
gaggcactgt tcaacgagct aaacagcatc gacctcacgc acatcttcat cagtcacaag  1140
aaactggaga ccatctcctc cgcgctgtgc gaccactggg acacgctcag gaacgcgctc  1200
tacgagcgcc gaatcagtga gctgacgggc aagatcacga agtccgcgaa ggagaaggtg  1260
cagcggtccc tcaagcacga ggacatcaac ctccaggaga tcatctcagc ggctgggaaa  1320
gagctgtccg aggcgttcaa gcagaaaacg agcgaaatcc tgtcccacgc gcacgcggcc  1380
ctggatcagc ctctgccgac gaccctcaag aaacaagaag aaaaggaaat cctcaagtcg  1440
cagctcgact cgctgctggg cctgtaccat ctcctcgact ggttcgccgt ggacgagagc  1500
aacgaggtgg accccgagtt ctccgcgcgg cttacgggga tcaagctgga gatggagccc  1560
agcctgtcct tctacaacaa ggcgcgcaac tacgccacca agaagcccta cagcgtggag  1620
aagttcaagc tcaacttcca gatgcccact ctcgcacgtg ggtgggacgt caaccgcgaa  1680
aaaaataatg gggcgatcct gttcgtcaag aacggcctgt actacttggg catcatgccg  1740
aaacagaagg gccgctacaa ggccctgagc ttcgaaccga ccgagaaaac gagcgagggg  1800
ttcgacaaga tgtactacga ctacttcccc gacgccgcga agatgattcc aaagtgctcc  1860
acgcagctta aggccgtgac ggcccacttc cagacgcaca cgacccccgat cctcctcagc  1920
aacaacttca tcgagcccct ggagatcacg aaggagatat acgacctgaa caacccggag  1980
aaggagccca agaaattcca gaccgcctac gccaagaaga caggcgacca aaagggttac  2040
agggaggccc tctgcaagtg gatcgacttc actagggact tcctgtccaa gtacaccaag  2100
actacctcta tcgacctgtc cagcctccgc ccgtcgtccc agtacaaaga tttgggcgag  2160
tattacgcgg agctgaaccc actgctctac cacatcagct tccagcgcat cgcggagaag  2220
gagatcatgg acgcagtgga gacgggcaag ctatacctat ttcagatata caacaaagac  2280
ttcgctaagg gacaccacgg caagcctaac ctgcacaccc tctactggac ggggctcttc  2340
agcccggaga acctcgccaa gacctcgatc aagctcaacg gccaggccga gctgttctac  2400
cggcccaagt cccgcatgaa gcggatggcc caccggctcg ggagaaaaat gctcaacaag  2460
aaattgaagg accaaaaaac gccgataccc gacaccctat accaggagct gtacgactat  2520
gtgaaccacc gcctgagcca cgacctcagc gacgaggcgc gggccctcct gccgaacgtc  2580
atcacaaagg aggtcagcca cgagatcatc aaggaccggc gcttcacctc cgacaagttt  2640
ttctttcacg tgcccatcac gctcaactac caggccgcca actcgccgtc caagttcaac  2700
cagcgcgtga acgcctacct caaggagcac cccgagaccc cgatcatcgg gattgaccga  2760
ggggagcgga acctcatcta catcaccgtc atcgacagca ccgggaagat ccttgaacag  2820
cggtcgctca acaccatcca gcagttcgac taccagaaga aactcgacaa ccgggagaag  2880
gagagagtgg cggcccgcca ggcttggtcc gtcgtcggga cgattaagga cttgaaacaa  2940
ggttacctgt cgcaagtgat ccacgagatc gttgacctga tgatccacta ccaagccgtc  3000
gtggtcctgg agaacctcaa cttcggcttc aagagcaaac gaaccggcat cgcggagaag  3060
gccgtgtacc agcagttcga aaaaatgctg atcgacaagc tgaactgcct cgtgctcaag  3120
gactaccccg ctgagaaggt cggcggggtg ctgaacccgt accagctcac tgaccagttc  3180
accagcttcg caaagatggg cacccagtcc ggcttcctgt tctacgtgcc tgcgccatac  3240
acctcgaaga tcgacccgct caccgggttc gtggacccct tcgtctggaa gaccatcaag  3300
aaccacgaga gccgcaagca cttcctggag ggcttcgact tcctccacta cgacgtcaag  3360
accggggact tcatcctgca cttcaagatg aaccgcaacc tcagtttcca gcgcggcctg  3420
ccggggttca tgcccgcttg ggatatagtc ttcgagaaga atgagacgca gttcgacgcg  3480
```

```
aagggcaccc cgttcatcgc cgggaagcgc atcgtgccgg tcatcgagaa ccaccggttc  3540
accgggcgct accgcgacct atacccggcg aacgagttga tcgccctcct ggaggagaag  3600
ggcatcgtgt tccgcgacgg ctccaacatc ctcccgaagc tgctcgaaaa cgacgactcc  3660
cacgccatcg acacgatggt cgcgctgatc cggtcggtgc tccagatgcg gaactccaac  3720
gccgcgacgg gcgaggacta catcaacagt ccggtccgcg atctgaacgg cgtctgcttc  3780
gactcccggt tccagaaccc cgagtggccg atggacgcgg acgcgaacgg cgcataccac  3840
atcgccctaa aagggcaatt gctgctcaac cacctcaagg aatccaaaga cctaaagctc  3900
cagaacggca tctccaacca ggactggctg gcgtacatcc aggaactgcg gaacgggagc  3960
aaaaaacgtc ggatcaagca agattga                                     3987

SEQ ID NO: 20           moltype = DNA  length = 3987
FEATURE                 Location/Qualifiers
source                  1..3987
                        mol_type = other DNA
                        organism = synthetic construct
SEQUENCE: 20
atggcgggct ccaagaaacg ccggattaag caagataccc agttcgaggg gttcacgaac  60
ctctaccaag tgagcaagac cctccgattc gaactgattc ctcaggggaa gaccctcaag  120
cacatccagg agcaagggtt catcgaggag gacaaggcgc ggaacgacca ctacaaggaa  180
ctcaaaccca tcatcgaccg catctacaag acctacgccg atcagtgcct ccagctcgtg  240
cagttggact gggagaacct cagcgcggcc attgactcct accggaagga gaaaacggag  300
gagacgcgca acgcgctcat cgaggaacag gcaacctatc gcaacgccat ccacgactac  360
ttcatcggga ggactgacaa cctcactgac gcgattaaca agcgccacgc ggagatatac  420
aagggactct tcaaagcgga gctgtttaac ggcaaggttc tcaagcaact cggcactgtg  480
accacgaccg agcatgagaa cgccctgctc cgctccttcg acaagttcac cacctacttc  540
tccgggttct accgcaaccg caagaatgtc ttcagcgcgg aggacatcag cacggccatt  600
ccacatcgaa tcgtccaaga taacttcccg aagttcaagg agaactgcca catcttcacc  660
cgactcatta ctgctgtacc gtcgttacgc gaacacttcg agaacgtcaa gaaggcaatt  720
ggaatcttcg tctctacgtc aatagaggag gtgttcagct tccctttcta caaccagctc  780
cttacgcaga cccagataga cctgtacaat cagctcctcg gtgggatcag ccgggaggcg  840
gggactgaga agattaaagg gctcaacgag gtcttgaacc tggccatcca aaaaaacgat  900
gagacggcgc acatcatcgc ctcgctgccc caccggttca tcccgctgtt caagcagatc  960
ctcagtgaca ggaacacctt gagctttatc ctagaggagt tcaagagcga cgaggaggtg  1020
atccagagct tctgcaagta caaaaccctg ctgaggaacg agaacgtcct ggagacggcg  1080
gaggcgctgt tcaacgagct gaactctatc gacttaactc acatattcat ctcgcacaag  1140
aagctggaga ctattagctc tgcactctgc gaccactggg acaccctccg caacgcgctc  1200
tacgagcgcc gcatctcgga gctgaccggg aagatcacca aatccgcgaa ggaaaaggtc  1260
cagcgttccc tcaaacacga ggatattaac ttacaggaga ttatctcagc ggctgggaag  1320
gagttgtcag aggcgttcaa gcagaaaact tccgagatcc tgagccacgc gcacgcagcg  1380
ctcgaccagc ctctgcccac caccctcaaa aagcaggaag aaaaagagat cctcaagagc  1440
cagttggact ccctgctggg gctctatcac cttctcgact ggttcgccgt cgatgagtcg  1500
aacgaggtgg accccgagtt ctccgcccgg ctgaccggca tcaagctaga gatggagccg  1560
tccctcagct tctacaataa ggcccgcaac tacgcgacca aaaaacccta cagcgtggag  1620
aagttcaagc tgaacttcca gatgccgacc ttagcacgcg gttgggacgt aaacagggag  1680
aagaacaatg gagccatcct gttcgtcaag aacgggcttt actacctcgg gataatgccc  1740
aagcagaagg gccgctacaa ggccctttcc ttcgagccga cggagaaaac ctccgagggg  1800
ttcgacaaga tgtactacga ctacttcccc gacgccgcca agatgatccc gaagtgctca  1860
acgcagctaa aagccgtgac cgcccacttc cagacccaca cgacgccgat cctgctgagc  1920
aacaacttca tcgagcccct tgagatcact aaggagatat acgacctgaa caaccccgag  1980
aaggagccca agaagtttca aaccgcctac gccaaaaaaa ctggcgacca aaagggctac  2040
agggaggcgc tgtgtaagtg gatcgacttc acacgcgact tcctttcgaa gtatacgaag  2100
acaacctcta ttgacctgag cagcctgcgt cctagctccc agtacaaaga tttgggcgag  2160
tactacgcgg agcttaatcc actactctac cacatctcat tccagcgcat cgctgagaag  2220
gaaatcatgg acgcggtgga gacaggcaaa ctgtacctct tccagatata caacaaagac  2280
ttcgctaagg ggcaccacgg gaagcccaac cttcatacgc tctactggac gggcctattc  2340
agccccgaaa atctggccaa gacctccatc aagctgaacg gccaagcgga gctgttctac  2400
agacccaaga gccggatgaa gcggatggcc cacaggctcg gcgagaaaat gcttaacaaa  2460
aagttgaagg accagaaaac ccctatcccc gacaccctct accaggaact gtacgactac  2520
gtgaaccaca ggctctcgca cgacctttcc gacgaggccc gtgccctact cccgaacgtc  2580
attaccaaag aggtttcgca cgagatcatc aaggaccggc ggttcacgag cgacaagttt  2640
ttctttcacg tccccatcac ccttaactac caggcggcca actccccatc caagttcaac  2700
cagcgtgtga atgcctacct caaggagcac ccagagaccc cgatcattgg gatcgaccgg  2760
ggcgagcgga acctgatcta catcaccgtc atcgactcga cgggcaagat tcttgagcag  2820
agatcgttga ataccataca gcagttcgac taccagaaga aactcgacaa ccgcgagaag  2880
gagcgcgtgg cggcccgcca ggcgtggtcc gtcgttggga cgattaagga cttgaaacaa  2940
ggttatctgt cccaagtcat ccacgagatc gttgatctga tgatccacta tcaggcagtg  3000
gtggtgctgg agaatctcaa cttcggcttc aagagtaagc ggacgggaat cgccgagaag  3060
gccgtgtacc agcagttcga gaagatgctg atcgacaagc tcaactgcct tgtgctgaaa  3120
gactacccgg ccgagaaggt cggcggcgtc ctcaacccgt accaacttac cgaccagttc  3180
acctccttcg ccaagatggg cactcagtcc gggttcttgt tctacgtccc cgcaccttac  3240
acctctaaga tcgaccctct gactggcttc gtagatccat tcgtgtggaa gaccattaag  3300
aaccacgaga gccgcaagca cttcctggag ggcttcgact tcctgcacta cgacgtgaag  3360
accggggact tcatccttca cttcaagatg aaccggaacc tcagcttcca gcggggcctg  3420
ccggggttca tgcccgcctg ggacatcgtg ttcgagaaga acgagaccca gttcgacgcg  3480
aagggcacgc ccttcatcgc cgggaagcgt atcgtgccgg tgatcgagaa ccatcgtttc  3540
acgggtcgct accgtgacct ctacccggcg aacgagctta tcgcactcct ggaggagaag  3600
ggcatcgtct tccgggacgg ctccaacatc ctcccgaaac tgctggaaaa cgacgactct  3660
cacgccatcg acacgatggt ggccctcatc cggtccgtgc tccaaatgcg gaacagcaac  3720
gccgccaccg gtgaggacta catcaacagc ccggtccggg atctgaacgg ggtgtgcttc  3780
```

```
gattcgcggt tccagaatcc tgagtggccg atggacgcgg atgcaaacgg ggcgtaccac  3840
atcgcgctca agggccagtt acttctgaac caccttaagg agtctaaaga tttgaaactc  3900
cagaacggga tctcgaacca ggactggctg gcctacatcc aagagttgcg gaacggcagc  3960
aagaagcggc ggattaagca agattag                                      3987

SEQ ID NO: 21          moltype = DNA  length = 1592
FEATURE                Location/Qualifiers
source                 1..1592
                       mol_type = other DNA
                       organism = Medicago truncatula
SEQUENCE: 21
actgttaata atttttaaac gtcagcgcac taaaaaaacg aaaagacgga cacgtgaaaa  60
taaaaaacac acactagttt atgacgcaat actattttac ttatgatttg ggtacattag  120
acaaaaccgt gaaagagatg tatcagctat gaaacctgta tacttcaata cagagactta  180
ctcatatcgg atacgtacgc acgaagtatc atattaatta ttttaatttt taataaatat  240
tttatcggat acttatgtga tactctacat atacacaagg atatttctaa gatactttat  300
agatacgtat cctagaaaaa catgaagagt aaaaaagtga gacaatgttg taaaaattca  360
ttataaatgt atatgattca attttagata tgcatcagta taattgattc tcgatgaaac  420
acttaaaatt atatttcttg tggaagaacg tagcgagaga ggtgattcag ttagacaaca  480
ttaaataaaa ttaatgttaa gttcttttaa tgatgtttct ctcaatatca catcatatga  540
aaatgtaata tgatttataa gaaaattttt aaaaaattta ttttaataat cacatgtact  600
atttttttaaa aattgtatct tttataataa tacaataata aagagtaatc agtgttaatt  660
tttcttcaaa tataagtttt attataaatc attgttaacg tatcataagt cattaccgta  720
tcgtatctta attttttttt aaaaaccgct aattcacgta cccgtattgt attgtacccg  780
cacctgtatc acaatcgatc ttagttagaa gaattgtctc gaggcggtgc aagacagcat  840
ataatagacg tggactctct tataccaaac gttgtcgtat cacaaagggt taggtaacaa  900
gtcacagttt gtccacgtgt cacgttttaa ttggaagagg tgccgttggc gtaatataac  960
agccaatcga tttttgctat aaaagcaaat caggtaaact aaacttcttc attcttttct  1020
tccccatcgc tacaaaaccg gttcctttgg aaaagagatt cattcaaacc tagcacccaa  1080
ttccgtttca aggtataatc tactttctat tcttcgatta ttttattatt attagctact  1140
atcgtttaat cgatcttttc ttttgatccg tcaaatttaa attcaattag ggttttgttc  1200
ttttctttca tctgattgaa atccttctga attgaaccgt ttacttgatt ttactgttta  1260
ttgtatgatt taatcctttg tttttcaaag acagtcttta gattgtgatt aggggttcat  1320
ataaattttt agatttggat ttttgtattg tatgattcaa aaaatacgtc ctttaattag  1380
attagtacat ggatattttt tacccgattt attgattgtc agggagaatt tgatgagcaa  1440
gttttttttga tgtctgttgt aaattgaatt gattataatt gctgatctgc tgcttccagt  1500
tttcataacc catattcttt taaccttgtt gtacacacaa tgaaaaattg gtgattgatt  1560
catttgtttt tctttgtttt ggattataca gg                                1592

SEQ ID NO: 22          moltype = DNA  length = 2000
FEATURE                Location/Qualifiers
source                 1..2000
                       mol_type = other DNA
                       organism = Zea mays
SEQUENCE: 22
gtcgtgcccc tctctagaga taaagagcat tgcatgtcta aagtataaaa aattaccaca  60
tattttttttg tcacacttat ttgaagtgta gtttatctat ctctatacat atatttaaac  120
ttcactctac aaataatata gtctataata ctaaaataat attagtgttt tagaggatca  180
tataaataaa ctgctagaca tggtctaaag gataattgaa tattttgaca atctacagtt  240
ttatcttttt agtgtgcatg tgatctctct gtttttttttg caaatagctt gacctatata  300
atacttcatc cattttatta gtacatccat ttaggattta gggttgatgg tttctataga  360
ctaattttta gtacatccat tttattcttt ttagtctcta aatttttttaa aactaaaact  420
ctattttagt tttttattta ataatttaga tataaaatga aataaaataa attgactaca  480
aataaaacaa atacccttta agaaataaaa aaactaagca aacattttttc ttgtttcgag  540
tagataatga caggctgttc aacgccgtcg acgagtctaa cggacaccaa ccagcgaacc  600
agcagcgtcg cgtcgggcca agcgaagcag acggcacggc atctctgtag ctgcctctgg  660
acccctctcg agagttccgc tccaccgttg gacttgctcc gctgtcggca tccagaaatt  720
gcgtggcgga gcggcagacg tgaggcggca cggcaggcgg cctcttcctc ctctcacggc  780
accggcagct acgggggatt cctttcccac cgctccttcg ctttcccttc ctcgcccgcc  840
gtaataaata gacaccccct ccacaccctc tttccccaac ctcgtgttcg ttcggagcgc  900
acacacacgc aaccagatct cccccaaatc cagccgtcgg cacctccgct tcaaggtacg  960
ccgctcatcc tccccccccc cctctctcta ccttctctag atcggcgatc cggtccatgg  1020
ttagggcccg gtagttctac ttctgttcat gtttgtgtta gagcaaacat gttcatgttc  1080
atgtttgtga tgatgtggtc tggttgggcg gtcgttctag atcggagtag gatactgttt  1140
caagctacct ggtggattta ttaattttgt atctgtatgt gtgtgccata catcttcata  1200
gttacgagtt taagatgatg gatggaaata tcgatctagg ataggtatac atgttgatgc  1260
gggttttact gatgcatata cagagatgct ttttttctcg cttggttgtg atgatatggt  1320
ctggttgggc ggtcgttcta gatcggagta gaatactgtt tcaaactacc tggtggattt  1380
attaaaggat aaagggtcgt tctagatcgg agtagaatac tgtttcaaac tacctggtgg  1440
atttattaaa ggatctgtat gtatgtgcct acatcttcat agttacgagt ttaagatgat  1500
ggatggaaat atcgatctag gataggtata catgttgatg cgggttttac tgatgcatat  1560
acagagatgc ttttttttcgc ttggttgtga tgatgtggtc tggttgggcg gtcgttctag  1620
atcggagtag aatactgttt caaactacct ggtggattta ttaattttgt atctttatgt  1680
gtgtgccata catcttcata gttacgagtt taagatgatg gatggaaata ttgatctagg  1740
ataggtatac atgttgatgt gggttttact gatgcatata catgatggca tatgcggcat  1800
ctattcatat gctctaacct tgagtaccta tctattataa taaacaagta tgttttataa  1860
ttattttgat cttgatatac ttggatgatg gcatatgcag cagctatatg tggatttttt  1920
agccctgcct tcatacgcta tttatttgct tggtactgtt tcttttgtcc gatgctcacc  1980
ctgttgtttg gtgatacttc                                              2000
```

```
SEQ ID NO: 23          moltype = AA  length = 228
FEATURE                Location/Qualifiers
source                 1..228
                       mol_type = protein
                       organism = Rattus norvegicus
SEQUENCE: 23
SSETGPVAVD PTLRRRIEPH EFEVFFDPRE LRKETCLLYE INWGGRHSIW RHTSQNTNKH  60
VEVNFIEKFT TERYFCPNTR CSITWFLSWS PCGECSRAIT EFLSRYPHVT LFIYIARLYH  120
HADPRNRQGL RDLISSGVTI QIMTEQESGY CWRNFVNYSP SNEAHWPRYP HLWVRLYVLE  180
LYCIILGLPP CLNILRRKQP QLTFFTIALQ SCHYQRLPPH ILWATGLK                228

SEQ ID NO: 24          moltype = AA  length = 199
FEATURE                Location/Qualifiers
source                 1..199
                       mol_type = protein
                       organism = Homo sapiens
SEQUENCE: 24
MEASPASGPR HLMDPHIFTS NFNNGIGRHK TYLCYEVERL DNGTSVKMDQ HRGFLHNQAK  60
NLLCGFYGRH AELRFLDLVP SLQLDPAQIY RVTWFISWSP CFSWGCAGEV RAFLQENTHV  120
RLRIFAARIY DYDPLYKEAL QMLRDAGAQV SIMTYDEFKH CWDTFVDHQG CPFQPWDGLD  180
EHSQALSGRL RAILQNQGN                                                199

SEQ ID NO: 25          moltype = DNA  length = 621
FEATURE                Location/Qualifiers
source                 1..621
                       mol_type = other DNA
                       organism = Petromyzon marinus
SEQUENCE: 25
acagatgcag agtatgtgag aattcacgaa aagctggaca tctatacctt caagaagcag  60
ttctttaaca ataagaagtc tgtgagccat aggtgctacg tgctgttcga gctgaagaga  120
aggggtgaaa gaagggcatg tttttggggg tatgctgtga acaagcccca gtctggaact  180
gagagaggca ttcacgccga aattttcagc atcagaaagg tggaggaata cctgagggat  240
aaccctggac agtttacaat taattggtat tctagctggt ctccatgcgc tgactgtgcc  300
gagaagatcc tggaatggta caaccaggag ctgagaggaa atggccatac cctgaagatt  360
tgggcctgca agctgtacta tgaaaagaac gcaagaaatc agatcggact gtggaacctg  420
agggataatg gtgtggggct gaacgtgatg gtgtccgagc actatcagtg ctgtagaaag  480
attttcattc agtcctcaca taatcagctg aacgagaata gatggctgga aaagactctg  540
aagagggctg agaagagaag gtccgaactg tcaattatga tccaggtgaa gatcctgcac  600
accactaagt cacctgccgt g                                             621

SEQ ID NO: 26          moltype = AA  length = 160
FEATURE                Location/Qualifiers
source                 1..160
                       mol_type = protein
                       organism = synthetic construct
SEQUENCE: 26
FERNYDPREL RKETYLLYEI KWGKSGKLWR HWCQNNRTQH AEVYFLENIF NARRFNPSTH  60
CSITWYLSWS PCAECSQKIV DFLKEHPNVL EIYVARLYYH EDERNRQGLR DLVNSGVTIR  120
IMDLPDYNYC WKTFVSDQGG DEDYWPGHFA PWIKQYSLKL                         160

SEQ ID NO: 27          moltype = AA  length = 207
FEATURE                Location/Qualifiers
source                 1..207
                       mol_type = protein
                       organism = synthetic construct
SEQUENCE: 27
TDAEYVRIHE KLDIYTFKKQ FSNNKKSVSH RCYVLFELKR RGERRACFWG YAVNKPQSGT  60
ERGIHAEIFS IRKVEEYLRD NPGQFTINWY SSWSPCADCA EKILEWYNQE LRGNGHTLKI  120
WVCKLYYEKN ARNQIGLWNL RDNGVGLNVM VSEHYQCCRK IFIQSSHNQL NENRWLEKTL  180
KRAEKRRSEL SIMFQVKILH TTKSPAV                                       207

SEQ ID NO: 28          moltype = AA  length = 228
FEATURE                Location/Qualifiers
source                 1..228
                       mol_type = protein
                       organism = synthetic construct
SEQUENCE: 28
SSKTGPVAVD PTLRRRIEPH EFEVFFDPRE LRKETCLLYE INWGGRHSIW RHTSQNTNKH  60
VEVNFIEKFT TERYFCPNTR CSITWFLSWS PCGECSRAIT EFLSRYPNVT LFIYIARLYH  120
LANPRNRQGL RDLISSGVTI QIMTEQESGY CWHNFVNYSP SNESHWPRYP HLWVRLYVLE  180
LYCIILGLPP CLNILRRKQS QLTSFTIALQ SCHYQRLPPH ILWATGLK                228

SEQ ID NO: 29          moltype = AA  length = 162
FEATURE                Location/Qualifiers
source                 1..162
                       mol_type = protein
                       organism = synthetic construct
SEQUENCE: 29
```

```
SFERNYDPRE LRKETYLLYE IKWGKSGKLW RHWCQNNRTQ HAEVYFLENI FNARRFNPST  60
HCSITWYLSW SPCAECSQKI VDFLKEHPNV NLEIYVARLY YPENERNRQG LRDLVNSGVT  120
IRIMDLPDYN YCWKTFVSDQ GGDEDYWPGH FAPWIKQYSL KL                    162

SEQ ID NO: 30          moltype = AA  length = 166
FEATURE                Location/Qualifiers
source                 1..166
                       mol_type = protein
                       organism = Escherichia coli
SEQUENCE: 30
SEVEFSHEYW MRHALTLAKR AWDEREVPVG AVLVHNNRVI GEGWNRPIGR HDPTAHAEIM  60
ALRQGGLVMQ NYRLIDATLY VTLEPCVMCA GAMIHSRIGR VVFGARDAKT GAAGSLMDVL  120
HHPGMNHRVE ITEGILADEC AALLSDFFRM RRQEIKAQKK AQSSTD                166

SEQ ID NO: 31          moltype = AA  length = 166
FEATURE                Location/Qualifiers
source                 1..166
                       mol_type = protein
                       organism = synthetic construct
SEQUENCE: 31
SEVEFSHEYW MRHALTLAKR ARDEREVPVG AVLVLNNRVI GEGWNRAIGL HDPTAHAEIM  60
ALRQGGLVMQ NYRLIDATLY VTFEPCVMCA GAMIHSRIGR VVFGVRNAKT GAAGSLMDVL  120
HYPGMNHRVE ITEGILADEC AALLCYFFRM PRQVFNAQKK AQSSTD                166

SEQ ID NO: 32          moltype = AA  length = 166
FEATURE                Location/Qualifiers
source                 1..166
                       mol_type = protein
                       organism = synthetic construct
SEQUENCE: 32
SEVEFSHEYW MRHALTLAKR AWDEREVPVG AVLVLNNRVI GEGWNRSIGL HDPTAHAEIM  60
ALRQGGLVMQ NYRLIDATLY VTFEPCVMCA GAMIHSRIGR VVFGVRNAKT GAAGSLMDVL  120
HYPGMNHRVE ITEGILADEC AALLCYFFRM RRQVFNAQKK AQSSTD                166

SEQ ID NO: 33          moltype = AA  length = 166
FEATURE                Location/Qualifiers
source                 1..166
                       mol_type = protein
                       organism = synthetic construct
SEQUENCE: 33
SEVEFSHEYW MRHALTLAKR ALDEREVPVG AVLVLNNRVI GEGWNRAIGL HDPTAHAEIM  60
ALRQGGLVMQ NYRLIDATLY VTFEPCVMCA GAMIHSRIGR VVFGVRNAKT GAAGSLMDVL  120
HYPGMNHRVE ITEGILADEC NALLCYFFRM RRQVFNAQKK AQSSTD                166

SEQ ID NO: 34          moltype = AA  length = 166
FEATURE                Location/Qualifiers
source                 1..166
                       mol_type = protein
                       organism = synthetic construct
SEQUENCE: 34
SEVEFSHEYW MRHALTLAKR ALDEREVPVG AVLVLNNRVI GEGWNRAIGL HDPTAHAEIM  60
ALRQGGLVMQ NYRLIDATLY VTFEPCVMCA GAMIHSRIGR VVFGVRNAKT GAAGSLMDVL  120
HYPGMNHRVE ITEGILADEC NALLCYFFRM PRQVFNAQKK AQSSTD                166

SEQ ID NO: 35          moltype = AA  length = 1763
FEATURE                Location/Qualifiers
source                 1..1763
                       mol_type = protein
                       organism = synthetic construct
SEQUENCE: 35
SEVEFSHEYW MRHALTLAKR AWDEREVPVG AVLVHNNRVI GEGWNRPIGR HDPTAHAEIM  60
ALRQGGLVMQ NYRLIDATLY VTLEPCVMCA GAMIHSRIGR VVFGARDAKT GAAGSLMDVL  120
HHPGMNHRVE ITEGILADEC AALLSDFFRM RRQEIKAQKK AQSSTDSGGS SGGSSGSETP  180
GTSESATPES SGGSSGGSSE VEFSHEYWMR HALTLAKRAR DEREVPVGAV LVLNNRVIGE  240
GWNRAIGLHD PTAHAEIMAL RQGGLVMQNY RLIDATLYVT FEPCVMCAGA MIHSRIGRVV  300
FGVRNAKTGA AGSLMDVLHY PGMNHRVEIT EGILADECAA LLCYFFRMPR QVFNAQKKAQ  360
SSTDSGGSSG GSSGSETPGT SESATPESSG GSSGGSDKKY SIGLAIGTNS VGWAVITDEY  420
KVPSKKFKVL GNTDRHSIKK NLIGALLFDS GETAEATRLK RTARRRYTRR KNRICYLQEI  480
FSNEMAKVDD SFFHRLEESF LVEEDKKHER HPIFGNIVDE VAYHEKYPTI YHLRKKLVDS  540
TDKADLRLIY LALAHMIKFR GHFLIEGDLN PDNSDVDKLF IQLVQTYNQL FEENPINASG  600
VDAKAILSAR LSKSRRLENL IAQLPGEKKN GLFGNLIALS LGLTPNFKSN FDLAEDAKLQ  660
LSKDTYDDDL DNLLAQIGDQ YADLFLAAKN LSDAILLSDI LRVNTEITKA PLSASMIKRY  720
DEHHQDLTLL KALVRQQLPE KYKEIFFDQS KNGYAGYIDG GASQEEFYKF IKPILEKMDG  780
TEELLVKLNR EDLLRKQRTF DNGSIPHQIH LGELHAILRR QEDFYPFLKD NREKIEKILT  840
FRIPYYVGPL ARGNSRFAWM TRKSEETITP WNFEEVVDKG ASAQSFIERM TNFDKNLPNE  900
KVLPKHSLLY EYFTVYNELT KVKYVTEGMR KPAFLSGEQK KAIVDLLFKT NRKVTVKQLK  960
EDYFKKIECF DSVEISGVED RFNASLGTYH DLLKIIKDKD FLDNEENEDI LEDIVLTLTL  1020
FEDREMIEER LKTYAHLFDD KVMKQLKRRR YTGWGRLSRK LINGIRDKQS GKTILDFLKS  1080
DGFANRNFMQ LIHDDSLTFK EDIQKAQVSG QGDSLHEHIA NLAGSPAIKK GILQTVKVVD  1140
```

```
ELVKVMGRHK PENIVIEMAR ENQTTQKGQK NSRERMKRIE EGIKELGSQI LKEHPVENTQ  1200
LQNEKLYLYY LQNGRDMYVD QELDINRLSD YDVDHIVPQS FLKDDSIDNK VLTRSDKNRG  1260
KSDNVPSEEV VKKMKNYWRQ LLNAKLITQR KFDNLTKAER GGLSELDKAG FIKRQLVETR  1320
QITKHVAQIL DSRMNTKYDE NDKLIREVKV ITLKSKLVSD FRKDFQFYKV REINNYHHAH  1380
DAYLNAVVGT ALIKKYPKLE SEFVYGDYKV YDVRKMIAKS EQEIGKATAK YFFYSNIMNF  1440
FKTEITLANG EIRKRPLIET NGETGEIVWD KGRDFATVRK VLSMPQVNIV KKTEVQTGGF  1500
SKESILPKRN SDKLIARKKD WDPKKYGGFD SPTVAYSVLV VAKVEKGKSK KLKSVKELLG  1560
ITIMERSSFE KNPIDFLEAK GYKEVKKDLI IKLPKYSLFE LENGRKRMLA SAGELQKGNE  1620
LALPSKYVNF LYLASHYEKL KGSPEDNEQK QLFVEQHKHY LDEIIEQISE FSKRVILADA  1680
NLDKVLSAYN KHRDKPIREQ AENIIHLFTL TNLGAPAAFK YFDTTIDRKR YTSTKEVLDA  1740
TLIHQSITGL YETRIDLSQL GGD                                         1763

SEQ ID NO: 36          moltype = AA  length = 1565
FEATURE                Location/Qualifiers
source                 1..1565
                       mol_type = protein
                       organism = synthetic construct
SEQUENCE: 36
SEVEFSHEYW MRHALTLAKR ARDEREVPVG AVLVLNNRVI GEGWNRAIGL HDPTAHAEIM  60
ALRQGGLVMQ NYRLIDATLY VTFEPCVMCA GAMIHSRIGR VVFGVRNSKR GAAGSLMNVL  120
NYPGMNHRVE ITEGILADEC AALLCDFYRM PRQVFNAQKK AQSSINSGGS SGGSSGSETP  180
GTSESATPES SGGSSGGSDK KYSIGLAIGT NSVGWAVITD EYKVPSKKFK VLGNTDRHSI  240
KKNLIGALLF DSGETAEATR LKRTARRRYT RRKNRICYLQ EIFSNEMAKV DDSFFHRLEE  300
SFLVEEDKKH ERHPIFGNIV DEVAYHEKYP TIYHLRKKLV DSTDKADLRL IYLALAHMIK  360
FRGHFLIEGD LNPDNSDVDK LFIQLVQTYN QLFEENPINA SGVDAKAILS ARLSKSRRLE  420
NLIAQLPGEK KNGLFGNLIA LSLGLTPNFK SNFDLAEDAK LQLSKDTYDD DLDNLLAQIG  480
DQYADLFLAA KNLSDAILLS DILRVNTEIT KAPLSASMIK RYDEHHQDLT LLKALVRQQL  540
PEKYKEIFFD QSKNGYAGYI DGGASQEEFY KFIKPILEKM DGTEELLVKL NREDLLRKQR  600
TFDNGSIPHQ IHLGELHAIL RRQEDFYPFL KDNREKIEKI LTFRIPYYVG PLARGNSRFA  660
WMTRKSEETI TPWNFEEVVD KGASAQSFIE RMTNFDKNLP NEKVLPKHSL LYEYFTVYNE  720
LTKVKYVTEG MRKPAFLSGE QKKAIVDLLF KTNRKVTVKQ LKEDYFKKIE CFDSVEISGV  780
EDRFNASLGT YHDLLKIIKD KDFLDNEENE DILEDIVLTL TLFEDREMIE ERLKTYAHLF  840
DDKVMKQLKR RRYTGWGRLS RKLINGIRDK QSGKTILDFL KSDGFANRNF MQLIHDDSLT  900
FKEDIQKAQV SGQGDSLHEH IANLAGSPAI KKGILQTVKV VDELVKVMGR HKPENIVIEM  960
ARENQTTQKG QKNSRERMKR IEEGIKELGS QILKEHPVEN TQLQNEKLYL YYLQNGRDMY  1020
VDQELDINRL SDYDVDHIVP QSFLKDDSID NKVLTRSDKN RGKSDNVPSE EVVKKMKNYW  1080
RQLLNAKLIT QRKFDNLTKA ERGGLSELDK AGFIKRQLVE TRQITKHVAQ ILDSRMNTKY  1140
DENDKLIREV KVITLKSKLV SDFRKDFQFY KVREINNYHH AHDAYLNAVV GTALIKKYPK  1200
LESEFVYGDY KVYDVRKMIA KSEQEIGKAT AKYFFYSNIM NFFKTEITLA NGEIRKRPLI  1260
ETNGETGEIV WDKGRDFATV RKVLSMPQVN IVKKTEVQTG GFSKESILPK RNSDKLIARK  1320
KDWDPKKYGG FDSPTVAYSV LVVAKVEKGK SKKLKSVKEL LGITIMERSS FEKNPIDFLE  1380
AKGYKEVKKD LIIKLPKYSL FELENGRKRM LASAGELQKG NELALPSKYV NFLYLASHYE  1440
KLKGSPEDNE QKQLFVEQHK HYLDEIIEQI SEFSKRVILA DANLDKVLSA YNKHRDKPIR  1500
EQAENIIHLF TLTNLGAPAA FKYFDTTIDR KRYTSTKEVL DATLIHQSIT GLYETRIDLS  1560
QLGGD                                                             1565

SEQ ID NO: 37          moltype = AA  length = 1565
FEATURE                Location/Qualifiers
source                 1..1565
                       mol_type = protein
                       organism = synthetic construct
SEQUENCE: 37
SEVEFSHEYW MRHALTLAKR ARDEREVPVG AVLVLNNRVI GEGWNRAIGL HDPTAHAEIM  60
ALRQGGLVMQ NYRLYDATLY STFEPCVMCA GAMIHSRIGR VVFGVRNAKT GAAGSLMDVL  120
HHPGMNHRVE ITEGILADEC AALLCRFFRM PRRVFNAQKK AQSSTDSGGS SGGSSGSETP  180
GTSESATPES SGGSSGGSDK KYSIGLAIGT NSVGWAVITD EYKVPSKKFK VLGNTDRHSI  240
KKNLIGALLF DSGETAEATR LKRTARRRYT RRKNRICYLQ EIFSNEMAKV DDSFFHRLEE  300
SFLVEEDKKH ERHPIFGNIV DEVAYHEKYP TIYHLRKKLV DSTDKADLRL IYLALAHMIK  360
FRGHFLIEGD LNPDNSDVDK LFIQLVQTYN QLFEENPINA SGVDAKAILS ARLSKSRRLE  420
NLIAQLPGEK KNGLFGNLIA LSLGLTPNFK SNFDLAEDAK LQLSKDTYDD DLDNLLAQIG  480
DQYADLFLAA KNLSDAILLS DILRVNTEIT KAPLSASMIK RYDEHHQDLT LLKALVRQQL  540
PEKYKEIFFD QSKNGYAGYI DGGASQEEFY KFIKPILEKM DGTEELLVKL NREDLLRKQR  600
TFDNGSIPHQ IHLGELHAIL RRQEDFYPFL KDNREKIEKI LTFRIPYYVG PLARGNSRFA  660
WMTRKSEETI TPWNFEEVVD KGASAQSFIE RMTNFDKNLP NEKVLPKHSL LYEYFTVYNE  720
LTKVKYVTEG MRKPAFLSGE QKKAIVDLLF KTNRKVTVKQ LKEDYFKKIE CFDSVEISGV  780
EDRFNASLGT YHDLLKIIKD KDFLDNEENE DILEDIVLTL TLFEDREMIE ERLKTYAHLF  840
DDKVMKQLKR RRYTGWGRLS RKLINGIRDK QSGKTILDFL KSDGFANRNF MQLIHDDSLT  900
FKEDIQKAQV SGQGDSLHEH IANLAGSPAI KKGILQTVKV VDELVKVMGR HKPENIVIEM  960
ARENQTTQKG QKNSRERMKR IEEGIKELGS QILKEHPVEN TQLQNEKLYL YYLQNGRDMY  1020
VDQELDINRL SDYDVDHIVP QSFLKDDSID NKVLTRSDKN RGKSDNVPSE EVVKKMKNYW  1080
RQLLNAKLIT QRKFDNLTKA ERGGLSELDK AGFIKRQLVE TRQITKHVAQ ILDSRMNTKY  1140
DENDKLIREV KVITLKSKLV SDFRKDFQFY KVREINNYHH AHDAYLNAVV GTALIKKYPK  1200
LESEFVYGDY KVYDVRKMIA KSEQEIGKAT AKYFFYSNIM NFFKTEITLA NGEIRKRPLI  1260
ETNGETGEIV WDKGRDFATV RKVLSMPQVN IVKKTEVQTG GFSKESILPK RNSDKLIARK  1320
KDWDPKKYGG FDSPTVAYSV LVVAKVEKGK SKKLKSVKEL LGITIMERSS FEKNPIDFLE  1380
AKGYKEVKKD LIIKLPKYSL FELENGRKRM LASAGELQKG NELALPSKYV NFLYLASHYE  1440
KLKGSPEDNE QKQLFVEQHK HYLDEIIEQI SEFSKRVILA DANLDKVLSA YNKHRDKPIR  1500
EQAENIIHLF TLTNLGAPAA FKYFDTTIDR KRYTSTKEVL DATLIHQSIT GLYETRIDLS  1560
QLGGD                                                             1565
```

```
SEQ ID NO: 38          moltype = AA  length = 364
FEATURE                Location/Qualifiers
source                 1..364
                       mol_type = protein
                       organism = synthetic construct
SEQUENCE: 38
SEVEFSHEYW MRHALTLAKR AWDEREVPVG AVLVHNNRVI GEGWNRPIGR HDPTAHAEIM  60
ALRQGGLVMQ NYRLIDATLY VTLEPCVMCA GAMIHSRIGR VVFGARDAKT GAAGSLMDVL  120
HHPGMNHRVE ITEGILADEC AALLSDFFRM RRQEIKAQKK AQSSTDSGGS SGGSSGSETP  180
GTSESATPES SGGSSGGSSE VEFSHEYWMR HALTLAKRAR DEREVPVGAV LVLNNRVIGE  240
GWNRAIGLHD PTAHAEIMAL RQGGLVMQNY RLIDATLYVT FEPCVMCAGA MIHSRIGRVV  300
FGVRNAKTGA AGSLMDVLHY PGMNHRVEIT EGILADECAA LLCYFFRMPR QVFNAQKKAQ  360
SSTD                                                                364

SEQ ID NO: 39          moltype = AA  length = 167
FEATURE                Location/Qualifiers
source                 1..167
                       mol_type = protein
                       organism = synthetic construct
SEQUENCE: 39
MSEVEFSHEY WMRHALTLAK RARDEREVPV GAVLVLNNRV IGEGWNRAIG LHDPTAHAEI  60
MALRQGGLVM QNYRLYDATL YSTFEPCVMC AGAMIHSRIG RVVFGVRNAK TGAAGSLMDV  120
LHHPGMNHRV EITEGILADE CAALLCRFFR MPRRVFNAQK KAQSSTD                 167

SEQ ID NO: 40          moltype = AA  length = 167
FEATURE                Location/Qualifiers
source                 1..167
                       mol_type = protein
                       organism = synthetic construct
SEQUENCE: 40
MSEVEFSHEY WMRHALTLAK RARDEREVPV GAVLVLNNRV IGEGWNRAIG LHDPTAHAEI  60
MALRQGGLVM QNYRLIDATL YVTFEPCVMC AGAMIHSRIG RVVFGVRNSK RGAAGSLMNV  120
LNYPGMNHRV EITEGILADE CAALLCDFYR MPRQVFNAQK KAQSSIN                 167

SEQ ID NO: 41          moltype = AA  length = 83
FEATURE                Location/Qualifiers
source                 1..83
                       mol_type = protein
                       organism = Bacillus phage AR9
SEQUENCE: 41
TNLSDIIEKE TGKQLVIQES ILMLPEEVEE VIGNKPESDI LVHTAYDEST DENVMLLTSD  60
APEYKPWALV IQDSNGENKI KML                                           83

SEQ ID NO: 42          moltype = AA  length = 24
FEATURE                Location/Qualifiers
source                 1..24
                       mol_type = protein
                       organism = synthetic construct
SEQUENCE: 42
EELLSKNYHL ENEVARLKKG SGSG                                          24

SEQ ID NO: 43          moltype = AA  length = 241
FEATURE                Location/Qualifiers
source                 1..241
                       mol_type = protein
                       organism = synthetic construct
SEQUENCE: 43
EEELLSKNYH LENEVARLKK GSGSGEELLS KNYHLENEVA RLKKGSGSGE ELLSKNYHLE  60
NEVARLKKGS GSGEELLSKN YHLENEVARL KKGSGSGEEL LSKNYHLENE VARLKKGSGS  120
GEELLSKNYH LENEVARLKK GSGSGEELLS KNYHLENEVA RLKKGSGSGE ELLSKNYHLE  180
NEVARLKKGS GSGEELLSKN YHLENEVARL KKGSGSGEEL LSKNYHLENE VARLKKGSGS  240
G                                                                   241

SEQ ID NO: 44          moltype = AA  length = 277
FEATURE                Location/Qualifiers
source                 1..277
                       mol_type = protein
                       organism = synthetic construct
SEQUENCE: 44
MGPDIVMTQS PSSLSASVGD RVTITCRSST GAVTTSNYAS WVQEKPGKLF KGLIGGTNNR  60
APGVPSRFSG SLIGDKATLT ISSLQPEDFA TYFCALWYSN HWVFGQGTKV ELKRGGGGSG  120
GGGSGGGGSS GGGSEVKLLE SGGGLVQPGG SLKLSCAVSG FSLTDYGVNW VRQAPGRGLE  180
WIGVIWGDGI TDYNSALKDR FIISKDNGKN TVYLQMSKVR SDDTALYYCV TGLFDYWGQG  240
TLVTVSSYPY DVPDYAGGGG GSGGGGSGGG GSGGGGS                            277

SEQ ID NO: 45          moltype = DNA  length = 66
FEATURE                Location/Qualifiers
source                 1..66
```

```
                        mol_type = other DNA
                        organism = Saccharomyces bayanus
SEQUENCE: 45
ttcttgtcgt acttatagat cgctacgtta tttcaatttt gaaaatctga gtcctgggag  60
tgcgga                                                             66

SEQ ID NO: 46           moltype = AA  length = 605
FEATURE                 Location/Qualifiers
source                  1..605
                        mol_type = protein
                        organism = Homo sapiens
SEQUENCE: 46
MSGWESYYKT EGDEEAEEEQ EENLEASGDY KYSGRDSLIF LVDASKAMFE SQSEDELTPF  60
DMSIQCIQSV YISKIISSDR DLLAWFYGTE KDKNSVNFKI YVLQELDNPG AKRILELDQF  120
KGQQGQKRFQ DMMGHGSDYS LSEVLWVCAN LFSDVQFKMS HKRIMLFTNE DNPHGNDSAK  180
ASRARTKAGD LRDTGIFLDL HLKKPGGFDI SLFYRDIISI AEDEDLRVHF EESSKLEDLL  240
RKVRAKETRK RALSRLKLKL NKDIVISVGI YNLVQKALKP PPIKLYRETN EPVKTKTRTF  300
NTSTGGLLLP SDTKRSQIYG SRQIILEKEE TEELKRFDDP GLMLMGFKPL VLLKKHHYLR  360
PSLFVYPEES LVIGSSTLFS ALLIKCLEKE VAALCRYTPR RNIPPYFVAL VPQEEELDDQ  420
KIQVTPPGFQ LVFLPFADDK RKMPFTEKIM ATPEQVGKMK AIVEKLRFTY RSDSFENPVL  480
QQHFRNLEAL ALDLMEPEQA VDLTLPKVEA MNKRLGSLVD EFKELVYPPD YNPEGKVTKR  540
KHDNEGSGSK RPKVEYSEEE LKTHISKGTL GKFTVPLKEA CRAYGLKSGL KKQELLEALT  600
KHFQD                                                              605

SEQ ID NO: 47           moltype = AA  length = 482
FEATURE                 Location/Qualifiers
source                  1..482
                        mol_type = protein
                        organism = synthetic construct
SEQUENCE: 47
MVRSGNKAAW LCMDVGFTMS NSIPGIESPF EQAKKVITMF VQRQVFAENK DEIALVLFGT  60
DGTDNPLSGG DQYQNITVHR HLMLPDFDLL EDIESKIQPG SQQADFLDAL IVSMDVIQHE  120
TIGKKFEKRH IEIFTDLSSR FSKSQLDIII HSLKKCDISE RHSIHWPCRL TIGSNLSIRI  180
AAYKSILQER VKKTTWDAKT LKKEDIQKET VYCLNDDDET EVLKEDIIQG FRYGSDIVPF  240
SKVDEEQMKY KSEGKCFSVL GFCKSSQVQR RFFMGNQVLK VFAARDDEAA AVALSSLIHA  300
LDDLDIWAIV RYAYDKRANP QVGVAFPHIK HNYECLVYVQ LPFMEDLRQY MFSSLKNSKK  360
YAPTEAQLNA VDALIDSMSL AKKDEKTDTL EDLFPTTKIP NPRFQRLFQC LLHRALHPRE  420
PLPPIQQHIW NMLNPPAEVT TKSQIPLSKI KTLFPLIEAK KKDQVTAQEI FQDNHEDGPT  480
AK                                                                 482

SEQ ID NO: 48           moltype = DNA  length = 10
FEATURE                 Location/Qualifiers
source                  1..10
                        mol_type = other DNA
                        organism = Methanobacterium thermoautotrophicum
SEQUENCE: 48
aatttttgga                                                         10

SEQ ID NO: 49           moltype = AA  length = 83
FEATURE                 Location/Qualifiers
source                  1..83
                        mol_type = protein
                        organism = Methanobacterium thermoautotrophicum
SEQUENCE: 49
GSVIDVSSQR VNVQRPLDAL GNSLNSPVII KLKGDREFRG VLKSFDLHMN LVLNDAEELE  60
DGEVTRRLGT VLIRGDNIVY ISP                                          83

SEQ ID NO: 50           moltype = DNA  length = 25
FEATURE                 Location/Qualifiers
source                  1..25
                        mol_type = other DNA
                        organism = Bacteriophage MS2
SEQUENCE: 50
gcgcacatga ggatcaccca tgtgc                                        25

SEQ ID NO: 51           moltype = AA  length = 116
FEATURE                 Location/Qualifiers
source                  1..116
                        mol_type = protein
                        organism = Bacteriophage MS2
SEQUENCE: 51
MASNFTQFVL VDNGGTGDVT VAPSNFANGI AEISSNSRSQ AYKVTCSVRQ SSAQNRKYTI  60
KVEVPKGAWR SYLNMELTIP IFATNSDCEL IVKAMQGLLK DGNPIPSAIA ANSGIY      116

SEQ ID NO: 52           moltype = DNA  length = 26
FEATURE                 Location/Qualifiers
source                  1..26
                        mol_type = other DNA
                        organism = Bacteriophage PP7
```

```
SEQUENCE: 52
ataaggagtt tatatggaaa ccctta                                      26

SEQ ID NO: 53          moltype = AA  length = 127
FEATURE                Location/Qualifiers
source                 1..127
                       mol_type = protein
                       organism = Bacteriophage PP7
SEQUENCE: 53
MSKTIVLSVG EATRTLTEIQ STADRQIFEE KVGPLVGRLR LTASLRQNGA KTAYRVNLKL  60
DQADWDCSTS VCGELPKVRY TQVWSHDVTI VANSTEASRK SLYDLTKSLV ATSQVEDLVV  120
NLVPLGR                                                           127

SEQ ID NO: 54          moltype = DNA  length = 19
FEATURE                Location/Qualifiers
source                 1..19
                       mol_type = other DNA
                       organism = Shigella phage
SEQUENCE: 54
ctgaatgcct gcgagcatc                                              19

SEQ ID NO: 55          moltype = AA  length = 62
FEATURE                Location/Qualifiers
source                 1..62
                       mol_type = protein
                       organism = Shigella phage
SEQUENCE: 55
MKSIRCKNCN KLLFKADSFD HIEIRCPRCK RHIIMLNACE HPTEKHCGKR EKITHSDETV  60
RY                                                                62

SEQ ID NO: 56          moltype = AA  length = 1367
FEATURE                Location/Qualifiers
source                 1..1367
                       mol_type = protein
                       organism = synthetic construct
SEQUENCE: 56
DKKYSIGLAI GTNSVGWAVI TDEYKVPSKK FKVLGNTDRH SIKKNLIGAL LFDSGETAEA  60
TRLKRTARRR YTRRKNRICY LQEIFSNEMA KVDDSFFHRL EESFLVEEDK KHERHPIFGN  120
IVDEVAYHEK YPTIYHLRKK LVDSTDKADL RLIYLALAHM IKFRGHFLIE GDLNPDNSDV  180
DKLFIQLVQT YNQLFEENPI NASGVDAKAI LSARLSKSRR LENLIAQLPG EKKNGLFGNL  240
IALSLGLTPN FKSNFDLAED AKLQLSKDTY DDDLDNLLAQ IGDQYADLFL AAKNLSDAIL  300
LSDILRVNTE ITKAPLSASM IKRYDEHHQD LTLLKALVRQ QLPEKYKEIF FDQSKNGYAG  360
YIDGGASQEE FYKFIKPILE KMDGTEELLV KLNREDLLRK QRTFDNGSIP HQIHLGELHA  420
ILRRQEDFYP FLKDNREKIE KILTFRIPYY VGPLARGNSR FAWMTRKSEE TITPWNFEEV  480
VDKGASAQSF IERMTNFDKN LPNEKVLPKH SLLYEYFTVY NELTKVKYVT EGMRKPAFLS  540
GEQKKAIVDL LFKTNRKVTV KQLKEDYFKK IECFDSVEIS GVEDRFNASL GTYHDLLKII  600
KDKDFLDNEE NEDILEDIVL TLTLFEDREM IEERLKTYAH LFDDKVMKQL KRRRYTGWGR  660
LSRKLINGIR DKQSGKTILD FLKSDGFANR NFMQLIHDDS LTFKEDIQKA QVSGQGDSLH  720
EHIANLAGSP AIKKGILQTV KVVDELVKVM GRHKPENIVI EMARENQTTQ KGQKNSRERM  780
KRIEEGIKEL GSQILKEHPV ENTQLQNEKL YLYYLQNGRD MYVDQELDIN RLSDYDVDHI  840
VPQSFLKDDS IDNKVLTRSD KNRGKSDNVP SEEVVKKMKN YWRQLLNAKL ITQRKFDNLT  900
KAERGGLSEL DKAGFIKRQL VETRQITKHV AQILDSRMNT KYDENDKLIR EVKVITLKSK  960
LVSDFRKDFQ FYKVREINNY HHAHDAYLNA VVGTALIKKY PKLESEFVYG DYKVYDVRKM  1020
IAKSEQEIGK ATAKYFFYSN IMNFFKTEIT LANGEIRKRP LIETNGETGE IVWDKGRDFA  1080
TVRKVLSMPQ VNIVKKTEVQ TGGFSKESIL PKRNSDKLIA RKKDWDPKKY GGFDSPTVAY  1140
SVLVVAKVEK GKSKKLKSVK ELLGITIMER SSFEKNPIDF LEAKGYKEVK KDLIIKLPKY  1200
SLFELENGRK RMLASAGELQ KGNELALPSK YVNFLYLASH YEKLKGSPED NEQKQLFVEQ  1260
HKHYLDEIIE QISEFSKRVI LADANLDKVL SAYNKHRDKP IREQAENIIH LFTLTNLGAP  1320
AAFKYFDTTI DRKRYTSTKE VLDATLIHQS ITGLYETRID LSQLGGD                1367

SEQ ID NO: 57          moltype = AA  length = 1367
FEATURE                Location/Qualifiers
source                 1..1367
                       mol_type = protein
                       organism = synthetic construct
SEQUENCE: 57
DKKYSIGLAI GTNSVGWAVI TDEYKVPSKK FKVLGNTDRH SIKKNLIGAL LFDSGETAEA  60
TRLKRTARRR YTRRKNRICY LQEIFSNEMA KVDDSFFHRL EESFLVEEDK KHERHPIFGN  120
IVDEVAYHEK YPTIYHLRKK LVDSTDKADL RLIYLALAHM IKFRGHFLIE GDLNPDNSDV  180
DKLFIQLVQT YNQLFEENPI NASGVDAKAI LSARLSKSRR LENLIAQLPG EKKNGLFGNL  240
IALSLGLTPN FKSNFDLAED AKLQLSKDTY DDDLDNLLAQ IGDQYADLFL AAKNLSDAIL  300
LSDILRVNTE ITKAPLSASM IKRYDEHHQD LTLLKALVRQ QLPEKYKEIF FDQSKNGYAG  360
YIDGGASQEE FYKFIKPILE KMDGTEELLV KLNREDLLRK QRTFDNGSIP HQIHLGELHA  420
ILRRQEDFYP FLKDNREKIE KILTFRIPYY VGPLARGNSR FAWMTRKSEE TITPWNFEEV  480
VDKGASAQSF IERMTNFDKN LPNEKVLPKH SLLYEYFTVY NELTKVKYVT EGMRKPAFLS  540
GEQKKAIVDL LFKTNRKVTV KQLKEDYFKK IECFDSVEIS GVEDRFNASL GTYHDLLKII  600
KDKDFLDNEE NEDILEDIVL TLTLFEDREM IEERLKTYAH LFDDKVMKQL KRRRYTGWGR  660
LSRKLINGIR DKQSGKTILD FLKSDGFANR NFMQLIHDDS LTFKEDIQKA QVSGQGDSLH  720
EHIANLAGSP AIKKGILQTV KVVDELVKVM GRHKPENIVI EMARENQTTQ KGQKNSRERM  780
```

KRIEEGIKEL GSQILKEHPV ENTQLQNEKL YLYYLQNGRD MYVDQELDIN RLSDYDVDHI 840
VPQSFLADDS IDNKVLTRSD KNRGKSDNVP SEEVVKKMKN YWRQLLNAKL ITQRKFDNLT 900
KAERGGLSEL DKAGFIKRQL VETRQITKHV AQILDSRMNT KYDENDKLIR EVKVITLKSK 960
LVSDFRKDFQ FYKVREINNY HHAHDAYLNA VVGTALIKKY PALESEFVYG DYKVYDVRKM 1020
IAKSEQEIGK ATAKYFFYSN IMNFFKTEIT LANGEIRKAP LIETNGETGE IVWDKGRDFA 1080
TVRKVLSMPQ VNIVKKTEVQ TGGFSKESIL PKRNSDKLIA RKKDWDPKKY GGFDSPTVAY 1140
SVLVVAKVEK GKSKKLKSVK ELLGITIMER SSFEKNPIDF LEAKGYKEVK KDLIIKLPKY 1200
SLFELENGRK RMLASAGELQ KGNELALPSK YVNFLYLASH YEKLKGSPED NEQKQLFVEQ 1260
HKHYLDEIIE QISEFSKRVI LADANLDKVL SAYNKHRDKP IREQAENIIH LFTLTNLGAP 1320
AAFKYFDTTI DRKRYTSTKE VLDATLIHQS ITGLYETRID LSQLGGD 1367

SEQ ID NO: 58 moltype = DNA length = 4101
FEATURE Location/Qualifiers
source 1..4101
mol_type = other DNA
organism = synthetic construct
SEQUENCE: 58
gacaagaagt acagcatcgg gctggcgatc gggaccaact ccgtcggctg ggctgtgatt 60
accgacgagt acaaggtgcc atccaagaag ttcaaggtcc tcggcaacac tgaccggcac 120
agcattaaga agaacctgat tggggcgctg ctgttcgatt cgggggagac tgcggaggcg 180
accaggctga agcggactgc gcgccggagg tacaccagga ggaagaatcg gatctgctac 240
ctccaggaga ttttctcgaa tgagatggcc aaggtggacg attccttctt ccatcgcctg 300
gaggagtcgt tcctcgttga ggaggacaag aagcatgaga ggcatcccat tttcgggaat 360
atcgttgacg aggtggctta ccatgagaag tacccgacca tctaccatct gcggaagaag 420
ctcgtcgatt cgaccgataa ggccgacctg cggctgatct acctggccct cgcgcacatg 480
attaagttcc ggggccattt cctcatcgag ggcgacctca acccggacaa ctcggacgtg 540
gataagctct tcattcagct cgtgcagaca tacaaccagc tcttcgagga gaatcccatt 600
aacgcctcgg gggtcgacgc taaggctatt ctctcggctc ggctgtcgaa gtcgcgccgg 660
ctggagaatc tcattgccca gctcccaggc gagaagaaga acggcctctt cggcaacctg 720
attgccctgt cgctggggct cacaccgaat ttcaagtcga acttcgacct cgccgaggac 780
gctaagctcc agctcagcaa ggatacttac gatgatgacc tcgataacct gctcgcccag 840
attggggatc agtacgcgga tctgttcctc gcggccaaga atctcagcga tgctattctc 900
ctgtcggaca ttctccgcgt caacacagag attactaagg ccccactgtc ggcgagcatg 960
attaagaggt acgatgagca tcatcaggac ctgacactgc tcaaggcgct ggtccggcag 1020
cagctccccg agaagtacaa ggagattttc ttcgatcagt caaagaatgg gtacgcgggc 1080
tacattgatg gcggcgcgtc ccaggaggag ttctacaagt tcattaagcc catcctggag 1140
aagatggacg ggaccgagga gctgctggtg aagctcaatc gggaggacct gctccggaag 1200
cagcgcacat tcgacaatgg ctcgattcct caccagattc acctgggcga gctgcacgcc 1260
attctccgca ggcaggagga cttctacccg ttcctcaagg acaaccgcga gaagatcgag 1320
aagatcctga ccttccggat tccatactac gtggggccgc tcgcgcgggg gaactcccgg 1380
ttcgcgtgga tgactcgcaa gtccgaagaa acgattacac cgtggaattt cgaggaggtc 1440
gtcgacaagg gcgctagtgc gcagtcattc attgagagga tgaccaattt cgataagaac 1500
ctgcctaacg agaaggtgct gccgaagcat tcgctgctct acgagtactt caccgtttac 1560
aatgagctga ccaaggtgaa gtatgtgact gagggcatga ggaagccagc gttcctgagc 1620
ggcgagcaga agaaggctat cgtggacctg ctcttcaaga ctaaccggaa ggtgactgtg 1680
aagcagctca aggaggacta cttcaagaag attgagtgct tcgattccgt tgagattagc 1740
ggggtggagg atcggttcaa tgcttcgctc gggacatacc acgatctcct gaagatcatt 1800
aaggataagg acttcctcga caacgaggag aacgaggaca ttctcgaaga tattgtcctg 1860
accctcaccc tcttcgagga tcgggagatg atcgaggaga ggctcaagac atacgctcat 1920
ctgttcgatg ataaggtcat gaagcagctg aagcgcaggc ggtacacagg gtgggggcgg 1980
ctgagccgga agctgatcaa cggattcgg gataagcagt ccgggaagac aattctcgac 2040
ttcctcaagt ccgacgggtt cgctaaccgg aacttcatgc agctcattca tgatgactcg 2100
ctgacattca aggaggatat tcagaaggcg caggtttcgg ggcagggcga ctcgctccac 2160
gagcatattg cgaatctggc gggctccccc gcgattaaga agggcattct gcaaaccgtc 2220
aaggtggttg atgagctggt caaggtcatg gggcggcata agccagagaa tattgtcatc 2280
gagatggcgc gggagaatca gaccacacag aaggggcaga agaactcacg ggagcggatg 2340
aagcgcatcg aggagggcat caaggagctg ggtcgcaga tcctgaagga gcatcccgtg 2400
gagaacactc agctgcaaaa tgagaagctg tacctctact acctccagaa cgggagggac 2460
atgtatgtgg atcaggagct ggatattaat aggctgagcg attacgatgt cgaccacatt 2520
gtcccacagt cgttcctgaa ggacgacagc attgacaaca aggtgctgac ccgctcggat 2580
aagaacaggg gcaagagcga taatgttcca agcgaggagg ttgtgaagaa gatgaagaac 2640
tactggcggc agctcctgaa cgcgaagctc atcacacagc ggaagttcga caacctcacc 2700
aaggctgagc gcgggggcct gagcgagctg gacaaggcgg ggttcattaa gaggcagctg 2760
gtcgagacac ggcagattac aaagcatgtt gcgcagattc tcgattcccg gatgaacacc 2820
aagtacgatg agaacgataa gctgattcgg gaggtcaagg taattaccct gaagtccaag 2880
ctggtgtccg acttcaggaa ggacttccag ttctacaagg ttcgggagat caacaactac 2940
caccacgcgc atgatgccta cctcaacgcg gtcgtgggga ccgctctcat caagaagtac 3000
ccaaagctgg agtcagagtt cgtctacggg gattacaagg tttacgacgt gcggaagatg 3060
atcgctaaga gcgagcagga gattggcaag gctaccgcta agtacttctt ctactccaac 3120
atcatgaact tcttcaagac agagattacc ctcgcgaatg gcgagatccg gaagaggccc 3180
ctcatcgaga caaatgggga gacaggggag attgtctggg ataaggggcg ggatttcgcg 3240
accgtccgga aggtcctgtc gatgccccag gttaatattg tcaagaagac tgaggtccag 3300
actggcggct tctcaaagga gtcgattctc ccaaagagga actccgataa gctcattgct 3360
cggaagaagg attgggaccc caagaagtac gggggattcg actcccccac tgttgcttac 3420
tctgttctgg ttgttgctaa ggtggagaag gggaagtcga agaagctgaa gagcgtgaag 3480
gagctgctcg ggattacaat tatggagagg tcatccttcg agaagaatcc catcgacttc 3540
ctggaggcca agggctacaa ggaggtgaag aaggacctga ttattaagct gcccaagtac 3600
tcgctcttcg agctggagaa tggcggaag cggatgctgg cgtccgcggg ggagctgcaa 3660
aaggggaacg agctggcgct cccctccaag tatgtgaact tcctctacct ggcgtcgcac 3720

```
tacgagaagc tgaaggggtc cccagaggat aatgagcaga agcagctctt cgtcgagcag  3780
cataagcact acctggacga gattatcgag cagattagcg agttctcgaa gcgggtcatc  3840
ctcgcggatg cgaacctgga taaggtgctc agcgcctaca ataagcaccg ggacaagccg  3900
attcgggagc aggcggagaa tattattcac ctcttcacac tcaccaacct cggggcacca  3960
gctgcgttca agtacttcga cactactatc gaccggaagc ggtacacctc gacgaaggag  4020
gtgctcgacg ccaccctcat tcaccagtcg atcacaggcc tgtacgagac acggattgac  4080
ctgtcccagc tcgggggcga c                                            4101

SEQ ID NO: 59          moltype = DNA  length = 4101
FEATURE                Location/Qualifiers
source                 1..4101
                       mol_type = other DNA
                       organism = synthetic construct
SEQUENCE: 59
gacaagaagt actccattgg cctggcgatt gggacaaact cggtggggtg ggccgtgatt  60
acggatgagt acaaggttcc aagcaagaag ttcaaggtcc tcgggaacac agatcggcat  120
tcgattaaga agaatctcat tggggcgctc ctcttcgact cgggggagac agcggaggct  180
accaggctca agcggacagc caggcggcgg tacacaaggc ggaagaatcg catctgctac  240
ctccaggaga ttttctcgaa tgagatggcg aaggtggacg acagcttctt ccatcggctg  300
gaggagtcct tcctggtgga ggaggataag aagcacgaga ggcatccaat tttcgggaac  360
atcgtggacg aggttgcgta ccatgagaag taccctacaa tctaccatct gcggaagaag  420
ctggttgact ccacagacaa ggcggacctg aggctgatct acctcgctct ggcccacatg  480
attaagttcc gcgggcattt cctgatcgag gggaacctga atcccgacaa ttcggatgtg  540
gacaagctct tcatccagct ggtgcagacc tacaaccagc tgttcgagga gaatcccatc  600
aatgcgtcgg gcgttgacgc taaggccatt ctgtccgcta ggctgtcgaa gagcaggagg  660
ctggagaacc tgatcgccca gctgccaggc gagaagaaga atgggctctt cgggaatctg  720
attgcgctct ccctggggct gacaccgaac ttcaagagca atttcgatct ggctgaggac  780
gcgaagctcc agctctcgaa ggacacttac gacgatgacc tcgataacct cctcgcgcag  840
atcggggacc agtacgctga tctcttcctc gccgctaaga acctctcgga tgctatcctg  900
ctctccgaca ttctccgggt taataccgag attacaaagg ccccactgtc ggcgtccatg  960
atcaagcggt acgatgagca tcatcaggat ctcaccctgc tcaaggccct cgtgcggcag  1020
cagctgcccg agaagtacaa ggagattttc ttcgaccaga gcaagaatgg gtacgctggc  1080
tacattgacg gcggggcctc acaggaggag ttctacaagt tcatcaagcc aatcctggag  1140
aagatggatg ggacagagga gctgctggtg aagctcaacc gggaggatct gctcaggaag  1200
cagcggacgt tcgacaacgg gtcgattccc catcagatcc acctgggga gctgcacgcg  1260
atcctgcgcc ggcaggagga tttctaccct ttcctgaagg ataatcggga gaagatcgag  1320
aagattctca ccttccggat tccctactac gtcgggccac tcgcgcgggg caatagcagg  1380
ttcgcctgga tgacacggaa gagcgaggag acaatcaccc cctggaactt cgaggaggtt  1440
gtcgacaagg gggcgtccgc ccagtcattc attgagcgga tgaccaattt cgacaagaat  1500
ctgccaaatg agaaggttct cccaaagcat agcctcctct acgagtactt cactgtttac  1560
aacgagctga ccaaggtgaa gtatgtgacc gagggcatgc ggaagcccgc gttcctgtcc  1620
ggcgagcaga agaaggccat tgtggacctc ctgttcaaga ccaatcgcaa ggtcacagtc  1680
aagcagctca aggaggatta cttcaagaag atcgagtgct tcgactcggt tgagattagc  1740
ggggtggagg atcggttcaa cgcgagcctc ggcacttacc acgacctcct gaagatcatc  1800
aaggataagg acttcctcga caacgaggag aacgaggata ttctggagga catcgtgctc  1860
accctgacgc tgttcgagga tcgggagatg atcgaggagc gcctgaagac ctacgctcat  1920
ctcttcgatg ataaggtcat gaagcagctg aagaggaggc ggtacaccgg gtggggccgc  1980
ctgagcagga agctcattaa cgggatcagg gacaagcaga gcggcaagac catcctggac  2040
ttcctcaaga gcgatggctt cgccaaccgg aatttcatgc agctcatcca cgacgactcc  2100
ctcaccttca aggaggacat tcagaaggct caggtcagcg gccagggcga ctcgctgcat  2160
gagcacatcg ctaacctggc gggcagccca gccatcaaga agggcatcct ccagacagtg  2220
aaggtcgtgg atgagctggt gaaggtcatg ggccggcata agcccgagaa tattgtgatt  2280
gagatggcgc gggagaatca gaccactcag aagggccaga agaactcgcg ggagcgcatg  2340
aagaggatcg aggaggggat taaggagctg ggcagccaga ttctcaagga gcacccccgtg  2400
gagaataccc agctccagaa cgagaagctg tacctctact acctccagaa tgggcgggac  2460
atgtatgttg atcaggagct ggacatcaat cgcctctcgg attacgacgt ggaccacatc  2520
gtgccccaga gcttcctgaa ggatgatagc atcgacaata aggtcctgac ccgctccgac  2580
aagaatcgcg gcaagagcga caacgtgccg agcgaggagg tcgtgaagaa gatgaagaac  2640
tactggcggc agctgctgaa cgcgaagctc attacacagc ggaagttcga taacctgacg  2700
aaggcggaga ggggcggcct ctccgagctg gacaaggcgg gcttcattaa gaggcagctc  2760
gtggagactc gccagatcac caagcacgtg gctcagatcc tcgatagccg gatgaatacg  2820
aagtacgatg agaatgacaa gctcatccgg gaggtgaagg taatcaccct gaagtcaaag  2880
ctcgttagcg atttccggaa ggacttccag ttctacaagg tgcgggagat taacaactac  2940
catcatgcgc acgatgcgta cctcaatgcg gtggtgggca cagccctgat taagaagtac  3000
cccaagctgg agagcgagtt cgtctacggg gactacaagg tgtacgatgt tcggaagatg  3060
atcgccaaga gcgagcagga gattgggaag gccaccgcta agtacttctt ctactcgaat  3120
attatgaatt tcttcaagac cgagatcaca ctcgctaatg gggagattcg gaagcggccc  3180
ctcatcgaga ctaacgggga gactggcgag attgtgtggg acaaggggcg cgacttcgct  3240
accgtgcgca aggtcctctc gatgccccag gttaatattg ttaagaagac agaggtgcag  3300
acgggcgggt tctccaagga gtctatcctg ccgaagcgga actcggacaa gctgatcgcc  3360
cgcaagaagg attgggaccc caagaagtac gggggattcg atagcccaac cgtggcttac  3420
agcgtcctgg tggtcgccaa ggttgagaag gggaagtcga agaagctcaa gagcgttaag  3480
gagctgctgg gcatcaccat catggagcgg tccagcttcg agaagaatcc tatcgacttc  3540
ctggaggcta aggggtacaa ggaggtcaag aaggacctga tcattaagct gcccaagtac  3600
tctctgttcg agctggagaa cggaggaag cggatgctgg cgtctgctgg cgagctacag  3660
aagggcaatg agctggcgct cccctcgaag tatgtcaact tcctctacct ggcttcccat  3720
tacgagaagc tgaagggctc gcccgaggat aatgagcaga agcagctctt cgtggagcag  3780
cacaagcact acctcgacga gatcattgag cagatttcgg agttctcgaa gcgggtcatt  3840
ctcgcggacg cgaacctcga caaggtcctc tcggcgtaca acaagcaccg ggacaagccc  3900
```

```
atccgggagc aggccgagaa cattatccac ctcttcacac tgaccaacct cggcgctccc  3960
gccgcgttca agtacttcga caccaccatt gaccgcaaga gatacacatc caccaaggag  4020
gtgctggacg cgaccctcat ccaccagagc atcacaggcc tctacgagac acggatcgac  4080
ctctcgcagc tcgggggcga t                                            4101

SEQ ID NO: 60          moltype = DNA  length = 4092
FEATURE                Location/Qualifiers
source                 1..4092
                       mol_type = other DNA
                       organism = synthetic construct
SEQUENCE: 60
gacaagaagt actcgatcgg cctggcgatt ggcacaaaca gcgtggggtg ggctgtgatc  60
actgatgagt acaaggtgcc atcgaagaag ttcaaggtgc tggggaatac agaccggcat  120
tcgatcaaga agaatctcat tggcgctctc ctcttcgatt ccggcgagac tgctgaggcg  180
acccgcctga agcgcaccgc ccggcggcgc tacactcggc ggaagaatag gatttgctac  240
ctccaggaga ttttctcgaa tgagatggcc aaggtggatg acagcttctt ccaccgcctg  300
gaggagtcgt tcctggtcga ggaggacaag aagcatgagc ggcaccctat cttcgggaat  360
atcgttgatg aggtcgccta ccacgagaag taccccacta tctaccatct ccgcaagaag  420
ctcgtggaca gcacagataa ggccgacctc cgcctgatct acctcgccct cgcgcacatg  480
attaagttcc gggggcactt cctcattgag gggdatctga atcccgataa ctccgacgtg  540
gacaagctgt tcatccagct ggtgcagaca tacaaccagc tgttcgagga gaatcccatc  600
aacgcgagcg gcgtggacgc taaggccatt ctgtcggcta ggctctcgaa gtcgaggcgg  660
ctggagaacc tgattgcgca gctccccggc gagaagaaga acgggctgtt cgggaatctc  720
atcgccctct ccctcggcct cacaccaaac ttcaagagca atttcgacct ggctgaggac  780
gctaagctgc aactctcaaa ggatacatac gatgacgacc tggacaatct cctggctcag  840
atcggcgacc agtacgctga cctgttcctc gcggccaaga atctgtcgga cgcgattctc  900
ctcagcgaca tcctgcgcgt caataccgag attacgaagg ctccactgtc tgcgtcaatg  960
attaagcggt acgatgagca tcaccaggat ctgaccctcc tgaaggcgct cgtgcggcag  1020
cagctgcccg agaagtacaa ggagattttc ttcgatcaga gcaagaatgg ctacgccggc  1080
tacatcgacg gggcgcgag ccaggaggag ttctacaagt tcatcaagcc catcctggag  1140
aagatggacg gcaccgagga gctactcgtg aagctcaatc gggaggatct cctccggaag  1200
cagcggacat tcgataacgg gtctatccca caccagatcc acctcggcga gctgcatgcg  1260
attctgcggc ggcaggagga tttctaccct ttcctgaagg acaaccggga gaagatcgag  1320
aagatcctca cattccggat tccatactac gtcggccccc tggcgagggg caatagccgg  1380
ttcgcgtgga tgacaaggaa gtccgaggag actattaccc cgtggaattt cgaggaggtg  1440
gttgacaagg gcgcttccgc gcagagcttc attgagcgga tgacaaactt cgacaagaat  1500
ctccccaacg agaaggtcct gccgaagcat agcctcctgt acgagtactt caccgtctac  1560
aatgagctaa ctaaggtcaa gtatgtgaca gagggcatga ggaagccagc cttcctctca  1620
ggcgagcaga agaaggccat tgtggacctc ctgttcaaga caaaccgcaa ggtgacagtg  1680
aagcagctga aggaggatta cttcaagaag attgagtgct tcgactcagt ggagatttca  1740
ggcgtggagg atcggttcaa cgcgagcctg gggacttacc acgacctgct gaagattatt  1800
aaggacaagg acttcctgga taacgaggag aatgaggaca tcctggagga tattgtgctc  1860
accctcaccc tgttcgagga cagggagatg attgaggaga ggctcaagac ctacgcgcac  1920
ctgttcgatg acaaggtcat gaagcagctg aagaggcggc gctacactgg gtggggccgc  1980
ctgtcgcgga agctgatcaa cggcattcgg gataagcagt ccgggaagac cattctggat  2040
ttcctgaagt cggacggctt cgccaacagg aatttcatgc agctgatcca cgacgactcc  2100
ctcaccttca aggaggacat tcagaaggcc caggttagcg gccagggga ctcactccac  2160
gagcatattg ccaatctggc cggctctcca gctatcaaga agggcatcct gcaaacagtt  2220
aaggttgttg acgagctggt taaggtcatg ggcggcata agcccgagaa cattgtcatc  2280
gagatggctc gggagaacca gacaactcag aagggccaga agaactccag ggagcgcatg  2340
aagcggattg aggagggcat taaggagctg gggtcccaga tcctcaagga gcaccctgtc  2400
gagaacactc agctgcaaaa cgagaagctc tacctgtact acctccagaa cgggcgggat  2460
atgtatgtgg atcaggagct ggacatcaac aggctctccg actacgacgt ggatcacatt  2520
gtcccacagt ctttcctcaa ggatgattcc atcgacaaca aggtgctgac gcgcagcgac  2580
aagaataggg ggaagtcgga caacgttccg agcgaggagg tcgtgaagaa gatgaagaat  2640
tactggaggc agctcctgaa tgcgaagctg atcactcaga ggaagttcga caatctgaca  2700
aaggcggaga ggggcggct ctcggagctg gataaggcgg gcttcatcaa gcggcagctc  2760
gttgaaaccc ggcagatcac caagcatgtc gcccagatcc tcgatagccg catgaacacc  2820
aagtacgatg agaacgacaa gctcattcgg gaggttaagg tcattacgct gaagtccaag  2880
ctcgtcagcg acttcaggaa ggatttccag ttctacaagg ttcgggagat taacaactac  2940
caccacgcgc atgatgcgta cctgaacgct gttgtcggca ctgctctcat caagaagtac  3000
ccaaagctgg agtccgagtt cgtctacggg gactacaagg tctacgatgt ccggaagatg  3060
atcgccaagt cggagcagga gatcgggaag gctactgcga agtacttctt ctacagcaac  3120
attatgaatt tcttcaagac ggagattacg ctggcgaacg gggagattag gaagaggccc  3180
ctcattgaga ctaatgggga gacaggcgag attgtttggg acaagggccg cgacttcgcg  3240
actgtgcgga aggtcctgtc catgccacag gtgaatattg ttaagaagac agaggtgcag  3300
actgggggct tctcgaagga gagcattctc ccaaagcgga acagcgataa gctcatcgcg  3360
cgcaagaagg attgggaccc taagaagtac ggcggcttcg attctcccac tgtggcctac  3420
tccgttctcg tggttgccaa ggttgagaag gggaagtcga agaagctgaa gtcggtcaag  3480
gagctgctcg ggattacaat catggagcgg agcagcttcg agaagaaccc tattgatttc  3540
ctggaggcca agggctacaa ggaggttaag aaggatctca ttatcaagct ccctaagtac  3600
tctctgttcg agctggagaa tggccggaag aggatgctgg cctcggctgg cgagctacag  3660
aaggggaatg agctggccct cccgtcgaag tatgtgaatt tcctgtacct cgcgtcgcac  3720
tacgagaagc tcaagggcag cccggaggat aatgagcaga agcagctctt cgtggagcag  3780
cataagcact acctggacga gatcattgag cagatcagcg agttctcgaa gcgggttatt  3840
ctggctgatg ctaacctgga caaggttctg agcgcctaca ataagcatcg cgacaagccg  3900
attcgcgagc aggcggagaa tattatccac ctgttcaccc tcactaacct cggggctccc  3960
gcggccttca agtacttcga taccacaata gataggaagc ggtacacctc gacgaaggag  4020
gtcctcgacg ccacactcat ccatcagtcg attacaggcc tgtacgagac acggattgac  4080
```

```
ctctcgcagc tg                                                4092

SEQ ID NO: 61          moltype = DNA  length = 4101
FEATURE                Location/Qualifiers
source                 1..4101
                       mol_type = other DNA
                       organism = synthetic construct
SEQUENCE: 61
gacaagaagt attccatagg cctggctatc ggcaccaaca gcgtgggctg ggccgtcatc  60
accgacgagt acaaagtgcc gagtaaaaag ttcaaagtgc tcggcaacac cgaccgccac  120
tccataaaga aaaacctgat cggggcgctc ctgttcgaca gcggcgagac ggcggaggcc  180
acccgcttga aacgcacggc ccgacggcgc tacacgcggc gcaagaaccg gatctgttac  240
ctacaggaga ttttctctaa cgagatggcg aaggtggacg actcgttctt tcaccgcctc  300
gaagagtcct tcctcgtgga ggaggacaag aaacacgagc gccacccgat cttcggcaac  360
atcgtggacg aggtggccta ccacgagaag tacccgacca tctaccacct ccggaagaaa  420
ctcgtggaca gcacggacaa ggccgacctg aggctcatct acctcgccct ggcgcacatg  480
attaagttcc ggggccactt cctgatcgag ggcgacctga acccggacaa cagcgacgtg  540
gacaagctgt tcatccagct agtccagacc tacaaccagc ttttcgagga aaacccccatc  600
aacgccagcg gggtggacgc gaaggcgatc ctgtccgccc ggctgagcaa gtcccggcgg  660
ctggagaacc tcatcgcgca gttgcccggc gagaagaaga acgggctgtt cgggaacctg  720
atcgccctct ccctggggct caccccgaac ttcaagtcca acttcgacct cgccgaggac  780
gccaaactac agctgagcaa ggacacctac gacgacgacc tcgacaacct gctggcccag  840
atcggggacc agtacgcaga cctgttcctc gccgccaaga acctctccga cgccatcctg  900
ctgtcggaca tcctgcgggt gaacacggag atcacgaagg ccccgctctc ggcctcgatg  960
attaaacgct acgacgagca ccaccaggac ttgaccctcc tcaaggcgct ggtccgccag  1020
cagcttcccg agaagtacaa ggaaatcttt ttcgatcaga gcaagaacgg gtacgccggg  1080
tacatcgacg gcggggcgtc ccaggaggag ttctacaagt tcatcaagcc catcctggag  1140
aaaatggacg ggaccgagga gctgctcgtg aagctcaacc gcgaagattt gctccgcaag  1200
cagcgcacgt tcgacaacgg gtcgatcccg caccagatcc acctgggcga gctgcacgcg  1260
atcctcaggc gtcaggaaga cttctacccc ttcctcaagg acaaccgcga gaagatagag  1320
aagattctga ccttcagaat tccttattac gtgggcccgc tggctcgggg caactcgcgc  1380
ttcgcctgga tgacgcgcaa gtccgaggag accatcaccc cgtggaactt cgaggaggtg  1440
gtggataagg gtgcctcggc ccagtccttc atcgagcgga tgaccaactt cgacaagaac  1500
ctgccgaacg agaaggtgct ccccaagcac agcctgctct acgaatattt cacggtgtac  1560
aacgagctga cgaaggtcaa gtacgtgacc gagggaatga ggaaacctgc attcctctcc  1620
ggggagcaga agaaagccat agtcgacctc ctgttcaaga ccaaccggaa ggtcaccgtc  1680
aagcagctca aggaggacta cttcaagaag atcgagtgct tcgattcagt ggagatcagc  1740
ggcgtcgagg accggttcaa cgccagcctg ggcacctacc acgacctgct caagatcatc  1800
aaggacaagg acttcctcga caacgaggag aacgaggaca tcctggagga catcgtgctg  1860
accctgacgc tcttcgagga ccgcgagatg atcgaggagc gcctcaagac ctacgcccac  1920
ctgttcgacg acaaggtgat gaagcagctc aagcggcgga gatatactgg gtggggccgc  1980
ctctcccgga agctcattaa cggtatcagg gataagcagt ccgggaagac gatcctcgac  2040
ttcctcaagt cggacgggtt cgccaaccgc aacttcatgc agctcatcca cgacgactcc  2100
ctgacgttca aggaggacat ccagaaggcc caagtgtctg gtcaaggtga ctcgctccac  2160
gagcacatcg ccaacctcgc gggcagcccg gccatcaaga agggaatact ccagaccgtc  2220
aaggtggtgg acgagctggt gaaggtcatg ggccgccaca agccggagaa catcgtcatc  2280
gagatggcgc gggagaacca gaccacgcag aaggggcaga aaaatagccg tgagcgcatg  2340
aagcgcatcg aggaggggat taaggagttg ggcagccaga tcctcaagga gcaccctgtg  2400
gagaacacgc agttgcaaaa cgagaagctc tacctgtact acctccagaa cgggagggat  2460
atgtacgtgg accaagaact ggacatcaac cgcctgtccg actacgacgt ggaccacatc  2520
gtgccgcaga gcttcctcaa ggacgacagc atcgacaaca aggtgctcac ccggtccgac  2580
aagaatcggg gcaagtccga caacgtgccc agcgaggagg tcgtcaaaaa gatgaaaaac  2640
tactggcgac aactactgaa cgccaagctc atcacccagc gcaagttcga caacctcaca  2700
aaagccgagc gcggcgggtt gagcgagctg gacaaggccg ggttcatcaa gcgccagctc  2760
gtcgagacgc gccagatcac gaagcacgtc gcgcagatac tcgacagccg gatgaacacc  2820
aagtacgacg agaacgacaa gctcatccgg gaggtgaagg tcatcaccct caagtcgaag  2880
ctcgtgagcg acttccgcaa ggacttccag ttctacaagg tccgggagat caacaactac  2940
caccacgccc acgatgctta tcttaacgcc gtggtgggga cggccctcat taagaaatac  3000
ccgaagctgg agtcggagtt cgtgtacggc gactacaagg tgtacgacgt caggaagatg  3060
atcgccaagt ccgaacagga gatcgggaag gccacggcga aatacttctt ctacagcaac  3120
atcatgaact tcttcaagac cgagatcacc ctcgccaacg gcgagatccg caagcgcccg  3180
ctcatcgaga cgaacgggga gaccggcgag atcgtctggg acaaggggcg cgacttcgcc  3240
actgtgcgga aggtgctgtc gatgccccag gtcaacatcg tcaagaagac ggaggtccag  3300
acgggcgggt tcagcaagga gagcatcctg ccgaagcgca acagcgacaa gctgatcgcc  3360
cgcaaaaagg actgggatcc aaaaaagtac ggcggcttcg acagccccac cgtcgcctac  3420
agcgtcctcg tcgtcgctaa agtcgagaag ggcaagtcca aaaagctcaa gagcgtcaag  3480
gagctgctcg ggatcaccat catggagcgg tccagcttcg agaagaaccc aattgatttc  3540
ctggaggcga agggctacaa ggaggtcaag aaagacctca tcataaagct gccgaagtac  3600
tcactcttcg agctggagaa cgggcgcaag cggatgctgg cgtcggccgg agagctccaa  3660
aagggcaacg agctggcgct gccgagcaag tacgtgaact tcctctacct ggcgtcccac  3720
tacgagaagc tcaagggcag tccagaggat aacgagcaga agcagctatt cgtggagcag  3780
cacaagcact acctggacga gatcatcgag cagatcagcg agttctccaa gcgcgtcatc  3840
ctggcggacg ccaacctgga caaggtgctg tccgcgtaca acaagcaccg cgacaagccg  3900
atccgcgagc aagccgagaa catcatccac ctgttcaccc tcacgaacct cggggcaccc  3960
gccgccttca aatatttcga cacgaccatc gaccgcaagc gctacaccag cacgaaggag  4020
gtgctcgacg ccaccctgat ccaccagagc atcaccgggc tgtacgagac ccgcatcgac  4080
ctctcgcagc tcggcgggga c                                      4101

SEQ ID NO: 62          moltype = DNA  length = 4101
```

```
FEATURE                 Location/Qualifiers
source                  1..4101
                        mol_type = other DNA
                        organism = synthetic construct
SEQUENCE: 62
gacaagaagt acagtattgg attggccatc gggacgaaca gcgtgggctg ggccgtcatc  60
accgacgagt acaaggtgcc atccaagaag tttaaggttc tggggaatac cgaccgccac  120
tcgatcaaga aaaatctcat cggggcgctg cttttcgaca gcggcgagac ggcggaagcg  180
acgcggctca agcggacggc tcgtcgccgt tacacccggc gtaagaaccg catctgttac  240
ctccaggaga tattcagcaa cgagatggcg aaggtggacg actccttttt ccaccgtctt  300
gaggagtcct tcctggtcga ggaggacaag aagcacgagc gccaccccgat cttcgggaac  360
atcgtggacg aggtggccta ccacgagaag taccccacga tctaccacct ccgcaaaaaa  420
ctcgtggact caactgacaa ggccgatttg aggcttatct acctcgccct cgcccacatg  480
attaagttcc gtgggcactt cctaatcgag ggtgacctca accccgacaa ctctgacgtg  540
gacaagctgt tcatccagct tgtgcagacc tacaatcagc tctttgagga gaatccgatc  600
aacgcatctg gtgtggacgc aaaggccatc ctcagcgcgc ggctgagcaa gtctaggcgg  660
ttggagaacc tgatcgccca actgcccggc gagaagaaaa atggcctctt cggcaacctg  720
atcgccctgt cgctggggct cacgccgaac ttcaagagta actttgacct ggcggaggac  780
gctaagctcc agctatctaa ggacacatac gacgacgacc tggacaacct gctggcccag  840
atcggcgacc agtacgccga cctcttccta gccgccaaga acctgtccga cgccatcctc  900
ctcagcgaca tcctgcgcgt gaacacggag atcacgaagg ctccgctcag cgcctccatg  960
attaagcggt acgacgagca ccaccaagac ctaactttac tcaaagccct cgtgcggcag  1020
cagcttcccg agaagtacaa agagatattt tttgatcagt ccaagaacgg ttatgcgggc  1080
tacatcgacg gcggcgcgag ccaggaggag ttctacaagt tcatcaagcc catcctggag  1140
aagatggacg gcacggagga gctgctcgtg aagctcaacc gtgaagacct cctgcgaaag  1200
cagcgaacct tcgacaacgg ttcgatcccg caccagatcc acctcgggga gctgcacgcc  1260
atcctgaggc gacaggagga cttctaccct ttcctaaagg acaaccgcga gaagattgaa  1320
aaaatcctga cgtttcgcat accctactac gtcggcccgc tggcgcgcgg caactcccgg  1380
ttcgcctgga tgacccgtaa gagcgaggag acgatcaccc cgtggaactt cgaggaggtc  1440
gtggacaagg gcgcgagcgc gcagagcttc atcgagcgca tgaccaactt cgacaagaac  1500
ctccccgaacg agaaggtgct cccaaagcac tccctcctgt acgagtattt caccgtgtac  1560
aacgagttga caaaggtgaa gtacgtgacg gagggaatgc ggaagcctgc gttcctctcg  1620
ggcgagcaga agaaggcaat cgtggacctg ctcttcaaga ccaaccggaa ggtgacggtg  1680
aagcagctca aggaggacta cttcaaaaaa atcgagtgct tcgactccgt ggagataagc  1740
ggcgtggagg accgattcaa cgcctccctc ggcacctacc acgacctcct taagatcatc  1800
aaggacaagg acttcctgga caacgaggag aacgaggaca tcctggagga catcgtgctc  1860
accctgaccc tcttcgagga ccgggagatg atcgaggagc gcctcaagac gtacgcccac  1920
ttgttcgacg acaaggtgat gaagcagctc aagcggcggc gatacaccgg gtggggccgc  1980
ctatcccgca aacttatcaa cggcatccgc gacaagcagt ccggcaagac gatcctggat  2040
ttcctcaagt cggacgggtt cgccaaccgg aacttcatgc agctcatcca cgacgacagc  2100
ctcacgttca aggaggacat ccagaaggcc caagtgagcg gtcaagggga cagcctccac  2160
gagcacattg cgaaccttgc tggagccct gcgatcaaga aggggatatt gcaaaccgtg  2220
aaggtcgtgg acgagttggt gaaggtcatg ggcgacacaa agcccgagaa catcgtgatc  2280
gagatggcca gggaaaatca gaccacgcag aagggccaaa aaaacagccg cgagcggatg  2340
aagcggatcg aggagggcat caaggagctg gggtcgcaga tcctcaagga gcacccggtg  2400
gagaacacgc agctccagaa cgagaagctg tacctctatt acctacagaa cgggcgggat  2460
atgtacgtgg accaggagct agacatcaac cgcctgtccg actacgacgt ggaccatatc  2520
gtcccgcagt cgttcttgaa ggacgacagc atcgacaaca aggtgctcac aagatcggat  2580
aagaatcgag gcaagtccga caacgtgccc tcggaggagg tggtcaagaa aatgaaaaac  2640
tactggcggc agttgctgaa cgccaagctc attacgcagc ggaagttcga caacctgacg  2700
aaggctgaac gtggtgggct cagcgagcta gacaaggcgg ggttcatcaa gcggcagctc  2760
gtcgagaccc ggcagatcac caagcacgtg gcgcagatcc tggactcgcg catgaacacc  2820
aagtacgacg agaacgacaa gctcatccgt gaggtgaagg tcatcaccct taagtctaag  2880
ctggtcagtg acttccgcaa ggacttccag ttctacaagg tccgggagat caacaactac  2940
caccacgcgc acgacgccta cctcaacgcg gtggtgggga cggcgcttat taagaaatat  3000
cccaagctgg aaagcgagtt cgtttacggc gactacaagg tgtacgacgt ccgcaagatg  3060
atcgcaaagt cggaacagga aatcggaaag gcgacggcca aatatttctt ttactccaac  3120
atcatgaatt tttttaagac ggagatcacc ctggcgaacg gggagatccg caagcggccc  3180
ctcatcgaga ccaacgggga gacgggcgag atcgtctggg acaagggccg ggacttcgcc  3240
accgtgcgga aggtgctttc tatgcctcaa gtcaatatcg tcaaaaagac agaggtgcag  3300
accggcgggt tcagcaagga gtctatcctg ccgaagcgca actcggacaa gctcatcgcg  3360
cgcaagaaag actgggaccc caaaaaatat ggcgggttcg actcgccgac cgtcgcctac  3420
agcgtcctcg tggtggctaa ggtcgagaag ggcaagagca aaaagctaaa gtcggtgaag  3480
gagctgctgg gcatcaccat catggagcgc tcgtctttcg agaagaatcc aatcgacttc  3540
ctagaggcga aggggtacaa ggaggtcaaa aaggatctta tcatcaaact gccgaagtac  3600
agtctgttcg agctggagaa cggcggaag cggatgctgg ctagtgcggg cgagttgcag  3660
aagggcaacg agttggcact gccctccaag tacgtgaact tcctgtacct ggcctcccac  3720
tacgagaagc tcaaggggag ccccgaggac aacgagcaga agcagctatt cgtcgagcag  3780
cacaagcact acctggacga gatcatcgag cagatcagtg agttctccaa gcgggtcatc  3840
ctcgcggacg ccaacctgga caaggtgctg agcgcgtaca acaagcacag ggacaagcca  3900
atcagggaac aggccgagaa catcatccac ctgttcaccc tgaccaacct gggtgcaccg  3960
gctgccttca agtactttga cacgaccatc gaccggaagc gctacacctc cacgaaggag  4020
gtgctggacg ccacgctgat ccaccagagc atcaccgggc tctacgagac acggatcgac  4080
ctgagccagc ttggcgggga c                                            4101

SEQ ID NO: 63           moltype = DNA  length = 4092
FEATURE                 Location/Qualifiers
source                  1..4092
                        mol_type = other DNA
```

```
                         organism = synthetic construct
SEQUENCE: 63
gacaaaaagt attccattgg actcgctatc ggcacgaaca gcgtcgggtg ggcggtcatc  60
actgacgagt acaaggtgcc gagcaagaag tttaaggtgc tgggaaacac cgacaggcac  120
tcgatcaaga aaaatcttat cggggcccta ctcttcgact ccggagaaac cgccgaggcc  180
acccggttga agcgcacggc ccgccgtcgc tacaccaggc gcaagaaccg gatctgctac  240
ctccaggaga tattcagcaa tgagatggcg aaggtggacg actcgttttt tcacaggcta  300
gaggagtctt tcctcgtgga ggaggacaag aaacacgagc gccaccccat cttcggcaac  360
atcgtggatg aggtggcata tcacgagaag tacccaacca tctaccacct ccgcaaaaag  420
ctcgtggact ctaccgacaa ggccgacctc cgtctgatct acctcgcgct ggcccacatg  480
attaagttcc gaggacactt tctgatcgag ggcgacctga acccagacaa cagcgacgtg  540
gacaagctgt tcatccaact tgtccagacc tacaatcagc tcttcgagga gaaccctatc  600
aacgcctcgg gcgtggacgc gaaggccatc ctgtccgccc gcctgagcaa gtcgcggcgg  660
ctggagaacc tgatcgccca gctccccggc gaaaaaaaga acggcctctt cggcaacctc  720
atcgcgttgt cgctggggct caccccgaac ttcaagtcca acttcgacct ggccgaggac  780
gctaaactcc agctctcgaa ggatacctac gacgacgacc tcgacaacct gctggcccag  840
atcggcgacc agtacgcgga ccttttcctg gcggccaaga acctgagcga cgcgatcctc  900
cttagcgaca tactccgtgt gaacaccgag atcacgaagg ccccgctctc cgcgtccatg  960
attaagcgct acgacgagca ccaccaagac cttaccctgc ttaaggcgct ggtcaggcag  1020
cagttaccgg agaagtacaa ggagatcttt tttgatcaat ctaagaacgg ttacgccggg  1080
tacatcgacg gcggcgcgtc ccaggaggag ttctacaagt tcatcaagcc gatcttggag  1140
aaaatggacg ggaccgagga gctgctcgtg aagctcaacc gcgaagacct cctccgcaag  1200
cagcgcacct tcgacaacgg gagcatcccg caccagatcc acctgggaga gctgcacgcg  1260
atcctgcgga gacaagagga cttctacccc ttcctcaagg acaaccggga gaagattgaa  1320
aaaatactta cttttcgtat cccgtactac gtcgggcccc ttgcgagggg caactccaga  1380
ttcgcgtgga tgacccgcaa gtccgaggag accatcaccc cgtggaactt cgaggaggtg  1440
gtggacaagg gcgcgtcggc ccagtcgttc atcgagcgca tgaccaactt cgacaagaac  1500
cttccgaacg agaaggtgct cccgaagcac agcctgctct acgaatattt tactgtgtac  1560
aacgagctga cgaaggtcaa gtacgttacg gaggggatga ggaagcccgc cttcctctcc  1620
ggcgagcaga agaaagccat tgtggatctc ctgttcaaga ccaaccgcaa ggtgacggtg  1680
aaacagctca aagaggacta cttcaagaag atcgagtgct tcgactccgt agagatcagc  1740
ggggtcgagg accgcttcaa cgcctcgctg ggcacgtacc acgacctgct aaagattatc  1800
aaggacaaag acttcctaga caatgaggag aacgaggaca ttctggagga catcgtgctg  1860
actctgacgc tgttcgaaga ccgcgagatg atcgaggagc ggcttaagac gtacgcccac  1920
ctgttcgacg acaaggtgat gaagcagttg aaacggcggc gctacaccgg gtggggccgc  1980
ctctcccgca agctcatcaa cggcatccgc gacaagcagt cggggaagac gatcctggac  2040
ttcctcaaga gcgacggctt cgccaaccga aacttcatgc agctaatcca cgacgacagc  2100
ctgacgttca aggaggacat ccagaaggcc caagtgagcg gccagggaga ctcgctacac  2160
gagcatatcg ccaacctggc tggcagcccg gcgattaaga aaggaatcct ccaaaccgtc  2220
aaagtggtgg acgagctggt gaaggtgatg ggccgccaca agcccgagaa cattgtgatc  2280
gagatggcgc gggagaacca gacgacgcag aagggccaaa aaaatagcag ggaaaggatg  2340
aagcgaatag aggaggggat caaggagctg gggagccaga ttctcaaaga gcacccggtc  2400
gagaacacac agctccagaa cgagaagctg tacctctact acctccaaaa cggccgcgat  2460
atgtacgtgg accaggaact agacatcaac cggctgagcg actatgacgt ggaccacatc  2520
gtgccgcagt ccttcctcaa ggacgactcg attgacaaca aagtgctcac tagatccgac  2580
aagaacagag gcaagagcga taacgtcccg tcggaggagg tcgtcaagaa aatgaaaaac  2640
tactggcggc agctcctaaa cgccaagctc atcacgcagc gtaagttcga caacctgacg  2700
aaggcggagc ggggcgggct gagcgagctg gacaaagcgg ggttcatcaa gcggcagctc  2760
gttgagacgc ggcagatcac aaagcacgtc gcgcaaatcc tcgactcccg catgaacacc  2820
aagtacgacg agaacgacaa gctcatccgg gaggtgaagg tcattaccct taaatcgaag  2880
ctcgtcagcg actttcgtaa ggacttccag ttctacaagg tcagagagat caacaactac  2940
caccacgccc acgacgccta tctgaacgcc gtggtgggca ccgcgcttat taagaagtac  3000
cccaagctgg agtccgagtt cgtgtacggc gactacaagg tttatgacgt caggaagatg  3060
atcgccaagt cggaacagga gatcggaaaa gctaccgcca aatatttctt ctatagcaac  3120
atcatgaact tcttcaaaac cgagatcacc ctcgccaacg gcgagatccg gaagcgcccg  3180
ctcatcgaga ccaacgggga gaccggggag atcgtctggg acaaggggcg ggacttcgct  3240
actgtccgaa aggtgctctc catgccacaa gtgaatatcg tcaagaaaac agaggtgcag  3300
accggagggt tcagtaagga gtccatcctg cccaagcgga actccgacaa gctaattgct  3360
cgcaaaaagg attgggatcc taaaaaatat ggcggcttcg actcgcccac ggtcgcctac  3420
tctgtgctgg tcgtggcgaa ggtggagaag ggcaagtcca agaagctcaa gagcgtcaag  3480
gagctgctgg ggatcacgat catggagcgt agttcgtttg agaagaatcc catcgacttc  3540
ctggaggcta agggctacaa ggaggtcaaa aaggacctca tcattaagct gccgaagtac  3600
agcctcttcg agctggagaa cgggcggaag cgtatgctcg cctccgctgg ggagttacaa  3660
aaggggaacg agctggcgct gccgtctaag tacgtcaact tcctgtacct ggcctcccac  3720
tacgagaagc tcaaggggtc gccggaggac aacgagcaga agcagctctt cgtagagcag  3780
cacaagcact acctggacga gatcatcgag cagatttcag agttctcaaa gcgggtcatc  3840
ctcgccgacg ccaacctgga caaggtgctc tcggcctaca acaagcaccg ggacaagccg  3900
atccgcgaac aggccgaaaa catcatccac ctgttcacgc tcaccaacct cggtgccccg  3960
gcggccttca agtactttga cacgaccatc gaccggaagc gctatacctc gacgaaggag  4020
gtgctggacg ccaccctgat ccaccagtcc atcaccgggc tttacgagac ccggatcgac  4080
ctctcgcagc ta                                                      4092

SEQ ID NO: 64            moltype = DNA  length = 4101
FEATURE                  Location/Qualifiers
source                   1..4101
                         mol_type = other DNA
                         organism = synthetic construct
SEQUENCE: 64
gacaagaagt atagtattgg actcgccatc ggaaccaact ctgtggggtg ggctgttatt  60
```

```
acagatgaat ataaggtgcc atccaaaaag tttaaagttc tgggcaatac tgatagacac  120
tcaatcaaga agaatctgat aggtgcactt ctgtttgata gtggagagac tgccgaggca  180
accagactta aaaggactgc aagaagaaga tataccagaa gaaagaatag gatttgctat  240
ttgcaggaaa tcttcagcaa cgaaatggcc aaggttgatg actcattttt ccataggttg  300
gaggagagtt ttcttgtgga ggaagataag aagcacgaaa gacacccaat tttcgggaat  360
atagtggacg aggtggctta tcatgagaag tatcccacta tctaccacct gagaaagaaa  420
cttgtggact caaccgataa ggctgatctt aggcttatat acttggccct tgcacatatg  480
atcaaattca ggggccattt tcttatcgaa ggcgatctta atcccgataa ctcagatgtg  540
gacaagctgt ttatacaact tgtgcaaacc tacaatcaac tcttcgagga gaatcccatt  600
aacgcctccg gcgtggatgc aaaagccata ctgtcagcca gactgagcaa aagtaggaga  660
ctggagaatc ttatagccca actgcccggt gaaaagaaga atgggctctt cggaaatctg  720
atcgctcttt cattggggtt gacacccaac tttaagagta actttgactt ggcagaagat  780
gcaaagttgc agctcagtaa agacacatat gacgatgacc ttgacaatct cttggcacaa  840
ataggggatc aatacgctga ccttttcctc gctgccaaga acctcagcga cgctatactg  900
ttgtccgaca ttcttagggt taataccgaa attacaaagg cccctcttag tgcaagtatg  960
atcaaaaggt atgatgagca tcaccaagac cttacactgc tgaaggctct ggttagacag  1020
caactccctg aaaagtataa ggaaatattc ttcgaccaaa gtaagaacgg gtacgccggt  1080
tatattgatg gggcgcaag tcaagaagaa ttttacaaat tcatcaagcc aattcttgaa  1140
aagatggacg ggactgagga attgctggtg aaactgaata gagaggacct tcttagaaaa  1200
cagaggacat ttgacaatgg gtccatccca caccagattc atctgggga actccacgca  1260
atattgagga gacaagaaga cttttaccca ttccttaagg ataatagaga gaaaatcgaa  1320
aaaatcctga ctttcaggat tccttactat gttgggccac tggccagggg gaactcaaga  1380
ttcgcttgga tgacaaggaa gtcagaagaa accataaccc cttggaattt tgaagaggtg  1440
gttgataagg gggcatcagc ccagtctttc atagagagga tgaccaactt tgataaaaat  1500
cttccaaatg agaaggtttt gccaaaacat agtcttttgt acgagtactt tactgtttat  1560
aacgaattga ccaaggtgaa gtatgtgacc gagggaatga ggaagccagc atttttgtcc  1620
ggggagcaaa agaaagcaat cgttgatctt ctcttcaaga ccaacagaaa agtgaccgtg  1680
aaacaactga aggaagacta cttcaaaaag atagaatgtt tcgattcagt ggaaattagc  1740
ggtgttgaag acaggttcaa tgcttcattg ggtacttacc acgacctgtt gaagataatc  1800
aaagacaagg actttctcga taatgaggag aacgaagaca tcttggaaga cattgtgctt  1860
acactcactt tgtttgagga cagggaaatg attgaggaaa gactcaaaac ttacgctcat  1920
ttgtttgatg ataaggttat gaaacaacta aaaagaagaa ggtacaccgg ctggggaaga  1980
ttgagtagga aactgatcaa cggtattaga gataaacaat ccggaaagac tatcctcgat  2040
ttccttaaga gtgatggctt tgcaaatagg aattttatgc agctgattca tgacgactca  2100
cttaccttca aagaagacat ccaaaaagct caggtgtctg ggcaaggcga cagtctgcat  2160
gaacatatag ctaacttggc tgggagtccc gccatcaaga aggggatact tcaaacagtt  2220
aaagttgtgg acgaattggt gaaggtaatg ggaaggcaca agcctgaaaa tatagtgata  2280
gaaatggcaa gggaaaatca aacaacccag aagggacaga agaacagtag ggaaaggatg  2340
aaaaggatag aagaggggat caaagagctt ggtagccaga tcctcaagga acatccagtg  2400
gagaataccc aacttcaaaa cgagaaactc tatttgtact acttgcagaa cggaagagat  2460
atgtatgtgg accaagagct tgatattaac aggctgagcg attatgacgt tgaccacata  2520
gtgccccaat cattcctcaa ggatgactct attgataata aggtgctgac aaggagtgac  2580
aagaatagag ggaaatccga caacgttcca tccgaggaag ttgtgaagaa gatgaagaac  2640
tactggaggc agttgctgaa cgctaagctc attacccaga ggaaattcga taacctgacc  2700
aaagcagaga gaggcgggct gagcgaactc gataaagcag gtttcatcaa gagacaactc  2760
gtggagacta ggcaaattac taagcacgtg gctcaaatac tcgacagcag gatgaacaca  2820
aagtacgacg agaacgacaa gctcattaga gaggttaagg ttattactct gaaaagtaaa  2880
ttggttagcg atttcagaaa ggatttccaa ttctataagg ttagagagat caacaattat  2940
catcatgcac atgatgccta tctgaatgct gtggttggta cagcccttat caagaagtac  3000
cctaagctag agagcgagtt tgtgtacgga gattataagg tgtatgatgt gaggaaaatg  3060
atcgctaaaa gtgagcaaga gattggaaag gctaccgcca aatacttctt ttattccaat  3120
attatgaatt tcttcaagac agaaatcacc ctggctaacg gcgagataag gaagaggccg  3180
cttatcgaaa ctaatgggga gacaggcgaa atagtgtggg acaaagggag ggatttcgca  3240
actgtgagga aggttttgag catgcctcag gtgaatatcg ttaagaaaac cgaagttcaa  3300
actggagggt tctctaagga aagcattctc cccaagagga actccgacaa gctgattgct  3360
agaaagaaag actgggaccc caagaagtat ggcggattcg actcacccac tgtggcatat  3420
agcgttctcg tggtggcaaa ggttgaaaag ggtaaatcca aaaaactcaa atccgtgaag  3480
gaactccttg gcataactat tatggaaagg agtagctttg aaaagaatcc catcgacttt  3540
ctcgaagcta agggctataa ggaagttaag aaggacctta taatcaaact tccaaaatac  3600
tcccttttg agttggaaaa cggcagaaag agaatgttgg ccagtgccgg ggagcttcaa  3660
aagggcaacg aactggctct gcctagcaaa tatgtgaact tttgtatct ggcatcacac  3720
tacgagaaac ttaaaggctc tcctgaggac aacgagcaaa aacagctctt tgttgaacag  3780
cataagcact acctcgacga gattattgag cagatcagcg agttctcaaa gagagttatt  3840
ctggctgacg ctaatcttga caaggtttg tccgcttaca acaaacacag ggataagcca  3900
atcagggagc aggcagaaaa cataatccat ctctttaccc tgacaaacct cggtgccccc  3960
gctgctttca agtattttga tactaccatt gacaggaaga gatatacttc cactaaggaa  4020
gtgctcgacg caaccctcat acaccaaagt atcacaggcc tctatgaaac taggatagat  4080
ttgtctcaac ttgggggcga t                                            4101
```

```
SEQ ID NO: 65          moltype = DNA  length = 4101
FEATURE                Location/Qualifiers
source                 1..4101
                       mol_type = other DNA
                       organism = synthetic construct
SEQUENCE: 65
gacaaaaagt attccatcgg gcttgctatc ggaaccaact ctgtggggtg ggcagttatt  60
accgacgaat acaaggtgcc cagcaagaag tttaaggttc tggggaacac agatagacat  120
agcataaaga aaaacctgat aggcgcactg ttgttcgact ccggggaaac agccgaagct  180
accaggctga agagaactgc aagaagaagg tacaccagaa gaaaaaacag aatatgttat  240
```

```
ctccaagaga ttttctctaa cgagatggcc aaggtggacg actcattctt tcacagactg  300
gaagaatctt tccttgtgga agaagataag aaacacgaga ggcaccctat ttttggcaat  360
atcgtggatg aggtggctta ccacgaaaaa taccctacaa tataccacct caggaaaaaa  420
ttggttgata gtacagacaa ggccgacctc aggctcatct atttggccct ggcccatatg  480
attaaattca gggggcactt tctcatcgag ggagatttga accccgacaa cagtgatgtt  540
gataagctct ttattcagct cgtgcagact tacaatcagt tgtttgagga aaaccccatt  600
aatgcttccg gggtggacgc caaggcaatc ctttctgcaa gactctcaaa gtcaaggaga  660
ctcgaaaatc tgatagcaca gcttccagga gagaagaaga acgggctctt tggaaacctg  720
atcgctctgt cactcggact cacacccaat ttcaaaagca attttgattt ggcagaggac  780
gctaagctgc aactcagtaa ggatacctac gacgatgact tggataatct gctcgcacaa  840
attggggacc agtatgcaga cctgtttctc gcagctaaga acttgagtga cgccatattg  900
ctcagtgaca tcctcagggt taataccgag attacaaaag ctccactctc tgcaagcatg  960
atcaagaggt atgacgagca ccatcaagac ctgacactcc ttaaggcgtt ggttaggcag  1020
caacttcctg aaaagtataa ggaaatcttc ttcgatcaaa gcaaaaacgg ctacgccggc  1080
tatatagacg gggagcatc ccaagaagaa ttttataagt tcataaaacc tatattggag  1140
aagatggacg ggacagagga attgctcgtg aaactgaaca gggaggatct cctcaggaag  1200
caaaggacct tcgacaatgg ctccatccca catcagattc acctcggcga actgcacgca  1260
atactgagaa gacaagagga cttttatcct ttcctgaagg acaacaggga gaaaatcgag  1320
aaaatcttga cattcagaat cccatactac gttgggcctc tggccagagg taacagtagg  1380
ttcgcctgga tgactaggaa atcagaggag actattacac cctggaactt tgaagaagtt  1440
gttgataagg gagcttcagc acaatcattc atcgaaagaa tgacaaactt tgacaaaaat  1500
ctgcctaatg agaaagtgct cccaaaacat tccctgctgt atgagtattt taccgtttat  1560
aacgagctta ccaaggtgaa atacgttact gaaggtatga gaaagccagc ttttctttca  1620
ggggagcaaa agaaggctat cgtggatctt ctctttaaga ccaacagaaa ggttaccgtg  1680
aagcagctta aggaagacta ctttaaaaag atcgagtgtt ttgactcagt ggaaataagc  1740
ggtgttgaag atagattcaa cgcatccttg ggaacttatc atgatcttct taagataatc  1800
aaggataaag actttctcga caacgaggaa aacgaagata tactggagga catagttctg  1860
acacttactt tgttcgagga tagggagatg atcgaggaaa gactgaaaac atatgctcac  1920
cttttcgacg acaaagttat gaaacaactc aagagaagga gatatacagg gtgggggaga  1980
ttgagcagga aactgattaa tggtatcaga gacaaacagt caggaaaaac aatactcgac  2040
tttttgaaat cagacgggtt cgcaaatagg aatttcatgc agcttataca cgacgattca  2100
cttactttta aagaggacat tcaaaaggct caagttagtg gacaaggtga ctccctccac  2160
gaacacatcg caaatctcgc tggcagccct gcaattaaga agggtatact ccagacagtt  2220
aaggttgttg acgagctggt taaagtgatg ggaagacaca aacccgagaa catagtgata  2280
gagatggcca gggaaaacca aaccactcaa aaagggcaga aaaattccag agagaggatg  2340
aaaaggattg aagaaggtat caaggagctg ggtagccaaa ttctgaaaga acatcctgtg  2400
gaaaacactc aactccagaa tgagaaactc tatctgtact atctgcaaaa tgggagagat  2460
atgtatgtgg accaggaact ggacataaac aggctctcag attacgatgt ggatcatatc  2520
gtgccacagt cctttcttaa ggatgatagc atcgacaata aggtgcttac caggtccgac  2580
aagaacaggg gaaagtcaga taacgtgcct tctgaagaag ttgttaaaaa gatgaagaac  2640
tactggagac agctgcttaa cgctaagctc ataacacaga ggaagtttga caacttgacc  2700
aaggccgaga gaggcggact ctcagaattg gataaggcag ggttcataaa aaggcagctg  2760
gtggaaacaa ggcagataac taaacatgtg gctcagatcc tcgatagtag gatgaataca  2820
aaatacgatg agaacgacaa gctcataagg gaggttaaag tgataactct gaaatccaaa  2880
ctggttagcg attttaggaa ggatttccag ttttacaaag ttagggagat caacaattat  2940
catcacgccc acgatgccta cttgaacgca gttgtgggta ctgcacttat caaaaagtac  3000
cctaagctgg aatccgagtt tgtttatgga gactataagg tgtacgacgt tagaaaaatg  3060
attgcaaagt cagagcagga gatagggaaa gccactgcaa aatatttctt ttatagcaat  3120
atcatgaatt tctttaagac agaaatcaca ctggccaatg gggaaataag gaagaggccc  3180
ctgatcgaaa ctaatggcga gacaggggag attgtgtggg ataaaggtag ggactttgca  3240
acagtgagga aagtgctgag catgccccaa gttaatatcg ttaaaaagac cgaggttcaa  3300
acagggggct ttagtaagga aagcattttg cccaagagga atagtgacaa attgattgct  3360
aggaaaaaag attgggaccc caaaaagtat ggcggatttg atagccccac tgttgcttac  3420
tccgtgctcg tggttgcaaa ggtggagaag ggaaagagca agaaactgaa gtcagttaag  3480
gaactccttg gtatcactat catggaaaga agctcctttg agaagaaccc tattgacttc  3540
ctggaggcta aagggtacaa agaggttaag aaagacctta tcattaaatt gcccaaatat  3600
agtcttttcg agcttgaaaa cggaagaaag aggatgcttg catccgctgg cgaattgcaa  3660
aagggcaatg agcttgctct cccttccaag tatgtgaact tcctttatct tgcctcacac  3720
tatgaaaaac tcaaaggttc acccgaagac aacgaacaaa agcaactatt tgtggaacaa  3780
cacaagcact acctggacga aatcattgag caaatttctg agttttcaaa aagggtaatc  3840
ttggctgacg caaatctcga caaagttttg tcagcttaca acaaacatag agataagcca  3900
attagagagc aagctgagaa tatcatccat ctgtttaccc tgactaacct tggagcgcct  3960
gctgctttta aatatttcga caccacaatc gacaggaaga ggtacactag cactaaggaa  4020
gttctcgacg ccaccctcat ccaccagagt attacaggcc tgtacgagac aagaattgat  4080
ctttctcaac ttggtggtga c                                            4101
```

```
SEQ ID NO: 66          moltype = DNA  length = 4101
FEATURE                Location/Qualifiers
source                 1..4101
                       mol_type = other DNA
                       organism = synthetic construct
SEQUENCE: 66
gataagaagt actcaatcgg tctggcaatc ggaaccaact ctgtgggttg ggcagtgatt  60
acagatgagt ataaggtgcc aagcaaaaaa ttcaaggtgc tgggtaatac cgacagacac  120
agcattaaga agaatttgat tggagcactc ctctttgact caggggaaac agcagaggca  180
acaaggctga agaggacagc aaggcggagg tacacaaggc ggaaaaacag gatatgctac  240
ctccaggaaa tctttagcaa cgagatggct aaagtggatg atagcttttt ccatagactc  300
gaagaatcct ttcttgttga agaggacaaa aagcatgaaa ggcatcccat cttcggcaat  360
atagttgatg aggttgcata ccatgagaag taccccacaa tctaccacct cagaaagaaa  420
```

```
cttgtggact ccacagataa agcagacctg aggctcatat acctcgcact cgcacacatg  480
atcaagttca gagggcactt tctcatcgaa ggtgacctga atccagataa ttcagatgtg  540
gataaactgt ttatacagct ggtgcaaaca tacaaccaac ttttcgagga aaacccaatc  600
aatgcctccg gtgttgatgc aaaggccatc ctgtcagcaa gactcagcaa aagcaggcgg  660
ctcgaaaacc tcatcgccca gcttcccggt gaaaagaaga acgggctctt tggtaatctc  720
atcgcattga gccttggtct tactccaaac ttcaagagca attttgatct ggcagaggat  780
gctaaactgc aactctcaaa ggacacatat gacgatgacc ttgacaatct gttggcccag  840
atcggggacc aatatgcaga cctcttcctg gccgcaaaga atctgtcaga tgcaatcctc  900
ttgtccgaca tactgagagt taacactgag atcacaaagg cacctctgtc cgcctccatg  960
attaagagat acgatgagca tcaccaggat ctgactttgc tcaaagccct cgttagacag  1020
cagttgccag aaaagtacaa agaaatattc tttgatcaat caaaaaacgg atatgcaggg  1080
tacatcgacg gtggggcaag ccaggaagag ttctacaaat tcatcaaacc tatcctggaa  1140
aagatggatg ggacagaaga gctgctggtt aagctgaata gggaagacct cctcagaaag  1200
cagaggacat ttgataacgg gagcatccct catcaaatcc acctcggtga actccatgct  1260
atcctgagaa ggcaggaaga cttttatcca tttttgaagg acaataggga gaaaatcgaa  1320
aaaatcctga cattcagaat cccatactac gttggtcctc tggcaagagg taacagtagg  1380
ttcgcatgga tgacaaggaa aagcgaggag acaatcacac cctggaattt tgaggaagtt  1440
gttgacaagg gtgccagcgc acaatccttt atcgaaagaa tgacaaattt cgacaagaat  1500
ctgcctaacg aaaaggttct cccaaagcat tcactcctgt acgaatattt tacagtttat  1560
aacgaactga ctaaagttaa atacgttacc gagggtatga ggaagccagc attcctttcc  1620
ggggaacaga agaaagctat tgtggacctc ctgttcaaga caaatagaaa agtgacagtt  1680
aagcaactca aagaggatta cttcaaaaag atcgaatgtt ttgactctgt ggagatcagc  1740
ggggtggagg atagattcaa cgccagcctg ggtacatatc atgatctcct gaaaatcatt  1800
aaagacaagg acttccttga caacgaggag aacgaggaca ttctggaaga cattgttctg  1860
accctcacac tctttgagga tagggagatg attgaggaaa gactgaagac ctacgcccac  1920
ctctttgacg ataaagtgat gaaacagctc aagagaagaa ggtatacagg ttgggggaga  1980
ctgagcagga agttgatcaa tgggattagg gacaaacagt ccgggaaaac aatcctcgat  2040
tttctgaagt cagacggttt cgcaaacaga aattttatgc agctcattca cgatgacagc  2100
ttgacattca aggaagacat ccaaaaggct caagtgagcg gccaagggga tagcctccac  2160
gagcatattg caaatctggc aggttcacca gccatcaaaa agggcatact tcagacagtt  2220
aaggttgtgg acgaattggt taaagttatg ggcaggcata agccagagaa tatcgttatc  2280
gaaatggcaa gggagaacca aacaactcaa aaagggcaga aaaatagcag agagaggatg  2340
aaaagaatcg aggaagggat caaggaactt gggtcccaaa tcctcaagga gcacccagtt  2400
gaaaatactc aactgcaaaa cgagaagctc tatctctact atctccaaaa cgggagggat  2460
atgtatgttg accaggagct ggatattaac agactgtcag attatgatgt tgatcatatc  2520
gtgccccagt cattcctgaa ggacgattcc atcgacaaca aagttctcac aaggtccgat  2580
aaaaacaggg gcaagtccga taacgttcca agcgaagaag tggtgaaaaa gatgaaaaac  2640
tattggagac aacttctgaa tgcaaagttg attactcaga gaaagtttga caacctcaca  2700
aaagcagaaa gaggcgggct tagcgaactc gataaggcag ggtttatcaa aagacagctg  2760
gttgagacaa ggcagatcac aaaacatgtg gcacagatcc ttgactcaag gatgaatacc  2820
aagtatgatg agaatgataa gttgatcagg gaggttaaag ttatcacact caaatccaaa  2880
ctggtgtcag acttcaggaa agactttcaa ttttataagg tgagggagat caataactac  2940
caccatgcac atgacgccta cctgaacgca gtggtgggta cagcattgat taaaaaatac  3000
cctaagctgg agtctgagtt tgtgtacggg gactacaagg tgtacgacgt gaggaaaatg  3060
atagccaagt ccgagcagga gatcgggaaa gcaacagcta agtatttctt ttacagtaat  3120
atcatgaatt tctttaaaac tgagattact ctggcaaacg gggagatcag gaaaagaccc  3180
ctcatcgaga ctaatggtga aacaggtgag atcgtttggg acaaggggag ggattttgct  3240
actgttagaa aagttctgag tatgccacaa gtgaatattg tgaaaaagac agaagttcag  3300
acaggtgggt tctccaaaga atccatcctg cccaagagaa attcagacaa gctcatcgca  3360
agaaagaagg actgggaccc taagaagtac ggaggatttg acagccccac cgtggcctat  3420
tccgtgcttg ttgtggcaaa ggtggagaaa gggaagagca aaaaactgaa atccgtgaaa  3480
gaactgctgg gaattaccat catggaaaga agctcctttg agaagaaccc aatcgacttc  3540
ctggaagcaa aggatataa ggaagtgaaa aaggacctca ttatcaagct cccaaaatac  3600
tcacttttcg agttggagaa cggtagaaag aggatgctgg caagcgcagg ggaacttcag  3660
aaaggcaatg agctggcatt gccatcaaag tatgtgaact tcctctactt ggccagccat  3720
tacgagaaac ttaaaggtag cccagaagat aacgagcaaa aacagctctt tgtggaacag  3780
cataagcatt atctggatga gatcatagaa caaatctcag agttttccaa gagagttatc  3840
ctcgcagatg caaacctgga taaggttctc tcagcctata ataagcatag agacaagcca  3900
attagagagc aagcagagaa cattatccac ttgttcactc ttacaaacct gggggcacca  3960
gccgccttca aatatttcga tacaacaata gacagaaaga ggtataccag caccaaagaa  4020
gttctcgacg ccacactgat ccatcaatca atcacaggcc tttacgaaac taggatcgac  4080
ttgtcacaac tgggtgggga t                                            4101
```

```
SEQ ID NO: 67          moltype = DNA  length = 3307
FEATURE                Location/Qualifiers
source                 1..3307
                       mol_type = other DNA
                       organism = synthetic construct
SEQUENCE: 67
gagcaaggac acctacgacg acgacttgga caacctattg gcccagatag gtgaccagta  60
tgcagacctc ttccttgcgg ccaagaactt gagtgacgct atactgctca gtgacatcct  120
gagggtgaac actgagatca ctaaggcccc tctctctgcc tcaatgatta agcgttacga  180
cgagcatcac caggatctca ccctgcttaa ggcccttgtt cggcagcagc tccctgagaa  240
gtacaaggag atattttttg accagtctaa gaacggctac gccggttaca ttgacggtgg  300
ggcaagccag gaggagttct acaagttcat caagccgatc cttgagaaga tggacggcac  360
cgaggagcta cttgtcaagt tgaaccggga agacctgctc cggaaacagc gtacattcga  420
caacggcagc atccctcacc agatccacct gggcgaacta cacgccatcc tccgacgtca  480
ggaggacttc tatccattct tgaaagataa cagggaaaaa atcgaaaaaa tacttacgtt  540
tcgaatacct tactacgtgg ggccccttgc tcggggaaac tccagattcg catggatgac  600
```

```
caggaagtca gaggagacca tcacaccctg gaactttgag gaggtggttg acaaaggtgc  660
ttctgcccag tccttcattg agcggatgac taacttcgac aagaacctgc ccaacgagaa  720
ggtgctgcca aagcacagcc tgctctacga atactttact gtgtacaatg agctgacgaa  780
ggtgaagtac gtgacagagg ggatgcggaa gcccgctttc ctgagcggcg agcaaaaaaa  840
agcaatcgtg gacctactgt tcaagaccaa ccgaaaggtg acagtgaagc agctcaagga  900
ggactacttc aaaaaaatcg agtgcttcga ctctgttgag ataagcggcg tggaggaccg  960
attcaacgcc tcattgggaa cctatcacga cctgctcaag atcattaagg acaaggactt  1020
cctggataat gaggagaatg aggacatcct ggaggatatt gtgctgaccc ttactctatt  1080
cgaggacagg gagatgatcg aggagcgact caagacctac gctcacctgt tcgacgacaa  1140
ggttatgaag caattgaagc gtaggcgata cacggggtgg ggaagactct cccgaaaact  1200
gataaacggc atcagggaca agcagtcagg gaagacgatc ttggacttcc tgaaatccga  1260
cgggttcgcc aaccgcaact tcatgcagct cattcacgac gactcactaa cgttcaaaga  1320
ggacattcag aaggctcaag tcagtggaca aggcgactcc ctgcacgagc acattgcaaa  1380
ccttgcgggc tccccggcga ttaaaaaggg cattctccaa acggttaagg tggtggacga  1440
gctggtgaag gtgatgggcc gacacaagcc tgagaacatc gtgatcgaga tggccaggga  1500
gaaccagact acccagaagg gtcagaagaa ctctcgggaa cgtatgaagc gtattgagga  1560
ggggattaag gagttgggct ctcaaatcct caaggagcac cctgtggaga acactcagct  1620
ccaaaacgag aagctgtacc tgtactacct gcaaaacggg cgcgatatgt acgtggatca  1680
ggagttggac atcaacaggc ttagcgatta cgacgtggac cacatcgtgc cacagtcatt  1740
cttaaaggac gacagcatcg acaacaaggt tctgacgagg agcgacaaga atcgagggaa  1800
aagtgacaat gttccatccg aggaggtggt caagaaaatg aagaactatt ggcgtcagct  1860
tctgaacgcc aagctcatca cccagcggaa attcgacaac ctgactaagg ctgagcgagg  1920
cggactctcc gagcttgaca aggctggctt catcaagcgg cagttggtcg aaacccgaca  1980
gataacgaag cacgttgccc agatacttga ctcccgtatg aacaccaagt acgacgagaa  2040
cgacaagctc atcagggagg tgaaggtcat tacccttaag tccaaactcg tcagcgactt  2100
tcgtaaggac ttccagttct acaaggtgcg cgagatcaat aactaccacc acgcacacga  2160
cgcctacctg aacgcagtgg ttggaaccgc gttgattaaa aagtacccca agttggagtc  2220
ggagttcgtt tacggggact acaaggtgta cgacgttcgg aagatgatcg ccaagtctga  2280
acaggagatc gggaaagcaa ccgccaagta tttcttctat agcaacatca tgaacttctt  2340
taaaaccgag atcacacttg ccaatggcga gatccgtaag aggccgctga tcgagacaaa  2400
tggggagact ggcgagatcg tgtgggacaa gggccgcgac ttcgcaaccg ttcggaaagt  2460
cttgtccatg cctcaagtca acatcgtcaa gaagactgag gtgcaaacag gcgggttctc  2520
gaaggagtcc atactgccca agaggaactc agacaagctc atagcacgca aaaaagactg  2580
ggatccaaag aaatacggcg ggttcgactc gccgacagtc gcatactccg tgttagtggt  2640
ggctaaagtg gaaaagggga agtccaagaa gctcaagtcc gtcaaggagt tgctcgggat  2700
caccattatg gaacggtcct cattcgagaa gaatcccatt gacttcctag aggcgaaggg  2760
ctacaaagag gtcaaaaagg acctaattat taagctcccc aagtattcac tcttcgaact  2820
tgaaaatggt cgtaagcgga tgttggcaag cgctggagag cttcagaagg ggaacgagct  2880
tgcactgcct tccaagtacg tgaacttcct gtacctcgcc tctcattacg agaagttgaa  2940
gggctcaccg gaggacaacg agcagaagca gttgttcgtg gagcagcaca agcactacct  3000
cgacgagatc attgagcaga taagtgagtt cagcaaacgg gtgatccttg ccgacgctaa  3060
cctggacaag gtgctgagcg cctacaacaa gcacagagac aagccgatcc gagagcaagc  3120
ggagaacatc atacacctgt tcaccctcac gaacctcggg gctcccgcag ccttcaaata  3180
ttttgacacg accatcgacc gtaaacgcta cactagcacg aaggaggtgc tggacgctac  3240
ccttatccac cagtccatca ccggcctgta cgagacgaga atcgacttgt cgcagctcgg  3300
tggtgac                                                           3307

SEQ ID NO: 68          moltype = DNA  length = 4101
FEATURE                Location/Qualifiers
source                 1..4101
                       mol_type = other DNA
                       organism = synthetic construct
SEQUENCE: 68
gacaaaaaat actcaattgg tctggcaatt gggaccaaca gtgtcggatg ggccgtgatt  60
accgacgagt acaaggtgcc gtccaaaaaa ttcaaggtgc ttgggaacac cgaccgccac  120
tcgatcaaga aaaacctaat cggtgcgttg cttttcgaca gtggggagac cgccgaggca  180
acacgcttaa aacgcacagc taggaggaga tatacacggc gcaagaaccg aatatgctac  240
ttacaggaga tattctccaa tgagatggcg aaggtggacg actctttctt ccatcggctt  300
gaggaatcct tcctggtcga ggaggacaag aagcacgagc gacacccgat attcgggaac  360
atcgttgatg aggtggcgta ccacgagaag tacccaacga tataccactt acgcaagaag  420
ctcgtggact ctacggacaa ggccgacttg cgccttatct acttggcact ggcccacatg  480
attaagttcc gaggccactt ccttatcgag ggtgacctga accccgataa ctccgacgtg  540
gacaagctct tcatccaact cgtccagaca tacaaccagc tattcgagga gaatcctatc  600
aacgcctctg gggtggacgc taaagctatc ctctcagccc gcctgtcaaa gtcgaggagg  660
ttggagaacc taatcgccca gcttccaggc gagaagaaaa atgggctgtt cggaaacctt  720
atcgcactct cactgggcct aaccccgaac ttcaagtcca acttcgacct ggcagaggac  780
gcgaaattgc agttgtcgaa agacacctat gacgatgacc tggacaacct gttggcccag  840
atagggggacc agtacgccga cctgttccta gcggccaaga acctgtccga cgccatcttg  900
ctgtcggata tactgcgggt gaacaccgag atcactaaag cacctctctc cgccagcatg  960
attaagcgtt acgacgagca ccaccaagat ttgaccctgc taaaggcact tgtacggcag  1020
cagcttcccg agaagtacaa ggagatcttt ttcgaccaaa gcaagaacgg ctacgccggg  1080
tacatcgacg gaggtgccag ccaggaggag ttctacaagt tcattaagcc catcctggag  1140
aagatggacg ggactgagga actacttgtg aagctgaacc gggaagactt actacggaag  1200
cagcgtacct tcgacaacgg ttctatccca catcagatcc atcttgggga gttgcacgcg  1260
atcctgcgac gccaggagga cttttacccc ttcctgaaag acaaccgcga gaaaatcgag  1320
aagatactga ccttcagaat accttactac gtcggacccc ttgcgcgagg caactcaaga  1380
ttcgcgtgga tgaccaggaa atcagaggag accatcacac cctggaattt cgaggaggtg  1440
gttgacaagg gtgcctccgc ccagtccttt atcgaacgaa tgaccaactt cgacaagaac  1500
ttgcccaacg agaaggtgct ccccaaacac agcctcctct acgaatattt cacagtgtac  1560
```

```
aacgagctta ctaaagttaa gtatgttact gagggcatga ggaaacccgc cttcctgtca  1620
ggcgagcaga agaaagctat tgtggacctc cttttcaaga ccaaccggaa ggtgacagtg  1680
aagcagctca aggaggacta cttcaagaag atagagtgct tcgacagcgt ggagatcagc  1740
ggggtggagg acagattcaa tgcctctctc ggaacatacc acgacttgct taagatcatc  1800
aaggacaagg acttcctcga caacgaggaa aacgaggata ttctggagga tattgttctg  1860
actcttaccc tgttcgagga ccgggagatg atcgaggagc gtctcaagac ctacgcccac  1920
ctgttcgacg acaaagttat gaagcagctc aagcgtcgga gatataccgg atggggccgt  1980
ctgtctcgga agctcatcaa cgggatcagg gacaagcagt cagggaagac gatcttagac  2040
ttccttaagt ctgacggctt cgccaacagg aacttcatgc agttgatcca cgacgacagc  2100
cttaccttca aggaggacat ccagaaggcc caagtgagtg gccagggtga cagcctccac  2160
gagcatattg ctaatcttgc gggttcccca gcgattaaaa agggcatact tcaaaccgtt  2220
aaggtggtgg acgagcttgt caaggtgatg gggcgacaca agcccgagaa catcgtgatc  2280
gagatggcca gggagaacca gaccacccag aaggggcaga agaatagccg agaacgcatg  2340
aagcgcatcg aggaggggat taaggagcta gggagccaga tcctcaagga acatcccgtc  2400
gagaacaccc agctccagaa cgagaagcta tacctctact acttgcaaaa cgggagggat  2460
atgtacgtgg atcaggagtt ggacattaac cgcctaagcg actacgacgt agatcacatc  2520
gtgcctcagt cattcctcaa agacgacagc attgacaaca aagtcttgac ccgatccgac  2580
aagaaccgag gaaaatccga caatgtgccc tcagaggagg tcgtcaagaa aatgaagaac  2640
tattggaggc agctacttaa cgccaaactc ataacccagc ggaagttcga caacctgaca  2700
aaggctgagc ggggtgggct cagcgagctt gacaaggctg gcttcatcaa gcggcagttg  2760
gtggagacaa gacagataac gaagcacgtg gctcagatcc tggactctcg catgaacacg  2820
aagtacgacg agaacgacaa attgatccgc gaggtcaagg ttattacgct caagagcaaa  2880
cttgtcagcg atttccgcaa ggacttccag ttctacaagg tgagggagat taacaactac  2940
caccatgcac atgatgccta cttgaacgca gtggtgggga ccgcgcttat taaaaagtac  3000
cctaagttgg agtcagagtt cgtttatggg gactacaagg tgtacgacgt ccggaagatg  3060
attgcaaagt ctgaacagga aatcgggaag gccaccgcca aatatttctt ctacagtaac  3120
attatgaatt tttttaagac tgaaattact ctcgcaaacg gcgagatcag gaagcgtccc  3180
ctcatcgaga caaacgggga gaccggggag atagtctggg acaaggggcg ggacttcgct  3240
acggtgagga aggtgctctc gatgccacaa gtgaacatcg tcaaaaagac agaggtgcag  3300
accggtggct tctcaaagga gtcaatcctg ccaaaacgta acagcgacaa gctcatcgcc  3360
cgcaagaaag actgggaccc taagaagtat ggtgggttcg actcaccgac ggtcgcatac  3420
tccgttctgg tcgtggcaaa ggtggaaaag ggcaagtcca aaaaactgaa atccgtgaag  3480
gagttgcttg gcattaccat catggaacgc agcagcttcg agaagaaccc cattgacttc  3540
ctggaggcta aagggtacaa ggaggtcaag aaagatttaa ttattaagct acctaagtac  3600
agcttgttcg agctggagaa cggccgaaaa cgaatgctcg catccgccgg ggaacttcaa  3660
aagggcaacg agcttgcgct gccctccaag tacgtgaact tcctgtactt ggcatcccac  3720
tacgagaaac tcaagggtag cccagaggac aacgagcaga agcagctatt cgtggagcag  3780
cacaagcact acctcgacga gataatcgag cagatcagtg agttcagtaa gcgggtgata  3840
ctcgcggacg ccaacttgga caaggtgctt agtgcctaca acaagcaccg tgacaagccc  3900
atccgagaac aggctgagaa catcatccac cttttcactc tgacaaacct cggtgctccc  3960
gccgccttca aatacttcga cactaccatc gacaggaagc gctacacatc tacgaaggaa  4020
gttcttgacg ctacgcttat tcatcagtct atcacagggc tgtacgagac aaggatcgac  4080
cttagccaac tcggcgggga t                                            4101

SEQ ID NO: 69          moltype = DNA  length = 7052
FEATURE                Location/Qualifiers
source                 1..7052
                       mol_type = genomic DNA
                       organism = Glycine max
SEQUENCE: 69
attggataca agggtatcta attcgcacat gtcatcattc aaataaagac aaaaccccat  60
ctctcatcca ctccttaata ctactatata gtctcaacct caaccaggag gcatcaagag  120
tccccccaaa accaaccaac caaattaaag cctcactctc tttctcttca tttgtagatt  180
cctatactgt tgcaaggaaa ataaaacaaa gatagtatat acatggtggt gttcatggat  240
tatttggaat ggttgtttgc aattccaagt gtcccttctg cttcagcaat gttcaccctg  300
cttgctttaa ttggaggatt gttggtttat ctgtatgcac cctattgggg gttaaggaag  360
gttccagggc caccatctct gccccttgta ggacaccttc ccttgctggc aaagtatggt  420
cctgatgtgt tctcagtcct cgccaagcaa tatggtccta tttacaggtt agtatgctta  480
catgtatttg gtgcaacata tatagtcaat tgatgattaa tttgatagta tatatttatg  540
ctatttttct tccccggctt tcattggatt gataacagaa aagggtcgtt agtcttgatt  600
ggatatcgat cttgttgtat ttatgtccat tcaaatgcct caaactcctt ttggagaatg  660
atatgatctt aggcagaatc acgatggcag actaaggttg gttggttgag tcttgtgtgt  720
ggttttggta ttgccccgga ggaactagct acaaatatta aaaaagtgat tattatatga  780
tccaagtgtc ctacttgttc ttgtttactc agatgcttgc ttgcttccat acaataaact  840
gaaaaagggc ccagcgccag cgtcgtatgc tttgatgtct ttctcgaccc gggcaataaa  900
accgaatatg tttaagagaa aatattttat gttgtaaaac tattttattt catcatctaa  960
ctataaattg ttatatcatc taatcacaaa taatatagac ttataatata taatactttc  1020
ctattcaatg aaaatctaaa actgttatgc acattttgag tatataattt attttctatt  1080
ttctaatatt tttttgttat taagcgattt ttatatgaag ccgccaaata aacagtgctg  1140
gattgggaat aagatctcta taacttaaga gtgtcgataa atgcctactt tggagagaaa  1200
ttatcatatg taatagtgta atacgattct caacaatttt tacatgatgt ataattgatt  1260
atttattaaa tttttaaatt aaaaacttaa ttaaatgtta catagaaatt aattgaaact  1320
attatgatca tagacaatct ctatatgagt aactcaatta tgtatcatgt atagattaac  1380
tgaaactata aaaatataag gtggtagccc tagaagacct aaatcatata ataatttatc  1440
cattgttaag ggtgggaaga tgacagtaaa aaaaaaaaag tggcaagatg catgggagat  1500
atgaagaaaa aatgtagaaa gaaagtgata aatgttaaaa gtaattcaat agaaaaagaa  1560
atgaaaagat ataaagaaaa tggagtaaaa ttgatatgga tcggaaaaga aaatgtctat  1620
tttgtaagag ttttagatat agtaggtgaa aaaagagtac aaaaacttat taaatacacg  1680
tggatgtgtt atattggtta tttgaaaagt tatataattt gtggaaataa agaaaagagt  1740
```

-continued

```
tttggatggg cgttcgtgca atctgttttc gtaacaaaca ggatttccaa atttataatt  1800
tttcatcatt taataggtcc taccacgatt gataaataac tactcctcct aaaacaggag  1860
tattatgtat tctattgcat cctgcaagga tattattggt ccttggtgct cataaattgt  1920
aggttccctt tatgtgaaaa tttcttggag tgactaccgt taagcaaatc atttcggaat  1980
ccgagctagt tattaatgtc ccacgataaa caaaaattac tatttaggca atctatctat  2040
cagcctctcc taaaataatt ccttttgttc ataaaattta gatttggtgt attgttaata  2100
taaaaattat atagacattt aagagaatat atcataatgt taattaatta taattagtat  2160
aaaaccttct tacatattgt accaaaacaa caacttttaa tattattgac attacattaa  2220
aataaattat catagttaag gtcttaagct ttgcttatat tgtgtctttt taaggcttta  2280
agcacaaaaa gtatgtttat tccacatttc aagtttataa aattaagctt tatatatata  2340
tttgttaaaa gtatttagtt attctagcaa gacattataa tttaatatat tgtatatggc  2400
atgtattgta accataattc caacagctaa ttatttacac aataacattt atcatctaac  2460
aaaatattaa taaactaata attaatattt attgataaaa agacacactc aacaaatagt  2520
gccagcagtg catgctagat gatagaagtg aaaagtggaa aaaatgaaga ataatcagca  2580
ctgattatca gtcattttta acaactcttt ttttcttttt ttattcttat taagcagcac  2640
gtgctaagtt tcataaaacc ttttggggtt ggcgcttcac acatatatac tagctagtag  2700
ttaacagtag ctgtttttttc ttagttgagc tgattcttta ttccatgatt ttcctggtta  2760
tggttgtaaa tgatgttctt attatttatt ggtgcagatt ccatatggga agacagccac  2820
taataattat agcagatgca gagctttgta aggaggctgg aataaaaaaa ttcaaagaca  2880
tttcaaacag aagtattccc tcaccaattt ctgcttcccc tcttcaccaa aagggcctct  2940
tcttcagccg gtatgcaaat tatgacccaa cagctttcaa taatagtaat gttatttcta  3000
caatttggta gtgtttgcca agtaatttca gcagttataa acaactttaa ctaacttata  3060
agttaatttg actaaaatta tattttctta aataatcact tacttttcat atattgtaga  3120
atgagaattt aagttataca atttcatttt attttccttt tatagcaaaa aaatattttc  3180
tctctttttt atcatcccca ataattattg atgtttttga aatgattttt ctaatcaaaa  3240
tttttaatct tcacatgtca agcccattgg gggaaagaag tataaaccaa acaggaaaat  3300
taacacgggt gctggtgctt tttttcccc cttcaaaact aagataatta gcaatgatta  3360
ttttcctcca aatatgagag gcatgaagtg acatcaagtt atacagtata ctagtaatat  3420
ttctctgtta ataatgccat aacatgaaaa aagtggtagc acgttgtgtt ggagttacat  3480
caaacaatta tgccaaatgc tattatatgc atacagcatg gtattgaaga tgaaaagaat  3540
gaatgagaat gagattaaaa aatataataa ttatataaca tttttttatt atatttctta  3600
tttgtcttat atttttcttt cctttcaatt ttatcttttt acatgttcta tttaatctgt  3660
cttgtaacta tagaaaaggg tcataaaaat ataatatatc aaacaaaaga ataactttaa  3720
ttaaatccga tatatcccca attaatgatg attcaatata ttataaatat atgagtaatt  3780
tatatctgta gtcaatttat catgcataaa tacatgacat tttactggtt cagcacagaa  3840
gttattatgc aattatttgt agacttcttg ccaaaagaag ttgtaatttt aagctggatc  3900
aattttagac ttttaatttg tgaattagac aaaataaatc agaatttgag ccttaaaaaa  3960
tgtgagtatg tagataggaa attaatgcat caccagtttt ttaagaactg cagaaaatct  4020
tagctaggta taattttata actttgagcc aagcaataat tggactttga accctgtata  4080
agatgttttg aaacagcaga tgatcgtaat gcaaatgtaa aacgttgcct gtttagcaaa  4140
taaatacaat agtacgttaa acaatccttt caataattaa aaatgaaggt acaaaagact  4200
accacatgca ttaacaacgg ctgataagag gttttacgaa attcttacaa agagaaatta  4260
ttaatttcaa gaatcaaatg taaatgttac tggcaaagtg ctacaacggc tgataagagg  4320
ttttacaaaa ttattactaa gagaaattat caattgcaag aatcaaatgt aaatgttact  4380
agcaaagtgc tagaattttt tgttgaaaat aaataattag tctatgtaat gttactcgtt  4440
ttaccgcttt attttatata tatatatatg gattttaagt tttatcttta tacctcagtc  4500
aaaaaaaact tttatctttg taattcttaa taaatgttga tctttgtttt ccatgaagaa  4560
cttatttatt tctaatagtg tttaattgac aaatcatcat tgcttaaggg aaaaaggtta  4620
atacaggtaa aagcatagga gtcaacatgc caataactaa aagaaagggg gtggggaata  4680
aagtaaaact acatgagtta actattaatt ttaaccacaa tctgttttgg taatgtcacc  4740
accgagtaaa aattgtatga tgcacacaag tgaatcacat gaaattttaa cggatctgcc  4800
tttaagttgt acaaaagcta ttctttagat actggtttct actttctagt ggtccactaa  4860
gttgaatatc attttctttt ccttttgtga tcattagtcg tgaaatccat acgtcagagc  4920
ccatgtgccc tgcatgttaa tgcttctcca aaaactatta tagtgctatg ctaatcctct  4980
ataatagtca aattcaaatt cacccaactt catttcaaat caaatattca aacagtttct  5040
tgcaaattga tggtgcaggg attcacaatg gtctaccatg cgaaacacta tattatcaat  5100
gtaccagcca tcatacttgt ccagattagt gccaacaatg cagtccttca tagaatctgc  5160
gactcaaaac cttgactctc aaaaagaaga cataattttc tccaacctgt ccctaagact  5220
agcaactgat gtgattggac atgcagcatt tggtgtcaac tttggccttt ctaggccaca  5280
ttcagtttgt gattccatca agagtgttaa tgttaacaat aacaataaca atgcaagtgc  5340
tagtagtagt agtaatgata atgaagtatc agatttcatc gaccaacaca tatactccac  5400
aacacagcta aagatggact tgtctggttc cttgtccatt atcttgggtc tgcttttgcc  5460
aatacttcag gagccattta ggcagattct gaagagaatt cctggcacca tggactggaa  5520
gattgagcgt accaaccaga aactaagtgg ccgtcttgat gagattgtgg agaagagaat  5580
gaaagacaag gcacgaagtt cgaaggattt cttgtcactc atacttaatg ccagagaaac  5640
aaaagctgtt tcagagaatg tgttcacacc tgactacata agtgctgtta cttacgagca  5700
cctacttgct ggctccgcaa ccacttcctt taccttgtct tctgttgtct atttggttgc  5760
tggacaccct gaagttgaga aaaagttgct tcatgagatt gatgggtttg gtccagtgga  5820
tcagataccc acttctcaag atcttcataa caagtttcct tatcttgatc aggtttgtta  5880
aaatgaatac caaaatctca agacaagttt gatgttccaa cttgcaaggg caaagtatgt  5940
agattcattg ttatactttt gtatgctcta actctattta attaatgcag gtgatcaaag  6000
aggccatgag gttttacact gtctctccct tagttgcaag agaaacatca aatgaagtag  6060
agattggagg ctatctcctt ccaaaggtaa tacaaaatac aaaatactag tactacacag  6120
ttacttataa aaaaagaaaa taaatccaat taaggaggta aaattaataa ataaaatctc  6180
ataattaagt taaataaacg tatggtgtgt ttggataaaa agatttcatg acttaaaatc  6240
aacttatata tttcaacttt cataaaaact ctatctttaa ctacttcaaa aacttttgtt  6300
taacttatcc acatgtcaag gtgctaattg ttaaaaaaat tatccaaaca gaccatccag  6360
gactgtcttt tttggtatac atactcttca caaatcacaa ccaaattaac gagagttttt  6420
acttgtgctg acactatata tggttttgtg tatgcagggg acttgggtct ggttagcgct  6480
```

```
tggagttcca gcaaaagacc ccaaaaactt tccagagcca gaaaagttca aaccagatag  6540
gtttgacccc aactgtgaag aaatgaaacg aaggcatcct tatgctttta taccatttgg  6600
aattggtcct cgggcttgca ttggtaaaca attttcccta caagagatca agatttctct  6660
gattcattta tatcgaaaat acttgtttcg gcattctccc aatatggaaa acccccttaga  6720
actccagtat gggatagtcc tcaacttcaa gcatggggtc aagctcagag tcataaaaag  6780
aacagagact tgctaagtaa acggttcaga catggcttat actagtacag agttcagaag  6840
atgaattata agatggagtg tgctaaaatc caataatgaa aaattgtaat gttacgcaga  6900
atcagccaat aagtgtttaa aataataagg tcaaagagtg tgtttgcatt tcccaaatat  6960
agaattgtaa gtttataaga gtaagagaca ctcttcctac aagattatga atgacattat  7020
catttgtggt aaaaaaaaac actcaaaagc at                                7052

SEQ ID NO: 70           moltype = DNA  length = 1584
FEATURE                 Location/Qualifiers
source                  1..1584
                        mol_type = other DNA
                        organism = Glycine max
SEQUENCE: 70
atggtggtgt tcatggatta tttggaatgg ttgtttgcaa ttccaagtgt cccttctgct  60
tcagcaatgt tcaccctgct tgctttaatt ggaggattgt tggtttatct gtatgcaccc  120
tattgggggt taaggaaggt tccagggcca ccatctctgc cccttgtagg acaccttccc  180
ttgctggcaa agtatggtcc tgatgtgttc tcagtcctcg ccaagcaata tggtcctatt  240
tacagattcc atatgggaag acagccacta ataattatag cagatgcaga gctttgtaag  300
gaggctggaa taaaaaaatt caaagacatt tcaaacagaa gtattccctc accaatttct  360
gcttcccctc ttcaccaaaa gggcctcttc ttcagccggg attcacaatg gtctaccatg  420
cgaaacacta tattatcaat gtaccagcca tcatacttgt ccagattagt gccaacaatg  480
cagtccttca tagaatctgc gactcaaaac cttgactctc aaaaagaaga cataattttc  540
tccaacctgt ccctaagact agcaactgat gtgattggac atgcagcatt tggtgtcaac  600
tttggccttt ctaggccaca ttcagtttgt gattccatca agatatcaga tttcatcgac  660
caacacatat actccacaac acagctaaag atggacttgt ctggttcctt gtccattatc  720
ttgggtctgc ttttgccaat acttcaggag ccatttaggc agattctgaa gagaattcct  780
ggcaccatgg actggaagat tgagcgtacc aaccagaaac taagtggccg tcttgatgag  840
attgtggaga agagaatgaa agacaaggca cgaagttcga aggatttctt gtcactcata  900
cttaatgcca gagaaacaaa agctgtttca gagaatgtgt tcacacctga ctacataagt  960
gctgttactt acgagcacct acttgctggc tccgcaacca cttcctttac cttgtcttct  1020
gttgtctatt tggttgctgg acaccctgaa gttgagaaaa agttgcttca tgagattgat  1080
gggtttggtc cagtggatca gatacccact tctcaagatc ttcataacaa gtttccttat  1140
cttgatcagg tgatcaaaga ggccatgagg ttttacactg tctctccctt agttgcaaga  1200
gaaacatcaa atgaagtaga gattggaggc tatctccttc caaaggggac ttgggtctgg  1260
ttagcgcttg gagttccagc aaaagacccc aaaaactttc cagagccaga aaagttcaaa  1320
ccagataggt ttgaccccaa ctgtgaagaa atgaaacgaa ggcatcctta tgcttttata  1380
ccatttggaa ttggtcctcg ggcttgcatt ggtaaacaat ttccctaca agagatcaag  1440
atttctctga ttcatttata tcgaaaatac ttgtttcggc attctcccaa tatggaaaac  1500
cccttagaac tccagtatgg gatagtcctc aacttcaagc atggggtcaa gctcagagtc  1560
ataaaaagaa cagagacttg ctaa                                        1584

SEQ ID NO: 71           moltype = AA  length = 527
FEATURE                 Location/Qualifiers
source                  1..527
                        mol_type = protein
                        organism = Glycine max
SEQUENCE: 71
MVVFMDYLEW LFAIPSVPSA SAMFTLLALI GGLLVYLYAP YWGLRKVPGP PSLPLVGHLP  60
LLAKYGPDVF SVLAKQYGPI YRFHMGRQPL IIIADAELCK EAGIKKFKDI SNRSIPSPIS  120
ASPLHQKGLF FSRDSQWSTM RNTILSMYQP SYLSRLVPTM QSFIESATQN LDSQKEDIIF  180
SNLSLRLATD VIGHAAFGVN FGLSRPHSVC DSIKISDFID QHIYSTTQLK MDLSGSLSII  240
LGLLLPILQE PFRQILKRIP GTMDWKIERT NQKLSGRLDE IVEKRMKDKA RSSKDFLSLI  300
LNARETKAVS ENVFTPDYIS AVTYEHLLAG SATTSFTLSS VVYLVAGHPE VEKKLLHEID  360
GFGPVDQIPT SQDLHNKFPY LDQVIKEAMR FYTVSPLVAR ETSNEVEIGG YLLPKGTWVW  420
LALGVPAKDP KNFPEPEKFK PDRFDPNCEE MKRRHPYAFI PFGIGPRACI GKQFSLQEIK  480
ISLIHLYRKY LFRHSPNMEN PLELQYGIVL NFKHGVKLRV IKRTETC                527

SEQ ID NO: 72           moltype = DNA  length = 349
FEATURE                 Location/Qualifiers
source                  1..349
                        mol_type = other DNA
                        organism = Glycine max
SEQUENCE: 72
agattcctat actgttgcaa ggaaaataaa acaaagatag tatatacatg gtggtgttca  60
tggattattt ggaatggttg tttgcaattc caagtgtccc ttctgcttca gcaatgttca  120
ccctgcttgc tttaattgga ggattgttgg tttatctgta tgcaccctat tgggggttaa  180
ggaaggttcc agggccacca tctctgcccc ttgtaggaca ccttcccttg ctggcaaagt  240
atggtcctga tgtgttctca gtcctcgcca agcaatatgg tcctatttac aggttagtat  300
gcttacatgt atttggtgca acatatatag tcaattgatg attaatttg              349

SEQ ID NO: 73           moltype = DNA  length = 269
FEATURE                 Location/Qualifiers
source                  1..269
                        mol_type = other DNA
                        organism = Glycine max
```

```
SEQUENCE: 73
tatatacatg gtggtgttca tggattattt ggaatggttg tttgcaattc caagtgtccc  60
ttctgcttca gcaatgttca ccctgcttgc tttaattgga ggattgttgg tttatctgta  120
tgcaccctat tgggggttaa ggaaggttcc agggccacca tctctgcccc ttgtaggaca  180
ccttcccttg ctggcaaagt atggtcctga tgtgttctca gtcctcgcca agcaatatgg  240
tcctatttac aggttagtat gcttacatg                                   269

SEQ ID NO: 74           moltype = DNA  length = 229
FEATURE                 Location/Qualifiers
source                  1..229
                        mol_type = other DNA
                        organism = Glycine max
SEQUENCE: 74
tggattattt ggaatggttg tttgcaattc caagtgtccc ttctgcttca gcaatgttca  60
ccctgcttgc tttaattgga ggattgttgg tttatctgta tgcaccctat tgggggttaa  120
ggaaggttcc agggccacca tctctgcccc ttgtaggaca ccttcccttg ctggcaaagt  180
atggtcctga tgtgttctca gtcctcgcca agcaatatgg tcctattta             229

SEQ ID NO: 75           moltype = DNA  length = 189
FEATURE                 Location/Qualifiers
source                  1..189
                        mol_type = other DNA
                        organism = Glycine max
SEQUENCE: 75
tttgcaattc caagtgtccc ttctgcttca gcaatgttca ccctgcttgc tttaattgga  60
ggattgttgg tttatctgta tgcaccctat tgggggttaa ggaaggttcc agggccacca  120
tctctgcccc ttgtaggaca ccttcccttg ctggcaaagt atggtcctga tgtgttctca  180
gtcctcgcc                                                         189

SEQ ID NO: 76           moltype = DNA  length = 223
FEATURE                 Location/Qualifiers
source                  1..223
                        mol_type = other DNA
                        organism = Glycine max
SEQUENCE: 76
agattcctat actgttgcaa ggaaaataaa acaaagatag tatatacatg gtggtgttca  60
tggattattt ggaatggttg tttgcaattc caagtgtccc ttctgcttca gcaatgttca  120
ccctgcttgc tttaattgga ggattgttgg tttatctgta tgcaccctat tgggggttaa  180
ggaaggttcc agggccacca tctctgcccc ttgtaggaca cct                   223

SEQ ID NO: 77           moltype = DNA  length = 143
FEATURE                 Location/Qualifiers
source                  1..143
                        mol_type = other DNA
                        organism = Glycine max
SEQUENCE: 77
tatatacatg gtggtgttca tggattattt ggaatggttg tttgcaattc caagtgtccc  60
ttctgcttca gcaatgttca ccctgcttgc tttaattgga ggattgttgg tttatctgta  120
tgcaccctat tgggggttaa gga                                         143

SEQ ID NO: 78           moltype = DNA  length = 103
FEATURE                 Location/Qualifiers
source                  1..103
                        mol_type = other DNA
                        organism = Glycine max
SEQUENCE: 78
tggattattt ggaatggttg tttgcaattc caagtgtccc ttctgcttca gcaatgttca  60
ccctgcttgc tttaattgga ggattgttgg tttatctgta tgc                   103

SEQ ID NO: 79           moltype = DNA  length = 63
FEATURE                 Location/Qualifiers
source                  1..63
                        mol_type = other DNA
                        organism = Glycine max
SEQUENCE: 79
tttgcaattc caagtgtccc ttctgcttca gcaatgttca ccctgcttgc tttaattgga  60
gga                                                               63

SEQ ID NO: 80           moltype = DNA  length = 223
FEATURE                 Location/Qualifiers
source                  1..223
                        mol_type = other DNA
                        organism = Glycine max
SEQUENCE: 80
ttgctttaat tggaggattg ttggtttatc tgtatgcacc ctattggggg ttaaggaagg  60
ttccagggcc accatctctg ccccttgtag gacaccttcc cttgctggca aagtatggtc  120
ctgatgtgtt ctcagtcctc gccaagcaat atggtcctat ttacaggtta gtatgcttac  180
atgtatttgg tgcaacatat atagtcaatt gatgattaat ttg                   223
```

```
SEQ ID NO: 81          moltype = DNA  length = 143
FEATURE                Location/Qualifiers
source                 1..143
                       mol_type = other DNA
                       organism = Glycine max
SEQUENCE: 81
ctattggggg ttaaggaagg ttccagggcc accatctctg ccccttgtag gacaccttcc  60
cttgctggca aagtatggtc ctgatgtgtt ctcagtcctc gccaagcaat atggtcctat  120
ttacaggtta gtatgcttac atg                                          143

SEQ ID NO: 82          moltype = DNA  length = 103
FEATURE                Location/Qualifiers
source                 1..103
                       mol_type = other DNA
                       organism = Glycine max
SEQUENCE: 82
ttccagggcc accatctctg ccccttgtag gacaccttcc cttgctggca aagtatggtc  60
ctgatgtgtt ctcagtcctc gccaagcaat atggtcctat tta                    103

SEQ ID NO: 83          moltype = DNA  length = 63
FEATURE                Location/Qualifiers
source                 1..63
                       mol_type = other DNA
                       organism = Glycine max
SEQUENCE: 83
ccccttgtag gacaccttcc cttgctggca aagtatggtc ctgatgtgtt ctcagtcctc  60
gcc                                                                63

SEQ ID NO: 84          moltype = DNA  length = 302
FEATURE                Location/Qualifiers
source                 1..302
                       mol_type = other DNA
                       organism = Glycine max
SEQUENCE: 84
atggtggtgt tcatggatta tttggaatgg ttgtttgcaa ttccaagtgt cccttctgct  60
tcagcaatgt tcaccctgct tgctttaatt ggaggattgt tggtttatct gtatgcaccc  120
tattgggggt taaggaaggt tccagggcca ccatctctgc cccttgtagg acaccttccc  180
ttgctggcaa agtatggtcc tgatgtgttc tcagtcctcg ccaagcaata tggtcctatt  240
tacagattcc atatgggaag acagccacta ataattatag cagatgcaga gctttgtaag  300
ga                                                                 302

SEQ ID NO: 85          moltype = DNA  length = 229
FEATURE                Location/Qualifiers
source                 1..229
                       mol_type = other DNA
                       organism = Glycine max
SEQUENCE: 85
tggattattt ggaatggttg tttgcaattc caagtgtccc ttctgcttca gcaatgttca  60
ccctgcttgc tttaattgga ggattgttgg tttatctgta tgcaccctat tgggggttaa  120
ggaaggttcc agggccacca tctctgcccc ttgtaggaca ccttcccttg ctggcaaagt  180
atggtcctga tgtgttctca gtcctcgcca agcaatatgg tcctattta              229

SEQ ID NO: 86          moltype = DNA  length = 189
FEATURE                Location/Qualifiers
source                 1..189
                       mol_type = other DNA
                       organism = Glycine max
SEQUENCE: 86
tttgcaattc caagtgtccc ttctgcttca gcaatgttca ccctgcttgc tttaattgga  60
ggattgttgg tttatctgta tgcaccctat tgggggttaa ggaaggttcc agggccacca  120
tctctgcccc ttgtaggaca ccttcccttg ctggcaaagt atggtcctga tgtgttctca  180
gtcctcgcc                                                          189

SEQ ID NO: 87          moltype = DNA  length = 176
FEATURE                Location/Qualifiers
source                 1..176
                       mol_type = other DNA
                       organism = Glycine max
SEQUENCE: 87
atggtggtgt tcatggatta tttggaatgg ttgtttgcaa ttccaagtgt cccttctgct  60
tcagcaatgt tcaccctgct tgctttaatt ggaggattgt tggtttatct gtatgcaccc  120
tattgggggt taaggaaggt tccagggcca ccatctctgc cccttgtagg acacct      176

SEQ ID NO: 88          moltype = DNA  length = 136
FEATURE                Location/Qualifiers
source                 1..136
                       mol_type = other DNA
                       organism = Glycine max
SEQUENCE: 88
```

```
atggtggtgt tcatggatta tttggaatgg ttgtttgcaa ttccaagtgt cccttctgct  60
tcagcaatgt tcaccctgct tgctttaatt ggaggattgt tggtttatct gtatgcaccc  120
tattgggggt taagga                                                   136

SEQ ID NO: 89          moltype = DNA  length = 223
FEATURE                Location/Qualifiers
source                 1..223
                       mol_type = other DNA
                       organism = Glycine max
SEQUENCE: 89
ttgctttaat tggaggattg ttggtttatc tgtatgcacc ctattggggg ttaaggaagg  60
ttccagggcc accatctctg ccccttgtag gacaccttcc cttgctggca aagtatggtc  120
ctgatgtgtt ctcagtcctc gccaagcaat atggtcctat ttacagattc catatgggaa  180
gacagccact aataattata gcagatgcag agctttgtaa gga                    223

SEQ ID NO: 90          moltype = DNA  length = 147
FEATURE                Location/Qualifiers
source                 1..147
                       mol_type = other DNA
                       organism = Glycine max
SEQUENCE: 90
caccctattg gggggttaagg aaggttccag ggccaccatc tctgcccctt gtaggacacc  60
ttcccttgct ggcaaagtat ggtcctgatg tgttctcagt cctcgccaag caatatggtc  120
ctatttacag attccatatg ggaagac                                       147

SEQ ID NO: 91          moltype = DNA  length = 107
FEATURE                Location/Qualifiers
source                 1..107
                       mol_type = other DNA
                       organism = Glycine max
SEQUENCE: 91
aaggttccag ggccaccatc tctgcccctt gtaggacacc ttcccttgct ggcaaagtat  60
ggtcctgatg tgttctcagt cctcgccaag caatatggtc ctattta                 107

SEQ ID NO: 92          moltype = AA  length = 100
FEATURE                Location/Qualifiers
source                 1..100
                       mol_type = protein
                       organism = Glycine max
SEQUENCE: 92
MVVFMDYLEW LFAIPSVPSA SAMFTLLALI GGLLVYLYAP YWGLRKVPGP PSLPLVGHLP  60
LLAKYGPDVF SVLAKQYGPI YRFHMGRQPL IIIADAELCK                        100

SEQ ID NO: 93          moltype = DNA  length = 10873
FEATURE                Location/Qualifiers
source                 1..10873
                       mol_type = genomic DNA
                       organism = Glycine max
SEQUENCE: 93
cccccccccc caaattaata aagccgctct ctttctcttc atttgtagat tcctatactg  60
ttgcaaggaa aataaaacaa acaaacacac atggtattca tggattattt ggaatggttg  120
cttccaattc caagtgtccc ttctgcttca gcaatgttca ccctgcttgc tttaatagga  180
ggattgttgg tttatctgta tgcaccctat tggggtgtaa ggaaggttcc aggcccacca  240
tctctgcccc ttgtgggaca ccttcctttg ttggctaagt atggtcctga tgtgttctca  300
gtccttgcca aacaatatgg tccgatttac aggttagttt acttacatat atattaatcg  360
tcaattgatg atgatgatca atttgttagt atatatttat gccatttttc ttccccttca  420
ctggattgat aaggaaaaag gttgttagtc ttgattggat atcgatcttt ttgtttttat  480
gtcctctcaa atgcctcaaa ctcctcttga agaatgatat gatcttaggc agaatcacga  540
tggcagataa attttgactt gagaaggttg gttagttgtg tcttgtgtgt ggttttggta  600
ttggtattgg tcgctgtctc tatgtctatg ccccgaaaga agtagataca aatattaaaa  660
aagtgattat tctatgatcc aagtgtcgta ctcgttcttt gattactcag atgcttgctt  720
gcctccatac attaaactga aaaagggccc agcaagcgtc ttatatgctt tggtgtcttt  780
ctcgactcag gcaataaacc aaatattttt atgataaaat attttatgtt gcgacttgga  840
agaatataaa actgttttttc atactcatct gattataaat tatcatatat ataataaatt  900
tattaatatt tataataaat attttaaaat ttttaatttt aatttattaa cagtgtaaat  960
tttattacat cgacaacata tgattacttt aaactttatt ttttaataag tttaataatt  1020
atatattaat aatataaagt aattttacat tgtggattaa ctacaaaata aggttgatga  1080
ttttgtaagt agtcatttta tgtaaaagtt aatatataat atataataat ctgtggtgga  1140
atgaaaacat aaaaatattt taaagagtaa atgtataatc tatatttttt tctttttta  1200
atattattct gtttctaatt ctgttattta gcgattttta tatgaagccg tcaaataaac  1260
agtgccggat tgggaataat atatctataa tttaagagtg accataaatg cctactttag  1320
agagaaattg tcatgtctaa tatgattcta aatttctttt acatgatgca taattgattc  1380
ttccttttgc tattatatga ctcaagttta aaataatttg ttttttttata atatttaact  1440
tataatattt cttttattaa ttatttttat attaaaatat tctttattaa aaaaagttaa  1500
tatattgaca aactagaaga gaaaaaaata ttaatgacaa aagtaatttt aaaaatatta  1560
taaatttaag ataaatttat tattatcaac taaataaatc actttcctta atcttaataa  1620
aataaataat tgagttttat gtaataacga agggagtatt tattaacttt ttaattaaaa  1680
cttaattaaa ttttatatag aaattaattg aaactattac tatcttaaac aacttctaca  1740
tgaataactc aattatgtat catggattaa ctgaaactat aaaaaaatat gcagtagtcc  1800
```

-continued

```
taaatcacat gataatttat ccatttttag atggattggg gtgggaagat gacaataaaa  1860
aaaaaaagtg ggaatatgcg cgactgcatg agagatgtga agaaaaaaaa agtagagata  1920
tgaagaaaaa aaagagtaga aagaaagtga tgaatataac aagtaatgca atggaaaaga  1980
aaagaaaaaa atggagtaaa attgagatgg aaaagaaaat gatttttttcg aaacagtttt  2040
aaatagtacg tgaacagaca gacagtacaa aaacttatta aatacacgtg ggtggttatt  2100
tgaaaagtta tatatttaat ggaaacaaag aaaagagttt tggatgcgcg ttggtgcaat  2160
ctattttcgt gacaaacagg atttccaaat ttatattttt tcatcattta ataggtccta  2220
ccactagtca tgtcaatgga ccgggctgcg gcgccaacta ctgtcccccct tcgcgttccc  2280
gcccttcaac taaccccgtc cttgtctctc atttttgttc taggattttt ttttctgttc  2340
ccattcctgc gggtttcttt agtcttctct tcgtggggcc tcaatttttt taaaaatatt  2400
aattttaaat ttcaatacaa atcaatttta agaagactta aaaaatccaa atactattaa  2460
acttaaataa ataaatatgg acaacaagtt taatttaaaa taatacaaac ataatattca  2520
ataataatat aaatagtttt aactacaaat attttcttat aatatcttaa acaaccagta  2580
aattgaagtc ctctaatttt gaaaccaaca agtcaataac tctctaatat tgtaagtcag  2640
taaattaata atatattagt atatcatcat tcatgttctc aacaatagat tcaaataaat  2700
gtgttatgtt tgaacaacct aacaaataaa aaatcaaata aactttcaag tcatttaaga  2760
aaattaagtg aattatatat atatatatat attaccttgc atttctttac gtaattaatt  2820
ttgggtacac attaaagctt ctaaatgatc tttgaaagaa ataaaaaaaa gcctaagtaa  2880
tcaaaacatg aaaacaaact tgaatttaaa ctaaaaactt gaatctgagc aaccaactaa  2940
ccaaagaaaa tataaaatta aaactttcaa atgtaaaaca taattttgaa atgatcaagc  3000
aaaatcatga gaaaaacaat aaagacgata tatagtaaac aaatctattg gtaagaagag  3060
agtaactagt acttacactt caaggtgact gtgggatttg ggaagaaata aacgacatgg  3120
caaggtttag gataaaaagt aaagtgaata agttatttga gagtttgagt tttaagagta  3180
attgagttgt taggattttt taaaatataa ggataatttt ataattttt caaatcaagt  3240
atacacggtg gtagggggtg atccttgtcc ctgccgtagc cgctcgaaaa tatttattcc  3300
tgtttccatt ctcgttgggg aaaaatccca atctattggg cccaaaacaa gacagaaatt  3360
tccgtttata atacaaattg acatccctac cattgataaa taactacatt attatatatt  3420
ctattacatc tttggaggat attattggtc cttggggcta ttaaattata ggttcccttt  3480
atatgaaaat ttattggagt gactatcgtt aagcaaatca tttcggaatc caagctaatt  3540
attaatgtgc cacgataaaa aaatcattta ttaaggcaat caatctatca tcctctccaa  3600
aaataatccc tttttcatca tagaatttag aattggtgta ttgttaatat aaaaattact  3660
atataaatat ttaagaggat atatcataat gttaaatagt ataaaacctt cttatatatt  3720
gtacaaaaat aataactttt aatattgaca ttacattaaa ataaattatt atatttaagg  3780
tattaagctt tgcttatatt gtctttttaa ggcttcaagc acaaaaagta tatgtttatt  3840
ctacacttaa gtttataaaa ataagctttt aaattatata tataatatac tttttgttaa  3900
aagtatttag ttattctaac aggacattat agtttaatat ataaagtatt ttatatagcg  3960
tgtactgtaa cgatacttta acacctaaat atatgcatga tagtattcac catttaacac  4020
aacaaataat tgatataaga ttaatttgat gaaaaaaaaa agaaaaagag attatacatt  4080
cacatttttg tgctaacaaa aagaagctaa caaagacaat aaattaataa ctgatatttt  4140
ttaattaaaa aaacactcaa caaacaaatt aatagctaat atttttaatt aaaaaaacac  4200
tcaacaaata gtaactgata tttttcaatt aaaaaaacac tcaacaaata gtaactgata  4260
tttttcaatt aaaaaaacac tcaacaaata gtgctagtag tgcatgctag atgatagaag  4320
gaaaaagtgg aaaaaatgaa aaataattag cacagtgtga tatcatatca atgtaccaaa  4380
aaatattatt atcagtaatt tttaagcagc acgtgttaag tttcacaaaa cttgttgggg  4440
ttggcgcttc atatatatat atataggtca ttgctccagt agaccatttt gatatatggt  4500
ctattttgga caagaattgt tagccgttag attaaatggt tattataggc tagcacaccg  4560
gattctgcaa ccctctccca ccaattttgt tgaggtccat ggccatgtgg taaaagatgt  4620
aggagaggca ttcaggttgt ggaggacgat ggtgtctggg ggatggagga ggaggtgctc  4680
gcgctagtta cagacgttgt cgatttggaa cccgaagaag agggccaacc agtccagaag  4740
gtggtcagag atggaggtgg tcgaatgggt gggggtaatc gaacgctgcc gccggaggga  4800
ggtgggggaa aaggcagaga aaggtaagct gccggagaaa tgagtgagag aggcttgcgg  4860
gattgagtat gctgatctat aataatcatt taatccaacg gctgaaaatt attatccata  4920
gtggacgatc tttcaagtgg tccacgctag ccttgatcat atatatatat atatgggagg  4980
gagtttactt gttctaaaga tattttttat ttttatcatt ttttttagat gatcttaaga  5040
aaataaataa taaaaataaa aaaattattt tttagagtaa atggatctct atatatatat  5100
atatttaaat gtaactgttt tttcttaaaa cgtggaagaa tttattttga attttttgac  5160
attttttag gtcacatgtt aaaatataag atataagaat ttttttatat ttttattcta  5220
gttataaaat cctatttaag ttcttgaatt ttactttcag acaaaaaataa taactctttt  5280
ttttttcaaa tgaaattaaa aaacaatatt ttttgacaaa agtgaaattt ttggattttt  5340
tttcttctaa aatccaacct caaactgatg ctcttaaaca ataatactaa taaatcataa  5400
gaagaagagt tcttcagctc aaaaaaccta acttaaaaat tcctattaac aatgttatta  5460
cttgcattgt ttctttatcc catgatttcc ctagttatgg tcgtaaatgc tgttcttatt  5520
atttattggt gcagattcca tatgggaaga cagccactaa taattatagc agatgcagag  5580
ctttgtaagg aggctggaat aaaaaaattc aaagacattt caaacagaag tattccctcc  5640
ccaatttctg cttctcctct tcaccaaaaa ggcctcttct tcagccggta cgcaaattac  5700
gactcaacag tgttcaataa tatagtaatg ttatttctac aactagtgta gtgtttgata  5760
agtaatttca gtactttata agttgttttg actagtttat aagttaattg aactaaaatt  5820
atactttctt aatttaatca cttccttttc atatatattg tagaatgaga tttaaaatta  5880
tactatttta ttttattttt ccttttaatg taaataaatt acagattttt ctctctctct  5940
ctctctctct tttatcataa aaaaccccat aactattgat tttttttaga tgcctttttt  6000
gaagaagttt agaaattttc aagcttttta atcttcacat gtcacgcctt attgggggaa  6060
aaaagtataa actaaacagg aaaacacggg tgctagtgct tgttttcctc ttcaaaaaaa  6120
taattattat agcaattggt tattttcctc caaatatgag aggaatatga agtgacataa  6180
acttatacag tataccagta agagttatat ttttcatact tcaattttta ggaactggat  6240
cctctccagc cctctccagc aaaagcatat gagccactgg attaattcaa tgattccaat  6300
tttaaaagaa aaacatgaca aacaaggatg catactcacg tttcttttgc cattcaaatc  6360
ttatcaatat taatacaaag aataagctat cgcagagcaa aactctaaac tccataataa  6420
aatattaaaa ttatatttca ccatcagtca tcgataatag taaacaaaaa ataattacaa  6480
aattatgtaa attagaaaat attaatgagt taaaaaatta agaacaaaaa tgaaaattga  6540
```

```
tctttttta cattatattc caatttaaat tatttatcat gaatataaaa tactactata  6600
ctctatatgg ttaaatatat tatttattat taatttaatt atatacaaat atttataatg  6660
tccgattgta atataaaatt tatattttaa ttaagaaggt ttcattctct aaattgtata  6720
ctttaatttt tataatatat aaataaatta taacttgaat aacttatttg attatttatc  6780
ttattatttt tgtttggttt gatttttat cgtttaaaaa gtttaattta attctttatc  6840
ttattttttt agtttaattc ttaatatttt taaaaaattt atttgatctt ttatcttttt  6900
tttcaaaaca ttttgttatt ttttttatt gtttagtttg gtctttgaat ttatttaaga  6960
ttgacatcat taaatttatt tatgattgac atcattaatt atttaaaaat atattttttt  7020
gttaagtttt ctccctttct tctccaattc attttgaaaa taaaaatttt attcttaaat  7080
gattaacaac attaatctta aatgcactga aagatcaatc tgaaaaaaaa agataaatga  7140
caaaattatt tttttaaaa gataaaagac taaattaaaa aaaatcaaat taaactttta  7200
aaaagataaa atactaaatt gtaaaaaaaa taagataaat aataaaatat ttttttaaa  7260
aaaatataaa aaactaaatt gaatcaaata ataagataaa aaaccaaata ttcgttctaa  7320
attatattat atctatacac atggtttagt ttggattata ttttaaaatt caaattagtg  7380
ttgttaaaaa gttcagtttt tttttcaag tcttaataat ttaatttttt taacttacac  7440
caattcataa ttatgttttt acctactatt gttattatta tttgtagtgg tccactatgt  7500
tgaatatcat tttctttccc ttttgtggtc attagtcgtg aaatccatac gtcagagccc  7560
atgtggcctg catgttaatg cttctccaaa aactatatat atatatatat atatatatat  7620
atatatatgt gtgtgtgtgt gtgtgtctgt catataatag tcaaattcaa atacaccgac  7680
ttaattcatt tcaaatcaaa attttaaaga gtttcttgca aattgatggt gcagggattc  7740
acaatggtct atcatgcgaa acactatatt atcaatgtac cagccatcat acttgtccag  7800
attagtgcca acaatgcagt ccttcataga atccgcgacc caaaacctcg actctcaaaa  7860
agaagacatt atattttcca acttgtccct aagactagca actgacgtga ttggacatgc  7920
agcatttggt gttaactttg gcctctctag tccccattca gtttgtgatt ccatcaagaa  7980
tgttaatgtt aacaataaca ataacaatgc aagtgctagt agtagtaata gtaatgataa  8040
tgaagtatca gatttcatca accaacacat atactctaca acacagctta agatggactt  8100
gtctggttcc ttgtccatta tcttgggtct gcttttgcca atacttcaag agccatttag  8160
gcagattctg aagagaattc ctggcaccat ggacaggaag attgagcata ccaaccagaa  8220
actaagtggt cgtcttgatg agatagtgga gaagagaatg aaagacaaga cacgaagttc  8280
gaaggatttc ttgtcactca tacttaatgc cagagaaaca aaatctgttt cagagaatgt  8340
gttcacacct gagtacataa gtgctgttac ttacgagcac ttacttgctg gctcagcaac  8400
cacgtccttt actttgtctt ctgttgtcta tttggttgct ggacaccctg aagttgagaa  8460
aaagttgctt catgagattg atgggtttgg tccagtggat cagataccaa cttctcaaga  8520
tcttcatgac aagtttcctt atcttgatca ggtttgttca aaatgaacac aaaatcttag  8580
acaagcttga tgttccaaca tgcaagggca gagtatgtag attcattatt ataattttgt  8640
aagctcttaa tttaattaat gcaggtgatc aaagaggcca tgaggtttta cactgtctcc  8700
ccattagttg caagagaaac atcaaatgaa gtagagattg ggggctatct tcttccaaag  8760
gtaatacaaa atactacaca attatcataa caggtgaata taaatttcat aaatgaggta  8820
aaataaataa gtatataaaa ttcatgatta agttaaaaaa atatatgacg tgtttgaata  8880
aacttgtcca tagcacttat aaaagaagaa aaaaataatt gaacttttcc atgacttatg  8940
tatttaaact tttacaaaaa cttttttatt taactacaaa aactcttctt taacttctcc  9000
acatgtcaag gtgcataatt gttataaata aaatataaaa aaatccaaac tgaccataca  9060
gaattattat tgtttggtat acacactctt cacaaatcac aatcaaatta acgagttttt  9120
acttatgctg tcactaaata tggttttatg taagcagggg acttgggtct ggttagcact  9180
tggagttcca gcaaaagacc ccagaaactt tcctgagcca gacaagttca aaccggagag  9240
gtttgacccc aactttgaag aaatgaaacg aagacatcct tatgctttta taccatttgg  9300
aattggtcct cgggcatgca ttggtagaca attttccctg caagagatca agctttctct  9360
gattcattta tatcgaaaat acttgtttcg gcattctccc aatatggaaa acccccttaga  9420
actccaatat gggatagtcc tcaacttcaa gcatggggtc aagctcagag ccataaaaag  9480
aaaagaggct tgctaagtaa acagttctga cttcgcatta tcgcatatac tagtaaagag  9540
ttcagaagat gaattatgca ttattatctt atagtaatat tgagtgcgct aaaatccaaa  9600
aacgaacaat tgtgatgtta catagaatca gccaataagt gtttaaaaat aataggtcaa  9660
cgagtgtgtt attagcattt cccaaatata gaatgcaagt ttataagagt aagagacact  9720
cttcctacaa gattatgaaa tggcattatc atttgtggta aaaaaaactc aagggacaaa  9780
aaaatccgtc taaatgtgtt aaccaaagga gtgtttcccc atatagttat gcttaagttg  9840
atttatctgg ataagcctct cagcactgag taatatcaaa acccacaaat aaacaattat  9900
acaaaatgga gacccctcac aagtattccc aaacacaaaa gctacttcta gccagctaac  9960
taactcaatt taaattgcat ggaacaacaa gatgttgaac ttcttggaaa aaaaaataat  10020
aacaataaat acacaaagat gtcgagcttc caccagattc tatccctttc accgtgccat  10080
cactgaactc ttgtccaagt gaagtggcct agaaaagttg attgaagggt cagaatccgc  10140
agtggagaaa accgctgccc tcttgaggaa ttgaaaccca tccatggatt gctgcctctg  10200
agctctatta tatacatgat tgccacttgt cttttgcttt gcctttgtgg actgagtcag  10260
gttcatgtaa ttaggcctag caacaacagc attaccatta ctatcctcag tcctgtcaca  10320
agtgttccca gacattggtg ttgtggatgt acaaatggaa gatgatgcag aactctcatc  10380
gtatcgaaac tcagaacttg gacttgagga taagcgagta gcttgcccaa caaggggtgg  10440
cctagctgaa atccttgttg tgacgttgtt cttcttgact ttgaccatgc tttgtttgga  10500
attagagctc acaaaggatt ccacaaactt ctttggaggt ggggttttat ctaaggcttc  10560
agcctgagat tgtgattgtt ccatcaatct actctcccaa ggctttgctg ccatccaacg  10620
ctccaaccaa ctccacccac agttagcttt gttcatctca tgactcttaa gagaggtaaa  10680
tgaggcacgt gttcgtggat tagggcttgg tattgatctg cattgctgga aattacatgc  10740
atatcaagaa tgttaaacat ctttctaaac tagaaaaaaa gtggcttagt ttatagtact  10800
ttgttatagc ctgtttgaat tcaaattata tatatgattt agaatgacat tgaaatgtca  10860
attaacatga ttt                                                     10873
```

```
SEQ ID NO: 94          moltype = DNA  length = 1854
FEATURE                Location/Qualifiers
source                 1..1854
                       mol_type = other DNA
                       organism = Glycine max
```

```
SEQUENCE: 94
atggtattca tggattattt ggaatggttg cttccaattc caagtgtccc ttctgcttca  60
gcaatgttca ccctgcttgc tttaatagga ggattgttgg tttatctgta tgcaccctat  120
tggggtgtaa ggaaggttcc aggcccacca tctctgcccc ttgtgggaca ccttcctttg  180
ttggctaagt atggtcctga tgtgttctca gtccttgcca aacaatatgg tccgatttac  240
agatgtagga gaggcattca ggttgtggag gacgatggtg tctgggggat ggaggaggag  300
gtgctcgcgc tagttacaga cgttgtcgat ttggaacccg aagaagaggg ccaaccagtc  360
cagaaggtgg tcagagatgg aggtggtcga atgggtgggg gtaatcgaac gctgccgccg  420
gagggaggtg gggaaaaagg cagagaaaga ttccatatgg gaagacagcc actaataatt  480
atagcagatg cagagctttg taaggaggct ggaataaaaa aattcaaaga catttcaaac  540
agaagtattc cctccccaat ttctgcttct cctcttcacc aaaaaggcct cttcttcagc  600
cgggattcac aatggtctat catgcgaaac actatattat caatgtacca gccatcatac  660
ttgtccagat tagtgccaac aatgcagtcc ttcatagaat ccgcgaccca aaacctcgac  720
tctcaaaaag aagacattat attttccaac ttgtccctaa gactagcaac tgacgtgatt  780
ggacatgcag catttggtgt taactttggc ctctctagtc cccattcagt ttgtgattcc  840
atcaagaatg ttaatgttaa caataacaat aacaatgcaa gtgctagtag tagtaatagt  900
aatgataatg aagtatcaga tttcatcaac caacacatat actctacaac acagcttaag  960
atggacttgt ctggttcctt gtccattatc ttgggtctgc ttttgccaat acttcaagag  1020
ccatttaggc agattctgaa gagaattcct ggcaccatgg acaggaagat tgagcatacc  1080
aaccagaaac taagtggtcg tcttgatgag atagtggaga agagaatgaa agacaagaca  1140
cgaagttcga aggatttctt gtcactcata cttaatgcca gagaaacaaa atctgtttca  1200
gagaatgtgt tcacacctga gtacataagt gctgttactt acgagcactt acttgctggc  1260
tcagcaacca cgtcctttac tttgtcttct gttgtctatt tggttgctgg acaccctgaa  1320
gttgagaaaa agttgcttca tgagattgat gggtttggtc cagtggatca gataccaact  1380
tctcaagatc ttcatgacaa gtttccttat cttgatcagg tgatcaaaga ggccatgagg  1440
ttttacactg tctccccatt agttgcaaga gaaacatcaa atgaagtaga gattgggggc  1500
tatcttcttc caaaggggac ttgggtctgg ttagcacttg gagttccagc aaaagacccc  1560
agaaactttc ctgagccaga caagttcaaa ccggagaggt ttgaccccaa ctttgaagaa  1620
atgaaacgaa gacatcctta tgcttttata ccatttggaa ttggtcctcg ggcatgcatt  1680
ggtagacaat ttccctgca agagatcaag ctttctctga ttcatttata tcgaaaatac  1740
ttgtttcggc attctcccaa tatggaaaac cccttagaac tccaatatgg gatagtcctc  1800
aacttcaagc atggggtcaa gctcagagcc ataaaaagaa aagaggcttg ctaa        1854

SEQ ID NO: 95          moltype = AA  length = 617
FEATURE                Location/Qualifiers
source                 1..617
                       mol_type = protein
                       organism = Glycine max
SEQUENCE: 95
MVFMDYLEWL LPIPSVPSAS AMFTLLALIG GLLVYLYAPY WGVRKVPGPP SLPLVGHLPL  60
LAKYGPDVFS VLAKQYGPIY RCRRGIQVVE DDGVWGMEEE VLALVTDVVD LEPEEEGQPV  120
QKVVRDGGGR MGGGNRTLPP EGGGGKGRER FHMGRQPLII IADAELCKEA GIKKFKDISN  180
RSIPSPISAS PLHQKGLFFS RDSQWSIMRN TILSMYQPSY LSRLVPTMQS FIESATQNLD  240
SQKEDIIFSN LSLRLATDVI GHAAFGVNFG LSSPHSVCDS IKNVNVNNNN NNASASSSNS  300
NDNEVSDFIN QHIYSTTQLK MDLSGSLSII LGLLLPILQE PFRQILKRIP GTMDRKIEHT  360
NQKLSGRLDE IVEKRMKDKT RSSKDFLSLI LNARETKSVS ENVFTPEYIS AVTYEHLLAG  420
SATTSFTLSS VVYLVAGHPE VEKKLLHEID GFGPVDQIPT SQDLHDKFPY LDQVIKEAMR  480
FYTVSPLVAR ETSNEVEIGG YLLPKGTWVW LALGVPAKDP RNFPEPDKFK PERFDPNFEE  540
MKRRHPYAFI PFGIGPRACI GRQFSLQEIK LSLIHLYRKY LFRHSPNMEN PLELQYGIVL  600
NFKHGVKLRA IKRKEAC                                                617

SEQ ID NO: 96          moltype = DNA  length = 349
FEATURE                Location/Qualifiers
source                 1..349
                       mol_type = other DNA
                       organism = Glycine max
SEQUENCE: 96
atttgtagat tcctatactg ttgcaaggaa aataaaacaa acaaacacac atggtattca  60
tggattattt ggaatggttg cttccaattc caagtgtccc ttctgcttca gcaatgttca  120
ccctgcttgc tttaatagga ggattgttgg tttatctgta tgcaccctat tggggtgtaa  180
ggaaggttcc aggcccacca tctctgcccc ttgtgggaca ccttcctttg ttggctaagt  240
atggtcctga tgtgttctca gtccttgcca aacaatatgg tccgatttac aggttagttt  300
acttacatat atattaatcg tcaattgatg atgatgatca atttgttag             349

SEQ ID NO: 97          moltype = DNA  length = 269
FEATURE                Location/Qualifiers
source                 1..269
                       mol_type = other DNA
                       organism = Glycine max
SEQUENCE: 97
acaaacacac atggtattca tggattattt ggaatggttg cttccaattc caagtgtccc  60
ttctgcttca gcaatgttca ccctgcttgc tttaatagga ggattgttgg tttatctgta  120
tgcaccctat tggggtgtaa ggaaggttcc aggcccacca tctctgcccc ttgtgggaca  180
ccttcctttg ttggctaagt atggtcctga tgtgttctca gtccttgcca aacaatatgg  240
tccgatttac aggttagttt acttacata                                   269

SEQ ID NO: 98          moltype = DNA  length = 229
FEATURE                Location/Qualifiers
source                 1..229
```

```
                        mol_type = other DNA
                        organism = Glycine max
SEQUENCE: 98
tggattattt ggaatggttg cttccaattc caagtgtccc ttctgcttca gcaatgttca  60
ccctgcttgc tttaatagga ggattgttgg tttatctgta tgcaccctat tggggtgtaa  120
ggaaggttcc aggcccacca tctctgcccc ttgtgggaca ccttcctttg ttggctaagt  180
atggtcctga tgtgttctca gtccttgcca aacaatatgg tccgattta            229

SEQ ID NO: 99           moltype = DNA  length = 189
FEATURE                 Location/Qualifiers
source                  1..189
                        mol_type = other DNA
                        organism = Glycine max
SEQUENCE: 99
cttccaattc caagtgtccc ttctgcttca gcaatgttca ccctgcttgc tttaatagga  60
ggattgttgg tttatctgta tgcaccctat tggggtgtaa ggaaggttcc aggcccacca  120
tctctgcccc ttgtgggaca ccttcctttg ttggctaagt atggtcctga tgtgttctca  180
gtccttgcc                                                          189

SEQ ID NO: 100          moltype = DNA  length = 223
FEATURE                 Location/Qualifiers
source                  1..223
                        mol_type = other DNA
                        organism = Glycine max
SEQUENCE: 100
atttgtagat tcctatactg ttgcaaggaa aataaaacaa acaaacacac atggtattca  60
tggattattt ggaatggttg cttccaattc caagtgtccc ttctgcttca gcaatgttca  120
ccctgcttgc tttaatagga ggattgttgg tttatctgta tgcaccctat tggggtgtaa  180
ggaaggttcc aggcccacca tctctgcccc ttgtgggaca cct                    223

SEQ ID NO: 101          moltype = DNA  length = 143
FEATURE                 Location/Qualifiers
source                  1..143
                        mol_type = other DNA
                        organism = Glycine max
SEQUENCE: 101
acaaacacac atggtattca tggattattt ggaatggttg cttccaattc caagtgtccc  60
ttctgcttca gcaatgttca ccctgcttgc tttaatagga ggattgttgg tttatctgta  120
tgcaccctat tggggtgtaa gga                                          143

SEQ ID NO: 102          moltype = DNA  length = 103
FEATURE                 Location/Qualifiers
source                  1..103
                        mol_type = other DNA
                        organism = Glycine max
SEQUENCE: 102
tggattattt ggaatggttg cttccaattc caagtgtccc ttctgcttca gcaatgttca  60
ccctgcttgc tttaatagga ggattgttgg tttatctgta tgc                    103

SEQ ID NO: 103          moltype = DNA  length = 63
FEATURE                 Location/Qualifiers
source                  1..63
                        mol_type = other DNA
                        organism = Glycine max
SEQUENCE: 103
cttccaattc caagtgtccc ttctgcttca gcaatgttca ccctgcttgc tttaatagga  60
gga                                                                63

SEQ ID NO: 104          moltype = DNA  length = 223
FEATURE                 Location/Qualifiers
source                  1..223
                        mol_type = other DNA
                        organism = Glycine max
SEQUENCE: 104
ttgctttaat aggaggattg ttggtttatc tgtatgcacc ctattggggt gtaaggaagg  60
ttccaggccc accatctctg ccccttgtgg gacaccttcc tttgttggct aagtatggtc  120
ctgatgtgtt ctcagtcctt gccaaacaat atggtccgat ttacaggtta gtttacttac  180
atatatatta atcgtcaatt gatgatgatg atcaatttgt tag                    223

SEQ ID NO: 105          moltype = DNA  length = 143
FEATURE                 Location/Qualifiers
source                  1..143
                        mol_type = other DNA
                        organism = Glycine max
SEQUENCE: 105
ctattggggt gtaaggaagg ttccaggccc accatctctg ccccttgtgg gacaccttcc  60
tttgttggct aagtatggtc ctgatgtgtt ctcagtcctt gccaaacaat atggtccgat  120
ttacaggtta gtttacttac ata                                          143
```

```
SEQ ID NO: 106          moltype = DNA  length = 103
FEATURE                 Location/Qualifiers
source                  1..103
                        mol_type = other DNA
                        organism = Glycine max
SEQUENCE: 106
ttccaggccc accatctctg ccccttgtgg gacaccttcc tttgttggct aagtatggtc  60
ctgatgtgtt ctcagtcctt gccaaacaat atggtccgat tta                    103

SEQ ID NO: 107          moltype = DNA  length = 63
FEATURE                 Location/Qualifiers
source                  1..63
                        mol_type = other DNA
                        organism = Glycine max
SEQUENCE: 107
ccccttgtgg gacaccttcc tttgttggct aagtatggtc ctgatgtgtt ctcagtcctt  60
gcc                                                                63

SEQ ID NO: 108          moltype = DNA  length = 299
FEATURE                 Location/Qualifiers
source                  1..299
                        mol_type = other DNA
                        organism = Glycine max
SEQUENCE: 108
atggtattca tggattattt ggaatggttg cttccaattc caagtgtccc ttctgcttca  60
gcaatgttca ccctgcttgc tttaatagga ggattgttgg tttatctgta tgcaccctat  120
tggggtgtaa ggaaggttcc aggcccacca tctctgcccc ttgtgggaca ccttcctttg  180
ttggctaagt atggtcctga tgtgttctca gtccttgcca aacaatatgg tccgatttac  240
agatgtagga gaggcattca ggttgtggag gacgatggtg tctgggggat ggaggagga   299

SEQ ID NO: 109          moltype = DNA  length = 229
FEATURE                 Location/Qualifiers
source                  1..229
                        mol_type = other DNA
                        organism = Glycine max
SEQUENCE: 109
tggattattt ggaatggttg cttccaattc caagtgtccc ttctgcttca gcaatgttca  60
ccctgcttgc tttaatagga ggattgttgg tttatctgta tgcaccctat tggggtgtaa  120
ggaaggttcc aggcccacca tctctgcccc ttgtgggaca ccttcctttg ttggctaagt  180
atggtcctga tgtgttctca gtccttgcca aacaatatgg tccgattta              229

SEQ ID NO: 110          moltype = DNA  length = 189
FEATURE                 Location/Qualifiers
source                  1..189
                        mol_type = other DNA
                        organism = Glycine max
SEQUENCE: 110
cttccaattc caagtgtccc ttctgcttca gcaatgttca ccctgcttgc tttaatagga  60
ggattgttgg tttatctgta tgcaccctat tggggtgtaa ggaaggttcc aggcccacca  120
tctctgcccc ttgtgggaca ccttcctttg ttggctaagt atggtcctga tgtgttctca  180
gtccttgcc                                                          189

SEQ ID NO: 111          moltype = DNA  length = 173
FEATURE                 Location/Qualifiers
source                  1..173
                        mol_type = other DNA
                        organism = Glycine max
SEQUENCE: 111
atggtattca tggattattt ggaatggttg cttccaattc caagtgtccc ttctgcttca  60
gcaatgttca ccctgcttgc tttaatagga ggattgttgg tttatctgta tgcaccctat  120
tggggtgtaa ggaaggttcc aggcccacca tctctgcccc ttgtgggaca cct         173

SEQ ID NO: 112          moltype = DNA  length = 223
FEATURE                 Location/Qualifiers
source                  1..223
                        mol_type = other DNA
                        organism = Glycine max
SEQUENCE: 112
ttgctttaat aggaggattg ttggtttatc tgtatgcacc ctattggggt gtaaggaagg  60
ttccaggccc accatctctg ccccttgtgg gacaccttcc tttgttggct aagtatggtc  120
ctgatgtgtt ctcagtcctt gccaaacaat atggtccgat ttacagatgt aggagaggca  180
ttcaggttgt ggaggacgat ggtgtctggg ggatggagga gga                    223

SEQ ID NO: 113          moltype = DNA  length = 143
FEATURE                 Location/Qualifiers
source                  1..143
                        mol_type = other DNA
                        organism = Glycine max
SEQUENCE: 113
```

-continued

```
ctattggggt gtaaggaagg ttccaggccc accatctctg ccccttgtgg gacaccttcc  60
tttgttggct aagtatggtc ctgatgtgtt ctcagtcctt gccaaacaat atggtccgat  120
ttacagatgt aggagaggca ttc                                          143

SEQ ID NO: 114         moltype = AA  length = 99
FEATURE                Location/Qualifiers
source                 1..99
                       mol_type = protein
                       organism = Glycine max
SEQUENCE: 114
MVFMDYLEWL LPIPSVPSAS AMFTLLALIG GLLVYLYAPY WGVRKVPGPP SLPLVGHLPL  60
LAKYGPDVFS VLAKQYGPIY RCRRGIQVVE DDGVWGMEE                         99

SEQ ID NO: 115         moltype = DNA  length = 2780
FEATURE                Location/Qualifiers
source                 1..2780
                       mol_type = genomic DNA
                       organism = Glycine max
SEQUENCE: 115
gcagatttca tatgggaaga caaccactaa tcttggtagc agatccagag ctttgtaaaa  60
aagtgggtat caaacaattc aaagacattc caaacagaag cattccctct cctatttctg  120
cttctcctct tcaccaaaaa ggtctcttct ttaccaggta tgcaattttg ttctcttcct  180
tttgtaacaa aagcataaag cataattatt aatttatgag acaagttatt attcaatgag  240
tttcagagaa tagataaatg ataatcatga gtattgaagg ttttcaaata tattatccta  300
gcataaaatt gttgaagtca cacttgagag acacaagata ttccatgtaa ttatatttct  360
ttacagattt atataagtta aaatgtagag aagttttatt tgttgagcac ttttgtgtaa  420
ctttttttctt gtggatttct gggtggggta gcattaggca taggcactac atgttagatg  480
tgatttccat tttgtgatca tcgtgccatg tcattaattt gagaaccaaa gattcgtagt  540
aatccaattc caatggttct ccaatatctc tgtcctccag tgagaaagaa caatggtttg  600
atacacaaaa tctaagcaca caaaagaaat tgatcatgca atgaatgatg atgatgatgt  660
gtgcagggac tcacgttggt cagccatgcg aaacacgatc ttgtcagtgt accagccatc  720
acacttggct agcttagtgc caatgatgca atcattcata gaatccgcaa cacaaaatct  780
tgatacccca aatgaggaca taatcttttc caatctttcc ctaaggctag caactgatgt  840
gattggagag gcagcatttg gtgtcaactt tggcctctct aagcccattt cagtttgtga  900
atcaatcaag agtgttagtg ttaacaatgt gagaaatgat gataatgata atggtgatga  960
tgaagtatca gatttcatca atcaacacat ttactccaca gcacaactta agatggactt  1020
gtctggttca ttctccatca tacttggtct acttgcacca atacttcagg agccatttag  1080
gcagattctg aagagaatac caggcacaat ggacaggaaa atagagagta ctaatgagaa  1140
acttagtggt cgtcttgatg agattgtcaa gaggagaatg gaaaacaaga atagaacttc  1200
aaagaatttc ttgtcactca ttttgaatgc aagagaatca aagaaagtat ctgaaaatgt  1260
cttttcacct gactacgtta gtgctgttac ttatgagcac ttacttgctg ggtcagctac  1320
tacagccttt accttgtcat ccattgtcta cttggttgct ggacacatag aagttgagaa  1380
aaagttgctt caagagattg atggatttgg tacacctgat aggattccca tagctcaaga  1440
tcttcatgac agttttcctt atcttgatca ggtcagctgc tagtgatact ttgtgagatt  1500
caagattttg tactttgaat ttgcaaggac caagaaataa tgatgtgaaa ttctcaattt  1560
aattaatgca ggtgattaaa gaggccatga ggttttacac tgtctcccca ttggttgcaa  1620
gagaagcatc aaatgaggtg gagataggag gttatcttct tccaaaggta gtgatataaa  1680
tttttggata gcattgggat ggataacatg taaagagaaa ataatatgtg aacagacaga  1740
gtaaaaagtt ttcatataac aatcaaatag aaatataaga taagtttgtt atcttttata  1800
attattatac attctttggt taagtgaaaa aaagagaaag aaaaagaaag gaaaaatatt  1860
aaaaagatac ttctttcttt ctcttgtttg gtaggataag gaaggaaagg aaaaaaatct  1920
atatggacct cacctattta ttctttcttt ctctccattt tggaaataaa aagagagaag  1980
agcttataaa agtacaaaga caaaaatatc cttatacgtt gtacatctct tttatttagg  2040
attttttttt tcattttgta tacatatctt ctgtcttttc ttccacttct aatacaacca  2100
atcagtttat attgtacttt tatttttctt tcactttctt tcttaaacca aacatactat  2160
aaaagtcaaa caatttttga ttgattagtg tgaaacttta taatgtgtct catttttcttt  2220
ctttgtttta gtacatgtgc aaaatttccc actttttctt gggagaggaa gacattgtat  2280
aatcttgatg aagggtttc tagttatgcc atcactgatg ttttgtacac gagcagggga  2340
cgtgggtatg gttagctctt ggagttctag caaaagatcc aagaaatttt ccagagcctg  2400
agaagtttaa accagagagg tttgacccca aatgtgaaga aatgaaaaga aggcatcctt  2460
atgcattcat accatttgga attggtcccc gggcatgtat tggtcagaaa ttttccctac  2520
aagagatcaa actttctctg attcatttgt accgaaaata tgtttttcgt cattcacttg  2580
acatggaaaa ccctgtagaa atggaatatg gtatggttct caacttcaag catggtctca  2640
agcttagagt cataagaaga acgtaatact gtgatgcaat ggatgaatta aaatctctct  2700
tcaatatgta gtgattgtaa acaatgcaaa atatgcttat gtaattcaaa caagtacaat  2760
tttgctgaga tgatacagga                                              2780

SEQ ID NO: 116         moltype = DNA  length = 1308
FEATURE                Location/Qualifiers
source                 1..1308
                       mol_type = other DNA
                       organism = Glycine max
SEQUENCE: 116
atgggaagac aaccactaat cttggtagca gatccagagc tttgtaaaaa agtgggtatc  60
aaacaattca aagacattcc aaacagaagc attccctctc ctatttctgc ttctcctctt  120
caccaaaaag gtctcttctt taccagggac tcacgttggt cagccatgcg aaacacgatc  180
ttgtcagtgt accagccatc acacttggct agcttagtgc caatgatgca atcattcata  240
gaatccgcaa cacaaaatct tgatacccca aatgaggaca taatcttttc caatctttcc  300
ctaaggctag caactgatgt gattggagag gcagcatttg gtgtcaactt tggcctctct  360
```

```
aagcccattt cagttttatc agatttcatc aatcaacaca tttactccac agcacaactt  420
aagatggact tgtctggttc attctccatc atacttggtc tacttgcacc aatacttcag  480
gagccattta ggcagattct gaagagaata ccaggcacaa tggacaggaa aatagagagt  540
actaatgaga aacttagtgg tcgtcttgat gagattgtca agaggagaat ggaaaacaag  600
aatagaactt caaagaattt cttgtcactc attttgaatg caagagaatc aaagaaagta  660
tctgaaaatg tcttttcacc tgactacgtt agtgctgtta cttatgagca cttacttgct  720
gggtcagcta ctacagcctt taccttgtca tccattgtct acttggttgc tggacacata  780
gaagttgaga aaaagttgct tcaagagatt gatggatttg gtacacctga taggattccc  840
atagctcaag atcttcatga cagttttcct tatcttgatc aggtgattaa agaggccatg  900
aggttttaca ctgtctcccc attggttgca agagaagcat caaatgaggt ggagatagga  960
ggttatcttc ttccaaaggg gacgtgggta tggttagctc ttggagttct agcaaaagat  1020
ccaagaaatt ttccagagcc tgagaagttt aaaccagaga ggtttgaccc caaatgtgaa  1080
gaaatgaaaa gaaggcatcc ttatgcattc ataccatttg gaattggtcc ccgggcatgt  1140
attggtcaga aattttccct acaagagatc aaactttctc tgattcattt gtaccgaaaa  1200
tatgtttttc gtcattcact tgacatggaa aaccctgtag aaatggaata tggtatggtt  1260
ctcaacttca agcatggtct caagcttaga gtcataagaa gaacgtaa              1308

SEQ ID NO: 117         moltype = AA  length = 435
FEATURE                Location/Qualifiers
source                 1..435
                       mol_type = protein
                       organism = Glycine max
SEQUENCE: 117
MGRQPLILVA DPELCKKVGI KQFKDIPNRS IPSPISASPL HQKGLFFTRD SRWSAMRNTI  60
LSVYQPSHLA SLVPMMQSFI ESATQNLDTP NEDIIFSNLS LRLATDVIGE AAFGVNFGLS  120
KPISVLSDFI NQHIYSTAQL KMDLSGSFSI ILGLLAPILQ EPFRQILKRI PGTMDRKIES  180
TNEKLSGRLD EIVKRRMENK NRTSKNFLSL ILNARESKKV SENVFSPDYV SAVTYEHLLA  240
GSATTAFTLS SIVYLVAGHI EVEKKLLQEI DGFGTPDRIP IAQDLHDSFP YLDQVIKEAM  300
RFYTVSPLVA REASNEVEIG GYLLPKGTWV WLALGVLAKD PRNFPEPEKF KPERFDPKCE  360
EMKRRHPYAF IPFGIGPRAC IGQKFSLQEI KLSLIHLYRK YVFRHSLDME NPVEMEYGMV  420
LNFKHGLKLR VIRRT                                                  435

SEQ ID NO: 118         moltype = DNA  length = 230
FEATURE                Location/Qualifiers
source                 1..230
                       mol_type = other DNA
                       organism = Glycine max
SEQUENCE: 118
gcagatttca tatgggaaga caaccactaa tcttggtagc agatccagag ctttgtaaaa  60
aagtgggtat caaacaattc aaagacattc caaacagaag cattccctct cctatttctg  120
cttctcctct tcaccaaaaa ggtctcttct ttaccaggta tgcaattttg ttctcttcct  180
tttgtaacaa aagcataaag cataattatt aatttatgag acaagttatt            230

SEQ ID NO: 119         moltype = DNA  length = 190
FEATURE                Location/Qualifiers
source                 1..190
                       mol_type = other DNA
                       organism = Glycine max
SEQUENCE: 119
gcagatttca tatgggaaga caaccactaa tcttggtagc agatccagag ctttgtaaaa  60
aagtgggtat caaacaattc aaagacattc caaacagaag cattccctct cctatttctg  120
cttctcctct tcaccaaaaa ggtctcttct ttaccaggta tgcaattttg ttctcttcct  180
tttgtaacaa                                                        190

SEQ ID NO: 120         moltype = DNA  length = 163
FEATURE                Location/Qualifiers
source                 1..163
                       mol_type = other DNA
                       organism = Glycine max
SEQUENCE: 120
tcatatggga agacaaccac taatcttggt agcagatcca gagctttgta aaaaagtggg  60
tatcaaacaa ttcaaagaca ttccaaacag aagcattccc tctcctattt ctgcttctcc  120
tcttcaccaa aaaggtctct tctttaccag gtatgcaatt ttg                   163

SEQ ID NO: 121         moltype = DNA  length = 123
FEATURE                Location/Qualifiers
source                 1..123
                       mol_type = other DNA
                       organism = Glycine max
SEQUENCE: 121
taatcttggt agcagatcca gagctttgta aaaaagtggg tatcaaacaa ttcaaagaca  60
ttccaaacag aagcattccc tctcctattt ctgcttctcc tcttcaccaa aaaggtctct  120
tct                                                               123

SEQ ID NO: 122         moltype = DNA  length = 170
FEATURE                Location/Qualifiers
source                 1..170
                       mol_type = other DNA
                       organism = Glycine max
```

```
SEQUENCE: 122
gcagatttca tatgggaaga caaccactaa tcttggtagc agatccagag ctttgtaaaa  60
aagtgggtat caaacaattc aaagacattc caaacagaag cattccctct cctatttctg  120
cttctcctct tcaccaaaaa ggtctcttct ttaccaggta tgcaattttg            170

SEQ ID NO: 123         moltype = DNA  length = 130
FEATURE                Location/Qualifiers
source                 1..130
                       mol_type = other DNA
                       organism = Glycine max
SEQUENCE: 123
gcagatttca tatgggaaga caaccactaa tcttggtagc agatccagag ctttgtaaaa  60
aagtgggtat caaacaattc aaagacattc caaacagaag cattccctct cctatttctg  120
cttctcctct                                                         130

SEQ ID NO: 124         moltype = DNA  length = 103
FEATURE                Location/Qualifiers
source                 1..103
                       mol_type = other DNA
                       organism = Glycine max
SEQUENCE: 124
tcatatggga agacaaccac taatcttggt agcagatcca gagctttgta aaaaagtggg  60
tatcaaacaa ttcaaagaca ttccaaacag aagcattccc tct                    103

SEQ ID NO: 125         moltype = DNA  length = 63
FEATURE                Location/Qualifiers
source                 1..63
                       mol_type = other DNA
                       organism = Glycine max
SEQUENCE: 125
taatcttggt agcagatcca gagctttgta aaaaagtggg tatcaaacaa ttcaaagaca  60
ttc                                                                63

SEQ ID NO: 126         moltype = DNA  length = 223
FEATURE                Location/Qualifiers
source                 1..223
                       mol_type = other DNA
                       organism = Glycine max
SEQUENCE: 126
tcatatggga agacaaccac taatcttggt agcagatcca gagctttgta aaaaagtggg  60
tatcaaacaa ttcaaagaca ttccaaacag aagcattccc tctcctattt ctgcttctcc  120
tcttcaccaa aaaggtctct tctttaccag gtatgcaatt ttgttctctt ccttttgtaa  180
caaaagcata aagcataatt attaatttat gagacaagtt att                    223

SEQ ID NO: 127         moltype = DNA  length = 143
FEATURE                Location/Qualifiers
source                 1..143
                       mol_type = other DNA
                       organism = Glycine max
SEQUENCE: 127
gagctttgta aaaaagtggg tatcaaacaa ttcaaagaca ttccaaacag aagcattccc  60
tctcctattt ctgcttctcc tcttcaccaa aaaggtctct tctttaccag gtatgcaatt  120
ttgttctctt ccttttgtaa caa                                          143

SEQ ID NO: 128         moltype = DNA  length = 103
FEATURE                Location/Qualifiers
source                 1..103
                       mol_type = other DNA
                       organism = Glycine max
SEQUENCE: 128
tatcaaacaa ttcaaagaca ttccaaacag aagcattccc tctcctattt ctgcttctcc  60
tcttcaccaa aaaggtctct tctttaccag gtatgcaatt ttg                    103

SEQ ID NO: 129         moltype = DNA  length = 61
FEATURE                Location/Qualifiers
source                 1..61
                       mol_type = other DNA
                       organism = Glycine max
SEQUENCE: 129
ccaaacagaa gcattccctc tcctatttct gcttctcctc ttcaccaaaa aggtctcttc  60
t                                                                  61

SEQ ID NO: 130         moltype = DNA  length = 219
FEATURE                Location/Qualifiers
source                 1..219
                       mol_type = other DNA
                       organism = Glycine max
SEQUENCE: 130
atgggaagac aaccactaat cttggtagca gatccagagc tttgtaaaaa agtgggtatc  60
```

```
aaacaattca aagacattcc aaacagaagc attccctctc ctatttctgc ttctcctctt  120
caccaaaaag gtctcttctt taccagggac tcacgttggt cagccatgcg aaacacgatc  180
ttgtcagtgt accagccatc acacttggct agcttagtg                         219

SEQ ID NO: 131         moltype = DNA  length = 179
FEATURE                Location/Qualifiers
source                 1..179
                       mol_type = other DNA
                       organism = Glycine max
SEQUENCE: 131
atgggaagac aaccactaat cttggtagca gatccagagc tttgtaaaaa agtgggtatc  60
aaacaattca aagacattcc aaacagaagc attccctctc ctatttctgc ttctcctctt  120
caccaaaaag gtctcttctt taccagggac tcacgttggt cagccatgcg aaacacgat   179

SEQ ID NO: 132         moltype = DNA  length = 143
FEATURE                Location/Qualifiers
source                 1..143
                       mol_type = other DNA
                       organism = Glycine max
SEQUENCE: 132
taatcttggt agcagatcca gagctttgta aaaaagtggg tatcaaacaa ttcaaagaca  60
ttccaaacag aagcattccc tctcctattt ctgcttctcc tcttcaccaa aaaggtctct  120
tctttaccag ggactcacgt tgg                                          143

SEQ ID NO: 133         moltype = DNA  length = 159
FEATURE                Location/Qualifiers
source                 1..159
                       mol_type = other DNA
                       organism = Glycine max
SEQUENCE: 133
atgggaagac aaccactaat cttggtagca gatccagagc tttgtaaaaa agtgggtatc  60
aaacaattca aagacattcc aaacagaagc attccctctc ctatttctgc ttctcctctt  120
caccaaaaag gtctcttctt taccagggac tcacgttgg                         159

SEQ ID NO: 134         moltype = DNA  length = 119
FEATURE                Location/Qualifiers
source                 1..119
                       mol_type = other DNA
                       organism = Glycine max
SEQUENCE: 134
atgggaagac aaccactaat cttggtagca gatccagagc tttgtaaaaa agtgggtatc  60
aaacaattca aagacattcc aaacagaagc attccctctc ctatttctgc ttctcctct   119

SEQ ID NO: 135         moltype = DNA  length = 99
FEATURE                Location/Qualifiers
source                 1..99
                       mol_type = other DNA
                       organism = Glycine max
SEQUENCE: 135
atgggaagac aaccactaat cttggtagca gatccagagc tttgtaaaaa agtgggtatc  60
aaacaattca aagacattcc aaacagaagc attccctct                         99

SEQ ID NO: 136         moltype = DNA  length = 143
FEATURE                Location/Qualifiers
source                 1..143
                       mol_type = other DNA
                       organism = Glycine max
SEQUENCE: 136
gagctttgta aaaaagtggg tatcaaacaa ttcaaagaca ttccaaacag aagcattccc  60
tctcctattt ctgcttctcc tcttcaccaa aaaggtctct tctttaccag ggactcacgt  120
tggtcagcca tgcgaaacac gat                                          143

SEQ ID NO: 137         moltype = DNA  length = 103
FEATURE                Location/Qualifiers
source                 1..103
                       mol_type = other DNA
                       organism = Glycine max
SEQUENCE: 137
tatcaaacaa ttcaaagaca ttccaaacag aagcattccc tctcctattt ctgcttctcc  60
tcttcaccaa aaaggtctct tctttaccag ggactcacgt tgg                    103

SEQ ID NO: 138         moltype = DNA  length = 63
FEATURE                Location/Qualifiers
source                 1..63
                       mol_type = other DNA
                       organism = Glycine max
SEQUENCE: 138
ttccaaacag aagcattccc tctcctattt ctgcttctcc tcttcaccaa aaaggtctct  60
tct                                                                63
```

```
SEQ ID NO: 139         moltype = AA  length = 73
FEATURE                Location/Qualifiers
source                 1..73
                       mol_type = protein
                       organism = Glycine max
SEQUENCE: 139
MGRQPLILVA DPELCKKVGI KQFKDIPNRS IPSPISASPL HQKGLFFTRD SRWSAMRNTI  60
LSVYQPSHLA SLV                                                     73

SEQ ID NO: 140         moltype = DNA  length = 6131
FEATURE                Location/Qualifiers
source                 1..6131
                       mol_type = genomic DNA
                       organism = Glycine max
SEQUENCE: 140
actcctctaa tttcaggaac caaaaaacct tagtctctgt ctctttcctt tggtatatac  60
acactgcaca tgccaaaata aaaatggtgt ccatagtatt ggaatggtta tttccttttc  120
catgtgtagc catgttcacc acccttctga tgttaatagg aggattattg ggttatcttt  180
atgggcccta ttgggggctt aggaaagttc caggcccacc aacgctgccg ctggtaggac  240
accttccctt actggctaaa tacggccctg atgtcttctc actccttgcc aagcaatatg  300
gcccaattta caggtttgta ctttacataa ttgaatctgg atagaaggca cttttttta  360
ccatattatt ggtataccga tactaatcat gggttggaga acttaatcac tcacttttat  420
agtgagatct ttctttttaa ttatgttttt ttctttcaca aatctcgaac ctagttcaat  480
attattcgaa ccaaaatgac ttactagtta gatagcagac aattacagct taatcaattt  540
gatttgttga gatcattctc attttcttca tcttcttctc ttcatgagaa gctaaaaaga  600
aaatctgtta ctgctgatat gatacccaac ttgaatatat gaaattcaaa atgcataaaa  660
gtcctgttgg gtgtggatga tatttggtca tgtaatgatg ggggttatat atggttgact  720
tgtgaagggt atatatatga ttatggtggt ggtgggacag tgttttagtg catattgcct  780
gggaagaagt agatataatc acataatttg gaaaaaaagt taacgttctg ttgtgatcta  840
tttgtgcttg tttgtcaact tgattaaata tgataagaaa caacattagc atcagcatgc  900
ccgtcctata gtaacatgat taaattgctc ttgataaata ttaagagtgt cctcaattgt  960
atgcacataa ccttctaaac aaagatcttg tcgttgtcct tgatggcaga agaatttgag  1020
tcctttaaaa gtgaacaaag catctaacac aaaaataaag gtaaatgcat agttgatttg  1080
aataaagtac tttataaatt tatttaattt tgagttagtg atggatgcac gcttactttt  1140
gtttatgtaa ataatgcata tttactttc tcattttgca caagtacttc gctagatcca  1200
tggtcataaa tgaatcaaga taagtagagt aatttaagtt taagcttgac atataaaaaa  1260
tattatttat ttaaatgaat caaagttaaa ctttagactt gtttgaagat agacagcctg  1320
aattagaatc tacttagttg ataatttaat ttttgttcct ttatcaaata ttttttgaa  1380
acatttttaa atttattaat ttattattta gtaaatgaat tttcgtacta aaaataaagt  1440
aaaaataaga gaaaaataat tagatgtaaa aattacatat taattattta taacaaaaaa  1500
tataatatat taaatatatc tttctcacat ttaatttttt ttatcttcag gcacacatat  1560
aacactcaca ctcaactttt tagtatcaag tttataaact ttgaactgga gtgattttta  1620
taattataaa tagaattaaa tttgagttta ttttcttaat aaaataaata aattttattg  1680
gacatttaat aaatcgaatc tggatagcaa aaatataagt tttagagctt aattttaaat  1740
tatttctcat tgataaaaaa atattattaa gataattatt ataaaaatta acaaattata  1800
atatataata atttgatact aaataacagt acaaattcta taagtgcata tatagtctac  1860
tctaaatttt atgcagttca attttacaac cctgatttat cattgggtga ttaatttct  1920
atccaacaga acaatttttt tttttttaga gaataaacct ttggttattc tggtaaacgc  1980
cttacgcgcg tctgattttc aaaactcaaa agtcaaaagg gacattttgc tgcgatttta  2040
atcattgtgt acggaaaact tctagcactg tttgcagagg attattaagt tattaaaaaa  2100
agtatacatt aaacataatt taacatggaa aaagaagaga aaggaaaaga tgaatacgaa  2160
ttaatgtgtg atttcatata ttattctcgt gaatttttcc attaacggct agttatattt  2220
aagatcgaat ttaattagca cgtagtgtta cttaattata gatcattatc agtttatgac  2280
caatatgtca ttttgagtga aatagtgcta aaaaatttta aacaaaattt caggttcttg  2340
tacataaaaa atttaattaa aaaatattta ttaaaagtga taaataaggt tctctcatca  2400
ataaaattaa taaatataca ctaataagat tcacgacttt tataatacga attattttaa  2460
atgtcatctt taaaatatta ttttaattga tcaagtgtgt tcaaatcagt ttatgaaaat  2520
taaattctat atttaatagt attttaaatt ttcattgtga aatcagtatc ataaatgctt  2580
gataaatcat ggcaacttca ttttatgctt atcaagccat cttctcactt taactgttga  2640
tgatgttgtt actatttgtt taatggagca gatttcatat gggaagacaa ccactaatct  2700
tggtagcaga tccagagctt tgtaaagaag tgggaataaa aaaattcaaa gacattccaa  2760
acagaagcat tccctctcct atttcagctt ccccccttca ccaaaaaggt ctcttcttta  2820
ccaggtatac aatttaattt ttttcttttc tttttgtaat aatagcataa acaataattg  2880
ttaatttacg agacaaacta ttattcaata agttagagaa tagataaatg aaaataatga  2940
gtattgaagg ttttcaaatg tattatccta tagcataaaa ctgtttgagt cacacttaga  3000
tagacaggaa aggtatttat tattgagtaa aaaaaattct gcactatatt tttatattgt  3060
tattcaatca cacattatta tgtataataa atttattaat ttttataatg attattttat  3120
aagttatatc aataataatt tgtgatgaaa tgagagtgtt aatgtatttt acactctagt  3180
tatatttctt tacaattgat agaagttaaa atatagagag gtctcatttg ttgagcactt  3240
ttgtgcaact tttttcttgt ggatttctgt gtggggtagc attagcatag gcactatatg  3300
ttaaatgtca tttccatttt gtgatcatcg tgtcatgtca ttaatttgag aatcaaagat  3360
tcgttgtaat ccaattccaa tggttctcca aaatctttgt cctctagtga gaaagaacaa  3420
tggtttgata caccaaatct aagaacacac aaaagaaatt gatcatgcaa tgatgatttg  3480
cagggactca cgttggtcaa ccatgcgaaa cacgatcttg tcagtgtacc agccatcaca  3540
cttggctagc ttagtgccaa cgatgcaatc attcatagaa tccgcaacac aaaatcttga  3600
caccccaaat gaggacataa tcttttccaa tctttcctta aggctagcaa ccgatgtgat  3660
tggagaggca gcatttggtg tcaattttgg cctctctaag ccacattcag tttgtgaatc  3720
aatcaagagt gttagtgtta acaatgtgag aaatgatgat gatgaggtat ctgatttcat  3780
```

```
caatcaacac atttactcca caacacaact taagatggac ttgtctggtt cattctccat  3840
catacttggt ctacttgcac caatacttca ggagccattt aggcagattc tgaagagaat  3900
accaggcaca atggacagca aaatagagag tactaatgag aagctgagtg gtcctcttga  3960
tgagattgtc aagaggagaa tggaagacaa gaatagaact tcaaagaatt tcttgtcact  4020
cattttgaat gcaagagaat caaagaaagt atctgaaaat gtcttttcac ctgattacat  4080
tagcgctgtt acttatgagc acttacttgc tgggtcagct accacagcct ttaccttgtc  4140
atccattgtc tacttggttg ctggacaccg agaggttgag aaaaagttgc ttcaagagat  4200
tgatggattt ggtccacctg ataggattcc cacagctcaa gatcttcatg acagttttcc  4260
ttatcttgat caggtcagct gatagtgata ctttgtgaga ttcaagattt tgtacgttga  4320
atttgcaagg accagcaata atgatgtaaa attctcaatt taattaacgc aggtgattaa  4380
agaggccatg aggttttaca cagtctcccc attggttgca agagaaacat cacatgaggt  4440
ggagatagga ggttaccttc ttccaaaggt agtaatacat ctttgtccag tgtcaaatat  4500
aattttttga tggcattggg agggataaca tgtaatgaga aaataatacg tgcatggacc  4560
ccgtaaagag tttttatatg ttcatcaaac aaaaatctag atataataaa tttgtagact  4620
tttataataa ttatatatta tttggtttac gtgaaaaaaa gagaaaggaa ggggaaatat  4680
taaaaaaata cttcttttcc ttgattagaa ggagtaagcc aaggaaggaa tggaaaaaaa  4740
aaatatatga accccaccta tttattctgt cttttcattg tgtatacata ccataccttc  4800
tttatttctt tctacttcta atgcaaccaa acaacttata aaatcatctt actttctact  4860
tatttttttct taaaccaaac atattataaa agtcaaacaa tttttaattg gtcgatagtg  4920
tgaaactttt atactaacat tacatagaaa tttgtctcat tttctttgtt ttagtacatg  4980
tgcaaaattt tccatttttct tgatgcaggg tattttagtt atgccaccac tgatgttttg  5040
tacatgagca ggggacatgg gtatggttag ctctaggagt tctagcaaaa gatccaagga  5100
attttccaga gcctgagaag ttcaaaccag agaggtttga ccccaaatgt gaagaaatga  5160
aacgaagaca tccttatgca ttcataccat ttggaattgg tccccgggca tgtattggtc  5220
agaaattttc cctacaagag atcaagctta ctctgattca tttgtaccag aaatatgttt  5280
ttcgtcattc agttgacatg gaaaaacctg tagaaatgga atatggtatg gttctcaact  5340
tcaagcatgg tatcaagctt agagtcataa gaagaacgta attatagagt gaccatgtat  5400
accaactaag attgtacttt gtgatgcaat ggatgaatta aaatctctct ttaatatgtt  5460
gtgattgtca acaaggcaaa atatgctaat tcaaacagga tattaaactt ttatgcaaat  5520
tttatgaaag aaagagtatc ttgactttga atgtgcctac aaaagcagat tcccccacta  5580
attgctgggt ctcactcttc aattttatac tttgtttagg ccttgcagtc tcttgataac  5640
ataaaaaatt aacaactgat tatacaaatg gagagacccc taaagtagta ttgcttaggg  5700
aaagcacaaa agctactgct acagttgtaa ttcaattaac agaccattga acaacaagtt  5760
gttgaagtgt ttgaacttct tgaaaataaa tacaacagag aggatcaatc aatagaatca  5820
agtcgctttt tcaccgtgaa ctcttatcca tgtaggttgg taggtaaagt ggcctagaaa  5880
agttggttga agggtcagaa gcattagaga aaactgctgt tcttttgaga aactggaact  5940
catccatgga ctgctgcctc tgagatctat tgtactgatg attgctggtt ttctgctttg  6000
ccttggttga ctcggtgagg ttcatgtaac taggcctaga gttgttacta tcctctgtcc  6060
tgtcacaagg tattggagtt gtagatgtgc agattgagga tgaattagag cagctctcat  6120
catagtgaaa c                                                       6131
```

```
SEQ ID NO: 141          moltype = DNA  length = 1486
FEATURE                 Location/Qualifiers
source                  1..1486
                        mol_type = other DNA
                        organism = Glycine max
SEQUENCE: 141
atggtgtcca tagtattgga atggttattt cctttccat gtgtagccat gttcaccacc  60
cttctgatgt taataggagg attattgggt tatctttatg ggccctattg ggggcttagg  120
aaagttccag gcccaccaac gctgccgctg gtaggacacc ttcccttact ggctaaatac  180
ggccctgatg tcttctcact ccttgccaag caatatggcc caatttacag atttcatatg  240
ggaagacaac cactaatctt ggtagcagat ccagagcttt gtaaagaagt gggaataaaa  300
aaattcaaag acattccaaa cagaagcatt ccctctccta tttcagcttc ccccttcac  360
caaaaaggtc tcttctttac cagggactca cgttggtcaa ccatgcgaaa cacgatcttg  420
tcagtgtacc agccatcaca cttggctagc ttagtgccaa cgatgcaatc attcatagaa  480
tccgcaacac aaaatcttga caccccaaat gaggacataa tcttttccaa tctttcctta  540
aggctagcaa ccgatgtgat tggagaggca gcatttggtg tcaattttgg cctctctaag  600
ccacattcag tatctgattt catcaatcaa cacatttact cccacaacaca acttaagatg  660
gacttgtctg gttcattctc catcatactt ggtctacttg caccaatact tcaggagcca  720
tttaggcaga ttctgaagag aataccaggc acaatggaca gcaaaataga gagtactaat  780
gagaagctga gtggtcctct tgatgagatt gtcaagagga gaatggaaga caagaataga  840
acttcaaaga atttcttgtc actcattttg aatgcaagag aatcaaagaa agtatctgaa  900
aatgtctttt cacctgatta cattagcgct gttacttatg agcacttact tgctgggtca  960
gctaccacag cctttacctt gtcatccatt gtctacttgg ttgctggaca ccgagaggtt  1020
gagaaaaagt tgcttcaaga gattgatgga tttggtccac ctgataggat tcccacagct  1080
caagatcttc atgacagttt tccttatctt gatcaggtga ttaaagaggc catgaggttt  1140
tacacagtct ccccattggt tgcaagagaa acatcacatg aggtggagat aggaggttac  1200
cttcttccaa aggggacatg ggtatggtta gctctaggag ttctagcaaa agatccaagg  1260
aattttccag agcctgagaa gttcaaacca gagaggtttg accccaaatg tgaagaaatg  1320
aaacgaagac atccttatgc attcatacca tttggaattg gtccccgggc atgtattggt  1380
cagaaatttt ccctacaaga gatcaagctt actctgattc atttgtacca gaaatatgtt  1440
tttcgtcatt cagttgacat ggaaaaacct gtagaaatgg aatatg                 1486
```

```
SEQ ID NO: 142          moltype = AA  length = 495
FEATURE                 Location/Qualifiers
source                  1..495
                        mol_type = protein
                        organism = Glycine max
SEQUENCE: 142
```

```
MVSIVLEWLF PFPCVAMFTT LLMLIGGLLG YLYGPYWGLR KVPGPPTLPL VGHLPLLAKY  60
GPDVFSLLAK QYGPIYRFHM GRQPLILVAD PELCKEVGIK KFKDIPNRSI PSPISASPLH  120
QKGLFFTRDS RWSTMRNTIL SVYQPSHLAS LVPTMQSFIE SATQNLDTPN EDIIFSNLSL  180
RLATDVIGEA AFGVNFGLSK PHSVSDFINQ HIYSTTQLKM DLSGSFSIIL GLLAPILQEP  240
FRQILKRIPG TMDSKIESTN EKLSGPLDEI VKRRMEDKNR TSKNFLSLIL NARESKKVSE  300
NVFSPDYISA VTYEHLLAGS ATTAFTLSSI VYLVAGHREV EKKLLQEIDG FGPPDRIPTA  360
QDLHDSFPYL DQVIKEAMRF YTVSPLVARE TSHEVEIGGY LLPKGTWVWL ALGVLAKDPR  420
NFPEPEKFKP ERFDPKCEEM KRRHPYAFIP FGIGPRACIG QKFSLQEIKL TLIHLYQKYV  480
FRHSVDMEKP VEMEY                                                 495

SEQ ID NO: 143         moltype = DNA  length = 333
FEATURE                Location/Qualifiers
source                 1..333
                       mol_type = other DNA
                       organism = Glycine max
SEQUENCE: 143
gtctctttcc tttggtatat acacactgca catgccaaaa taaaaatggt gtccatagta  60
ttggaatggt tatttccttt tccatgtgta gccatgttca ccacccttct gatgttaata  120
ggaggattat tgggttatct ttatgggccc tattgggggc ttaggaaagt tccaggccca  180
ccaacgctgc cgctggtagg acaccttccc ttactggcta aatacggccc tgatgtcttc  240
tcactccttg ccaagcaata tggcccaatt tacaggtttg tactttacat aattgaatct  300
ggatagaagg cacttttttt taccatatta ttg                             333

SEQ ID NO: 144         moltype = DNA  length = 254
FEATURE                Location/Qualifiers
source                 1..254
                       mol_type = other DNA
                       organism = Glycine max
SEQUENCE: 144
taaaaatggt gtccatagta ttggaatggt tatttccttt tccatgtgta gccatgttca  60
ccacccttct gatgttaata ggaggattat tgggttatct ttatgggccc tattgggggc  120
ttaggaaagt tccaggccca ccaacgctgc cgctggtagg acaccttccc ttactggcta  180
aatacggccc tgatgtcttc tcactccttg ccaagcaata tggcccaatt tacaggtttg  240
tactttacat aatt                                                  254

SEQ ID NO: 145         moltype = DNA  length = 214
FEATURE                Location/Qualifiers
source                 1..214
                       mol_type = other DNA
                       organism = Glycine max
SEQUENCE: 145
ttggaatggt tatttccttt tccatgtgta gccatgttca ccacccttct gatgttaata  60
ggaggattat tgggttatct ttatgggccc tattgggggc ttaggaaagt tccaggccca  120
ccaacgctgc cgctggtagg acaccttccc ttactggcta aatacggccc tgatgtcttc  180
tcactccttg ccaagcaata tggcccaatt taca                            214

SEQ ID NO: 146         moltype = DNA  length = 174
FEATURE                Location/Qualifiers
source                 1..174
                       mol_type = other DNA
                       organism = Glycine max
SEQUENCE: 146
tccatgtgta gccatgttca ccacccttct gatgttaata ggaggattat tgggttatct  60
ttatgggccc tattgggggc ttaggaaagt tccaggccca ccaacgctgc cgctggtagg  120
acaccttccc ttactggcta aatacggccc tgatgtcttc tcactccttg ccaa      174

SEQ ID NO: 147         moltype = DNA  length = 223
FEATURE                Location/Qualifiers
source                 1..223
                       mol_type = other DNA
                       organism = Glycine max
SEQUENCE: 147
gtctctttcc tttggtatat acacactgca catgccaaaa taaaaatggt gtccatagta  60
ttggaatggt tatttccttt tccatgtgta gccatgttca ccacccttct gatgttaata  120
ggaggattat tgggttatct ttatgggccc tattgggggc ttaggaaagt tccaggccca  180
ccaacgctgc cgctggtagg acaccttccc ttactggcta aat                  223

SEQ ID NO: 148         moltype = DNA  length = 143
FEATURE                Location/Qualifiers
source                 1..143
                       mol_type = other DNA
                       organism = Glycine max
SEQUENCE: 148
taaaaatggt gtccatagta ttggaatggt tatttccttt tccatgtgta gccatgttca  60
ccacccttct gatgttaata ggaggattat tgggttatct ttatgggccc tattgggggc  120
ttaggaaagt tccaggccca cca                                        143

SEQ ID NO: 149         moltype = DNA  length = 103
FEATURE                Location/Qualifiers
```

```
source                  1..103
                        mol_type = other DNA
                        organism = Glycine max
SEQUENCE: 149
ttggaatggt tatttccttt tccatgtgta gccatgttca ccacccttct gatgttaata  60
ggaggattat tgggttatct ttatgggccc tattgggggc tta                    103

SEQ ID NO: 150          moltype = DNA  length = 63
FEATURE                 Location/Qualifiers
source                  1..63
                        mol_type = other DNA
                        organism = Glycine max
SEQUENCE: 150
tccatgtgta gccatgttca ccacccttct gatgttaata ggaggattat tgggttatct  60
tta                                                                63

SEQ ID NO: 151          moltype = DNA  length = 223
FEATURE                 Location/Qualifiers
source                  1..223
                        mol_type = other DNA
                        organism = Glycine max
SEQUENCE: 151
gatgttaata ggaggattat tgggttatct ttatgggccc tattgggggc ttaggaaagt  60
tccaggccca ccaacgctgc cgctggtagg acaccttccc ttactggcta aatacggccc  120
tgatgtcttc tcactccttg ccaagcaata tggcccaatt tacaggtttg tactttacat  180
aattgaatct ggatagaagg cacttttttt taccatatta ttg                    223

SEQ ID NO: 152          moltype = DNA  length = 144
FEATURE                 Location/Qualifiers
source                  1..144
                        mol_type = other DNA
                        organism = Glycine max
SEQUENCE: 152
tattgggggc ttaggaaagt tccaggccca ccaacgctgc cgctggtagg acaccttccc  60
ttactggcta aatacggccc tgatgtcttc tcactccttg ccaagcaata tggcccaatt  120
tacaggtttg tactttacat aatt                                         144

SEQ ID NO: 153          moltype = DNA  length = 104
FEATURE                 Location/Qualifiers
source                  1..104
                        mol_type = other DNA
                        organism = Glycine max
SEQUENCE: 153
tccaggccca ccaacgctgc cgctggtagg acaccttccc ttactggcta aatacggccc  60
tgatgtcttc tcactccttg ccaagcaata tggcccaatt taca                   104

SEQ ID NO: 154          moltype = DNA  length = 64
FEATURE                 Location/Qualifiers
source                  1..64
                        mol_type = other DNA
                        organism = Glycine max
SEQUENCE: 154
cgctggtagg acaccttccc ttactggcta aatacggccc tgatgtcttc tcactccttg  60
ccaa                                                               64

SEQ ID NO: 155          moltype = DNA  length = 288
FEATURE                 Location/Qualifiers
source                  1..288
                        mol_type = other DNA
                        organism = Glycine max
SEQUENCE: 155
atggtgtcca tagtattgga atggttattt ccttttccat gtgtagccat gttcaccacc  60
cttctgatgt taataggagg attattgggt tatctttatg ggccctattg ggggcttagg  120
aaagttccag gcccaccaac gctgccgctg gtaggacacc ttcccttact ggctaaatac  180
ggccctgatg tcttctcact ccttgccaag caatatggcc caatttacag atttcatatg  240
ggaagacaac cactaatctt ggtagcagat ccagagcttt gtaaagaa               288

SEQ ID NO: 156          moltype = DNA  length = 248
FEATURE                 Location/Qualifiers
source                  1..248
                        mol_type = other DNA
                        organism = Glycine max
SEQUENCE: 156
atggtgtcca tagtattgga atggttattt ccttttccat gtgtagccat gttcaccacc  60
cttctgatgt taataggagg attattgggt tatctttatg ggccctattg ggggcttagg  120
aaagttccag gcccaccaac gctgccgctg gtaggacacc ttcccttact ggctaaatac  180
ggccctgatg tcttctcact ccttgccaag caatatggcc caatttacag atttcatatg  240
ggaagaca                                                           248
```

```
SEQ ID NO: 157          moltype = DNA  length = 213
FEATURE                 Location/Qualifiers
source                  1..213
                        mol_type = other DNA
                        organism = Glycine max
SEQUENCE: 157
ttggaatggt tatttccttt tccatgtgta gccatgttca ccacccttct gatgttaata  60
ggaggattat tgggttatct ttatgggccc tattgggggc ttaggaaagt tccaggccca  120
ccaacgctgc cgctggtagg acaccttccc ttactggcta aatacggccc tgatgtcttc  180
tcactccttg ccaagcaata tggcccaatt tac                               213

SEQ ID NO: 158          moltype = DNA  length = 173
FEATURE                 Location/Qualifiers
source                  1..173
                        mol_type = other DNA
                        organism = Glycine max
SEQUENCE: 158
tccatgtgta gccatgttca ccacccttct gatgttaata ggaggattat tgggttatct  60
ttatgggccc tattgggggc ttaggaaagt tccaggccca ccaacgctgc cgctggtagg  120
acaccttccc ttactggcta aatacggccc tgatgtcttc tcactccttg cca         173

SEQ ID NO: 159          moltype = DNA  length = 178
FEATURE                 Location/Qualifiers
source                  1..178
                        mol_type = other DNA
                        organism = Glycine max
SEQUENCE: 159
atggtgtcca tagtattgga atggttattt cctttttccat gtgtagccat gttcaccacc  60
cttctgatgt taataggagg attattgggt tatctttatg ggccctattg ggggcttagg  120
aaagttccag gcccaccaac gctgccgctg gtaggacacc ttcccttact ggctaaat    178

SEQ ID NO: 160          moltype = DNA  length = 138
FEATURE                 Location/Qualifiers
source                  1..138
                        mol_type = other DNA
                        organism = Glycine max
SEQUENCE: 160
atggtgtcca tagtattgga atggttattt cctttttccat gtgtagccat gttcaccacc  60
cttctgatgt taataggagg attattgggt tatctttatg ggccctattg ggggcttagg  120
aaagttccag gcccacca                                                138

SEQ ID NO: 161          moltype = DNA  length = 103
FEATURE                 Location/Qualifiers
source                  1..103
                        mol_type = other DNA
                        organism = Glycine max
SEQUENCE: 161
ttggaatggt tatttccttt tccatgtgta gccatgttca ccacccttct gatgttaata  60
ggaggattat tgggttatct ttatgggccc tattgggggc tta                    103

SEQ ID NO: 162          moltype = DNA  length = 63
FEATURE                 Location/Qualifiers
source                  1..63
                        mol_type = other DNA
                        organism = Glycine max
SEQUENCE: 162
tccatgtgta gccatgttca ccacccttct gatgttaata ggaggattat tgggttatct  60
tta                                                                63

SEQ ID NO: 163          moltype = DNA  length = 223
FEATURE                 Location/Qualifiers
source                  1..223
                        mol_type = other DNA
                        organism = Glycine max
SEQUENCE: 163
gatgttaata ggaggattat tgggttatct ttatgggccc tattgggggc ttaggaaagt  60
tccaggccca ccaacgctgc cgctggtagg acaccttccc ttactggcta aatacggccc  120
tgatgtcttc tcactccttg ccaagcaata tggcccaatt tacagatttc atatgggaag  180
acaaccacta atcttggtag cagatccaga gctttgtaaa gaa                    223

SEQ ID NO: 164          moltype = DNA  length = 143
FEATURE                 Location/Qualifiers
source                  1..143
                        mol_type = other DNA
                        organism = Glycine max
SEQUENCE: 164
tattgggggc ttaggaaagt tccaggccca ccaacgctgc cgctggtagg acaccttccc  60
ttactggcta aatacggccc tgatgtcttc tcactccttg ccaagcaata tggcccaatt  120
tacagatttc atatgggaag aca                                          143
```

```
SEQ ID NO: 165          moltype = AA  length = 96
FEATURE                 Location/Qualifiers
source                  1..96
                        mol_type = protein
                        organism = Glycine max
SEQUENCE: 165
MVSIVLEWLF PFPCVAMFTT LLMLIGGLLG YLYGPYWGLR KVPGPPTLPL VGHLPLLAKY  60
GPDVFSLLAK QYGPIYRFHM GRQPLILVAD PELCKE                            96

SEQ ID NO: 166          moltype = DNA  length = 23
FEATURE                 Location/Qualifiers
source                  1..23
                        mol_type = other DNA
                        organism = synthetic construct
SEQUENCE: 166
ttctgcttca gcaatgttca ccc                                          23

SEQ ID NO: 167          moltype = DNA  length = 23
FEATURE                 Location/Qualifiers
source                  1..23
                        mol_type = other DNA
                        organism = synthetic construct
SEQUENCE: 167
cttgctggca aagtatggtc ctg                                          23

SEQ ID NO: 168          moltype = DNA  length = 23
FEATURE                 Location/Qualifiers
source                  1..23
                        mol_type = other DNA
                        organism = synthetic construct
SEQUENCE: 168
tttgttggct aagtatggtc ctg                                          23

SEQ ID NO: 169          moltype = DNA  length = 23
FEATURE                 Location/Qualifiers
source                  1..23
                        mol_type = other DNA
                        organism = synthetic construct
SEQUENCE: 169
ccacccttct gatgttaata gga                                          23

SEQ ID NO: 170          moltype = DNA  length = 23
FEATURE                 Location/Qualifiers
source                  1..23
                        mol_type = other DNA
                        organism = synthetic construct
SEQUENCE: 170
ttactggcta aatacggccc tga                                          23

SEQ ID NO: 171          moltype = DNA  length = 23
FEATURE                 Location/Qualifiers
source                  1..23
                        mol_type = other DNA
                        organism = synthetic construct
SEQUENCE: 171
gagctttgta aaaaagtggg tat                                          23

SEQ ID NO: 172          moltype = DNA  length = 23
FEATURE                 Location/Qualifiers
source                  1..23
                        mol_type = other DNA
                        organism = synthetic construct
SEQUENCE: 172
tctcctattt ctgcttctcc tct                                          23

SEQ ID NO: 173          moltype = DNA  length = 8218
FEATURE                 Location/Qualifiers
source                  1..8218
                        mol_type = other DNA
                        organism = synthetic construct
SEQUENCE: 173
atatttatat gatgtttcta tttctcattc actctgtctt ttatcacttt atctatcact  60
tatggcatta tgacatattt catttcgttc ttcgtgcctt tcaccagatt gatataccta  120
gcaagcgtgt atctgttcag caccaatcca tggtctgaag aatatttgcg gtagaatttg  180
aaatttctga tgatttttta ttcatctatc aagtttcagt aattacttgt aaggattctt  240
acgctttaag tagtacgtaa aagagacgat gaattatgtg taaaattaga gcgtgtttaa  300
tttttacttg ttaagcatac ttaaaagtta taagaccctc ctaagatata gattggtgtt  360
cagtgtgtta tgacgtgtta ttaaatagtg cccctgaatt gaattcctta atttgtgggt  420
```

-continued

```
gcccattact aacaatccta ggtcatgatg cagtatctcg cattctcctc gcctctattc  480
tagttctgta catataatat tgtcaagaag gttctggagt gacctgaaac atttccctgt  540
ggtccaataa tagttaattg agcctgatac gtgttagcat gtttggttaa ataggcctac  600
aacagtatca tttttcaata ttttattgat aataatggtc ataattaata tataaactat  660
tcttataact gtgtgtgaca acgtatattc aaagtggatt ccacagcaaa cagaaagcat  720
aaatgctgat caaaacaacc aaattaagta gaagagggtt catacttgat ggtgagtctt  780
atatactgta tatattatcc ctgtagtatt taggctaagg ataaagcaat taattatctg  840
agctatcggt gtcgtgaata aaccacgcct cattttcatg cctgggtata ggaataggat  900
gcatagtgga tagtgttgac tgtgtgttcc gattcaggtg aacgtgcatt tatacccccca  960
cccacacact ctcagaaatt aaagtccaca agtagtaaca ctcaacacat gcacgagctg  1020
cactaggtat agtatctttt caaccgaaaa ggatgcctcc tcccaatgct agctagctaa  1080
attattattt atttttcct tgccatgaaa acccataata aataaaaaga agatcttttt  1140
attattatat gacgaaaaga atgaagaagg aaacggattg gatacaaggg tatctaattc  1200
gcacatgtca tcattcaaat aaagacaaaa ccccatctct catccactcc ttaatactac  1260
tatatagtct caacctcaac caggaggcat caagagtccc cccaaaacca accaaccaaa  1320
ttaaagcctc actctctttc tcttcatttg tagattccta tactgttgca aggaaaataa  1380
aacaaagata gtatatacat ggtggtgttc atggattatt tggaatggtt gtttgcaatt  1440
ccaagtgtcc cttctgcttc agcaatgttc accctgcttg ctttaattgg aggattgttg  1500
gtttatctgt atgcacccta ttgggggtta aggaaggttc cagggccacc atctctgccc  1560
cttgtaggac accttccctt gctggcaaag ttgtgttctc agtcctcgcc aagcaatatg  1620
gtcctattta caggttagta tgcttacatg tatttggtgc aacatatata gtcaattgat  1680
gattaatttg atagtatata tttatgctat ttttcttccc cggctttcat tggattgata  1740
acagaaaagg gtcgttagtc ttgattggat atcgatcttg ttgtatttat gtccattcaa  1800
atgcctcaaa ctccttttgg agaatgatat gatcttaggc agaatcacga tggcagacta  1860
aggttggttg gttgagtctt gtgtgtggtt ttggtattgc cccggaggaa ctagctacaa  1920
atattaaaaa agtgattatt atatgatcca agtgtcctac ttgttcttgt ttactcagat  1980
gcttgcttgc ttccatacaa taaactgaaa aagggcccag cgccagcgtc gtatgctttg  2040
atgtctttct cgacccgggc aataaaaccg aatatgttta agagaaaata ttttatgttg  2100
taaaactatt ttatttcatc atctaactat aaattgttat atcatctaat cacaaataat  2160
atagacttat aatatataat actttcctat tcaatgaaaa tctaaaactg ttatgcacat  2220
tttgagtata taatttattt tctattttct aatatttttt tgttattaag cgatttttat  2280
atgaagccgc caaataaaca gtgctggatt gggaataaga tctctataac ttaagagtgt  2340
cgataaatgc ctactttgga gagaaattat catatgtaat agtgtaatac gattctcaac  2400
aatttttaca tgatgtataa ttgattattt attaaatttt taaattaaaa acttaattaa  2460
atgttacata gaaattaatt gaaactatta tgatcataga caatctctat atgagtaact  2520
caattatgta tcatgtatag attaactgaa actataaaaa tataaggtgg tagccctaga  2580
agacctaaat catataataa tttatccatt gttaagggtg ggaagatgac agtaaaaaaa  2640
aaaaagtggc aagatgcatg ggagatatga agaaaaaatg tagaaagaaa gtgataaatg  2700
ttaaaagtaa ttcaatagaa aaagaaatga aaagatataa agaaaatgga gtaaaattga  2760
tatggatcgg aaaagaaaat gtctattttg taagagtttt agatatagta ggtgaaaaaa  2820
gagtacaaaa acttattaaa tacacgtgga tgtgttatat tggttatttg aaaagttata  2880
taatttgtgg aaataaagaa aagagttttg gatgggcgtt cgtgcaatct gttttcgtaa  2940
caaacaggat ttccaaattt ataattttc atcatttaat aggtcctacc acgattgata  3000
aataactact cctcctaaaa caggagtatt atgtattcta ttgcatcctg caaggatatt  3060
attggtcctt ggtgctcata aattgtaggt tccctttatg tgaaaatttc ttggagtgac  3120
taccgttaag caaatcattt cggaatccga gctagttatt aatgtcccac gataaacaaa  3180
aattactatt taggcaatct atctatcagc ctctcctaaa ataattcctt ttgttcataa  3240
aatttagatt tggtgtattg ttaatataaa aattatatag acatttaaga gaatatatca  3300
taatgttaat taattataat tagtataaaa ccttcttaca tattgtacca aaacaacaac  3360
ttttaatatt attgacatta cattaaaata aattatcata gttaaggtct taagctttgc  3420
ttatattgtg tctttttaag gctttaagca caaaaagtat gtttattcca catttcaagt  3480
ttataaaatt aagctttata tatatatttg ttaaaagtat ttagttattc tagcaagaca  3540
ttataattta atatattgta tatggcatgt attgtaacca taattccaac agctaattat  3600
ttacacaata acatttatca tctaacaaaa tattaataaa ctaataatta atatttattg  3660
ataaaaagac acactcaaca aatagtgcca gcagtgcatg ctagatgata gaagtgaaaa  3720
gtggaaaaaa tgaagaataa tcagcactga ttatcagtca tttttaacaa ctctttttttt  3780
cttttttat tcttattaag cagcacgtgc taagtttcat aaaacctttt ggggttggcg  3840
cttcacacat atatactagc tagtagttaa cagtagctgt tttttcttag ttgagctgat  3900
tctttattcc atgattttcc tggttatggt tgtaaatgat gttcttatta tttattggtg  3960
cagattccat atgggaagac agccactaat aattatagca gatgcagagc tttgtaagga  4020
ggctggaata aaaaaattca aagacatttc aaacagaagt attccctcac caatttctgc  4080
ttcccctctt caccaaaagg gcctcttctt cagccggtat gcaaattatg acccaacagc  4140
tttcaataat agtaatgtta tttctacaat ttggtagtgt ttgccaagta atttcagcag  4200
ttataaacaa ctttaactaa cttataagtt aatttgacta aaattatatt ttcttaaata  4260
atcacttact tttcatatat tgtagaatga gaatttaagt tatacaattt cattttattt  4320
tcctttata gcaaaaaaat atttctctc tttttatca tccccaataa ttattgatgt  4380
ttttgaaatg atttttctaa tcaaaatttt taatcttcac atgtcaagcc cattgggggga  4440
aagaagtata aaccaaacag gaaaattaac acgggtgctg gtgcttttt ttccccccttc  4500
aaaactaaga taattagcaa tgattatttt cctccaaata tgagaggcat gaagtgacat  4560
caagttatac agtatactag taatatttct ctgttaataa tgccataaca tgaaaaaagt  4620
ggtagcacgt tgtgttggag ttacatcaaa caattatgcc aaatgctatt atatgcatac  4680
agcatggtat tgaagatgaa aagaatgaat gagaatgaga ttaaaaaata taataattat  4740
ataacatttt tttattatat ttcttatttg tcttatattt ttctttcctt tcaattttat  4800
ctttttacat gttctattta atctgtcttg taactataga aaagggtcat aaaaatataa  4860
tatatcaaac aaaagaataa ctttaattaa atccgatata tccccaatta atgatgattc  4920
aatatattat aaatatatga gtaatttata tctgtagtca atttatcatg cataaataca  4980
tgacatttta ctggttcagc acagaagtta ttatgcaatt atttgtagac ttcttgccaa  5040
aagaagttgt aattttaagc tggatcaatt ttagactttt aatttgtgaa ttagacaaaa  5100
taaatcagaa tttgagcctt aaaaaatgtg agtatgtaga taggaaatta atgcatcacc  5160
```

```
agttttttaa gaactgcaga aaatcttagc taggtataat tttataactt tgagccaagc  5220
aataattgga ctttgaaccc tgtataagat gttttgaaac agcagatgat cgtaatgcaa  5280
atgtaaaacg ttgcctgttt agcaaataaa tacaatagta cgttaaacaa tcctttcaat  5340
aattaaaaat gaaggtacaa aagactacca catgcattaa caacggctga taagaggttt  5400
tacgaaattc ttacaaagag aaattattaa tttcaagaat caaatgtaaa tgttactggc  5460
aaagtgctac aacggctgat aagaggtttt acaaaattat tactaagaga aattatcaat  5520
tgcaagaatc aaatgtaaat gttactagca aagtgctaga attttttgtt gaaaataaat  5580
aattagtcta tgtaatgtta ctcgttttac cgctttattt tatatatata tatatggatt  5640
ttaagtttta tctttatacc tcagtcaaaa aaaactttta tctttgtaat tcttaataaa  5700
tgttgatctt tgttttccat gaagaactta tttatttcta atagtgttta attgacaaat  5760
catcattgct taagggaaaa aggttaatac aggtaaaagc ataggagtca acatgccaat  5820
aactaaaaga aagggggtgg ggaataaagt aaaactacat gagttaacta ttaattttaa  5880
ccacaatctg ttttggtaat gtcaccaccg agtaaaaatt gtatgatgca cacaagtgaa  5940
tcacatgaaa ttttaacgga tctgccttta agttgtacaa aagctattct ttagatactg  6000
gtttctactt tctagtggtc cactaagttg aatatcattt tcttttcctt ttgtgatcat  6060
tagtcgtgaa atccatacgt cagagcccat gtgccctgca tgttaatgct tctccaaaaa  6120
ctattatagt gctatgctaa tcctctataa tagtcaaatt caaattcacc caacttcatt  6180
tcaaatcaaa tattcaaaca gtttcttgca aattgatggt gcagggattc acaatggtct  6240
accatgcgaa acactatatt atcaatgtac cagccatcat acttgtccag attagtgcca  6300
acaatgcagt ccttcataga atctgcgact caaaaccttg actctcaaaa agaagacata  6360
attttctcca acctgtccct aagactagca actgatgtga ttggacatgc agcatttggt  6420
gtcaactttg gcctttctag gccacattca gtttgtgatt ccatcaagag tgttaatgtt  6480
aacaataaca ataacaatgc aagtgctagt agtagtagta atgataatga agtatcagat  6540
ttcatcgacc aacacatata ctccacaaca cagctaaaga tggacttgtc tggttccttg  6600
tccattatct tgggtctgct tttgccaata cttcaggagc catttaggca gattctgaag  6660
agaattcctg gcaccatgga ctggaagatt gagcgtacca accagaaact aagtggccgt  6720
cttgatgaga ttgtggagaa gagaatgaaa gacaaggcac gaagttcgaa ggatttcttg  6780
tcactcatac ttaatgccag agaaacaaaa gctgtttcag agaatgtgtt cacacctgac  6840
tacataagtg ctgttactta cgagcaccta cttgctggct ccgcaaccac ttcctttacc  6900
ttgtcttctg ttgtctattt ggttgctgga caccctgaag ttgagaaaaa gttgcttcat  6960
gagattgatg ggtttggtcc agtggatcag atacccactt ctcaagatct tcataacaag  7020
tttccttatc ttgatcaggt ttgttaaaat gaataccaaa atctcaagac aagtttgatg  7080
ttccaacttg caagggcaaa gtatgtagat tcattgttat acttttgtat gctctaactc  7140
tatttaatta atgcaggtga tcaaagaggc catgaggttt tacactgtct ctcccttagt  7200
tgcaagagaa acatcaaatg aagtagagat tggaggctat ctccttccaa aggtaataca  7260
aaatacaaaa tactagtact acacagttac ttataaaaaa agaaaataaa tccaattaag  7320
gaggtaaaat taataaataa aatctcataa ttaagttaaa taaacgtatg gtgtgtttgg  7380
ataaaaagat ttcatgactt aaaatcaact tatatatttc aactttcata aaaactctat  7440
ctttaactac ttcaaaaact tttgtttaac ttatccacat gtcaaggtgc taattgttaa  7500
aaaaattatc caaacagacc atccaggact gtcttttttg gtatacatac tcttcacaaa  7560
tcacaaccaa attaacgaga gtttttactt gtgctgacac tatatatggt tttgtgtatg  7620
caggggactt gggtctggtt agcgcttgga gttccagcaa aagaccccaa aaactttcca  7680
gagccagaaa agttcaaacc agataggttt gaccccaact gtgaagaaat gaaacgaagg  7740
catccttatg cttttatacc atttggaatt ggtcctcggg cttgcattgg taaacaattt  7800
tccctacaag agatcaagat ttctctgatt catttatatc gaaaatactt gtttcggcat  7860
tctcccaata tggaaaaccc cttagaactc cagtatggga tagtcctcaa cttcaagcat  7920
ggggtcaagc tcagagtcat aaaaagaaca gagacttgct aagtaaacgg ttcagacatg  7980
gcttatacta gtacagagtt cagaagatga attataagat ggagtgtgct aaaatccaat  8040
aatgaaaaat tgtaatgtta cgcagaatca gccaataagt gtttaaaata ataaggtcaa  8100
agagtgtgtt tgcatttccc aaatatagaa ttgtaagttt ataagagtaa gagacactct  8160
tcctacaaga ttatgaatga cattatcatt tgtggtaaaa aaaaacactc aaaagcat    8218
```

```
SEQ ID NO: 174          moltype = AA  length = 86
FEATURE                 Location/Qualifiers
source                  1..86
                        mol_type = protein
                        organism = synthetic construct
SEQUENCE: 174
MVVFMDYLEW LFAIPSVPSA SAMFTLLALI GGLLVYLYAP YWGLRKVPGP PSLPLVGHLP  60
LLAKLCSQSS PSNMVLFTDS IWEDSH                                     86
```

```
SEQ ID NO: 175          moltype = DNA  length = 10866
FEATURE                 Location/Qualifiers
source                  1..10866
                        mol_type = other DNA
                        organism = synthetic construct
SEQUENCE: 175
cccccccccc caaattaata aagccgctct ctttctcttc atttgtagat tcctatactg  60
ttgcaaggaa aataaaacaa acaaacacac atggtattca tggattattt ggaatggttg  120
cttccaattc caagtgtccc ttctgcttca gcaattgctt gctttaatag gaggattgtt  180
ggtttatctg tatgcaccct attggggtgt aaggaaggtt ccaggcccac catctctgcc  240
ccttgtggga caccttcctt tgttggctaa gtatggtcct gatgtgttct cagtccttgc  300
caaacaatat ggtccgattt acaggttagt ttacttacat atatattaat cgtcaattga  360
tgatgatgat caatttgtta gtatatattt atgccatttt tcttcccctt cactggattg  420
ataaggaaaa aggttgttag tcttgattgg atatcgatct ttttgttttt atgtcctctc  480
aaatgcctca aactcctctt gaagaatgat atgatcttag gcagaatcac gatggcagat  540
aaattttgac ttgagaaggt tggttagttg tgtcttgtgt gtggttttgg tattggtatt  600
ggtcgctgtc tctatgtcta tgccccgaaa gaagtagata caaatattaa aaaagtgatt  660
attctatgat ccaagtgtcg tactcgttct ttgattactc agatgcttgc ttgcctccat  720
```

-continued acattaaact gaaaaagggc ccagcaagcg tcttatatgc tttggtgtct ttctcgactc 780
aggcaataaa ccaaatattt ttatgataaa atattttatg ttgcgacttg gaagaatata 840
aaactgtttt tcatactcat ctgattataa attatcatat atataataaa tttattaata 900
tttataataa atattttaaa atttttaatt ttaatttatt aacagtgtaa attttattac 960
atcgacaaca tatgattact ttaaacttta ttttttaata agtttaataa ttatatatta 1020
ataatataaa gtaattttac attgtggatt aactacaaaa taaggttgat gattttgtaa 1080
gtagtcattt tatgtaaaag ttaatatata atatataata atctgtggtg gaatgaaaac 1140
ataaaaatat tttaaagagt aaatgtataa tctatatttt tttctttttt taatattatt 1200
ctgtttctaa ttctgttatt tagcgatttt tatatgaagc cgtcaaataa acagtgccgg 1260
attgggaata atatatctat aatttaagag tgaccataaa tgcctacttt agagagaaat 1320
tgtcatgtct aatatgattc taaatttctt ttacatgatg cataattgat tcttcctttt 1380
gctattatat gactcaagtt taaaataatt tgttttttta taatatttaa cttataatat 1440
ttcttttatt aattattttt atattaaaat attctttatt aaaaaaagtt aatatattga 1500
caaactagaa gagaaaaaaa tattaatgac aaaagtaatt ttaaaaatat tataaattta 1560
agataaattt attattatca actaaataaa tcactttcct taatcttaat aaaataaata 1620
attgagtttt atgtaataac gaagggagta tttattaact ttttaattaa aacttaatta 1680
aattttatat agaaattaat tgaaactatt actatcttaa acaacttcta catgaataac 1740
tcaattatgt atcatggatt aactgaaact ataaaaaaat atgcagtagt cctaaatcac 1800
atgataattt atccattttt agatggattg gggtgggaag atgacaataa aaaaaaaaag 1860
tgggaatatg cgcgactgca tgagagatgt gaagaaaaaa aaagtagaga tatgaagaaa 1920
aaaaagagta gaaagaaagt gatgaatata acaagtaatg caatggaaaa gaaaagaaaa 1980
aaatggagta aaattgagat ggaaaagaaa atgatttttt cgaaacagtt ttaaatagta 2040
cgtgaacaga cagacagtac aaaaacttat taaatacacg tgggtggtta tttgaaaagt 2100
tatatattta atggaaacaa agaaaagagt tttggatgcg cgttggtgca atctattttc 2160
gtgacaaaca ggatttccaa atttatattt tttcatcatt taataggtcc taccactagt 2220
catgtcaatg gaccgggctg cggcgccaac tactgtcccc cttcgcgttc ccgcccttca 2280
actaaccccg tccttgtctc tcatttttgt tctaggattt ttttttctgt tcccattcct 2340
gcgggtttct ttagtcttct cttcgtgggg cctcaatttt tttaaaaata ttaattttaa 2400
atttcaatac aaatcaattt taagaagact taaaaaatcc aaatactatt aaacttaaat 2460
aaataaatat ggacaacaag tttaatttaa aataatacaa acataatatt caataataat 2520
ataaatagtt ttaactacaa atattttctt ataatatctt aaacaaccag taaattgaag 2580
tcctctaatt ttgaaaccaa caagtcaata actctctaat attgtaagtc agtaaattaa 2640
taatatatta gtatatcatc attcatgttc tcaacaatag attcaaataa atgtgttatg 2700
tttgaacaac ctaacaaata aaaaatcaaa taaactttca agtcatttaa gaaaattaag 2760
tgaattatat atatatatat atattacctt gcatttcttt acgtaattaa ttttgggtac 2820
acattaaagc ttctaaatga tctttgaaag aaataaaaaa aagcctaagt aatcaaaaca 2880
tgaaaacaaa cttgaattta aactaaaaac ttgaatctga gcaaccaact aaccaaagaa 2940
aatataaaat taaaactttc aaatgtaaaa cataattttg aaatgatcaa gcaaaatcat 3000
gagaaaaaca ataaagacga tatatagtaa acaaatctat tggtaagaag agagtaacta 3060
gtacttacac ttcaaggtga ctgtgggatt tgggaagaaa taaacgacat ggcaaggttt 3120
aggataaaaa gtaaagtgaa taagttattt gagagtttga gttttaagag taattgagtt 3180
gttaggattt tttaaaatat aaggataatt ttataatttt ttcaaatcaa gtatacacgg 3240
tggtaggggg tgatccttgt ccctgccgta gccgctcgaa aatatttatt cctgtttcca 3300
ttctcgttgg ggaaaaatcc caatctattg ggcccaaaac aagacagaaa tttccgttta 3360
taatacaaat tgacatccct accattgata aataactaca ttattatata ttctattaca 3420
tctttggagg atattattgg tccttggggc tattaaatta taggttccct ttatatgaaa 3480
atttattgga gtgactatcg ttaagcaaat catttcggaa tccaagctaa ttattaatgt 3540
gccacgataa aaaaatcatt tattaaggca atcaatctat catcctctcc aaaaataatc 3600
cctttttcat catagaattt agaattggtg tattgttaat ataaaaatta ctatataaat 3660
atttaagagg atatatcata atgttaaata gtataaaacc ttcttatata ttgtacaaaa 3720
ataataactt ttaatattga cattacatta aaataaatta ttatatttaa ggtattaagc 3780
tttgcttata ttgtcttttt aaggcttcaa gcacaaaaag tatatgttta ttctacactt 3840
aagtttataa aaataagctt ttaaattata tatataatat actttttgtt aaaagtattt 3900
agttattcta acaggacatt atagtttaat atataaagta ttttatatag cgtgtactgt 3960
aacgatactt taacacctaa atatatgcat gatagtattc accatttaac acaacaaata 4020
attgatataa gattaatttg atgaaaaaaa aaagaaaaag agattataca ttcacatttt 4080
tgtgctaaca aaaagaagct aacaaagaca ataaattaat aactgatatt ttttaattaa 4140
aaaaacactc aacaaacaaa ttaatagcta atatttttaa ttaaaaaaac actcaacaaa 4200
tagtaactga tatttttcaa ttaaaaaaac actcaacaaa tagtaactga tatttttcaa 4260
ttaaaaaaac actcaacaaa tagtgctagt agtgcatgct agatgataga aggaaaaagt 4320
ggaaaaaatg aaaaataatt agcacagtgt gatatcatat caatgtacca aaaaatatta 4380
ttatcagtaa tttttaagca gcacgtgtta agtttcacaa aacttgttgg ggttggcgct 4440
tcatatatat atatataggt cattgctcca gtagaccatt ttgatatatg gtctattttg 4500
gacaagaatt gttagccgtt agattaaatg gttattatag gctagcacac cggattctgc 4560
aaccctctcc caccaatttt gttgaggtcc atggccatgt ggtaaaagat gtaggagagg 4620
cattcaggtt gtggaggacg atggtgtctg gggggatggag gaggaggtgc tcgcgctagt 4680
tacagacgtt gtcgatttgg aacccgaaga agagggccaa ccagtccaga aggtggtcag 4740
agatggaggt ggtcgaatgg gtgggggtaa tcgaacgctg ccgccggagg gaggtggggg 4800
aaaaggcaga gaaaggtaag ctgccggaga aatgagtgag agaggcttgc gggattgagt 4860
atgctgatct ataataatca tttaatccaa cggctgaaaa ttattatcca tagtggacga 4920
tctttcaagt ggtccacgct agccttgatc atatatatat atatatggga gggagtttac 4980
ttgttctaaa gatatttttt atttttatca tttttttttag atgatcttaa gaaaataaat 5040
aataaaaata aaaaaattat tttttagagt aaatggatct ctatatatat atatatttaa 5100
atgtaactgt tttttcttaa aacgtggaag aatttatttt gaattttttg acattttttt 5160
aggtcacatg ttaaaatata agatataaga atttttttat atttttattc tagttataaa 5220
atcctattta agttcttgaa ttttactttc agacaaaaat aataactctt ttttttttca 5280
aatgaaatta aaaaacaata tttttgaca aaagtgaaat ttttggattt tttttcttct 5340
aaaatccaac ctcaaactga tgctcttaaa caataatact aataaatcat aagaagaaga 5400
gttcttcagc tcaaaaaacc taacttaaaa attcctatta acaatgttat tacttgcatt 5460

```
gtttctttat cccatgattt ccctagttat ggtcgtaaat gctgttctta ttatttattg  5520
gtgcagattc catatgggaa gacagccact aataattata gcagatgcag agctttgtaa  5580
ggaggctgga ataaaaaaat tcaaagacat ttcaaacaga agtattccct ccccaatttc  5640
tgcttctcct cttcaccaaa aaggcctctt cttcagccgg tacgcaaatt acgactcaac  5700
agtgttcaat aatatagtaa tgttatttct acaactagtg tagtgtttga taagtaattt  5760
cagtacttta taagttgttt tgactagttt ataagttaat tgaactaaaa ttatactttc  5820
ttaatttaat cacttccttt tcatatatat tgtagaatga gatttaaaat tatactattt  5880
tattttattt ttcctttttaa tgtaaataaa ttacagattt ttctctctct ctctctctct  5940
cttttatcat aaaaaaaccc ataactattg attttttttta gatgcctttt ttgaagaagt  6000
ttagaaattt tcaagctttt taatcttcac atgtcacgcc ttattggggg aaaaaagtat  6060
aaactaaaca ggaaaacacg ggtgctagtg cttgttttcc tcttcaaaaa aataattatt  6120
atagcaattg gttattttcc tccaaatatg agaggaatat gaagtgacat aaacttatac  6180
agtataccag taagagttat atttttcata cttcaatttt taggaactgg atcctctcca  6240
gccctctcca gcaaaagcat atgagccact ggattaattc aatgattcca attttaaaag  6300
aaaaacatga caaacaagga tgcatactca cgtttctttt gccattcaaa tcttatcaat  6360
attaatacaa agaataagct atcgcagagc aaaactctaa actccataat aaaatattaa  6420
aattatattt caccatcagt catcgataat agtaaacaaa aaataattac aaaattatgt  6480
aaattagaaa atattaatga gttaaaaaat taagaacaaa aatgaaaatt gatctttttt  6540
tacattatat tccaatttaa attatttatc atgaatataa aatactacta tactctatat  6600
ggttaaatat attatttatt attaatttaa ttatatacaa atatttataa tgtccgattg  6660
taatataaaa tttatatttt aattaagaag gtttcattct ctaaattgta tactttaatt  6720
tttataatat ataaataaat tataacttga ataacttatt tgattattta tcttattatt  6780
tttgtttggt ttgatttttt atcgtttaaa aagtttaatt taattcttta tcttattttt  6840
ttagtttaat tcttaatatt tttaaaaaat ttatttgatc ttttatcttt tttttcaaaa  6900
cattttgtta tttttttttta ttgtttagtt tggtctttga atttatttaa gattgacatc  6960
attaaattta tttatgattg acatcattaa ttatttaaaa atatattttt ttgttaagtt  7020
ttctcccttt cttctccaat tcattttgaa aataaaaatt ttattcttaa atgattaaca  7080
acattaatct taaatgcact gaaagatcaa tctgaaaaaa aaagataaat gacaaaatta  7140
tttttttttaa aagataaaag actaaattaa aaaaaatcaa attaaacttt taaaaagata  7200
aaatactaaa ttgtaaaaaa aataagataa ataataaaat atttttttta aaaaaatata  7260
aaaaactaaa ttgaatcaaa taataagata aaaaaccaaa tattcgttct aaattatatt  7320
atatctatac acatggttta gtttggatta tattttaaaa ttcaaattag tgttgttaaa  7380
aagttcagtt tttttttttca agtcttaata atttaatttt tttaacttac accaattcat  7440
aattatgttt ttacctacta ttgttattat tatttgtagt ggtccactat gttgaatatc  7500
attttcttttc ccttttgtgg tcattagtcg tgaaatccat acgtcagagc ccatgtggcc  7560
tgcatgttaa tgcttctcca aaaactatat atatatatat atatatatat atatatatat  7620
gtgtgtgtgt gtgtgtgtct gtcatataat agtcaaattc aaatacaccg acttaattca  7680
tttcaaatca aaattttaaa gagtttcttg caaattgatg gtgcagggat tcacaatggt  7740
ctatcatgcg aaacactata ttatcaatgt accagccatc atacttgtcc agattagtgc  7800
caacaatgca gtccttcata gaatccgcga cccaaaacct cgactctcaa aaagaagaca  7860
ttatattttc caacttgtcc ctaagactag caactgacgt gattggacat gcagcatttg  7920
gtgttaactt tggcctctct agtccccatt cagtttgtga ttccatcaag aatgttaatg  7980
ttaacaataa caataacaat gcaagtgcta gtagtagtaa tagtaatgat aatgaagtat  8040
cagatttcat caaccaacac atatactcta caacacagct taagatggac ttgtctggtt  8100
ccttgtccat tatcttgggt ctgcttttgc caatacttca agagccattt aggcagattc  8160
tgaagagaat tcctggcacc atggacagga agattgagca taccaaccag aaactaagtg  8220
gtcgtcttga tgagatagtg gagaagagaa tgaaagacaa gacacgaagt tcgaaggatt  8280
tcttgtcact catacttaat gccagagaaa caaaatctgt ttcagagaat gtgttcacac  8340
ctgagtacat aagtgctgtt acttacgagc acttacttgc tggctcagca accacgtcct  8400
ttactttgtc ttctgttgtc tatttggttg ctggacaccc tgaagttgag aaaaagttgc  8460
ttcatgagat tgatgggttt ggtccagtgg atcagatacc aacttctcaa gatcttcatg  8520
acaagtttcc ttatcttgat caggtttgtt caaaatgaac acaaaatctt agacaagctt  8580
gatgttccaa catgcaaggg cagagtatgt agattcatta ttataatttt gtaagctctt  8640
aatttaatta atgcaggtga tcaaagaggc catgaggttt tacactgtct ccccattagt  8700
tgcaagagaa acatcaaatg aagtagagat tgggggctat cttcttccaa aggtaataca  8760
aaatactaca caattatcat aacaggtgaa tataaatttc ataaatgagg taaaataaat  8820
aagtatataa aattcatgat taagttaaaa aaatatatga cgtgtttgaa taaacttgtc  8880
catagcactt ataaaagaag aaaaaaataa ttgaactttt ccatgactta tgtatttaaa  8940
cttttacaaa aactttttta tttaactaca aaaactcttc tttaacttct ccacatgtca  9000
aggtgcataa ttgttataaa taaaatataa aaaaatccaa actgaccata cagaattatt  9060
attgtttggt atacacactc ttcacaaatc acaatcaaat taacgagttt ttacttatgc  9120
tgtcactaaa tatggtttta tgtaagcagg ggacttgggt ctggttagca cttggagttc  9180
cagcaaaaga ccccagaaac tttcctgagc cagacaagtt caaaccggag aggtttgacc  9240
ccaactttga agaaatgaaa cgaagacatc cttatgcttt tataccattt ggaattggtc  9300
ctcgggcatg cattggtaga caattttccc tgcaagagat caagctttct ctgattcatt  9360
tatatcgaaa atacttgttt cggcattctc ccaatatgga aaacccctta gaactccaat  9420
atgggatagt cctcaacttc aagcatgggg tcaagctcag agccataaaa agaaaagagg  9480
cttgctaagt aaacagttct gacttcgcat tatcgcatat actagtaaag agttcagaag  9540
atgaattatg cattattatc ttatagtaat attgagtgcg ctaaaatcca aaaacgaaca  9600
attgtgatgt tacatagaat cagccaataa gtgtttaaaa ataataggtc aacgagtgtg  9660
ttattagcat ttcccaaata tagaatgcaa gtttataaga gtaagagaca ctcttcctac  9720
aagattatga aatggcatta tcatttgtgg taaaaaaaac tcaagggaca aaaaaatccg  9780
tctaaatgtg ttaaccaaag gagtgtttcc ccatatagtt atgcttaagt tgatttatct  9840
ggataagcct ctcagcactg agtaatatca aaacccacaa ataaacaatt atacaaaatg  9900
gagacccctc acaagtattc ccaaacacaa aagctacttc tagccagcta actaactcaa  9960
tttaaattgc atggaacaac aagatgttga acttcttgga aaaaaaaata ataacaataa  10020
atacacaaag atgtcgagct tccaccagat tctatccctt tcaccgtgcc atcactgaac  10080
tcttgtccaa gtgaagtggc ctagaaaagt tgattgaagg gtcagaatcc gcagtggaga  10140
aaaccgctgc cctcttgagg aattgaaacc catccatgga ttgctgcctc tgagctctat  10200
```

-continued

```
tatatacatg attgccactt gtcttttgct ttgcctttgt ggactgagtc aggttcatgt  10260
aattaggcct agcaacaaca gcattaccat tactatcctc agtcctgtca caagtgttcc  10320
cagacattgg tgttgtggat gtacaaatgg aagatgatgc agaactctca tcgtatcgaa  10380
actcagaact tggacttgag gataagcgag tagcttgccc aacaaggggt ggcctagctg  10440
aaatccttgt tgtgacgttg ttcttcttga ctttgaccat gctttgtttg gaattagagc  10500
tcacaaagga ttccacaaac ttctttggag gtggggtttt atctaaggct tcagcctgag  10560
attgtgattg ttccatcaat ctactctccc aaggctttgc tgccatccaa cgctccaacc  10620
aactccaccc acagttagct ttgttcatct catgactctt aagagaggta aatgaggcac  10680
gtgttcgtgg attagggctt ggtattgatc tgcattgctg gaaattacat gcatatcaag  10740
aatgttaaac atctttctaa actagaaaaa aagtggctta gtttatagta ctttgttata  10800
gcctgtttga attcaaatta tatatatgat ttagaatgac attgaaatgt caattaacat  10860
gatttt                                                            10866

SEQ ID NO: 176         moltype = AA  length = 59
FEATURE                Location/Qualifiers
source                 1..59
                       mol_type = protein
                       organism = synthetic construct
SEQUENCE: 176
MVFMDYLEWL LPIPSVPSAS AIACFNRRIV GLSVCTLLGC KEGSRPTISA PCGTPSFVG   59

SEQ ID NO: 177         moltype = DNA  length = 6482
FEATURE                Location/Qualifiers
source                 1..6482
                       mol_type = other DNA
                       organism = synthetic construct
SEQUENCE: 177
actcctctaa tttcaggaac caaaaaacct tagtctctgt ctctttcctt tggtatatac  60
acactgcaca tgccaaaata aaaatggtgt ccatagtatt ggaatggtta tttccttttc  120
catgtgtagc catgttcacc acccattggg ttatctttat gggccctatt gggggcttag  180
gaaagttcca ggcccaccaa cgctgccgct ggtaggacac cttcccttac tggctaaata  240
cggccctgat gtcttctcac tccttgccaa gcaatatggc ccaatttaca ggtttgtact  300
ttacataatt gaatctggat agaaggcact ttttttacc atattattgg tataccgata  360
ctaatcatgg gttggagaac ttaatcactc actttatag tgagatcttt ctttttaatt  420
atgtttttt ctttcacaaa tctcgaacct agttcaatat tattcgaacc aaaatgactt  480
actagttaga tagcagacaa ttacagctta atcaatttga tttgttgaga tcattctcat  540
tttcttcatc ttcttctctt catgagaagc taaaaagaaa atctgttact gctgatatga  600
tacccaactt gaatatatga aattcaaaat gcataaaagt cctgttgggt gtggatgata  660
tttggtcatg taatgatggg ggttatatat ggttgacttg tgaagggtat atatatgatt  720
atggtggtgg tgggacagtg ttttagtgca tattgcctgg gaagaagtag atataatcac  780
ataatttgga aaaaaagtta acgttctgtt gtgatctatt tgtgcttgtt tgtcaacttg  840
attaaatatg ataagaaaca acattagcat cagcatgccc gtcctatagt aacatgatta  900
aattgctctt gataaatatt aagagtgtcc tcaattgtat gcacataacc ttctaaacaa  960
agatcttgtc gttgtccttg atggcagaag aatttgagtc ctttaaaagt gaacaaagca  1020
tctaacacaa aaataaaggt aaatgcatag ttgatttgaa taaagtactt tataaattta  1080
tttaattttg agttagtgat ggatgcacgc ttacttttgt ttatgtaaat aatgcatatt  1140
tacttttctc attttgcaca agtacttcgc tagatccatg gtcataaatg aatcaagata  1200
agtagagtaa tttaagttta agcttgacat ataaaaaata ttatttattt aaatgaatca  1260
aagttaaact ttagacttgt ttgaagatag acagcctgaa ttagaatcta cttagttgat  1320
aatttaattt ttgttccttt atcaaatatt tttttgaaac atttttaaat ttattaattt  1380
attatttagt aaatgaattt tcgtactaaa aataaagtaa aaataagaga aaaataatta  1440
gatgtaaaaa ttacatatta attatttata acaaaaaata taatatatta aatatatctt  1500
tctcacattt aattttttt atcttcaggc acacatataa cactcacact caactttta  1560
gtatcaagtt tataaacttt gaactggagt gatttttata attataaata gaattaaatt  1620
tgagtttatt ttcttaataa aataaaataa ttttattgga catttaataa atcgaatctg  1680
gatagcaaaa atataagttt tagagcttaa ttttaaatta tttctcattg ataaaaaaat  1740
attattaaga taattattat aaaaattaac aaattataat atataataat ttgatactaa  1800
ataacagtac aaattctata agtgcatata tagtctactc taaattttat gcagttcaat  1860
tttacaaccc tgatttatca ttgggtgatt aattttctat ccaacagaac aattttttt  1920
tttttagaga ataaaccttt ggttattctg gtaaacgcct tacgcgcgtc tgattttcaa  1980
aactcaaaag tcaaaaggga cattttgctg cgattttaat cattgtgtac ggaaaacttc  2040
tagcactgtt tgcagaggat tattaagtta ttaaaaaaag tatacattaa acataattta  2100
acatggaaaa agaagagaaa ggaaaagatg aatacgaatt aatgtgtgat ttcatatatt  2160
attctcgtga atttttccat taacggctag ttatatttaa gatcgaattt aattagcacg  2220
tagtgttact taattataga tcattatcag tttatgacca atatgtcatt ttgagtgaaa  2280
tagtgctaaa aaattttaaa caaaatttca ggttcttgta cataaaaaat ttaattaaaa  2340
aatatttatt aaaagtgata aataaggttc tctcatcaat aaaattaata aatatacact  2400
aataagattc acgactttta taatacgaat tattttaaat gtcatcttta aaatattatt  2460
ttaattgatc aagtgtgttc aaatcagttt atgaaaatta aattctatat ttaatagtat  2520
tttaaatttt cattgtgaaa tcagtatcat aaatgcttga taaatcatgg caacttcatt  2580
ttatgcttat caagccatct tctcacttta actgttgatg atgttgttac tatttgttta  2640
atggagcaga tttcatatgg gaagacaacc actaatcttg gtagcagatc cagagctttg  2700
taaagaagtg ggaataaaaa aattcaaaga cattccaaac agaagcattc cctctcctat  2760
ttcagcttcc ccccttcacc aaaaaggtct cttctttacc aggtatacaa tttaattttt  2820
ttcttttctt tttgtaataa tagcataaac aataattgtt aatttacgag acaaactatt  2880
attcaataag ttagagaata gataaatgaa aataatgagt attgaaggtt ttcaaatgta  2940
ttatcctata gcataaaact gtttgagtca cacttagata gacaggaaag gtatttatta  3000
ttgagtaaaa aaaattctgc actatatttt tatattgtta ttcaatcaca cattattatg  3060
tataataaat ttattaattt ttataatgat tattttataa gttatatcaa taataatttg  3120
```

```
tgatgaaatg agagtgttaa tgtattttac actctagtta tatttcttta caattgatag  3180
aagttaaaat atagagaggt ctcatttgtt gagcactttt gtgcaacttt tttcttgtgg  3240
atttctgtgt ggggtagcat tagcataggc actatatgtt aaatgtcatt tccattttgt  3300
gatcatcgtg tcatgtcatt aatttgagaa tcaaagattc gttgtaatcc aattccaatg  3360
gttctccaaa atctttgtcc tctagtgaga aagaacaatg gtttgataca ccaaatctaa  3420
gaacacacaa aagaaattga tcatgcaatg atgatttgca gggactcacg ttggtcaacc  3480
atgcgaaaca cgatcttgtc agtgtaccag ccatcacact tggctagctt agtgccaacg  3540
atgcaatcat tcatagaatc cgcaacacaa aatcttgaca ccccaaatga ggacataatc  3600
ttttccaatc tttccttaag gctagcaacc gatgtgattg gagaggcagc atttggtgtc  3660
aattttggcc tctctaagcc acattcagtt tgtgaatcaa tcaagagtgt tagtgttaac  3720
aatgtgagaa atgatgatga tgaggtatct gatttcatca atcaacacat ttactccaca  3780
acacaactta agatggactt gtctggttca ttctccatca tacttggtct acttgcacca  3840
atacttcagg agccatttag gcagattctg aagagaatac caggcacaat ggacagcaaa  3900
atagagagta ctaatgagaa gctgagtggt cctcttgatg agattgtcaa gaggagaatg  3960
gaagacaaga atagaacttc aaagaatttc ttgtcactca ttttgaatgc aagagaatca  4020
aagaaagtat ctgaaaatgt cttttcacct gattacatta gcgctgttac ttatgagcac  4080
ttacttgctg ggtcagctac cacagccttt accttgtcat ccattgtcta cttggttgct  4140
ggacaccgag aggttgagaa aaagttgctt caagagattg atggatttgg tccacctgat  4200
aggattccca cagctcaaga tcttcatgac agttttcctt atcttgatca ggtcagctga  4260
tagtgatact ttgtgagatt caagattttg tacgttgaat ttgcaaggac cagcaataat  4320
gatgtaaaat tctcaattta attaacgcag gtgattaaag aggccatgag gttttacaca  4380
gtctccccat tggttgcaag agaaacatca catgaggtgg agataggagg ttaccttctt  4440
ccaaaggtag taatacatct ttgtccagtg tcaaatataa tttttttgatg gcattgggag  4500
ggataacatg taatgagaaa ataatacgtg catggacccc gtaaagagtt tttatatgtt  4560
catcaaacaa aaatctagat ataataaatt tgtagacttt tataataatt atatattatt  4620
tggtttacgt gaaaaaaaga gaaaggaagg ggaaatatta aaaaaatact tcttttcctt  4680
gattagaagg agtaagccaa ggaaggaatg gaaaaaaaaa atatatgaac cccacctatt  4740
tattctgtct tttcattgtg tatacatacc ataccttctt tatttctttc tacttctaat  4800
gcaaccaaac aacttataaa atcatcttac tttctactta ttttttctta aaccaaacat  4860
attataaaag tcaaacaatt tttaattggt cgatagtgtg aaacttttat actaacatta  4920
catagaaatt tgtctcattt tctttgtttt agtacatgtg caaaattttc cattttcttg  4980
atgcagggta ttttagttat gccaccactg atgttttgta catgagcagg ggacatgggt  5040
atggttagct ctaggagttc tagcaaaaga tccaaggaat tttccagagc ctgagaagtt  5100
caaaccagag aggtttgacc ccaaatgtga agaaatgaaa cgaagacatc cttatgcatt  5160
cataccattt ggaattggtc cccgggcatg tattggtcag aaattttccc tacaagagat  5220
caagcttact ctgattcatt tgtaccagaa atatgttttt cgtcattcag ttgacatgga  5280
aaaacctgta gaaatggaat atggtatggt tctcaacttc aagcatggta tcaagcttag  5340
agtcataaga agaacgtaat tatagagtga ccatgtatac caactaagat tgtactttgt  5400
gatgcaatgg atgaattaaa atctctcttt aatatgttgt gattgtcaac aaggcaaaat  5460
atgctaattc aaacaggata ttaaactttt atgcaaattt tatgaaagaa agagtatctt  5520
gactttgaat gtgcctacaa aagcagattc ccccactaat tgctgggtct cactcttcaa  5580
ttttatactt tgtttaggcc ttgcagtctc ttgataacat aaaaaattaa caactgatta  5640
tacaaatgga gagaccccta aagtagtatt gcttagggaa agcacaaaag ctactgctac  5700
agttgtaatt caattaacag accattgaac aacaagttgt tgaagtgttt gaacttcttg  5760
aaaataaata caacagagag gatcaatcaa tagaatcaag tcgcttttttc accgtgaact  5820
cttatccatg taggttggta ggtaaagtgg cctagaaaag ttggttgaag ggtcagaagc  5880
attagagaaa actgctgttc ttttgagaaa ctggaactca tccatggact gctgcctctg  5940
agatctattg tactgatgat tgctggtttt ctgctttgcc ttggttgact cggtgaggtt  6000
catgtaacta ggcctagagt tgttactatc ctctgtcctg tcacaaggta ttggagttgt  6060
agatgtgcag attgaggatg aattagagca gctctcatca tagtgaaact cagaacttgg  6120
actcgacgac aagcgagtag cttgtccaat atggggaggt ctagcagaaa tccttgtgct  6180
gacattgttc tttctgattt taatattgca tagttctgat gtttttgaat tggaggagtc  6240
aacacatttc tttggtggag gaggaggagg ggtcttctct gtggcatcag catgatgggt  6300
ttgttccatt aatctactct cccatggttt agctgccatc caacgttcca accaactcca  6360
tccccagttc gccttgtcca tctcgtgatt gttgagagcg gcgtttgctc ttgaattaga  6420
gatgggggtt gatctccatt gctgcaaaag ccaaggatta cacatgtttc ttaatataag  6480
ca                                                                6482
```

```
SEQ ID NO: 178         moltype = AA  length = 43
FEATURE                Location/Qualifiers
source                 1..43
                       mol_type = protein
                       organism = synthetic construct
SEQUENCE: 178
MVSIVLEWLF PFPCVAMFTT HWVIFMGPIG GLGKFQAHQR CRW                 43
```

```
SEQ ID NO: 179         moltype = DNA  length = 6496
FEATURE                Location/Qualifiers
source                 1..6496
                       mol_type = other DNA
                       organism = synthetic construct
SEQUENCE: 179
actcctctaa tttcaggaac caaaaaacct tagtctctgt ctctttcctt tggtatatac  60
acactgcaca tgccaaaata aaaatggtgt ccatagtatt ggaatggtta tttccttttc  120
catgtgtagc catgttcacc acccttctga tgtggattat tgggttatct ttatgggccc  180
tattgggggc ttaggaaagt tccaggccca ccaacgctgc cgctggtagg acaccttccc  240
ttactggcta aatacggccc tgatgtcttc tcactccttg ccaagcaata tggcccaatt  300
tacaggtttg tactttacat aattgaatct ggatagaagg cacttttttt taccatatta  360
ttggtatacc gatactaatc atgggttgga gaacttaatc actcactttt atagtgagat  420
```

```
ctttcttttt aattatgttt ttttctttca caaatctcga acctagttca atattattcg  480
aaccaaaatg acttactagt tagatagcag acaattacag cttaatcaat ttgatttgtt  540
gagatcattc tcattttctt catcttcttc tcttcatgag aagctaaaaa gaaaatctgt  600
tactgctgat atgataccca acttgaatat atgaaattca aaatgcataa aagtcctgtt  660
gggtgtggat gatatttggt catgtaatga tgggggttat atatggttga cttgtgaagg  720
gtatatatat gattatggtg gtggtgggac agtgttttag tgcatattgc ctgggaagaa  780
gtagatataa tcacataatt tggaaaaaaa gttaacgttc tgttgtgatc tatttgtgct  840
tgtttgtcaa cttgattaaa tatgataaga aacaacatta gcatcagcat gcccgtccta  900
tagtaacatg attaaattgc tcttgataaa tattaagagt gtcctcaatt gtatgcacat  960
aaccttctaa acaaagatct tgtcgttgtc cttgatggca gaagaatttg agtcctttaa  1020
aagtgaacaa agcatctaac acaaaaaataa aggtaaatgc atagttgatt tgaataaagt  1080
actttataaa tttatttaat tttgagttag tgatggatgc acgcttactt ttgtttatgt  1140
aaataatgca tatttacttt tctcattttg cacaagtact tcgctagatc catggtcata  1200
aatgaatcaa gataagtaga gtaatttaag tttaagcttg acatataaaa aatattattt  1260
atttaaatga atcaaagtta aactttagac ttgtttgaag atagacagcc tgaattagaa  1320
tctacttagt tgataattta atttttgttc ctttatcaaa tattttttttg aaacattttt  1380
aaatttatta atttattatt tagtaaatga attttcgtac taaaaaataaa gtaaaaaataa  1440
gagaaaaata attagatgta aaaattacat attaattatt tataacaaaa aatataatat  1500
attaaatata tctttctcac atttaatttt ttttatcttc aggcacacat ataacactca  1560
cactcaactt tttagtatca agtttataaa ctttgaactg gagtgatttt tataattata  1620
aatagaatta aatttgagtt tattttctta ataaaataaa taaattttat tggacattta  1680
ataaatcgaa tctggatagc aaaaatataa gttttagagc ttaattttaa attatttctc  1740
attgataaaa aaatattatt aagataatta ttataaaaat taacaaatta taatatataa  1800
taatttgata ctaaataaca gtacaaattc tataagtgca tatatagtct actctaaatt  1860
ttatgcagtt caattttaca accctgattt atcattgggt gattaatttt ctatccaaca  1920
gaacaatttt ttttttttta gagaataaac ctttggttat tctggtaaac gccttacgcg  1980
cgtctgattt tcaaaactca aaagtcaaaa gggacatttt gctgcgattt taatcattgt  2040
gtacggaaaa cttctagcac tgtttgcaga ggattattaa gttattaaaa aaagtataca  2100
ttaaacataa tttaacatgg aaaaagaaga gaaaggaaaa gatgaatacg aattaatgtg  2160
tgatttcata tattattctc gtgaattttt ccattaacgg ctagttatat ttaagatcga  2220
atttaattag cacgtagtgt tacttaatta tagatcatta tcagtttatg accaatatgt  2280
cattttgagt gaaatagtgc taaaaaattt taaacaaaat ttcaggttct tgtacataaa  2340
aaatttaatt aaaaaatatt tattaaaagt gataaataag gttctctcat caataaaatt  2400
aataaatata cactaataag attcacgact tttataatac gaattatttt aaatgtcatc  2460
tttaaaatat tattttaatt gatcaagtgt gttcaaatca gtttatgaaa attaaattct  2520
atatttaata gtattttaaa ttttcattgt gaaatcagta tcataaatgc ttgataaatc  2580
atggcaactt cattttatgc ttatcaagcc atcttctcac tttaactgtt gatgatgttg  2640
ttactatttg tttaatggag cagatttcat atgggaagac aaccactaat cttggtagca  2700
gatccagagc tttgtaaaga agtgggaata aaaaaattca aagacattcc aaacagaagc  2760
attccctctc ctatttcagc ttcccccctt caccaaaaag gtctcttctt taccaggtat  2820
acaatttaat tttttctttt tctttttgta ataatagcat aaacaataat tgttaattta  2880
cgagacaaac tattattcaa taagttagag aatagataaa tgaaaataat gagtattgaa  2940
ggttttcaaa tgtattatcc tatagcataa aactgtttga gtcacactta gatagacagg  3000
aaaggtattt attattgagt aaaaaaaatt ctgcactata tttttatatt gttattcaat  3060
cacacattat tatgtataat aaatttatta atttttataa tgattatttt ataagttata  3120
tcaataataa tttgtgatga aatgagagtg ttaatgtatt ttacactcta gttatatttc  3180
tttacaattg atagaagtta aaatatagag aggtctcatt tgttgagcac ttttgtgcaa  3240
cttttttctt gtggatttct gtgtggggta gcattagcat aggcactata tgttaaatgt  3300
catttccatt ttgtgatcat cgtgtcatgt cattaatttg agaatcaaag attcgttgta  3360
atccaattcc aatggttctc caaaatcttt gtcctctagt gagaaagaac aatggtttga  3420
tacaccaaat ctaagaacac acaaaagaaa ttgatcatgc aatgatgatt tgcagggact  3480
cacgttggtc aaccatgcga aacacgatct tgtcagtgta ccagccatca cacttggcta  3540
gcttagtgcc aacgatgcaa tcattcatag aatccgcaac acaaaatctt gacaccccaa  3600
atgaggacat aatcttttcc aatctttcct taaggctagc aaccgatgtg attggagagg  3660
cagcatttgg tgtcaatttt ggcctctcta agccacattc agtttgtgaa tcaatcaaga  3720
gtgttagtgt taacaatgtg agaaatgatg atgatgaggt atctgatttc atcaatcaac  3780
acatttactc cacaacacaa cttaagatgg acttgtctgg ttcattctcc atcatacttg  3840
gtctacttgc accaatactt caggagccat ttaggcagat tctgaagaga ataccaggca  3900
caatggacag caaaatagag agtactaatg agaagctgag tggtcctctt gatgagattg  3960
tcaagaggag aatggaagac aagaatagaa cttcaaagaa tttcttgtca ctcattttga  4020
atgcaagaga atcaaagaaa gtatctgaaa atgtcttttc acctgattac attagcgctg  4080
ttacttatga gcacttactt gctgggtcag ctaccacagc ctttaccttg tcatccattg  4140
tctacttggt tgctggacac cgagaggttg agaaaaagtt gcttcaagag attgatggat  4200
ttggtccacc tgataggatt cccacagctc aagatcttca tgacagtttt ccttatcttg  4260
atcaggtcag ctgatagtga tactttgtga gattcaagat tttgtacgtt gaatttgcaa  4320
ggaccagcaa taatgatgta aaattctcaa tttaattaac gcaggtgatt aaagaggcca  4380
tgaggtttta cacagtctcc ccattggttg caagagaaac atcacatgag gtggagatag  4440
gaggttacct tcttccaaag gtagtaatac atctttgtcc agtgtcaaat ataatttttt  4500
gatggcattg ggagggataa catgtaatga gaaaataata cgtgcatgga ccccgtaaag  4560
agtttttata tgttcatcaa acaaaaatct agatataata aatttgtaga cttttataat  4620
aattatatat tatttggttt acgtgaaaaa aagagaaagg aaggggaaat attaaaaaaa  4680
tacttctttt ccttgattag aaggagtaag ccaaggaagg aatggaaaaa aaaaatatat  4740
gaaccccacc tatttattct gtcttttcat tgtgtataca taccatacct tctttatttc  4800
tttctacttc taatgcaacc aaacaactta taaaatcatc ttactttcta cttatttttt  4860
cttaaaccaa acatattata aaagtcaaac aatttttaat tggtcgatag tgtgaaactt  4920
ttatactaac attacataga aatttgtctc attttctttg ttttagtaca tgtgcaaaat  4980
tttccatttt cttgatgcag ggtattttag ttatgccacc actgatgttt tgtacatgag  5040
caggggacat gggtatggtt agctctagga gttctagcaa aagatccaag gaattttcca  5100
gagcctgaga agttcaaacc agagaggttt gaccccaaat gtgaagaaat gaaacgaaga  5160
```

```
catccttatg cattcatacc atttggaatt ggtccccggg catgtattgg tcagaaattt  5220
tccctacaag agatcaagct tactctgatt catttgtacc agaaatatgt ttttcgtcat  5280
tcagttgaca tggaaaaacc tgtagaaatg gaatatggta tggttctcaa cttcaagcat  5340
ggtatcaagc ttagagtcat aagaagaacg taattataga gtgaccatgt ataccaacta  5400
agattgtact ttgtgatgca atggatgaat taaaatctct ctttaatatg ttgtgattgt  5460
caacaaggca aaatatgcta attcaaacag gatattaaac ttttatgcaa attttatgaa  5520
agaaagagta tcttgacttt gaatgtgcct acaaaagcag attcccccac taattgctgg  5580
gtctcactct tcaattttat actttgttta ggccttgcag tctcttgata acataaaaaa  5640
ttaacaactg attatacaaa tggagagacc cctaaagtag tattgcttag ggaaagcaca  5700
aaagctactg ctacagttgt aattcaatta acagaccatt gaacaacaag ttgttgaagt  5760
gtttgaactt cttgaaaata aatacaacag agaggatcaa tcaatagaat caagtcgctt  5820
tttcaccgtg aactcttatc catgtaggtt ggtaggtaaa gtggcctaga aaagttggtt  5880
gaagggtcag aagcattaga gaaaactgct gttcttttga gaaactggaa ctcatccatg  5940
gactgctgcc tctgagatct attgtactga tgattgctgg ttttctgctt tgccttggtt  6000
gactcggtga ggttcatgta actaggccta gagttgttac tatcctctgt cctgtcacaa  6060
ggtattggag ttgtagatgt gcagattgag gatgaattag agcagctctc atcatagtga  6120
aactcagaac ttggactcga cgacaagcga gtagcttgtc caatatgggg aggtctagca  6180
gaaatccttg tgctgacatt gttctttctg attttaatat tgcatagttc tgatgttttt  6240
gaattggagg agtcaacaca tttctttggt ggaggaggag gaggggtctt ctctgtggca  6300
tcagcatgat gggtttgttc cattaatcta ctctcccatg gtttagctgc catccaacgt  6360
tccaaccaac tccatcccca gttcgccttg tccatctcgt gattgttgag agcggcgttt  6420
gctcttgaat tagagatggg ggttgatctc cattgctgca aaagccaagg attacacatg  6480
tttcttaata taagca                                                6496

SEQ ID NO: 180         moltype = AA  length = 36
FEATURE                Location/Qualifiers
source                 1..36
                       mol_type = protein
                       organism = synthetic construct
SEQUENCE: 180
MVSIVLEWLF PFPCVAMFTT LLMWIIGLSL WALLGA                          36

SEQ ID NO: 181         moltype = DNA  length = 6503
FEATURE                Location/Qualifiers
source                 1..6503
                       mol_type = other DNA
                       organism = synthetic construct
SEQUENCE: 181
actcctctaa tttcaggaac caaaaaacct tagtctctgt ctctttcctt tggtatatac  60
acactgcaca tgccaaaata aaaatggtgt ccatagtatt ggaatggtta tttccttttc  120
catgtgtagc catgttcacc acccttctga tgttaatagg aggattattg ggttatcttt  180
atgggcccta ttgggggctt aggaaagttc caggcccacc aacgctgccg ctggtaggac  240
accttccctt actggctaaa tacggcctga tgtcttctca ctccttgcca agcaatatgg  300
cccaatttac aggtttgtac tttacataat tgaatctgga tagaaggcac tttttttttac  360
catattattg gtataccgat actaatcatg ggttggagaa cttaatcact cacttttata  420
gtgagatctt tctttttaat tatgtttttt tctttcacaa atctcgaacc tagttcaata  480
ttattcgaac caaaatgact tactagttag atagcagaca attacagctt aatcaatttg  540
atttgttgag atcattctca ttttcttcat cttcttctct tcatgagaag ctaaaaagaa  600
aatctgttac tgctgatatg atacccaact tgaatatatg aaattcaaaa tgcataaaag  660
tcctgttggg tgtggatgat atttggtcat gtaatgatgg gggttatata tggttgactt  720
gtgaagggta tatatatgat tatggtggtg gtgggacagt gttttagtgc atattgcctg  780
ggaagaagta gatataatca cataatttgg aaaaaaagtt aacgttctgt tgtgatctat  840
ttgtgcttgt ttgtcaactt gattaaatat gataagaaac aacattagca tcagcatgcc  900
cgtcctatag taacatgatt aaattgctct tgataaatat taagagtgtc ctcaattgta  960
tgcacataac cttctaaaca aagatcttgt cgttgtcctt gatggcagaa gaatttgagt  1020
cctttaaaag tgaacaaagc atctaacaca aaaataaagg taaatgcata gttgatttga  1080
ataaagtact ttataaattt atttaatttt gagttagtga tggatgcacg cttacttttg  1140
tttatgtaaa taatgcatat ttacttttct catttttgcac aagtacttcg ctagatccat  1200
ggtcataaat gaatcaagat aagtagagta atttaagttt aagcttgaca tataaaaaat  1260
attatttatt taaatgaatc aaagttaaac tttagacttg tttgaagata gacagcctga  1320
attagaatct acttagttga taatttaatt tttgttcctt tatcaaatat tttttttgaaa  1380
catttttaaa tttattaatt tattatttag taaatgaatt ttcgtactaa aaataaagta  1440
aaaataagag aaaaataatt agatgtaaaa attacatatt aattatttat aacaaaaaaat  1500
ataatatatt aaatatatct ttctcacatt taattttttt tatcttcagg cacacatata  1560
acactcacac tcaacttttt agtatcaagt ttataaactt tgaactggag tgatttttat  1620
aattataaat agaattaaat ttgagtttat tttcttaata aaataaataa attttattgg  1680
acatttaata aatcgaatct ggatagcaaa aatataagtt ttagagctta attttaaatt  1740
atttctcatt gataaaaaaa tattattaag ataattatta taaaaattaa caaattataa  1800
tatataataa tttgatacta aataacagta caaattctat aagtgcatat atagtctact  1860
ctaaatttta tgcagttcaa ttttacaacc ctgatttatc attgggtgat taattttcta  1920
tccaacagaa caattttttt ttttttagag aataaacctt tggttattct ggtaaacgcc  1980
ttacgcgcgt ctgattttca aaactcaaaa gtcaaaaggg acattttgct gcgattttaa  2040
tcattgtgta cggaaaactt ctagcactgt ttgcagagga ttattaagtt attaaaaaaa  2100
gtatacatta aacataattt aacatggaaa aagaagagaa aggaaaagat gaatacgaat  2160
taatgtgtga tttcatatat tattctcgtg aatttttcca ttaacggcta gttatattta  2220
agatcgaatt taattagcac gtagtgttac ttaattatag atcattatca gtttatgacc  2280
aatatgtcat tttgagtgaa atagtgctaa aaaattttaa acaaaatttc aggttcttgt  2340
acataaaaaa tttaattaaa aaatatttat taaaagtgat aaataaggtt ctctcatcaa  2400
taaaattaat aaatatacac taataagatt cacgactttt ataatacgaa ttattttaaa  2460
```

```
tgtcatcttt aaaatattat tttaattgat caagtgtgtt caaatcagtt tatgaaaatt  2520
aaattctata tttaatagta ttttaaattt tcattgtgaa atcagtatca taaatgcttg  2580
ataaatcatg gcaacttcat tttatgctta tcaagccatc ttctcacttt aactgttgat  2640
gatgttgtta ctatttgttt aatggagcag atttcatatg ggaagacaac cactaatctt  2700
ggtagcagat ccagagcttt gtaaagaagt gggaataaaa aaattcaaag acattccaaa  2760
cagaagcatt ccctctccta tttcagcttc ccccttcac caaaaaggtc tcttctttac  2820
caggtataca atttaatttt tttcttttct ttttgtaata atagcataaa caataattgt  2880
taatttacga gacaaactat tattcaataa gttagagaat agataaatga aaataatgag  2940
tattgaaggt tttcaaatgt attatcctat agcataaaac tgtttgagtc acacttagat  3000
agacaggaaa ggtatttatt attgagtaaa aaaaattctg cactatattt ttatattgtt  3060
attcaatcac acattattat gtataataaa tttattaatt tttataatga ttattttata  3120
agttatatca ataataattt gtgatgaaat gagagtgtta atgtatttta cactctagtt  3180
atatttcttt acaattgata gaagttaaaa tatagagagg tctcatttgt tgagcacttt  3240
tgtgcaactt ttttcttgtg gatttctgtg tggggtagca ttagcatagg cactatatgt  3300
taaatgtcat ttccatttttg tgatcatcgt gtcatgtcat taatttgaga atcaaagatt  3360
cgttgtaatc caattccaat ggttctccaa aatctttgtc ctctagtgag aaagaacaat  3420
ggtttgatac accaaatcta agaacacaca aaagaaattg atcatgcaat gatgatttgc  3480
agggactcac gttggtcaac catgcgaaac acgatcttgt cagtgtacca gccatcacac  3540
ttggctagct tagtgccaac gatgcaatca ttcatagaat ccgcaacaca aaatcttgac  3600
accccaaatg aggacataat cttttccaat ctttccttaa ggctagcaac cgatgtgatt  3660
ggagaggcag catttggtgt caattttggc ctctctaagc cacattcagt ttgtgaatca  3720
atcaagagtg ttagtgttaa caatgtgaga aatgatgatg atgaggtatc tgatttcatc  3780
aatcaacaca tttactccac aacacaactt aagatggact tgtctggttc attctccatc  3840
atacttggtc tacttgcacc aatacttcag gagccattta ggcagattct gaagagaata  3900
ccaggcacaa tggacagcaa aatagagagt actaatgaga agctgagtgg tcctcttgat  3960
gagattgtca agaggagaat ggaagacaag aatagaactt caaagaattt cttgtcactc  4020
attttgaatg caagagaatc aaagaaagta tctgaaaatg tcttttcacc tgattacatt  4080
agcgctgtta cttatgagca cttacttgct gggtcagcta ccacagcctt taccttgtca  4140
tccattgtct acttggttgc tggacaccga gaggttgaga aaaagttgct tcaagagatt  4200
gatggatttg gtccacctga taggattccc acagctcaag atcttcatga cagttttcct  4260
tatcttgatc aggtcagctg atagtgatac tttgtgagat tcaagatttt gtacgttgaa  4320
tttgcaagga ccagcaataa tgatgtaaaa ttctcaattt aattaacgca ggtgattaaa  4380
gaggccatga ggttttacac agtctcccca ttggttgcaa gagaaacatc acatgaggtg  4440
gagataggag gttaccttct tccaaaggta gtaatacatc tttgtccagt gtcaaatata  4500
attttttgat ggcattggga gggataacat gtaatgagaa aataatacgt gcatggaccc  4560
cgtaaagagt ttttatatgt tcatcaaaca aaaatctaga tataataaat ttgtagactt  4620
ttataataat tatatattat ttggtttacg tgaaaaaaag agaaaggaag gggaaatatt  4680
aaaaaaatac ttcttttcct tgattagaag gagtaagcca aggaaggaat ggaaaaaaaa  4740
aatatatgaa ccccacctat ttattctgtc ttttcattgt gtatacatac catacttcct  4800
ttatttcttt ctacttctaa tgcaaccaaa caacttataa aatcatctta ctttctactt  4860
attttttctt aaaccaaaca tattataaaa gtcaaacaat ttttaattgg tcgatagtgt  4920
gaaacttttta tactaacatt acatagaaat ttgtctcatt ttctttgttt tagtacatgt  4980
gcaaaatttt ccattttctt gatgcagggt attttagtta tgccaccact gatgttttgt  5040
acatgagcag gggacatggg tatggttagc tctaggagtt ctagcaaaag atccaaggaa  5100
ttttccagag cctgagaagt tcaaaccaga gaggtttgac cccaaatgtg aagaaatgaa  5160
acgaagacat ccttatgcat tcataccatt tggaattggt ccccgggcat gtattggtca  5220
gaaattttcc ctacaagaga tcaagcttac tctgattcat ttgtaccaga aatatgtttt  5280
tcgtcattca gttgacatgg aaaaacctgt agaaatggaa tatggtatgg ttctcaactt  5340
caagcatggt atcaagctta gagtcataag aagaacgtaa ttatagagtg accatgtata  5400
ccaactaaga ttgtactttg tgatgcaatg gatgaattaa aatctctctt taatatgttg  5460
tgattgtcaa caaggcaaaa tatgctaatt caaacaggat attaaacttt tatgcaaatt  5520
ttatgaaaga aagagtatct tgactttgaa tgtgcctaca aaagcagatt cccccactaa  5580
ttgctgggtc tcactcttca attttatact ttgtttaggc cttgcagtct cttgataaca  5640
taaaaaatta acaactgatt atacaaatgg agagacccct aaagtagtat tgcttaggga  5700
aagcacaaaa gctactgcta cagttgtaat tcaattaaca gaccattgaa caacaagttg  5760
ttgaagtgtt tgaacttctt gaaaataaat acaacagaga ggatcaatca atagaatcaa  5820
gtcgcttttt caccgtgaac tcttatccat gtaggttggt aggtaaagtg gcctagaaaa  5880
gttggttgaa gggtcagaag cattagagaa aactgctgtt cttttgagaa actggaactc  5940
atccatggac tgctgcctct gagatctatt gtactgatga ttgctggttt tctgctttgc  6000
cttggttgac tcggtgaggt tcatgtaact aggcctagag ttgttactat cctctgtcct  6060
gtcacaaggt attggagttg tagatgtgca gattgaggat gaattagagc agctctcatc  6120
atagtgaaac tcagaacttg gactcgacga caagcgagta gcttgtccaa tatggggagg  6180
tctagcagaa atccttgtgc tgacattgtt ctttctgatt ttaatattgc atagttctga  6240
tgtttttgaa ttggaggagt caacacattt ctttggtgga ggaggaggag gggtcttctc  6300
tgtggcatca gcatgatggg tttgttccat taatctactc tcccatggtt tagctgccat  6360
ccaacgttcc aaccaactcc atccccagtt cgccttgtcc atctcgtgat tgttgagagc  6420
ggcgtttgct cttgaattag agatgggggt tgatctccat tgctgcaaaa gccaaggatt  6480
acacatgttt cttaatataa gca                                           6503
```

```
SEQ ID NO: 182          moltype = AA  length = 84
FEATURE                 Location/Qualifiers
source                  1..84
                        mol_type = protein
                        organism = synthetic construct
SEQUENCE: 182
MVSIVLEWLF PFPCVAMFTT LLMLIGGLLG YLYGPYWGLR KVPGPPTLPL VGHLPLLAKY  60
GLMSSHSLPS NMAQFTDFIW EDNH                                          84
```

```
SEQ ID NO: 183          moltype = DNA  length = 6515
```

```
FEATURE                Location/Qualifiers
source                 1..6515
                       mol_type = other DNA
                       organism = synthetic construct
SEQUENCE: 183
actcctctaa tttcaggaac caaaaaacct tagtctctgt ctctttcctt tggtatatac  60
acactgcaca tgccaaaata aaaatggtgt ccatagtatt ggaatggtta tttccttttc  120
catgtgtagc catgttcacc acccttctga aggattattg ggttatcttt atgggcccta  180
ttgggggctt aggaaagttc caggcccacc aacgctgccg ctggtaggac accttccctt  240
actggnnnnn nnnnnnnnnn nnnnnnctaa atacggccct gatgtcttct cactccttgc  300
caagcaatat ggcccaattt acaggtttgt actttacata attgaatctg gatagaaggc  360
actttttttt accatattat tggtataccg atactaatca tgggttggag aacttaatca  420
ctcactttta tagtgagatc tttctttttta attatgtttt tttctttcac aaatctcgaa  480
cctagttcaa tattattcga accaaaatga cttactagtt agatagcaga caattacagc  540
ttaatcaatt tgatttgttg agatcattct catttttcttc atcttcttct cttcatgaga  600
agctaaaaag aaaatctgtt actgctgata tgatacccaa cttgaatata tgaaattcaa  660
aatgcataaa agtcctgttg ggtgtggatg atatttggtc atgtaatgat gggggttata  720
tatggttgac ttgtgaaggg tatatatatg attatggtgg tggtgggaca gtgttttagt  780
gcatattgcc tgggaagaag tagatataat cacataattt ggaaaaaaag ttaacgttct  840
gttgtgatct atttgtgctt gtttgtcaac ttgattaaat atgataagaa acaacattag  900
catcagcatg cccgtcctat agtaacatga ttaaattgct cttgataaat attaagagtg  960
tcctcaattg tatgcacata accttctaaa caaagatctt gtcgttgtcc ttgatggcag  1020
aagaatttga gtcctttaaa agtgaacaaa gcatctaaca caaaaataaa ggtaaatgca  1080
tagttgattt gaataaagta ctttataaat ttatttaatt ttgagttagt gatggatgca  1140
cgcttacttt tgtttatgta aataatgcat atttactttt ctcattttgc acaagtactt  1200
cgctagatcc atggtcataa atgaatcaag ataagtagag taatttaagt ttaagcttga  1260
catataaaaa atattattta tttaaatgaa tcaaagttaa actttagact tgtttgaaga  1320
tagacagcct gaattagaat ctacttagtt gataatttaa tttttgttcc tttatcaaat  1380
attttttga aacattttta aatttattaa tttattattt agtaaatgaa ttttcgtact  1440
aaaaataaag taaaaataag agaaaaataa ttagatgtaa aaattacata ttaattattt  1500
ataacaaaaa atataatata ttaaatatat ctttctcaca tttaattttt tttatcttca  1560
ggcacacata taacactcac actcaacttt ttagtatcaa gtttataaac tttgaactgg  1620
agtgattttt ataattataa atagaattaa atttgagttt attttcttaa taaaataaat  1680
aaattttatt ggacatttaa taaatcgaat ctggatagca aaaatataag ttttagagct  1740
taattttaaa ttatttctca ttgataaaaa aatattatta agataattat tataaaaatt  1800
aacaaattat aatatataat aatttgatac taaataacag tacaaattct ataagtgcat  1860
atatagtcta ctctaaattt tatgcagttc aattttacaa ccctgattta tcattgggtg  1920
attaattttc tatccaacag aacaattttt ttttttttag agaataaacc tttggttatt  1980
ctggtaaacg ccttacgcgc gtctgatttt caaaactcaa aagtcaaaag ggacattttg  2040
ctgcgatttt aatcattgtg tacggaaaac ttctagcact gtttgcagag gattattaag  2100
ttattaaaaa aagtatacat taaacataat ttaacatgga aaaagaagag aaaggaaaag  2160
atgaatacga attaatgtgt gatttcatat attattctcg tgaatttttc cattaacggc  2220
tagttatatt taagatcgaa tttaattagc acgtagtgtt acttaattat agatcattat  2280
cagtttatga ccaatatgtc attttgagtg aaatagtgct aaaaaatttt aaacaaaatt  2340
tcaggttctt gtacataaaa aatttaatta aaaaatattt attaaaagtg ataaataagg  2400
ttctctcatc aataaaatta ataaatatac actaataaga ttcacgactt ttataatacg  2460
aattatttta aatgtcatct ttaaaatatt attttaattg atcaagtgtg ttcaaatcag  2520
tttatgaaaa ttaaattcta tatttaatag tattttaaat tttcattgtg aaatcagtat  2580
cataaatgct tgataaatca tggcaacttc attttatgct tatcaagcca tcttctcact  2640
ttaactgttg atgatgttgt tactatttgt ttaatggagc agatttcata tgggaagaca  2700
accactaatc ttggtagcag atccagagct ttgtaaagaa gtgggaataa aaaaattcaa  2760
agacattcca aacagaagca ttccctctcc tatttcagct tcccccccttc accaaaaagg  2820
tctcttcttt accaggtata caatttaatt tttttctttt ctttttgtaa taatagcata  2880
aacaataatt gttaatttac gagacaaact attattcaat aagttagaga atagataaat  2940
gaaaataatg agtattgaag gttttcaaat gtattatcct atagcataaa actgtttgag  3000
tcacacttag atagacagga aaggtattta ttattgagta aaaaaaattc tgcactatat  3060
ttttatattg ttattcaatc acacattatt atgtataata aatttattaa tttttataat  3120
gattatttta taagttatat caataataat ttgtgatgaa atgagagtgt taatgtattt  3180
tacactctag ttatatttct ttacaattga tagaagttaa aatatagaga ggtctcattt  3240
gttgagcact tttgtgcaac tttttttcttg tggatttctg tgtggggtag cattagcata  3300
ggcactatat gttaaatgtc atttccattt tgtgatcatc gtgtcatgtc attaatttga  3360
gaatcaaaga ttcgttgtaa tccaattcca atggttctcc aaaatctttg tcctctagtg  3420
agaaagaaca atggtttgat acaccaaatc taagaacaca caaaagaaat tgatcatgca  3480
atgatgattt gcagggactc acgttggtca accatgcgaa acacgatctt gtcagtgtac  3540
cagccatcac acttggctag cttagtgcca acgatgcaat cattcataga atccgcaaca  3600
caaaatcttg acaccccaaa tgaggacata atcttttcca atctttcctt aaggctagca  3660
accgatgtga ttggagaggc agcatttggt gtcaattttg gcctctctaa gccacattca  3720
gtttgtgaat caatcaagag tgttagtgtt aacaatgtga gaaatgatga tgatgaggta  3780
tctgatttca tcaatcaaca catttactcc acaacacaac ttaagatgga cttgtctggt  3840
tcattctcca tcatacttgg tctacttgca ccaatacttc aggagccatt taggcagatt  3900
ctgaagagaa taccaggcac aatggacagc aaaatagaga gtactaatga gaagctgagt  3960
ggtcctcttg atgagattgt caagaggaga atggaagaca agaatagaac ttcaaagaat  4020
ttcttgtcac tcattttgaa tgcaagagaa tcaaagaaag tatctgaaaa tgtcttttca  4080
cctgattaca ttagcgctgt tacttatgag cacttacttg ctgggtcagc taccacagcc  4140
tttaccttgt catccattgt ctacttggtt gctggacacc gagaggttga gaaaaagttg  4200
cttcaagaga ttgatggatt tggtccacct gataggattc ccacagctca agatcttcat  4260
gacagttttc cttatcttga tcaggtcagc tgatagtgat actttgtgag attcaagatt  4320
ttgtacgttg aatttgcaag gaccagcaat aatgatgtaa aattctcaat ttaattaacg  4380
caggtgatta aagaggccat gaggttttac acagtctccc cattggttgc aagagaaaca  4440
```

-continued

```
tcacatgagg tggagatagg aggttacctt cttccaaagg tagtaataca tctttgtcca  4500
gtgtcaaata taattttttg atggcattgg gagggataac atgtaatgag aaaataatac  4560
gtgcatggac cccgtaaaga gtttttatat gttcatcaaa caaaaatcta gatataataa  4620
atttgtagac ttttataata attatatatt atttggttta cgtgaaaaaa agagaaagga  4680
aggggaaata ttaaaaaaat acttcttttc cttgattaga aggagtaagc caaggaagga  4740
atggaaaaaa aaaatatatg aaccccacct atttattctg tcttttcatt gtgtatacat  4800
accatacctt ctttatttct ttctacttct aatgcaacca aacaacttat aaaatcatct  4860
tactttctac ttattttttc ttaaaccaaa catattataa aagtcaaaca atttttaatt  4920
ggtcgatagt gtgaaacttt tatactaaca ttacatagaa atttgtctca ttttctttgt  4980
tttagtacat gtgcaaaatt ttccattttc ttgatgcagg gtattttagt tatgccacca  5040
ctgatgtttt gtacatgagc aggggacatg ggtatggtta gctctaggag ttctagcaaa  5100
agatccaagg aattttccag agcctgagaa gttcaaacca gagaggtttg accccaaatg  5160
tgaagaaatg aaacgaagac atccttatgc attcatacca tttggaattg gtccccgggc  5220
atgtattggt cagaaatttt ccctacaaga gatcaagctt actctgattc atttgtacca  5280
gaaatatgtt tttcgtcatt cagttgacat ggaaaaacct gtagaaatgg aatatggtat  5340
ggttctcaac ttcaagcatg gtatcaagct tagagtcata agaagaacgt aattatagag  5400
tgaccatgta taccaactaa gattgtactt tgtgatgcaa tggatgaatt aaaatctctc  5460
tttaatatgt tgtgattgtc aacaaggcaa aatatgctaa ttcaaacagg atattaaact  5520
tttatgcaaa ttttatgaaa gaaagagtat cttgactttg aatgtgccta caaaagcaga  5580
ttcccccact aattgctggg tctcactctt caattttata ctttgtttag gccttgcagt  5640
ctcttgataa cataaaaaat taacaactga ttatacaaat ggagagaccc ctaaagtagt  5700
attgcttagg gaaagcacaa aagctactgc tacagttgta attcaattaa cagaccattg  5760
aacaacaagt tgttgaagtg tttgaacttc ttgaaaataa atacaacaga gaggatcaat  5820
caatagaatc aagtcgcttt ttcaccgtga actcttatcc atgtaggttg gtaggtaaag  5880
tggcctagaa aagttggttg aagggtcaga agcattagag aaaactgctg ttcttttgag  5940
aaactggaac tcatccatgg actgctgcct ctgagatcta ttgtactgat gattgctggt  6000
tttctgcttt gccttggttg actcggtgag gttcatgtaa ctaggcctag agttgttact  6060
atcctctgtc ctgtcacaag gtattggagt tgtagatgtg cagattgagg atgaattaga  6120
gcagctctca tcatagtgaa actcagaact tggactcgac gacaagcgag tagcttgtcc  6180
aatatgggga ggtctagcag aaatccttgt gctgacattg ttctttctga ttttaatatt  6240
gcatagttct gatgttttg aattggagga gtcaacacat ttctttggtg gaggaggagg  6300
aggggtcttc tctgtggcat cagcatgatg ggtttgttcc attaatctac tctcccatgg  6360
tttagctgcc atccaacgtt ccaaccaact ccatccccag ttcgccttgt ccatctcgtg  6420
attgttgaga gcggcgtttg ctcttgaatt agagatgggg gttgatctcc attgctgcaa  6480
aagccaagga ttacacatgt ttcttaatat aagca                              6515

SEQ ID NO: 184         moltype = AA  length = 47
FEATURE                Location/Qualifiers
source                 1..47
                       mol_type = protein
                       organism = synthetic construct
SEQUENCE: 184
MVSIVLEWLF PFPCVAMFTT LLKDYWVIFM GPIGGLGKFQ AHQRCRW                 47

SEQ ID NO: 185         moltype = DNA  length = 10
FEATURE                Location/Qualifiers
source                 1..10
                       mol_type = other DNA
                       organism = Glycine max
SEQUENCE: 185
atggtcctga                                                          10

SEQ ID NO: 186         moltype = DNA  length = 22
FEATURE                Location/Qualifiers
source                 1..22
                       mol_type = other DNA
                       organism = Glycine max
SEQUENCE: 186
ttctgatgtt aataggagga tt                                            22

SEQ ID NO: 187         moltype = DNA  length = 10
FEATURE                Location/Qualifiers
source                 1..10
                       mol_type = other DNA
                       organism = Glycine max
SEQUENCE: 187
tgttaatagg                                                          10
```

METHODS AND COMPOSITIONS FOR IMPROVING PLANT ARCHITECTURE AND YIELD TRAITS

STATEMENT OF PRIORITY

This application claims the benefit, under 35 U.S.C. § 119 (e), of U.S. Provisional Application No. 63/240,132 filed on Sep. 2, 2021, the entire contents of which is incorporated by reference herein.

STATEMENT REGARDING ELECTRONIC FILING OF A SEQUENCE LISTING

A Sequence Listing in XML text format, entitled 1499-72_ST26.xml, 352,003 bytes in size, generated on Aug. 19, 2022 and filed herewith, is hereby incorporated by reference into the specification for its disclosures.

FIELD OF THE INVENTION

This invention relates to compositions and methods for modifying More Axillary Growth 1 (MAX1) genes in plants, optionally to improve plant architecture and/or yield traits. The invention further relates to plants having improved plant architecture and/or improved yield traits produced using the methods and compositions of the invention.

BACKGROUND OF THE INVENTION

Intensive breeding across row crops has led to incremental increases in plant yield. However, genetic gain from breeding has started to plateau and assembling multiple small-effect genes in a breeding program has substantially increased research and development costs. Single gene solutions have been challenging for a complex trait such as yield, where background genetics and environment combine to reduce the impact of individual genes. Breeding has been successful by combining many individual genes with small contributing effects but is requiring greater resources to find unique combinations with improved effects. To increase the rate of yield gain, novel variation needs to be introduced in important genes and pathways that contribute to yield.

Transgenic approaches involving stable transformation to increase yield have largely been unsuccessful and there are no commercially relevant single gene approaches that have successfully created a step change in yield.

The present invention addresses these shortcomings in the art by providing new compositions and methods for improving plant architecture and/or improving/enhancing yield traits in plants, including in soybean and other plant species.

SUMMARY OF THE INVENTION

One aspect of the invention provides a plant or plant part thereof comprising at least one mutation in an endogenous More Axillary Growth 1 (MAX1) gene encoding a cytochrome P450 monooxygenase (MAX1) polypeptide), optionally wherein the at least one mutation may be a non-natural mutation.

A second aspect of the invention provides a plant cell, comprising an editing system the editing system comprising: (a) a CRISPR-Cas effector protein; and (b) a guide nucleic acid comprising a spacer sequence with complementarity to an endogenous target gene encoding a cytochrome P450 monooxygenase (MAX1) polypeptide.

A third aspect of the invention provides a plant cell comprising at least one non-natural mutation within an endogenous More Axillary Growth 1 (MAX1) gene, wherein the at least one mutation is a base substitution, base insertion, or base deletion that is introduced using an editing system that comprises a nucleic acid binding domain that binds to a target site in the endogenous MAX1 gene), optionally wherein the at least one mutation may be a non-natural mutation.

A fourth aspect of the invention provides a method of producing/breeding a transgene-free edited plant, comprising: crossing the plant of the invention with a transgene free plant, thereby introducing the at least one mutation into the plant that is transgene-free; and selecting a progeny plant that comprises the at least one mutation and is transgene-free, thereby producing a transgene free edited plant), optionally wherein the at least one mutation may be a non-natural mutation.

A fifth aspect of the invention provides a method of providing a plurality of plants having one or more improved yield traits, the method comprising planting two or more plants of the invention in a growing area, thereby providing a plurality of plants having improved plant architecture (e.g., increased branching, increased number of nodes, reduced internode length, and/or a reduced or semi-dwarf stature) and/or one or more improved yield traits (optionally increased seed size (e.g., seed area and/or seed weight), increased number of seed pods and/or increase number of flowers) as compared to a plurality of control plants not comprising the at least one mutation.

A sixth aspect provides a method for editing a specific site in the genome of a plant cell, the method comprising: cleaving, in a site-specific manner, a target site within an endogenous More Axillary Growth 1 (MAX1) gene in the plant cell, the endogenous MAX1 gene: (a) comprising a nucleotide sequence having at least 80% sequence identity to any one of SEQ ID NOs:69, 70, 93, 94, 115, 116, 140 or 141, (b) comprising a region having at least 90% sequence identity to any one of SEQ ID NOs:72-91, 96-113, 118-138, or 143-164, (c) encoding an amino acid sequence having at least 80% sequence identity to any one of SEQ ID NOs:71, 95, 117, or 142, and/or (d) encoding a region having at least 90% sequence identity to an amino acid sequence of any one of SEQ ID NOs:92, 114, 139 or 165, thereby generating an edit in the endogenous MAX1 gene of the plant cell and producing a plant cell comprising the edit in the endogenous MAX1 gene.

A seventh aspect provides a method for making a plant, the method comprising: (a) contacting a population of plant cells comprising an endogenous More Axillary Growth 1 (MAX1) gene with a nuclease linked to a nucleic acid binding domain (e.g., editing system) that binds to a sequence (i) having at least 80% sequence identity to a nucleotide sequence of any one of SEQ ID NOs:69, 70, 93, 94, 115, 116, 140 or 141, (ii) comprising a region having at least 90% identity to any one of SEQ ID NOs:72-91, 96-113, 118-138, or 143-164; (iii) encoding an amino acid sequence having at least 80% sequence identity to any one of SEQ ID NOs:71, 95, 117, or 142, and/or (iv) encoding a region having at least 90% sequence identity to any one of SEQ ID NOs:92, 114, 139 or 165, and/or; (b) selecting a plant cell from the population of plant cells in which an endogenous MAX1 gene has been mutated, thereby producing a plant cell comprising a mutation in the endogenous MAX1 gene; and (c) growing the selected plant cell into a plant.

An eighth aspect provides a method for improving one or more yield traits in a plant, comprising: (a) contacting a plant cell comprising an endogenous More Axillary Growth 1 (MAX1) gene with a nuclease targeting the endogenous MAX1 gene, wherein the nuclease is linked to a nucleic acid binding domain (e.g., editing system) that binds to a target site in the endogenous MAX1 gene, wherein the endogenous MAX1 gene: (i) comprises a sequence having at least 80% sequence identity to the nucleotide sequence of any one of SEQ ID NOs:69, 70, 93, 94, 115, 116, 140 or 141; (ii) comprises a region having at least 90% identity to any one of SEQ ID NOs:72-91, 96-113, 118-138, or 143-164; (iii) encodes an amino acid sequence having at least 80% sequence identity to any one of SEQ ID NOs:71, 95, 117, or 142; and/or (iv) encodes an amino acid sequence comprising a region having at least 90% sequence identity to any one of SEQ ID NOs:92, 114, 139 or 165 to produce a plant cell comprising a mutation in the endogenous MAX1 gene; and (b) growing the plant cell into a plant comprising the mutation in the endogenous MAX1 gene thereby producing a plant having a mutated endogenous MAX1 gene and improved plant architecture and/or one or more improved yield traits.

A ninth aspect provides a method of producing a plant or part thereof comprising at least one cell having a mutated More Axillary Growth 1 (MAX1) gene, the method comprising contacting a target site in an endogenous MAX1 gene in the plant or plant part with a nuclease comprising a cleavage domain and a nucleic acid binding domain, wherein the nucleic acid binding domain binds to a target site in the endogenous MAX1 gene, wherein the endogenous MAX1 gene (a) comprises a sequence having at least 80% sequence identity to a nucleotide sequence of any one of SEQ ID NOs:69, 70, 93, 94, 115, 116, 140 or 141; (b) comprises a region having at least 90% identity to any one of SEQ ID NOs:72-91, 96-113, 118-138, or 143-164; (c) encodes an amino acid sequence having at least 80% sequence identity to any one of SEQ ID NOs:71, 95, 117, or 142; and/or (d) encodes an amino acid sequence comprising a region having at least 90% identity to any one of SEQ ID NOs:92, 114, 139 or 165, thereby producing the plant or part thereof comprising at least one cell having a mutation in the endogenous MAX1 gene.

A tenth aspect of the invention provides a method for producing a plant or part thereof comprising a mutated endogenous More Axillary Growth 1 (MAX1) gene and exhibiting improved plant architecture and/or one or more improved yield traits, the method comprising contacting a target site in an endogenous MAX1 gene in the plant or plant part with a nuclease comprising a cleavage domain and a nucleic acid binding domain, wherein the nucleic acid binding domain binds to a target site in the endogenous MAX1 gene, wherein the endogenous MAX1 gene: (a) comprises a sequence having at least 80% sequence identity to a nucleotide sequence of any one of SEQ ID NOs:69, 70, 93, 94, 115, 116, 140 or 141; (b) comprises a region having at least 90% identity to any one of SEQ ID NOs:72-91, 96-113, 118-138, or 143-164; (c) encodes an amino acid sequence having at least 80% sequence identity to any one of SEQ ID NOs:71, 95, 117, or 142; and/or (d) encodes an amino acid sequence comprising a region having at least 90% identity to any one of SEQ ID NOs:92, 114, 139 or 165, thereby producing the plant or part thereof comprising an endogenous MAX1 gene having a mutation and exhibiting improved plant architecture and/or one or more improved yield traits.

An eleventh aspect provides a guide nucleic acid that binds to a target site in a More Axillary Growth 1 (MAX1) gene, wherein the target site is in a region of the MAX1 gene having at least 90% sequence identity to any one of SEQ ID NOs:72-91, 96-113, 118-138, or 143-164, optionally a region of the MAX1 gene having at least 90% sequence identity to any one of SEQ ID NOs:77-79, 81-83, 88, 90, 91, 101-103, 105-107, 113, 121, 124, 125, 127-129, 132-138, 148-150, 152-154, or 160-164.

In a twelfth aspect, a system is provided that comprises a guide nucleic acid of the invention and a CRISPR-Cas effector protein that associates with the guide nucleic acid.

A thirteenth aspect provides a gene editing system comprising a CRISPR-Cas effector protein in association with a guide nucleic acid, wherein the guide nucleic acid comprises a spacer sequence that binds to an endogenous More Axillary Growth 1 (MAX1) gene.

In a fourteenth aspect, a complex comprising a guide nucleic acid and a CRISPR-Cas effector protein comprising a cleavage domain is provided, wherein the guide nucleic acid binds to a target site in a More Axillary Growth 1 (MAX1) gene, wherein the endogenous MAX1 gene: (a) comprises a sequence having at least 80% sequence identity to a nucleotide sequence of any one of SEQ ID NOs:69, 70, 93, 94, 115, 116, 140 or 141; (b) comprises a region having at least 90% identity to any one of SEQ ID NOs:72-91, 96-113, 118-138, or 143-164; (c) encodes an amino acid sequence having at least 80% sequence identity to any one of SEQ ID NOs:71, 95, 117, or 142; and/or (d) encodes an amino acid sequence comprising a region having at least 90% identity to any one of SEQ ID NOs:92, 114, 139 or 165, and the cleavage domain cleaves a target strand in the MAX1 gene.

In a fifteenth aspect, an expression cassette is provided, the expression cassette comprising (a) a polynucleotide encoding CRISPR-Cas effector protein comprising a cleavage domain and (b) a guide nucleic acid that binds to a target site in an endogenous More Axillary Growth 1 (MAX1) gene, wherein the guide nucleic acid comprises a spacer sequence that is complementary to and binds to (i) a portion of a nucleic acid having at least 80% sequence identity to any one of SEQ ID NOs:69, 70, 93, 94, 115, 116, 140 or 141; (ii) a portion of a nucleic acid having at least 90% sequence identity to any one of SEQ ID NOs:72-91, 96-113, 118-138, or 143-164; (iii) a portion of a nucleic acid encoding an amino acid sequence having at least 80% sequence identity to any one of SEQ ID NOs:71, 95, 117, or 142; and/or (iv) a portion of a nucleic acid encoding an amino acid sequence having at least 90% identity to any one SEQ ID NOs:92, 114, 139 or 165.

In an additional aspect, a method of creating a mutation in an endogenous More Axillary Growth 1 (MAX1) gene in a plant is provided, the method comprising: (a) targeting a gene editing system to a portion of the endogenous MAX1 gene that (i) comprises a sequence having at least 90% sequence identity to any one of SEQ ID NOs:72-91, 96-113, 118-138, or 143-164; and/or (ii) encodes a sequence having at least 90% identity to any one of SEQ ID NOs:92, 114, 139 or 165, and (b) selecting a plant that comprises a modification located in a region of the endogenous MAX1 gene having at least 90% sequence identity to any one of SEQ ID NOs:72-91, 96-113, 118-138, or 143-164, optionally located in a region of the endogenous MAX1 gene having at least 90% sequence identity to any one of SEQ ID NOs:77-79, 81-83, 88, 90, 91, 101-103, 105-107, 113, 121, 124, 125, 127-129, 132-138, 148-150, 152-154, or 160-164.

In another aspect, plants are provided that comprise in their genome one or more mutated More Axillary Growth 1 (MAX1) genes produced by the methods of the invention.

A further aspect of the invention provides a soybean plant or plant part thereof comprising at least one mutation in at least one endogenous More Axillary Growth 1 (MAX1) gene having the gene identification number (gene ID) of Glyma.04g052100 (MAX1a), Glyma.06g052700 (MAX1b), Glyma.14g096900 (MAX1c) and/or Glyma.17g227500 (MAX1d), optionally wherein the at least one mutation may be a non-natural mutation.

In a further aspect, a guide nucleic acid is provided that binds to target nucleic acid in a More Axillary Growth 1 (MAX1) gene having the gene identification number (gene ID) of Glyma.04g052100 (MAX1a), Glyma.06g052700 (MAX1b), Glyma.14g096900 (MAX1c) and/or Glyma.17g227500 (MAX1d). Also provided herein are mutated MAX1 nucleic acids and polypeptides as described herein.

Further provided are polypeptides, polynucleotides, nucleic acid constructs, expression cassettes and vectors for making a plant of this invention.

These and other aspects of the invention are set forth in more detail in the description of the invention below.

BRIEF DESCRIPTION OF THE SEQUENCES

SEQ ID NOs:1-17 are exemplary Cas12a amino acid sequences useful with this invention.

SEQ ID NOs:18-20 are exemplary Cas12a nucleotide sequences useful with this invention.

SEQ ID NO:21-22 are exemplary regulatory sequences encoding a promoter and intron.

SEQ ID NOs:23-29 are exemplary cytosine deaminase sequences useful with this invention.

SEQ ID NOs:30-40 are exemplary adenine deaminase amino acid sequences useful with this invention.

SEQ ID NO:41 is an exemplary uracil-DNA glycosylase inhibitor (UGI) sequences useful with this invention.

SEQ ID NOs:42-44 provide example peptide tags and affinity polypeptides useful with this invention.

SEQ ID NOs:45-55 provide example RNA recruiting motifs and corresponding affinity polypeptides useful with this invention.

SEQ ID NOs:56-57 are exemplary Cas9 polypeptide sequences useful with this invention.

SEQ ID NOs:58-68 are exemplary Cas9 polynucleotide sequences useful with this invention.

SEQ ID NO:69 is an example MAX1a genomic sequence from soybean.

SEQ ID NO:70 is an example MAX1a coding sequence from soybean.

SEQ ID NO:71 is an example MAX1a polypeptide sequence from soybean.

SEQ ID NOs:72-91 are example portions or regions of a soybean MAX1a genomic and coding sequences.

SEQ ID NO:92 is an example portion or region of MAX1a polypeptide from soybean.

SEQ ID NO:93 is an example MAX1b genomic sequence from soybean.

SEQ ID NO:94 is an example MAX1b coding sequence from soybean.

SEQ ID NO:95 is an example MAX1b polypeptide sequence from soybean.

SEQ ID NOs:96-113 are example portions or regions of a soybean MAX1b genomic and coding sequences.

SEQ ID NO:114 is an example portion or region of MAX1b polypeptide from soybean.

SEQ ID NO:115 is an example MAX1c genomic sequence from soybean.

SEQ ID NO:116 is an example MAX1c coding sequence from soybean.

SEQ ID NO:117 is an example MAX1c polypeptide sequence from soybean.

SEQ ID NOs:118-138 are example portions or regions of a soybean MAX1c genomic and coding sequences.

SEQ ID NO:139 is an example portion or region of MAX1c polypeptide from soybean.

SEQ ID NO:140 is an example MAX1d genomic sequence from soybean.

SEQ ID NO:141 is an example MAX1d coding sequence from soybean.

SEQ ID NO:142 is an example MAX1d polypeptide sequence from soybean.

SEQ ID NOs:143-164 are example portions or regions of a soybean MAX1d genomic and coding sequences.

SEQ ID NO:165 is an example portion or region of MAX1d polypeptide from soybean.

SEQ ID NOs:166-168 and 169-172 are example spacer sequences for nucleic acid guides useful with this invention.

SEQ ID NOs:173, 175, 177, 179, 181, and 183 show example edited MAX1 genes.

SEQ ID NOs:174, 176, 178, 180, 182, and 184 show example truncated polypeptides encoded by the mutated MAX1 genes of SEQ ID NOs:173, 175, 177, 179, 181, and 183, respectively.

SEQ ID NOs:185-187 show example portions or regions deleted from MAX1 genes using the methods described herein.

DETAILED DESCRIPTION

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms “a,” “an” and “the” are intended to include the plural forms as well, unless the context clearly indicates otherwise.

Also as used herein, “and/or” refers to and encompasses any and all possible combinations of one or more of the associated listed items, as well as the lack of combinations when interpreted in the alternative (“or”).

The term “about,” as used herein when referring to a measurable value such as an amount or concentration and the like, is meant to encompass variations of ±10%, ±5%, ±1%, ±0.5%, or even ±0.1% of the specified value as well as the specified value. For example, “about X” where X is the measurable value, is meant to include X as well as variations of ±10%, ±5%, ±1%, ±0.5%, or even ±0.1% of X. A range provided herein for a measurable value may include any other range and/or individual value therein.

As used herein, phrases such as “between X and Y” and “between about X and Y” should be interpreted to include X and Y. As used herein, phrases such as “between about X and Y” mean “between about X and about Y” and phrases such as “from about X to Y” mean “from about X to about Y.”

Recitation of ranges of values herein are merely intended to serve as a shorthand method of referring individually to each separate value falling within the range, unless otherwise indicated herein, and each separate value is incorporated into the specification as if it were individually recited herein. For example, if the range 10 to15 is disclosed, then 11, 12, 13, and 14 are also disclosed.

The term “comprise,” “comprises” and “comprising” as used herein, specify the presence of the stated features, integers, steps, operations, elements, and/or components, but do not preclude the presence or addition of one or more other features, integers, steps, operations, elements, components, and/or groups thereof.

As used herein, the transitional phrase “consisting essentially of” means that the scope of a claim is to be interpreted to encompass the specified materials or steps recited in the claim and those that do not materially affect the basic and novel characteristic(s) of the claimed invention. Thus, the term “consisting essentially of” when used in a claim of this invention is not intended to be interpreted to be equivalent to “comprising.”

As used herein, the terms “increase,” “increasing,” “increased,” “enhance,” “enhanced,” “enhancing,” and “enhancement” (and grammatical variations thereof) describe an elevation of at least about 5%, 10%, 15%, 20%, 25%, 50%, 75%, 100%, 150%, 200%, 300%, 400%, 500% or more as compared to a control. For example, a plant comprising a mutation in a More Axillary Growth 1 (MAX1) gene as described herein can exhibit an improved yield trait (e.g., one or more improved yield traits, including, but not limited to, an increase in yield (bu/acre), an increase in biomass, an increase in the number of flowers, an increase in seed size, an increase in seed weight, an increased number of pods, an increased number of pods per node, an increased number of seeds per pod) and/or improved plant architecture (e.g., one or more traits associated with improved plant architecture, including, but not limited to, increased branching increased number of nodes, and/or reduced internode length as compared to a control plant devoid of the at least one mutation. A control plant is typically the same plant as the edited plant, but the control plant has not been similarly edited and therefore is devoid of the mutation. A control plant maybe an isogenic plant and/or a wild type plant. Thus, a control plant can be the same breeding line, variety, or cultivar as the subject plant into which a mutation as described herein is introgressed, but the control breeding line, variety, or cultivar is free of the mutation. In some embodiments, a comparison between a plant of the invention and a control plant is made under the same growth conditions, e.g., the same environmental conditions (soil, hydration, light, heat, nutrients, and the like).

As used herein, the terms “reduce,” “reduced,” “reducing,” “reduction,” “diminish,” and “decrease” (and grammatical variations thereof), describe, for example, a decrease of at least about 5%, 10%, 15%, 20%, 25%, 35%, 50%, 75%, 80%, 85%, 90%, 95%, 96%, 97%, 98%, 99%, 99.5%, 99.6%, 99.7%, 99.8%, 99.9%, or 100% as compared to a control. In particular embodiments, the reduction can result in no or essentially no (i.e., an insignificant amount, e.g., less than about 10% or even 5%) detectable activity or amount. In some embodiments, an improved plant architecture can include reduced stature (e.g., semi-dwarf, e.g., shorter than a control plant by about 5% to about 50%).

As used herein, the terms “express,” “expresses,” “expressed” or “expression,” and the like, with respect to a nucleic acid molecule and/or a nucleotide sequence (e.g., RNA or DNA) indicates that the nucleic acid molecule and/or a nucleotide sequence is transcribed and, optionally, translated. Thus, a nucleic acid molecule and/or a nucleotide sequence may express a polypeptide of interest or, for example, a functional untranslated RNA.

A “heterologous” or a “recombinant” nucleotide sequence is a nucleotide sequence not naturally associated with a host cell into which it is introduced, including non-naturally occurring multiple copies of a naturally occurring nucleotide sequence. A “heterologous” nucleotide/polypeptide may originate from a foreign species, or, if from the same species, is substantially modified from its native form in composition and/or genomic locus by deliberate human intervention.

A “native” or “wild type” nucleic acid, nucleotide sequence, polypeptide or amino acid sequence refers to a naturally occurring or endogenous nucleic acid, nucleotide sequence, polypeptide or amino acid sequence. In some contexts, a “wild type” nucleic acid is a nucleic acid that is not edited as described herein and can differ from an “endogenous” gene that may be edited as described herein (e.g., a mutated endogenous gene). In some contexts, a “wild type” nucleic acid (e.g., unedited) may be heterologous to the organism in which the wild type nucleic acid is found (e.g., a transgenic organism). As an example, a “wild type endogenous More Axillary Growth 1 (MAX1) gene” is a MAX1 gene that is naturally occurring in or endogenous to the reference organism, e.g., a plant, e.g., a soybean plant, a canola plant, and may be subject to modification as described herein, after which, such a modified endogenous gene is no longer wild type. In some embodiments, an endogenous MAX1 gene is an endogenous MAX1a gene, an endogenous MAX1b gene, an endogenous MAX1b gene, or an endogenous MAX1d gene, optionally wherein the modification may be in one or more than one of a MAX1a gene, MAX1b gene, MAX1c gene, and/or MAX1d gene.

As used herein, the term “heterozygous” refers to a genetic status wherein different alleles reside at corresponding loci on homologous chromosomes.

As used herein, the term "homozygous" refers to a genetic status wherein identical alleles reside at corresponding loci on homologous chromosomes.

As used herein, the term "allele" refers to one of two or more different nucleotides or nucleotide sequences that occur at a specific locus.

A "null allele" is a nonfunctional allele caused by a genetic mutation that results in a complete lack of production of the corresponding protein or produces a protein that is non-functional.

A "recessive mutation" is a mutation in a gene that produces a phenotype when homozygous but the phenotype is not observable when the locus is heterozygous.

A "dominant mutation" is a mutation in a gene that produces a mutant phenotype in the presence of a non-mutated copy of the gene. A dominant mutation may be a loss or a gain of function mutation, a hypomorphic mutation, a hypermorphic mutation or a weak loss of function or a weak gain of function.

A "dominant negative mutation" is a mutation that produces an altered gene product (e.g., having an aberrant function relative to wild type), which gene product adversely affects the function of the wild-type allele or gene product. For example, a "dominant negative mutation" may block a function of the wild type gene product. A dominant negative mutation may also be referred to as an "antimorphic mutation."

A "semi-dominant mutation" refers to a mutation in which the penetrance of the phenotype in a heterozygous organism is less than that observed for a homozygous organism.

A "weak loss-of-function mutation" is a mutation that results in a gene product having partial function or reduced function (partially inactivated) as compared to the wildtype gene product.

A "hypomorphic mutation" is a mutation that results in a partial loss of gene function, which may occur through reduced expression (e.g., reduced protein and/or reduced RNA) or reduced functional performance (e.g., reduced activity), but not a complete loss of function/activity. A "hypomorphic" allele is a semi-functional allele caused by a genetic mutation that results in production of the corresponding protein that functions at anywhere between 1% and 99% of normal efficiency.

A "hypermorphic mutation" is a mutation that results in increased expression of the gene product and/or increased activity of the gene product.

A "locus" is a position on a chromosome where a gene or marker or allele is located. In some embodiments, a locus may encompass one or more nucleotides.

As used herein, the terms "desired allele," "target allele" and/or "allele of interest" are used interchangeably to refer to an allele associated with a desired trait. In some embodiments, a desired allele may be associated with either an increase or a decrease (relative to a control) of or in a given trait, depending on the nature of the desired phenotype.

A marker is "associated with" a trait when said trait is linked to it and when the presence of the marker is an indicator of whether and/or to what extent the desired trait or trait form will occur in a plant/germplasm comprising the marker. Similarly, a marker is "associated with" an allele or chromosome interval when it is linked to it and when the presence of the marker is an indicator of whether the allele or chromosome interval is present in a plant/germplasm comprising the marker.

As used herein, the terms "backcross" and "backcrossing" refer to the process whereby a progeny plant is crossed back to one of its parents one or more times (e.g., 1, 2, 3, 4, 5, 6, 7, 8, etc.). In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. *Marker-assisted Backcrossing: A Practical Example, in* Techniques et Utilisations des Marqueurs Moleculaires Les Colloques, Vol. 72, pp. 45-56 (1995); and Openshaw et al., *Marker-assisted Selection in Backcross Breeding, in* Proceedings of the Symposium "Analysis of Molecular Marker Data," pp. 41-43 (1994). The initial cross gives rise to the F1 generation. The term "BC1" refers to the second use of the recurrent parent, "BC2" refers to the third use of the recurrent parent, and so on.

As used herein, the terms "cross" or "crossed" refer to the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

As used herein, the terms "introgression," "introgressing" and "introgressed" refer to both the natural and artificial transmission of a desired allele or combination of desired alleles of a genetic locus or genetic loci from one genetic background to another. For example, a desired allele at a specified locus can be transmitted to at least one (e.g., one or more) progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele may be a selected allele of a marker, a QTL, a transgene, or the like. Offspring comprising the desired allele can be backcrossed one or more times (e.g., 1, 2, 3, 4, or more times) to a line having a desired genetic background, selecting for the desired allele, with the result being that the desired allele becomes fixed in the desired genetic background. For example, a marker associated with increased yield under non-water stress conditions may be introgressed from a donor into a recurrent parent that does not comprise the marker and does not exhibit increased yield under non-water stress conditions. The resulting offspring could then be backcrossed one or more times and selected until the progeny possess the genetic marker(s) associated with increased yield under non-water stress conditions in the recurrent parent background.

A "genetic map" is a description of genetic linkage relationships among loci on one or more chromosomes within a given species, generally depicted in a diagrammatic or tabular form. For each genetic map, distances between loci are measured by the recombination frequencies between them. Recombination between loci can be detected using a variety of markers. A genetic map is a product of the mapping population, types of markers used, and the polymorphic potential of each marker between different populations. The order and genetic distances between loci can differ from one genetic map to another.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) of one or more known loci that the individual has inherited from its parents. The term genotype can be used to refer to an individual's genetic constitution at a single locus, at multiple loci, or more generally, the term genotype can be used to refer to an individual's genetic make-up for all the genes in its genome. Genotypes can be indirectly characterized, e.g., using markers and/or directly characterized by nucleic acid sequencing.

As used herein, the term "germplasm" refers to genetic material of or from an individual (e.g., a plant), a group of individuals (e.g., a plant line, variety or family), or a clone derived from a line, variety, species, or culture. The germplasm can be part of an organism or cell or can be separate from the organism or cell. In general, germplasm provides genetic material with a specific genetic makeup that provides a foundation for some or all of the hereditary qualities of an organism or cell culture. As used herein, germplasm includes cells, seed or tissues from which new plants may be grown, as well as plant parts that can be cultured into a whole plant (e.g., leaves, stems, buds, roots, pollen, cells, etc.).

As used herein, the terms "cultivar" and "variety" refer to a group of similar plants that by structural or genetic features and/or performance can be distinguished from other varieties within the same species.

As used herein, the terms "exotic," "exotic line" and "exotic germplasm" refer to any plant, line or germplasm that is not elite. In general, exotic plants/germplasms are not derived from any known elite plant or germplasm, but rather are selected to introduce one or more desired genetic elements into a breeding program (e.g., to introduce novel alleles into a breeding program).

As used herein, the term "hybrid" in the context of plant breeding refers to a plant that is the offspring of genetically dissimilar parents produced by crossing plants of different lines or breeds or species, including but not limited to the cross between two inbred lines.

As used herein, the term "inbred" refers to a substantially homozygous plant or variety. The term may refer to a plant or plant variety that is substantially homozygous throughout the entire genome or that is substantially homozygous with respect to a portion of the genome that is of particular interest.

A "haplotype" is the genotype of an individual at a plurality of genetic loci, i.e., a combination of alleles. Typically, the genetic loci that define a haplotype are physically and genetically linked, i.e., on the same chromosome segment. The term "haplotype" can refer to polymorphisms at a particular locus, such as a single marker locus, or polymorphisms at multiple loci along a chromosomal segment.

A plant in which at least one (e.g., one or more, e.g., 1, 2, 3, or 4, or more) endogenous MAX1 gene (e.g., an endogenous MAX1a gene, an endogenous MAX1b gene, an endogenous MAX1c gene, an endogenous MAX1d gene) is modified as described herein (e.g., comprises a modification as described herein, e.g., see SEQ ID NOs:173-184 edited MAX1 genes and their corresponding truncated polypeptides that they encode) may have improved yield traits as compared to a plant that does not comprise (is devoid of) the modification in the at least one endogenous MAX1 gene. As used herein, "improved yield traits" refers to any plant trait associated with growth, for example, biomass, yield, nitrogen use efficiency (NUE), inflorescence size/weight, fruit yield, fruit quality, fruit size, seed size (e.g., seed area, seed size), seed number, foliar tissue weight, nodulation number, nodulation mass, nodulation activity, number of seed heads, number of tillers, number of branches, number of flowers, number of tubers, tuber mass, bulb mass, number of seeds, total seed mass, rate of leaf emergence, rate of tiller/branch emergence, rate of seedling emergence, length of roots, number of roots, size and/or weight of root mass, or any combination thereof. In some aspects, "improved yield traits" may include, but are not limited to, increased inflorescence production, increased fruit production (e.g., increased number, weight and/or size of fruit; e.g., increased number, weight, and/or length of ears for, e.g., maize), increased fruit quality, increased number, size and/or weight of roots, increased meristem size, increased seed size (e.g., seed area and/or seed weight), increased biomass, increased leaf size, increased nitrogen use efficiency, increased height, increased internode number and/or increased internode length as compared to a control plant or part thereof (e.g., a plant that does not comprise a mutated endogenous MAX1 nucleic acid as described herein). In some aspects, improved yield traits can be expressed as quantity of grain/seed produced per area of land (e.g., bushels per acre of land). In some embodiments, the one or more improved yield traits is an increase in seed number.

As used herein, an "increased seed size" can mean a seed that is increased in area and/or an increase in seed weight (e.g., 100-seed weight). In some embodiments, a seed may be increased in area by up to about 70% (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 45, 46, 47, 48, 49, 50, 51, 52, 53, 54, 55, 56, 57, 58, 59, 60, 61, 62, 63, 64, 65, 66, 67, 68, 69, 70%) as compared to a seed from a control plant (e.g., a plant not comprising the mutation in an endogenous MAX1 gene as described herein). In some embodiments, an seed may be increased in weight by up to about 50% (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 45, 46, 47, 48, 49, or 50%) as compared to a seed from a control plant (e.g., a plant not comprising the mutation in an endogenous MAX1 gene as described herein). In some embodiments, an increase in seed size can include an increase in both seed area and seed size. An increased seed size may be measured, for example, by 100-seed weight.

As used herein a "control plant" means a plant that does not contain an edited MAX1 gene or gene as described herein that imparts an enhanced/improved trait (e.g., yield trait) or altered phenotype. A control plant is used to identify and select a plant edited as described herein and that has an enhanced trait or altered phenotype as compared to the control plant. A suitable control plant can be a plant of the parental line used to generate a plant comprising a mutated MAX1 gene(s), for example, a wild type plant devoid of an edit in an endogenous MAX1 gene as described herein. A suitable control plant can also be a plant that contains recombinant nucleic acids that impart other traits, for example, a transgenic plant having enhanced herbicide tolerance. A suitable control plant can in some cases be a progeny of a heterozygous or hemizygous transgenic plant line that is devoid of the mutated MAX1 gene as described herein, known as a negative segregant, or a negative isogenic line.

An enhanced trait (e.g., improved yield trait) may include, for example, decreased days from planting to maturity, increased stalk size, increased number of leaves, increased plant height growth rate in vegetative stage, increased ear size, increased ear dry weight per plant, increased number of kernels per ear, increased weight per kernel, increased number of kernels per plant, decreased ear void, extended grain fill period, reduced plant height, increased number of root branches, increased total root length, increased yield, increased nitrogen use efficiency, and/or increased water use efficiency as compared to a control plant. An altered phenotype may be, for example, plant height, biomass, canopy area, anthocyanin content, chlorophyll content, water applied, water content, and water use efficiency.

In some embodiments, a plant of this invention may comprise one or more improved yield traits including, but not limited to, In some embodiments, the one or more improved yield traits includes higher yield (bu/acre), increased biomass, increased plant height, increased stem diameter, increased leaf area, increased number of flowers, increased kernel row number, optionally wherein ear length is not substantially reduced, increased kernel number, increased kernel size, increased ear length, decreased tiller number, decreased tassel branch number, increased number of pods, including an increased number of pods per node and/or an increased number of pods per plant, increased number of seeds per pod, increased number of seeds, increased seed size, and/or increased seed weight (e.g., increase in 100-seed weight) as compared to a control plant devoid of the at least one mutation. In some embodiments, a plant of this invention may comprise one or more improved yield traits including, but not limited to, optionally an increase in yield (bu/acre), seed size (including kernel size), seed weight (including kernel weight), increased kernel row number (optionally wherein ear length is not substantially reduced), increased number of pods, increased number of seeds per pod and an increase in ear length as compared to a control plant or part thereof.

As used herein a "trait" is a physiological, morphological, biochemical, or physical characteristic of a plant or particular plant material or cell. In some instances, this characteristic is visible to the human eye and can be measured mechanically, such as seed or plant size, weight, shape, form, length, height, growth rate and development stage, or can be measured by biochemical techniques, such as detecting the protein, starch, certain metabolites, or oil content of seed or leaves, or by observation of a metabolic or physiological process, for example, by measuring tolerance to water deprivation or particular salt or sugar concentrations, or by the measurement of the expression level of a gene or genes, for example, by employing Northern analysis, RT-PCR, microarray gene expression assays, or reporter gene expression systems, or by agricultural observations such as hyperosmotic stress tolerance or yield. However, any technique can be used to measure the amount of, the comparative level of, or the difference in any selected chemical compound or macromolecule in the transgenic plants.

As used herein an "enhanced trait" means a characteristic of a plant resulting from mutations in a MAX1 gene(s) as described herein. Such traits include, but are not limited to, an enhanced agronomic trait characterized by enhanced plant morphology, physiology, growth and development, yield, nutritional enhancement, disease or pest resistance, or environmental or chemical tolerance. In some embodiments, an enhanced trait/altered phenotype may be, for example, decreased days from planting to maturity, increased stalk size, increased number of leaves, increased plant height growth rate in vegetative stage, increased ear size, increased ear dry weight per plant, increased number of kernels per ear, increased weight per kernel, increased number of kernels per plant, decreased ear void, extended grain fill period, reduced plant height, increased number of root branches, increased total root length, drought tolerance, increased water use efficiency, cold tolerance, increased nitrogen use efficiency, and/or increased yield. In some embodiments, a trait is increased yield under nonstress conditions or increased yield under environmental stress conditions. Stress conditions can include both biotic and abiotic stress, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability and high plant density. "Yield" can be affected by many properties including without limitation, plant height, plant biomass, pod number, pod position on the plant, number of internodes, incidence of pod shatter, grain size, ear size, ear tip filling, kernel abortion, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Yield can also be affected by efficiency of germination (including germination in stressed conditions), growth rate (including growth rate in stressed conditions), flowering time and duration, ear number, ear size, ear weight, seed number per ear or pod, seed size, composition of seed (starch, oil, protein) and characteristics of seed fill.

Also used herein, the term "trait modification" encompasses altering the naturally occurring trait by producing a detectable difference in a characteristic in a plant comprising a mutation in an endogenous MAX1 gene as described herein relative to a plant not comprising the mutation, such as a wild-type plant, or a negative segregant. In some cases, the trait modification can be evaluated quantitatively. For example, the trait modification can entail an increase or decrease in an observed trait characteristic or phenotype as compared to a control plant. It is known that there can be natural variations in a modified trait. Therefore, the trait modification observed can entail a change of the normal distribution and magnitude of the trait characteristics or phenotype in the plants as compared to a control plant.

The present disclosure relates to a plant with improved economically relevant characteristics, more specifically increased yield and or an improved plant architecture (which can contribute to improved yield traits). More specifically the present disclosure relates to a plant comprising a mutation(s) in a MAX1 gene(s) as described herein, wherein the plant has increased yield as compared to a control plant devoid of said mutation(s). In some embodiments, plants produced as described herein exhibit increased yield or improved yield trait components as compared to a control plant, optionally an improved plant architecture (e.g., increased branching, increased number of nodes, reduced internode length, semi-dwarf stature). In some embodiments, a plant of the present disclosure exhibits an improved trait that is related to yield, including but not limited to increased nitrogen use efficiency, increased nitrogen stress tolerance, increased water use efficiency and/or increased drought tolerance, as defined and discussed infra.

Yield can be defined as the measurable produce of economic value from a crop. Yield can be defined in the scope of quantity and/or quality. Yield can be directly dependent on several factors, for example, the number and size of organs (e.g., number of flowers), plant architecture (such as the number of branches, plant biomass, e.g., increased root biomass, steeper root angle and/or longer roots, and the like), flowering time and duration, grain fill period. Root architecture and development, photosynthetic efficiency, nutrient uptake, stress tolerance, early vigor, delayed senescence and functional stay green phenotypes may be factors in determining yield. Optimizing the above-mentioned factors can therefore contribute to increasing crop yield.

Reference herein to an increase/improvement in yield-related traits can also be taken to mean an increase in biomass (weight) of one or more parts of a plant, which can include above ground and/or below ground (harvestable) plant parts. In particular, such harvestable parts are seeds, and performance of the methods of the disclosure results in plants with increased yield and in particular increased seed yield relative to the seed yield of suitable control plants. The term "yield" of a plant can relate to vegetative biomass (root and/or shoot biomass), to reproductive organs, and/or to propagules (such as seeds) of that plant.

Increased yield of a plant of the present disclosure can be measured in a number of ways, including test weight, seed number per plant, seed weight, seed number per unit area (for example, seeds, or weight of seeds, per acre), bushels per acre, tons per acre, or kilo per hectare. Increased yield can result from improved utilization of key biochemical compounds, such as nitrogen, phosphorous and carbohydrate, or from improved responses to environmental stresses, such as cold, heat, drought, salt, shade, high plant density, and attack by pests or pathogens.

"Increased yield" can manifest as one or more of the following: (i) increased plant biomass (weight) of one or more parts of a plant, particularly aboveground (harvestable) parts, of a plant, increased root biomass (increased number of roots, increased root thickness, increased root length) or increased biomass of any other harvestable part; or (ii) increased early vigor, defined herein as an improved seedling aboveground area approximately three weeks post-germination.

"Early vigor" refers to active healthy plant growth especially during early stages of plant growth, and can result from increased plant fitness due to, for example, the plants being better adapted to their environment (for example, optimizing the use of energy resources, uptake of nutrients and partitioning carbon allocation between shoot and root). Early vigor, for example, can be a combination of the ability of seeds to germinate and emerge after planting and the ability of the young plants to grow and develop after emergence. Plants having early vigor also show increased seedling survival and better establishment of the crop, which often results in highly uniform fields with the majority of the plants reaching the various stages of development at substantially the same time, which often results in increased yield. Therefore, early vigor can be determined by measuring various factors, such as kernel weight, percentage germination, percentage emergence, seedling growth, seedling height, root length, root and shoot biomass, canopy size and color and others.

Further, increased yield can also manifest as increased total seed yield, which may result from one or more of an increase in seed biomass (seed weight) due to an increase in the seed weight on a per plant and/or on an individual seed basis an increased number of, for example, flowers/panicles per plant; an increased number of pods; an increased number of nodes; an increased number of flowers ("florets") per panicle/plant; increased seed fill rate; an increased number of filled seeds; increased seed size (length, width, area, perimeter, and/or weight), which can also influence the composition of seeds; and/or increased seed volume, which can also influence the composition of seeds. In one embodiment, increased yield can be increased seed yield, for example, increased seed weight; increased number of filled seeds; and/or increased harvest index.

Increased yield can also result in modified architecture, or can occur because of modified plant architecture.

Increased yield can also manifest as increased harvest index, which is expressed as a ratio of the yield of harvestable parts, such as seeds, over the total biomass The disclosure also extends to harvestable parts of a plant such as, but not limited to, seeds, leaves, fruits, flowers, bolls, pods, siliques, nuts, stems, rhizomes, tubers and bulbs. The disclosure furthermore relates to products derived from a harvestable part of such a plant, such as dry pellets, powders, oil, fat and fatty acids, starch or proteins.

The present disclosure provides a method for increasing "yield" of a plant or "broad acre yield" of a plant or plant part defined as the harvestable plant parts per unit area, for example seeds, or weight of seeds, per acre, pounds per acre, bushels per acre, tones per acre, tons per acre, kilo per hectare.

As used herein "nitrogen use efficiency" refers to the processes which lead to an increase in the plant's yield, biomass, vigor, and growth rate per nitrogen unit applied. The processes can include the uptake, assimilation, accumulation, signaling, sensing, retranslocation (within the plant) and use of nitrogen by the plant.

As used herein "increased nitrogen use efficiency" refers to the ability of plants to grow, develop, or yield faster or better than normal when subjected to the same amount of available/applied nitrogen as under normal or standard conditions; ability of plants to grow, develop, or yield normally, or grow, develop, or yield faster or better when subjected to less than optimal amounts of available/applied nitrogen, or under nitrogen limiting conditions.

As used herein "nitrogen limiting conditions" refers to growth conditions or environments that provide less than optimal amounts of nitrogen needed for adequate or successful plant metabolism, growth, reproductive success and/or viability.

As used herein the "increased nitrogen stress tolerance" refers to the ability of plants to grow, develop, or yield normally, or grow, develop, or yield faster or better when subjected to less than optimal amounts of available/applied nitrogen, or under nitrogen limiting conditions.

Increased plant nitrogen use efficiency can be translated in the field into either harvesting similar quantities of yield, while supplying less nitrogen, or increased yield gained by supplying optimal/sufficient amounts of nitrogen. The increased nitrogen use efficiency can improve plant nitrogen stress tolerance and can also improve crop quality and biochemical constituents of the seed such as protein yield and oil yield. The terms "increased nitrogen use efficiency", "enhanced nitrogen use efficiency", and "nitrogen stress tolerance" are used inter-changeably in the present disclosure to refer to plants with improved productivity under nitrogen limiting conditions.

As used herein "water use efficiency" refers to the amount of carbon dioxide assimilated by leaves per unit of water vapor transpired. It constitutes one of the most important traits controlling plant productivity in dry environments. "Drought tolerance" refers to the degree to which a plant is adapted to arid or drought conditions. The physiological responses of plants to a deficit of water include leaf wilting, a reduction in leaf area, leaf abscission, and the stimulation of root growth by directing nutrients to the underground parts of the plants. Typically, plants are more susceptible to drought during flowering and seed development (the reproductive stages), as plant's resources are deviated to support root growth. In addition, abscisic acid (ABA), a plant stress hormone, induces the closure of leaf stomata (microscopic pores involved in gas exchange), thereby reducing water loss through transpiration, and decreasing the rate of photosynthesis. These responses improve the water-use efficiency of the plant on the short term. The terms "increased water use efficiency", "enhanced water use efficiency", and "increased drought tolerance" are used inter-changeably in the present disclosure to refer to plants with improved productivity under water-limiting conditions.

As used herein "increased water use efficiency" refers to the ability of plants to grow, develop, or yield faster or better than normal when subjected to the same amount of available/applied water as under normal or standard conditions; ability of plants to grow, develop, or yield normally, or grow, develop, or yield faster or better when subjected to reduced amounts of available/applied water (water input) or under conditions of water stress or water deficit stress.

As used herein "increased drought tolerance" refers to the ability of plants to grow, develop, or yield normally, or grow, develop, or yield faster or better than normal when subjected to reduced amounts of available/applied water and/or under conditions of acute or chronic drought; ability of plants to grow, develop, or yield normally when subjected to reduced amounts of available/applied water (water input) or under conditions of water deficit stress or under conditions of acute or chronic drought.

As used herein, "drought stress" refers to a period of dryness (acute or chronic/prolonged) that results in water deficit and subjects plants to stress and/or damage to plant tissues and/or negatively affects grain/crop yield; a period of dryness (acute or chronic/prolonged) that results in water deficit and/or higher temperatures and subjects plants to stress and/or damage to plant tissues and/or negatively affects grain/crop yield.

As used herein, "water deficit" refers to the conditions or environments that provide less than optimal amounts of water needed for adequate/successful growth and development of plants.

As used herein, "water stress" refers to the conditions or environments that provide improper (either less/insufficient or more/excessive) amounts of water than that needed for adequate/successful growth and development of plants/crops thereby subjecting the plants to stress and/or damage to plant tissues and/or negatively affecting grain/crop yield.

As used herein "water deficit stress" refers to the conditions or environments that provide less/insufficient amounts of water than that needed for adequate/successful growth and development of plants/crops thereby subjecting the plants to stress and/or damage to plant tissues and/or negatively affecting grain yield.

As used herein, the terms "nucleic acid," "nucleic acid molecule," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made.

As used herein, the term "nucleotide sequence" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "nucleic acid construct," "oligonucleotide" and "polynucleotide" are also used interchangeably herein to refer to a heteropolymer of nucleotides. Nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25. A "5' region" as used herein can mean the region of a polynucleotide that is nearest the 5' end of the polynucleotide. Thus, for example, an element in the 5' region of a polynucleotide can be located anywhere from the first nucleotide located at the 5' end of the polynucleotide to the nucleotide located halfway through the polynucleotide. A "3' region" as used herein can mean the region of a polynucleotide that is nearest the 3' end of the polynucleotide. Thus, for example, an element in the 3' region of a polynucleotide can be located anywhere from the first nucleotide located at the 3' end of the polynucleotide to the nucleotide located halfway through the polynucleotide.

As used herein with respect to nucleic acids, the term "fragment" or "portion" refers to a nucleic acid that is reduced in length relative (e.g., reduced by 1, 2, 3, 4, 5, 6, 7, 8, 9, 10, 11, 12, 13, 14, 15, 16, 17, 18, 19, 20, 20, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 400, 450, 500, 550, 600, 650, 700, 750, 800, 850, or 900 or more nucleotides or any range or value therein) to a reference nucleic acid and that comprises, consists essentially of and/or consists of a nucleotide sequence of contiguous nucleotides identical or almost identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to a corresponding portion of the reference nucleic acid. Such a nucleic acid fragment may be, where appropriate, included in a larger polynucleotide of which it is a constituent. As an example, a repeat sequence of guide nucleic acid of this invention may comprise a "portion" of a wild type CRISPR-Cas repeat sequence (e.g., a wild type CRISPR-Cas repeat; e.g., a repeat from the CRISPR Cas system of, for example, a Cas9, Cas12a (Cpf1), Cas12b, Cas12c (C2c3), Cas12d (CasY), Cas12e (CasX), Cas12g, Cas12h, Cas12i, C2c4, C2c5, C2c8, C2c9, C2c10, Cas14a, Cas14b, and/or a Cas14c, and the like).

In some embodiments, a nucleic acid fragment may comprise, consist essentially of or consist of about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 320, 330, 340, 350, 360, 370, 380, 390, 395, 400, 410, 415, 420, 425, 430, 435, 440, 445, 450, 500, 550, 600, 650, 700, 750, 800, 850, 900, 950, 1000, 1100, 1150, 1200, 1250, 1300, 1350, 1400, 1450, 1500, 1550, 1600, 1650, 1700, 1750, 1800, 1900, 2000, 3000, 4000 or 5000 or more consecutive nucleotides, or any range or value therein, of a nucleic acid encoding a MAX1 polypeptide, optionally a fragment of a MAX1 gene may be about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 115, 120, 125, 130, 135, 140, 145, 150 consecutive nucleotides to about 155, 160, 165, 170, 175, 180, 185, 190, 195, 200, 205, 210, 215, 220, 225, 230, 240, 245, 250, 255, 260, 265, 270, 275, 280, 285, 290, 295, 300, 305, 310, 315, 320, 325, 330, 340, 345, 350, 355, 360, 365, 370, 375, 380, 385, 390, 395, or 400, or more consecutive nucleotides in length, or any range or value therein (e.g., a fragment or portion of any one of SEQ ID NOs:69, 70, 93, 94, 115, 116, 140 or 141 (e.g., of SEQ ID NOs:72-91, 96-113, 118-138, or 143-164).

In some embodiments, a "sequence-specific nucleic acid binding domain" may bind to one or more fragments or portions of nucleotide sequences (e.g., DNA, RNA) encoding, for example, a cytochrome P450 monooxygenase (MAX1) polypeptide as described herein.

As used herein with respect to polypeptides, the term "fragment" or "portion" may refer to a polypeptide that is reduced in length relative to a reference polypeptide and that comprises, consists essentially of and/or consists of an amino acid sequence of contiguous amino acids identical or almost identical (e.g., 90%, 91%, 92%, 93%, 94%, 95%, 96%, 97%, 98%, 99% identical) to a corresponding portion of the reference polypeptide. Such a polypeptide fragment may be, where appropriate, included in a larger polypeptide of which it is a constituent. In some embodiments, a polypeptide fragment may comprise, consist essentially of, or consist of at least about 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 125, 150, 175, 200, 225, 250, 260, 270, 280, or 290 or more consecutive amino acids of a reference polypeptide. In some embodiments, a polypeptide fragment may comprise, consist essentially of or consist of about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 230, 240, or 250 or more consecutive amino acid residues, or any range or value therein, of a MAX1 polypeptide (e.g., a fragment or a portion of any one of SEQ ID NOs:71, 95, 117, or 142 (e.g., SEQ ID NOs:92, 114, 139 or 165)). In some embodiments, a fragment of a MAX1 polypeptide can be the N-terminus of the polypeptide or a portion thereof (see, e.g., SEQ ID NOs:92, 114, 139 or 165). In some embodiments, a fragment of a MAX1 polypeptide may be the result of a mutation generated in at least one endogenous gene encoding a MAX1 polypeptide (e.g., a MAX1a gene, a MAX1b gene, a MAX1c gene and/or a MAX1d gene) as described herein (e.g., a deletion, insertion and the like, in one or more of the endogenous MAX1 genes in a plant) (see, e.g., SEQ ID NOs:174, 176, 178, 180, 182, or 184, which show truncated polypeptides encoded by the mutated MAX1 genes of SEQ ID NOs:173, 175, 177, 179, 181, or 183, respectively).

In some embodiments, such a deletion when comprised in a plant can result in the plant exhibiting improved plant architecture and/or one or more improved yield traits, as compared to a plant not comprising said deletion. A MAX1 gene may be edited in one or more than one location (and using one or more different editing tools), thereby providing a MAX1 gene comprising one or more than one mutation. In some embodiments, a MAX1 polypeptide mutated as described herein may comprise one or more than one edit that may result in a polypeptide having a deletion of one or more amino acid residues (e.g., a deletion of 1, 2, 3, 4, 5, 6, 7, 8, 9, 10, 11, 12, 13, 14, 15, 16, 17, 18, 19, 20, 30, 40, 50, 60, 70, 80, 90, 100, 150, 200, 250, 300, 350, 400, 450, 500, 550, 600 or more consecutive amino acid residue, and any range or value therein (e.g., a truncated polypeptide), optionally a deletion of about 100 to about 600 consecutive amino acid residues (e.g., about 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, or 600, and any range or value therein).

In some embodiments, a "portion" or "region" in reference to a nucleic acid means at least 1, 2, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135,140, 145, 150, 155, 160, 165, 170, 175, 180, 185, 190, 195, 200, 210, 220, 230, 240, 250, 260, 270, 280, 285, 290, 300, 310, 320, 330, 340, 350, 360, 370, 380, 390, 395, 400, 405, 410, 415, 420, 425, 430, 435, 440, 445, 450, 500, 600, 700, 800, 900, 1000, 1100, 1200, 1300, 1400, 1500, 1600, 1700, 1800, 1900, 2000, 2500, 3000, 3500, 4000, 4500, or 5000 or more consecutive nucleotides from a gene (e.g., consecutive nucleotides from a MAX1 gene), optionally a "portion" or "region" of a MAX1 gene may be about 1 nucleotide, or 2, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, or 150 consecutive nucleotides to about 155, 160, 165, 170, 175, 180, 185, 190, 195, 200, 205, 210, 215, 220, 225, 230, 240, 245, 250, 255, 260, 265, 270, 275, 280, 285, 290, 295, 300, 305, 310, 315, 320, 325, 330, 340, 345, 350, 355, 360, 365, 370, 375, 380, 385, 390, 395, or 400, or more consecutive nucleotides in length, or any range or value therein (e.g., a portion or region of any one of SEQ ID NOs:69, 70, 93, 94, 115, 116, 140 or 141 (e.g., SEQ ID NOs:72-91, 96-113, 118-138, or 143-164, optionally SEQ ID NOs:77-79, 81-83, 88, 90, 91, 101-103, 105-107, 113, 121, 124, 125, 127-129, 132-138, 148-150, 152-154, or 160-164).

In some embodiments, a "portion" or "region" of a MAX1 polypeptide sequence may be about 5 to about 250 or more consecutive amino acid residues in length (e.g., about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 120, 130, 140, 141, 142, 143, 144, 145, 150, 160, 170, 180, 190, 200, 210, 220, 230, 240, or 250, or more consecutive amino acid residues in length (e.g., a portion of any one of SEQ ID NOs:71, 95, 117, or 142 (e.g., an N-terminal portion of a MAX1 polypeptide (e.g., SEQ ID NOs:92, 114, 139 or 165)) (see, e.g., SEQ ID NOs:174, 176, 178, 180, 182, or 184, which show truncated polypeptides encoded by the mutated MAX1 genes of SEQ ID NOs:173, 175, 177, 179, 181, or 183, respectively).

As used herein with respect to nucleic acids, the term "functional fragment" refers to nucleic acid that encodes a functional fragment of a polypeptide.

The term "gene," as used herein, refers to a nucleic acid molecule capable of being used to produce mRNA, antisense RNA, miRNA, anti-microRNA antisense oligodeoxyribonucleotide (AMO) and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

The term "mutation" refers to point mutations (e.g., missense, or nonsense, or insertions or deletions of single base pairs that result in frame shifts), insertions, deletions, inversions and/or truncations. When the mutation is a substitution of a residue within an amino acid sequence with another residue, or a deletion or insertion of one or more residues within a sequence, the mutations are typically described by identifying the original residue followed by the position of the residue within the sequence and by the identity of the newly substituted residue. A truncation can include a truncation at the C-terminal end of a polypeptide or at the N-terminal end of a polypeptide. A truncation of a polypeptide can be the result of a deletion of the corresponding 5' end or 3' end of the gene encoding the polypeptide. A frameshift mutation can occur when deletions or insertions of one or more base pairs are introduced into a gene, optionally resulting in an out-of-frame mutation or an in-frame mutation. Frameshift mutations in a gene can result in the production of a polypeptide that is longer, shorter or the same length as the wild type polypeptide depending on when the first stop codon occurs following the mutated region of the gene. As an example, an out-of-frame mutation that produces a premature stop codon can produce a polypeptide that is shorter that the wild type polypeptide, or, in some embodiments, the polypeptide may be absent/undetectable. A DNA inversion is the result of a rotation of a genetic fragment within a region of a chromosome.

The terms "complementary" or "complementarity," as used herein, refer to the natural binding of polynucleotides under permissive salt and temperature conditions by base-pairing. For example, the sequence "A-G-T" (5' to 3') binds to the complementary sequence "T-C-A" (3' to 5'). Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

"Complement," as used herein, can mean 100% complementarity with the comparator nucleotide sequence or it can mean less than 100% complementarity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like, complementarity) to the comparator nucleotide sequence.

Different nucleic acids or proteins having homology are referred to herein as "homologues." The term homologue includes homologous sequences from the same and from other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence of this invention has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to said nucleotide sequence of the invention.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent sequence identity" can refer to the percentage of identical amino acids in an amino acid sequence as compared to a reference polypeptide.

As used herein, the phrase "substantially identical," or "substantial identity" in the context of two nucleic acid molecules, nucleotide sequences, or polypeptide sequences, refers to two or more sequences or subsequences that have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% nucleotide or amino acid residue identity, when compared and aligned for maximum correspondence, as measured using one of the following sequence comparison algorithms or by visual inspection. In some embodiments of the invention, the substantial identity exists over a region of consecutive nucleotides of a nucleotide sequence of the invention that is about 10 nucleotides to about 20 nucleotides, about 10 nucleotides to about 25 nucleotides, about 10 nucleotides to about 30 nucleotides, about 15 nucleotides to about 25 nucleotides, about 30 nucleotides to about 40 nucleotides, about 50 nucleotides to about 60 nucleotides, about 70 nucleotides to about 80 nucleotides, about 90 nucleotides to about 100 nucleotides, about 100 nucleotides to about 200 nucleotides, about 100 nucleotides to about 300 nucleotides, about 100 nucleotides to about 400 nucleotides, about 100 nucleotides to about 500 nucleotides, about 100 nucleotides to about 600 nucleotides, about 100 nucleotides to about 800 nucleotides, about 100 nucleotides to about 900 nucleotides, or more in length, or any range therein, up to the full length of the sequence. In some embodiments, nucleotide sequences can be substantially identical over at least about 20 nucleotides (e.g., about 20, 21, 22, 23, 24, 25, 26, 27, 28, 29, 30, 31, 32, 33, 34, 35, 36, 37, 38, 39, 40, 50, 60, 70, or 80 nucleotides or more).

In some embodiments of the invention, the substantial identity exists over a region of consecutive amino acid residues of a polypeptide of the invention that is about 3 amino acid residues to about 20 amino acid residues, about 5 amino acid residues to about 25 amino acid residues, about 7 amino acid residues to about 30 amino acid residues, about 10 amino acid residues to about 25 amino acid residues, about 15 amino acid residues to about 30 amino acid residues, about 20 amino acid residues to about 40 amino acid residues, about 25 amino acid residues to about 40 amino acid residues, about 25 amino acid residues to about 50 amino acid residues, about 30 amino acid residues to about 50 amino acid residues, about 40 amino acid residues to about 50 amino acid residues, about 40 amino acid residues to about 70 amino acid residues, about 50 amino acid residues to about 70 amino acid residues, about 60 amino acid residues to about 80 amino acid residues, about 70 amino acid residues to about 80 amino acid residues, about 90 amino acid residues to about 100 amino acid residues, or more amino acid residues in length, and any range therein, up to the full length of the sequence. In some embodiments, polypeptide sequences can be substantially identical to one another over at least about 8 consecutive amino acid residues (e.g., about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 130, 140, 150, 175, 200, 225, 250, 300, 350 or more amino acids in length or more consecutive amino acid residues). In some embodiments, two or more MAX1 polypeptides may be identical or substantially identical (e.g., at least 70% to 99.9% identical; e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%. 99.9% identical or any range or value therein) over at least 8 consecutive amino acids to about 350 consecutive amino acids. In some embodiments, two or more MAX1 polypeptides may be identical or substantially identical over at least 8, 9, 10, 11, 12, 13, 14, or 15 consecutive amino acids to about 20, 21, 22, 23, 24, 25, 26, 27, 28, 29, 30, 31, 32, 33, 34, 35, 36, 37, 38, 39, or 40 consecutive amino acids).

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, CA). An "identity fraction" for aligned segments of a test sequence and a reference sequence is the number of identical components which are shared by the two aligned sequences divided by the total number of components in the reference sequence segment, e.g., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Two nucleotide sequences may also be considered substantially complementary when the two sequences hybridize to each other under stringent conditions. In some embodiments, two nucleotide sequences considered to be substantially complementary hybridize to each other under highly stringent conditions.

"Stringent hybridization conditions" and "stringent hybridization wash conditions" in the context of nucleic acid hybridization experiments such as Southern and Northern hybridizations are sequence dependent and are different under different environmental parameters. An extensive guide to the hybridization of nucleic acids is found in Tijssen *Laboratory Techniques in Biochemistry and Molecular Biology-Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

A polynucleotide and/or recombinant nucleic acid construct of this invention (e.g., expression cassettes and/or vectors) may be codon optimized for expression. In some embodiments, the polynucleotides, nucleic acid constructs, expression cassettes, and/or vectors of the editing systems of the invention (e.g., comprising/encoding a sequence-specific nucleic acid binding domain (e.g., a sequence-specific nucleic acid binding domain (e.g., DNA binding domain) from a polynucleotide-guided endonuclease, a zinc finger nuclease, a transcription activator-like effector nuclease (TALEN), an Argonaute protein, and/or a CRISPR-Cas endonuclease (e.g., CRISPR-Cas effector protein) (e.g., a Type I CRISPR-Cas effector protein, a Type II CRISPR-Cas effector protein, a Type III CRISPR-Cas effector protein, a Type IV CRISPR-Cas effector protein, a Type V CRISPR-Cas effector protein or a Type VI CRISPR-Cas effector protein)), a nuclease (e.g., an endonuclease (e.g., Fok1), a polynucleotide-guided endonuclease, a CRISPR-Cas endonuclease (e.g., CRISPR-Cas effector protein), a zinc finger nuclease, and/or a transcription activator-like effector nuclease (TALEN)), deaminase proteins/domains (e.g., adenine deaminase, cytosine deaminase), a polynucleotide encoding a reverse transcriptase protein or domain, a polynucleotide encoding a 5'-3' exonuclease polypeptide, and/or affinity polypeptides, peptide tags, etc.) may be codon optimized for expression in a plant. In some embodiments, the codon optimized nucleic acids, polynucleotides, expression cassettes, and/or vectors of the invention have about 70% to about 99.9% (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%. 99.9% or 100%) identity or more to the reference nucleic acids, polynucleotides, expression cassettes, and/or vectors that have not been codon optimized.

In any of the embodiments described herein, a polynucleotide or nucleic acid construct of the invention may be operatively associated with a variety of promoters and/or other regulatory elements for expression in a plant and/or a cell of a plant. Thus, in some embodiments, a polynucleotide or nucleic acid construct of this invention may further comprise one or more promoters, introns, enhancers, and/or terminators operably linked to one or more nucleotide sequences. In some embodiments, a promoter may be operably associated with an intron (e.g., Ubi1 promoter and intron). In some embodiments, a promoter associated with an intron maybe referred to as a "promoter region" (e.g., Ubi1 promoter and intron).

By "operably linked" or "operably associated" as used herein in reference to polynucleotides, it is meant that the indicated elements are functionally related to each other and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, nucleic acid sequences can be present between a promoter and the nucleotide sequence, and the promoter can still be considered "operably linked" to the nucleotide sequence.

As used herein, the term "linked," in reference to polypeptides, refers to the attachment of one polypeptide to another. A polypeptide may be linked to another polypeptide (at the N-terminus or the C-terminus) directly (e.g., via a peptide bond) or through a linker.

The term "linker" is art-recognized and refers to a chemical group, or a molecule linking two molecules or moieties, e.g., two domains of a fusion protein, such as, for example, a nucleic acid binding polypeptide or domain and peptide tag and/or a reverse transcriptase and an affinity polypeptide that binds to the peptide tag; or a DNA endonuclease polypeptide or domain and peptide tag and/or a reverse transcriptase and an affinity polypeptide that binds to the peptide tag. A linker may be comprised of a single linking molecule or may comprise more than one linking molecule. In some embodiments, the linker can be an organic molecule, group, polymer, or chemical moiety such as a bivalent organic moiety. In some embodiments, the linker may be an amino acid or it may be a peptide. In some embodiments, the linker is a peptide.

In some embodiments, a peptide linker useful with this invention may be about 2 to about 100 or more amino acids in length, for example, about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 2 to about 40, about 2 to about 50, about 2 to about 60, about 4 to about 40, about 4 to about 50, about 4 to about 60, about 5 to about 40, about 5 to about 50, about 5 to about 60, about 9 to about 40, about 9 to about 50, about 9 to about 60, about 10 to about 40, about 10 to about 50, about 10 to about 60, or about 2, 3, 4, 5, 6, 7, 8, 9, 10, 11, 12, 13, 14, 15, 16, 17, 18, 19, 20, 21, 22, 23, 24, 25 amino acids to about 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 105, 110, 115, 120, 130, 140 150 or more amino acids in length). In some embodiments, a peptide linker may be a GS linker.

As used herein, the term "linked," or "fused" in reference to polynucleotides, refers to the attachment of one polynucleotide to another. In some embodiments, two or more polynucleotide molecules may be linked by a linker that can be an organic molecule, group, polymer, or chemical moiety such as a bivalent organic moiety. A polynucleotide may be linked or fused to another polynucleotide (at the 5' end or the 3' end) via a covalent or non-covenant linkage or binding, including e.g., Watson-Crick base-pairing, or through one or more linking nucleotides. In some embodiments, a polynucleotide motif of a certain structure may be inserted within another polynucleotide sequence (e.g., extension of the hairpin structure in the guide RNA). In some embodiments, the linking nucleotides may be naturally occurring nucleotides. In some embodiments, the linking nucleotides may be non-naturally occurring nucleotides.

A "promoter" is a nucleotide sequence that controls or regulates the transcription of a nucleotide sequence (e.g., a coding sequence) that is operably associated with the promoter. The coding sequence controlled or regulated by a promoter may encode a polypeptide and/or a functional RNA. Typically, a "promoter" refers to a nucleotide sequence that contains a binding site for RNA polymerase II and directs the initiation of transcription. In general, promoters are found 5', or upstream, relative to the start of the coding region of the corresponding coding sequence. A promoter may comprise other elements that act as regulators of gene expression; e.g., a promoter region. These include a TATA box consensus sequence, and often a CAAT box consensus sequence (Breathnach and Chambon, (1981) *Annu. Rev. Biochem.* 50:349). In plants, the CAAT box may be substituted by the AGGA box (Messing et al., (1983) in *Genetic Engineering of Plants*, T. Kosuge, C. Meredith and A. Hollaender (eds.), Plenum Press, pp. 211-227).

Promoters useful with this invention can include, for example, constitutive, inducible, temporally regulated, developmentally regulated, chemically regulated, tissue-preferred and/or tissue-specific promoters for use in the preparation of recombinant nucleic acid molecules, e.g., "synthetic nucleic acid constructs" or "protein-RNA complex." These various types of promoters are known in the art.

The choice of promoter may vary depending on the temporal and spatial requirements for expression, and also may vary based on the host cell to be transformed. Promoters for many different organisms are well known in the art. Based on the extensive knowledge present in the art, the appropriate promoter can be selected for the particular host organism of interest. Thus, for example, much is known about promoters upstream of highly constitutively expressed genes in model organisms and such knowledge can be readily accessed and implemented in other systems as appropriate.

In some embodiments, a promoter functional in a plant may be used with the constructs of this invention. Non-limiting examples of a promoter useful for driving expression in a plant include the promoter of the RubisCo small subunit gene 1 (PrbcS1), the promoter of the actin gene (Pactin), the promoter of the nitrate reductase gene (Pnr) and the promoter of duplicated carbonic anhydrase gene 1 (Pdca1) (See, Walker et al. *Plant Cell Rep.* 23:727-735 (2005); Li et al. Gene 403:132-142 (2007); Li et al. *Mol Biol. Rep.* 37:1143-1154 (2010)). PrbcS1 and Pactin are constitutive promoters and Pnr and Pdca1 are inducible promoters. Pnr is induced by nitrate and repressed by ammonium (Li et al. Gene 403:132-142 (2007)) and Pdca1 is induced by salt (Li et al. *Mol Biol. Rep.* 37:1143-1154 (2010)). In some embodiments, a promoter useful with this invention is RNA polymerase II (Pol II) promoter. In some embodiments, a U6 promoter or a 7SL promoter from *Zea mays* may be useful with constructs of this invention. In some embodiments, the U6c promoter and/or 7SL promoter from *Zea mays* may be useful for driving expression of a guide nucleic acid. In some embodiments, a U6c promoter, U6i promoter and/or 7SL promoter from *Glycine max* may be useful with constructs of this invention. In some embodiments, the U6c promoter, U6i promoter and/or 7SL promoter from *Glycine max* may be useful for driving expression of a guide nucleic acid.

Examples of constitutive promoters useful for plants include, but are not limited to, cestrum virus promoter (cmp) (U.S. Pat. No. 7,166,770), the rice actin 1 promoter (Wang et al. (1992) *Mol. Cell. Biol.* 12:3399-3406; as well as U.S. Pat. No. 5,641,876), CaMV 35S promoter (Odell et al. (1985) Nature 313:810-812), CaMV 19S promoter (Lawton et al. (1987) *Plant Mol. Biol.* 9:315-324), nos promoter (Ebert et al. (1987) Proc. Natl. Acad. Sci USA 84:5745-5749), Adh promoter (Walker et al. (1987) *Proc. Natl. Acad. Sci. USA* 84:6624-6629), sucrose synthase promoter (Yang & Russell (1990) Proc. Natl. Acad. Sci. USA 87:4144-4148), and the ubiquitin promoter. The constitutive promoter derived from ubiquitin accumulates in many cell types. Ubiquitin promoters have been cloned from several plant species for use in transgenic plants, for example, sunflower (Binet et al., 1991. *Plant Science* 79: 87-94), maize (Christensen et al., 1989. *Plant Molec. Biol.* 12: 619-632), and *Arabidopsis* (Norris et al. 1993. *Plant Molec. Biol.* 21:895-906). The maize ubiquitin promoter (UbiP) has been developed in transgenic monocot systems and its sequence and vectors constructed for monocot transformation are disclosed in the patent publication EP 0 342 926. The ubiquitin promoter is suitable for the expression of the nucleotide sequences of the invention in transgenic plants, especially monocotyledons. Further, the promoter expression cassettes described by McElroy et al. (*Mol. Gen. Genet.* 231: 150-160 (1991)) can be easily modified for the expression of the nucleotide sequences of the invention and are particularly suitable for use in monocotyledonous hosts.

In some embodiments, tissue specific/tissue preferred promoters can be used for expression of a heterologous polynucleotide in a plant cell. Tissue specific or preferred expression patterns include, but are not limited to, green tissue specific or preferred, root specific or preferred, stem specific or preferred, flower specific or preferred or pollen specific or preferred. Promoters suitable for expression in green tissue include many that regulate genes involved in photosynthesis and many of these have been cloned from both monocotyledons and dicotyledons. In one embodiment, a promoter useful with the invention is the maize PEPC promoter from the phosphoenol carboxylase gene (Hudspeth & Grula, *Plant Molec. Biol.* 12:579-589 (1989)). Non-limiting examples of tissue-specific promoters include those associated with genes encoding the seed storage proteins (such as β-conglycinin, cruciferin, napin and phaseolin), zein or oil body proteins (such as oleosin), or proteins involved in fatty acid biosynthesis (including acyl carrier protein, stearoyl-ACP desaturase and fatty acid desaturases (fad 2-1)), and other nucleic acids expressed during embryo development (such as Bce4, see, e.g., Kridl et al. (1991) *Seed Sci. Res.* 1:209-219; as well as EP Patent No. 255378). Tissue-specific or tissue-preferential promoters useful for the expression of the nucleotide sequences of the invention in plants, particularly maize, include but are not limited to those that direct expression in root, pith, leaf or pollen. Such promoters are disclosed, for example, in WO 93/07278, herein incorporated by reference in its entirety. Other non-limiting examples of tissue specific or tissue preferred promoters useful with the invention the cotton rubisco promoter disclosed in U.S. Pat. No. 6,040,504; the rice sucrose synthase promoter disclosed in U.S. Pat. No. 5,604,121; the root specific promoter described by de Framond (FEBS 290:103-106 (1991); EP 0 452 269 to Ciba-Geigy); the stem specific promoter described in U.S. Pat. No. 5,625,136 (to Ciba-Geigy) and which drives expression of the maize trpA gene; the cestrum yellow leaf curling virus promoter disclosed in WO 01/73087; and pollen specific or preferred promoters including, but not limited to, ProOsLPS10 and ProOsLPS11 from rice (Nguyen et al. *Plant Biotechnol. Reports* 9(5):297-306 (2015)), ZmSTK2_USP from maize (Wang et al. *Genome* 60(6):485-495 (2017)), LAT52 and LAT59 from tomato (Twell et al. *Development* 109(3):705-713 (1990)), Zm13 (U.S. Pat. No. 10,421,972), $PLA_2$-δ promoter from *Arabidopsis* (U.S. Pat. No. 7,141,424), and/or the ZmC5 promoter from maize (International PCT Publication No. WO1999/042587.

Additional examples of plant tissue-specific/tissue preferred promoters include, but are not limited to, the root hair-specific cis-elements (RHEs) (Kim et al. *The Plant Cell* 18:2958-2970 (2006)), the root-specific promoters RCc3 (Jeong et al. *Plant Physiol.* 153:185-197 (2010)) and RB7 (U.S. Pat. No. 5,459,252), the lectin promoter (Lindstrom et al. (1990) *Der. Genet.* 11:160-167; and Vodkin (1983) *Prog. Clin. Biol. Res.* 138:87-98), corn alcohol dehydrogenase 1 promoter (Dennis et al. (1984) *Nucleic Acids Res.* 12:3983-4000), S-adenosyl-L-methionine synthetase (SAMS) (Vander Mijnsbrugge et al. (1996) *Plant and Cell Physiology,* 37(8):1108-1115), corn light harvesting complex promoter (Bansal et al. (1992) Proc. Natl. Acad. Sci. USA 89:3654-3658), corn heat shock protein promoter (O'Dell et al. (1985) *EMBO J.* 5:451-458; and Rochester et al. (1986) *EMBO J.* 5:451-458), pea small subunit RuBP carboxylase promoter (Cashmore, "Nuclear genes encoding the small subunit of ribulose-1,5-bisphosphate carboxylase" pp. 29-39 In: *Genetic Engineering of Plants* (Hollaender ed., Plenum Press 1983; and Poulsen et al. (1986) Mol. Gen. Genet. 205:193-200), Ti plasmid mannopine synthase promoter (Langridge et al. (1989) *Proc. Natl. Acad. Sci. USA* 86:3219-3223), Ti plasmid nopaline synthase promoter (Langridge et al. (1989), supra), petunia chalcone isomerase promoter (van Tunen et al. (1988) *EMBO J.* 7:1257-1263), bean glycine rich protein 1 promoter (Keller et al. (1989) *Genes Dev.* 3:1639-1646), truncated CaMV 35S promoter (O'Dell et al. (1985) *Nature* 313:810-812), potato patatin promoter (Wenzler et al. (1989) *Plant Mol. Biol.* 13:347-354), root cell promoter (Yamamoto et al. (1990) *Nucleic Acids Res.* 18:7449), maize zein promoter (Kriz et al. (1987) Mol. Gen. Genet. 207:90-98; Langridge et al. (1983) *Cell* 34:1015-1022; Reina et al. (1990) *Nucleic Acids Res.* 18:6425; Reina et al. (1990) *Nucleic Acids Res.* 18:7449; and Wandelt et al. (1989) *Nucleic Acids Res.* 17:2354), globulin-1 promoter (Belanger et al. (1991) *Genetics* 129:863-872), α-tubulin cab promoter (Sullivan et al. (1989) *Mol. Gen. Genet.* 215:431-440), PEPCase promoter (Hudspeth & Grula (1989) *Plant Mol. Biol.* 12:579-589), R gene complex-associated promoters (Chandler et al. (1989) *Plant Cell* 1:1175-1183), and chalcone synthase promoters (Franken et al. (1991) *EMBO J.* 10:2605-2612).

Useful for seed-specific expression is the pea vicilin promoter (Czako et al. (1992) *Mol. Gen. Genet.* 235:33-40; as well as the seed-specific promoters disclosed in U.S. Pat. No. 5,625,136. Useful promoters for expression in mature leaves are those that are switched at the onset of senescence, such as the SAG promoter from *Arabidopsis* (Gan et al. (1995) *Science* 270:1986-1988).

In addition, promoters functional in chloroplasts can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

Additional regulatory elements useful with this invention include, but are not limited to, introns, enhancers, termination sequences and/or 5' and 3' untranslated regions.

An intron useful with this invention can be an intron identified in and isolated from a plant and then inserted into an expression cassette to be used in transformation of a plant. As would be understood by those of skill in the art, introns can comprise the sequences required for self-excision and are incorporated into nucleic acid constructs/expression cassettes in frame. An intron can be used either as a spacer to separate multiple protein-coding sequences in one nucleic acid construct, or an intron can be used inside one protein-coding sequence to, for example, stabilize the mRNA. If they are used within a protein-coding sequence, they are inserted "in-frame" with the excision sites included. Introns may also be associated with promoters to improve or modify expression. As an example, a promoter/intron combination useful with this invention includes but is not limited to that of the maize Ubi1 promoter and intron (see, e.g., SEQ ID NO:21 and SEQ ID NO:22).

Non-limiting examples of introns useful with the present invention include introns from the ADHI gene (e.g., Adh1-S introns 1, 2 and 6), the ubiquitin gene (Ubi1), the RuBisCO small subunit (rbcS) gene, the RuBisCO large subunit (rbcL) gene, the actin gene (e.g., actin-1 intron), the pyruvate dehydrogenase kinase gene (pdk), the nitrate reductase gene (nr), the duplicated carbonic anhydrase gene 1 (Tdca1), the psbA gene, the atpA gene, or any combination thereof.

In some embodiments, a polynucleotide and/or a nucleic acid construct of the invention can be an "expression cassette" or can be comprised within an expression cassette. As used herein, "expression cassette" means a recombinant nucleic acid molecule comprising, for example, a one or more polynucleotides of the invention (e.g., a polynucleotide encoding a sequence-specific nucleic acid binding domain, a polynucleotide encoding a deaminase protein or domain, a polynucleotide encoding a reverse transcriptase protein or domain, a polynucleotide encoding a 5'-3' exonuclease polypeptide or domain, a guide nucleic acid and/or reverse transcriptase (RT) template), wherein polynucleotide(s) is/are operably associated with one or more control sequences (e.g., a promoter, terminator and the like). Thus, in some embodiments, one or more expression cassettes may be provided, which are designed to express, for example, a nucleic acid construct of the invention (e.g., a polynucleotide encoding a sequence-specific nucleic acid binding domain, a polynucleotide encoding a nuclease polypeptide/domain, a polynucleotide encoding a deaminase protein/domain, a polynucleotide encoding a reverse transcriptase protein/domain, a polynucleotide encoding a 5'-3' exonuclease polypeptide/domain, a polynucleotide encoding a peptide tag, and/or a polynucleotide encoding an affinity polypeptide, and the like, or comprising a guide nucleic acid, an extended guide nucleic acid, and/or RT template, and the like). When an expression cassette of the present invention comprises more than one polynucleotide, the polynucleotides may be operably linked to a single promoter that drives expression of all of the polynucleotides or the polynucleotides may be operably linked to one or more separate promoters (e.g., three polynucleotides may be driven by one, two or three promoters in any combination). When two or more separate promoters are used, the promoters may be the same promoter, or they may be different promoters. Thus, a polynucleotide encoding a sequence specific nucleic acid binding domain, a polynucleotide encoding a nuclease protein/domain, a polynucleotide encoding a CRISPR-Cas effector protein/domain, a polynucleotide encoding an deaminase protein/domain, a polynucleotide encoding a reverse transcriptase polypeptide/domain (e.g., RNA-dependent DNA polymerase), and/or a polynucleotide encoding a 5'-3' exonuclease polypeptide/domain, a guide nucleic acid, an extended guide nucleic acid and/or RT template when comprised in a single expression cassette may each be operably linked to a single promoter, or separate promoters in any combination.

An expression cassette comprising a nucleic acid construct of the invention may be chimeric, meaning that at least one (e.g., one or more) of its components is heterologous with respect to at least one of its other components (e.g., a promoter from the host organism operably linked to a polynucleotide of interest to be expressed in the host organism, wherein the polynucleotide of interest is from a different organism than the host or is not normally found in association with that promoter). An expression cassette may also be one that is naturally occurring but has been obtained in a recombinant form useful for heterologous expression.

An expression cassette can optionally include a transcriptional and/or translational termination region (i.e., termination region) and/or an enhancer region that is functional in the selected host cell. A variety of transcriptional terminators and enhancers are known in the art and are available for use in expression cassettes. Transcriptional terminators are responsible for the termination of transcription and correct mRNA polyadenylation. A termination region and/or the enhancer region may be native to the transcriptional initiation region, may be native to, for example, a gene encoding a sequence-specific nucleic acid binding protein, a gene encoding a nuclease, a gene encoding a reverse transcriptase, a gene encoding a deaminase, and the like, or may be native to a host cell, or may be native to another source (e.g., foreign or heterologous to, for example, to a promoter, to a gene encoding a sequence-specific nucleic acid binding protein, a gene encoding a nuclease, a gene encoding a reverse transcriptase, a gene encoding a deaminase, and the like, or to the host cell, or any combination thereof).

An expression cassette of the invention also can include a polynucleotide encoding a selectable marker, which can be used to select a transformed host cell. As used herein, "selectable marker" means a polynucleotide sequence that when expressed imparts a distinct phenotype to the host cell expressing the marker and thus allows such transformed cells to be distinguished from those that do not have the marker. Such a polynucleotide sequence may encode either a selectable or screenable marker, depending on whether the marker confers a trait that can be selected for by chemical means, such as by using a selective agent (e.g., an antibiotic and the like), or on whether the marker is simply a trait that one can identify through observation or testing, such as by screening (e.g., fluorescence). Many examples of suitable selectable markers are known in the art and can be used in the expression cassettes described herein.

In addition to expression cassettes, the nucleic acid molecules/constructs and polynucleotide sequences described herein can be used in connection with vectors. The term "vector" refers to a composition for transferring, delivering or introducing a nucleic acid (or nucleic acids) into a cell. A vector comprises a nucleic acid construct (e.g., expression cassette(s)) comprising the nucleotide sequence(s) to be transferred, delivered or introduced. Vectors for use in transformation of host organisms are well known in the art. Non-limiting examples of general classes of vectors include viral vectors, plasmid vectors, phage vectors, phagemid vectors, cosmid vectors, fosmid vectors, bacteriophages, artificial chromosomes, minicircles, or *Agrobacterium* binary vectors in double or single stranded linear or circular form which may or may not be self-transmissible or mobilizable. In some embodiments, a viral vector can include, but is not limited, to a retroviral, lentiviral, adenoviral, adeno-associated, or herpes simplex viral vector. A vector as defined herein can transform a prokaryotic or eukaryotic host either by integration into the cellular genome or exist extrachromosomally (e.g., autonomous replicating plasmid with an origin of replication). Additionally, included are shuttle vectors by which is meant a DNA vehicle capable, naturally or by design, of replication in two different host organisms, which may be selected from actinomycetes and related species, bacteria and eukaryotic (e.g., higher plant, mammalian, yeast or fungal cells). In some embodiments, the nucleic acid in the vector is under the control of, and operably linked to, an appropriate promoter or other regulatory elements for transcription in a host cell. The vector may be a bi-functional expression vector which functions in multiple hosts. In the case of genomic DNA, this may contain its own promoter and/or other regulatory elements and in the case of cDNA this may be under the control of an appropriate promoter and/or other regulatory elements for expression in the host cell. Accordingly, a nucleic acid or polynucleotide of this invention and/or expression cassettes comprising the same may be comprised in vectors as described herein and as known in the art.

As used herein, "contact," "contacting," "contacted," and grammatical variations thereof, refer to placing the components of a desired reaction together under conditions suitable for carrying out the desired reaction (e.g., transformation, transcriptional control, genome editing, nicking, and/or cleavage). As an example, a target nucleic acid may be contacted with a sequence-specific nucleic acid binding protein (e.g., polynucleotide-guided endonuclease, a CRISPR-Cas endonuclease (e.g., CRISPR-Cas effector protein), a zinc finger nuclease, a transcription activator-like effector nuclease (TALEN) and/or an Argonaute protein)) and a deaminase or a nucleic acid construct encoding the same, under conditions whereby the sequence-specific nucleic acid binding protein, the reverse transcriptase and/or the deaminase are expressed and the sequence-specific nucleic acid binding protein binds to the target nucleic acid, and the reverse transcriptase and/or deaminase may be fused to either the sequence-specific nucleic acid binding protein or recruited to the sequence-specific nucleic acid binding protein (via, for example, a peptide tag fused to the sequence-specific nucleic acid binding protein and an affinity tag fused to the reverse transcriptase and/or deaminase) and thus, the deaminase and/or reverse transcriptase is positioned in the vicinity of the target nucleic acid, thereby modifying the target nucleic acid. Other methods for recruiting reverse transcriptase and/or deaminase may be used that take advantage of other protein-protein interactions, and also RNA-protein interactions and chemical interactions may be used for protein-protein and protein-nucleic acid recruitment.

As used herein, "modifying" or "modification" in reference to a target nucleic acid includes editing (e.g., mutating), covalent modification, exchanging/substituting nucleic acids/nucleotide bases, deleting, cleaving, nicking, and/or altering transcriptional control of a target nucleic acid. In some embodiments, a modification may include one or more single base changes (SNPs) of any type.

"Introducing," "introduce," "introduced" (and grammatical variations thereof) in the context of a polynucleotide of interest means presenting a nucleotide sequence of interest (e.g., polynucleotide, RT template, a nucleic acid construct, and/or a guide nucleic acid) to a plant, plant part thereof, or cell thereof, in such a manner that the nucleotide sequence gains access to the interior of a cell.

The terms "transformation" or transfection" may be used interchangeably and as used herein refer to the introduction of a heterologous nucleic acid into a cell. Transformation of a cell may be stable or transient. Thus, in some embodiments, a host cell or host organism (e.g., a plant) may be stably transformed with a polynucleotide/nucleic acid molecule of the invention. In some embodiments, a host cell or host organism may be transiently transformed with a polynucleotide/nucleic acid molecule of the invention.

"Transient transformation" in the context of a polynucleotide means that a polynucleotide is introduced into the cell and does not integrate into the genome of the cell.

By "stably introducing" or "stably introduced" in the context of a polynucleotide introduced into a cell is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein includes the nuclear and the plastid genome, and therefore includes integration of the nucleic acid into, for example, the chloroplast or mitochondrial genome. Stable transformation as used herein can also refer to a transgene that is maintained extrachromasomally, for example, as a minichromosome or a plasmid.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a host organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

Accordingly, in some embodiments, nucleotide sequences, polynucleotides, nucleic acid constructs, and/or expression cassettes of the invention may be expressed transiently and/or they can be stably incorporated into the genome of the host organism. Thus, in some embodiments, a nucleic acid construct of the invention (e.g., one or more expression cassettes comprising polynucleotides for editing as described herein) may be transiently introduced into a cell with a guide nucleic acid and as such, no DNA is maintained in the cell.

A nucleic acid construct of the invention may be introduced into a plant cell by any method known to those of skill in the art. Non-limiting examples of transformation methods include transformation via bacterial-mediated nucleic acid delivery (e.g., via Agrobacteria), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. Procedures for transforming both eukaryotic and prokaryotic organisms are well known and routine in the art and are described throughout the literature (See, for example, Jiang et al. 2013. *Nat. Biotechnol.* 31:233-239; Ran et al. *Nature Protocols* 8:2281-2308 (2013)). General guides to various plant transformation methods known in the art include Miki et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell. Mol. Biol. Lett.* 7:849-858 (2002)).

In some embodiments of the invention, transformation of a cell may comprise nuclear transformation. In other embodiments, transformation of a cell may comprise plastid transformation (e.g., chloroplast transformation). In still further embodiments, nucleic acids of the invention may be introduced into a cell via conventional breeding techniques. In some embodiments, one or more of the polynucleotides, expression cassettes and/or vectors may be introduced into a plant cell via *Agrobacterium* transformation.

A polynucleotide therefore can be introduced into a plant, plant part, plant cell in any number of ways that are well known in the art. The methods of the invention do not depend on a particular method for introducing one or more nucleotide sequences into a plant, only that they gain access to the interior the cell. Where more than polynucleotide is to be introduced, they can be assembled as part of a single nucleic acid construct, or as separate nucleic acid constructs, and can be located on the same or different nucleic acid constructs. Accordingly, the polynucleotide can be introduced into the cell of interest in a single transformation event, or in separate transformation events, or, alternatively, a polynucleotide can be incorporated into a plant as part of a breeding protocol.

The present invention is directed to modification of More Axillary Growth 1 (MAX1) genes (e.g., MAX1a genes, MAX1b genes, MAX1c genes, MAX1d genes) in plants through editing technology to provide plants that exhibit one or more improved yield traits and/or improved plant architecture. MAX1 is a strigolactone pathway gene that encodes a strigolactone biosynthetic enzyme. Specifically, MAX1 genes encode cytochrome P450 family member polypeptides (e.g., cytochrome p450 monooxygenases (MAX1 polypeptides)) belonging to the CYP711 clan. These MAX1 polypeptides act downstream of CCD7 (MAX3)/CCD8 (MAX4) to produce a carotenoid-derived branch inhibiting hormone and require MAX2 for the perception of this hormone (Booker et al. *Dev. Cell.* 8:443-449 (2005)). In soybean, MAX1 genes include MAX1a (Glyma.04g052100), MAX1b (Glyma.06g052700), MAX1c (Glyma.14g096900) and MAX1d (Glyma.17g227500), each of which may be targeted in a plant. Thus, an editing strategy useful for this invention can include generating a mutation in one or more than one (e.g., 1, 2, 3, and/or 4) MAX1 gene. As an example, one or more mutations may be generated in a MAX1a gene and a MAX1b gene of a plant. In some embodiments, one or more mutations may be generated in a MAX1c gene and a MAX1d gene. In some embodiments, one or more mutations may be generated in a MAX1a gene and at least one of a MAX1d gene and/or a MAX1c gene. In some embodiments, one or more mutations may be generated in a MAX1b gene and at least one of a MAX1c gene and/or a MAX1d gene. In some embodiments, one or more mutations may be generated in a MAX1a gene, a MAX1b gene, a MAX1c gene and a MAX1d gene. Mutations that may be useful for producing plants with one or more improved yield traits include, for example, substitutions, deletions, and/or insertions. In some aspects, a mutation generated by the editing technology can be a point mutation. In some embodiments, a mutation in one or more than one MAX1 gene as described herein results in knock-down of expression of the one or more than one MAX1 gene. In some embodiments, the at least one mutation may be a non-natural mutation.

In some embodiments, a mutation generated by the methods of the invention results in a mutated MAX1 gene comprising an edited nucleotide sequence having at least 90% sequence identity to any one of SEQ ID NOs:173, 175, 177, 179, 181, or 183, optionally wherein the mutation in the mutated MAX1 gene is a non-natural mutation.

In some embodiments, the invention provides a plant or plant part thereof comprising at least one mutation in an endogenous More Axillary Growth 1 (MAX1) gene (e.g., in one or more than one MAX1 gene) encoding a cytochrome P450 monooxygenase (MAX1) polypeptide. In some embodiments, an endogenous MAX1 gene is an endogenous MAX1a gene, an endogenous MAX1b gene, an endogenous MAX1c gene, or an endogenous MAX1d gene, wherein the encoded MAX1 polypeptide is a MAX1a polypeptide, a MAX1b polypeptide, a MAX1c polypeptide, or a MAX1d polypeptide, respectively. In some embodiments, the at least one mutation may be a non-natural mutation. In some embodiments, the at least one mutation may be a recessive mutation and/or a null mutation. In some embodiments, a mutation may be a knock-out mutation or a knock-down mutation. As used herein, a knock-out mutation results in little or no expression and/or zero percent activity of the encoded polypeptide. In some embodiments, the plant or part thereof comprises a mutated MAX1 gene having at least 90% sequence identity to any one of SEQ ID NOs:173, 175, 177, 179, 181, or 183.

In some embodiments, a knock-down mutation results in a reduction in activity of at least 5% (e.g., a reduction in activity of about 5, 6, 7, 8, 9, 10, 11, 12, 13, 14, 15, 16, 17, 18, 19, 20, 21, 22, 23, 24, 25, 26, 27, 28, 29, 30, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, and any range or value therein).

As used herein, a "non-natural mutation" refers to a mutation that is generated though human intervention and differs from mutations found in the same gene that have occurred in nature (e.g., occurred naturally)).

In some embodiments, a plant cell is provided, the plant cell comprising an editing system, the editing system comprising: (a) a CRISPR-Cas effector protein; and (b) a guide nucleic acid (e.g., gRNA, gDNA, crRNA, crDNA, sgRNA, sgDNA) comprising a spacer sequence with complementarity to an endogenous target gene encoding a cytochrome P450 monooxygenase (MAX1) polypeptide. The editing system may be used to generate a mutation in the endogenous target gene encoding a MAX1 polypeptide. In some embodiments, the endogenous target gene is an endogenous More Axillary Growth 1 (MAX1) gene (e.g., one or more than one endogenous MAX1 gene), optionally an endogenous MAX1a gene, an endogenous MAX1b gene, an endogenous MAX1c gene, and/or an endogenous MAX1d gene, and the MAX1 polypeptide is a MAX1a polypeptide, a MAX1b polypeptide, a MAX1c polypeptide, or a MAX1d polypeptide, respectively. In some embodiments, the mutation is a non-natural mutation. In some embodiments, the endogenous target gene: (a) comprises a nucleotide sequence having at least 80% sequence identity to any one of SEQ ID NOs:69, 70, 93, 94, 115, 116, 140 or 141, (b) comprises a region having at least 90% sequence identity to any one of SEQ ID NOs:72-91, 96-113, 118-138, or 143-164, (c) encodes a sequence having at least 80% sequence identity to any one of SEQ ID NOs:71, 95, 117, or 142, or (d) encodes a region having at least 90% sequence identity to any one of SEQ ID NOs:92, 114, 139 or 165. In some embodiments, a guide nucleic acid of an editing system may comprise the nucleotide sequence (a spacer sequence, e.g., one or more spacers) of any one of SEQ ID NOs:166-172 (e.g., SEQ ID NO:166 (PWsp1482), SEQ ID NO:167 (PWsp1483), SEQ ID NO:168 (PWsp1484), SEQ ID NO:169 (PWsp1485), SEQ ID NO:170 (PWsp1486), SEQ ID NO:171 (PWsp1487) and/or SEQ ID NO:172 (PWsp1488)).

A mutation in a MAX1 gene of the plant, plant part thereof, or the plant cell useful for this invention may be any type of mutation, including a base substitution, a base deletion, and/or a base insertion. In some embodiments, a mutation may comprise a base substitution to an A, a T, a G, or a C. In some embodiments, a mutation may be a deletion of at least one base pair (e.g., 1 base pair to about 100 base pairs; e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 consecutive base pairs; e.g., 1 to about 50 consecutive base pairs, 1 to about 30 consecutive base pairs, 1 to about 15 consecutive base pairs) or an insertion of at least one base pair (e.g., 1 base pair to about 15 base pairs; e.g., 1, 2, 3, 4, 5, 6, 7, 8, 9, 10, 11, 12, 13, 14, or 15 consecutive base pairs), optionally wherein the deletion or insertion may be an out-of-frame deletion or an out-of-frame insertion. In some embodiments, a mutation may be an insertion of at least one base pair (e.g., 1 base pair to about 16 base pairs; e.g., 1, 2, 3, 4, 5, 6, 7, 8, 9, 10, 11, 12, 13, 14, 15, or 16 consecutive base pairs; optionally 1, 2, 4, 5, 7, 8, 10, 11, 13, 14, or 16 consecutive base pairs, optionally wherein the insertion is an out-of-frame insertion. In some embodiments, a mutation in a MAX1 gene of a plant or plant part thereof may be a non-natural mutation.

A mutation in a MAX1 gene may be located in the 5' region of the MAX1 gene (e.g., a MAX1a gene, a MAX1b gene, a MAX1c gene, and/or a MAX1d gene), optionally in the 5' region of the MAX1 gene that encodes the N-terminal region of the encoded MAX1 polypeptide (e.g., the 5' coding regions (exons)). In some embodiments, the mutation in a MAX1 gene may be a non-natural mutation. In some embodiments, the mutation may be an out-of-frame deletion or an out-of-frame insertion that may result in a truncated polypeptide, or little or no detectible polypeptide. In some embodiments, the out-of-frame deletion or out-of-frame insertion may be a recessive mutation and/or a null mutation.

In some embodiments, a mutation located in the 5' region of the MAX1 gene may be a deletion or an insertion that results in a premature stop codon (e.g., an out-of-frame base insertion or an out-of-frame base deletion) and a truncated MAX1 polypeptide or, optionally resulting in little or no detectable MAX1 polypeptide. In some embodiments, the mutation results in a truncated MAX1 polypeptide, optionally a C-terminal truncation of the MAX1 polypeptide, optionally wherein the C-terminal truncation results in a deletion of about 100 amino acid residues to about 600 amino acid residues (e.g., 100, 150, from the C-terminus of the MAX1 polypeptide The types of editing tools that may be used to generate these and other mutations in MAX1 genes include any base editors or cutters, which are guided to a target site using spacers having at least 80% complementarity to a portion or a region of a MAX1 gene (e.g., one or more than one MAX1 gene, e.g., a MAX1a gene, a MAX1b gene, a MAX1c gene, and/or a MAX1d gene) as described herein.

In some embodiments, a mutation of a MAX1 gene is within a portion or region of the endogenous MAX1 gene having at least 90% sequence identity to any one of the nucleotide sequences of SEQ ID NOs:72-91, 96-113, 118-138, or 143-164, optionally a portion or region of the endogenous MAX1 gene having at least 90% sequence identity to any one of the nucleotide sequences of SEQ ID NOs:77-79, 81-83, 88, 90, 91, 101-103, 105-107, 113, 121, 124, 125, 127-129, 132-138, 148-150, 152-154, or 160-164.

An endogenous MAX1 gene useful with this invention (e.g., an endogenous target gene) encodes a cytochrome P450 monooxygenase (MAX1) polypeptide, and includes an endogenous MAX1a gene, an endogenous MAX1b gene, an endogenous MAX1c gene, or an endogenous MAX1d gene, which encode a MAX1a polypeptide, a MAX1b polypeptide, a MAX1c polypeptide, or a MAX1d polypeptide, respectively. In some embodiments, an endogenous MAX1 gene (e.g., endogenous target gene) (1) may comprise a nucleic acid sequence having at least 80% sequence identity to any one of SEQ ID NOs:69, 70, 93, 94, 115, 116, 140 or 141, (2) may comprise a region of a MAX1 gene having at least 90% sequence identity to any one of SEQ ID NOs:72-91, 96-113, 118-138, or 143-164, (3) may encode a polypeptide having at least 80% sequence identity to any one of SEQ ID NOs:71, 95, 117, or 142, and/or (4) may encode a region of a MAX1 polypeptide having at least 90% sequence identity to any one of SEQ ID NOs:92, 114, 139 or 165.

In some embodiments, a plant (e.g., a soybean plant) comprising at least one (e.g., one or more) mutation in an endogenous MAX1 gene (in at least one endogenous MAX1 gene, e.g., in one or more MAX1 genes) exhibits improved plant architecture and/or one or more improved yield traits as compared to a plant devoid of the at least one mutation (e.g., an isogenic plant (e.g., wild type unedited plant or a null segregant). In some embodiments the at least one mutation may be a non-natural mutation. In some embodiments, improved plant architecture includes but not limited to increased branching, increased number of nodes, reduced internode length, and/or a reduced or semi-dwarf stature. In some embodiments, the one or more improved yield traits include, but are not limited to, increased yield (bu/acre), increased biomass, increased flower number, altered flowering time (earlier or later), increased kernel number, increased kernel size, increased number of pods, including an increased number of pods per node and/or an increased number of pods per plant, increased number of seeds per pod, increased number of seeds, increased seed size, and/or increased seed weight (e.g., increase in 100-seed weight). In some embodiments, the one or more improved yield traits may include, but is not limited to, an increased flower number, increased seed size, increased seed weight, increased number of pods, and/or increased number of seeds per pod. In some embodiments, the plant comprising at least one mutation in an endogenous MAX1 gene and exhibiting improved plant architecture and/or one or more improved yield traits may comprise a mutated MAX1 gene having at least 90% sequence identity to any one of SEQ ID NOs:173, 175, 177, 179, 181, and/or 183.

As used herein, the term "semi-dwarf" refers to a plant produced by the methods of this invention having a shortened stature as compared to a control plant not comprising the mutation in a MAX1 gene as described herein. In some embodiments, a semi-dwarf plant may be reduced in stature by about 5% to about 50% (e.g., about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 45, 46, 47, 48, 49, or 50% shorter, and any range or value therein, when compared to a control plant (e.g., a plant devoid of the mutation in the endogenous MAX1 gene). In some embodiments, a plant produced by the methods of this invention, including a semi-dwarf plant, may comprise a bushier habit than a control plant due to increased branching as well as shorter internodes resulting from the at least one mutation in an endogenous MAX1 gene.

An "increased number of nodes" and an "increased number of branches" as used herein, means an increase in the number of nodes and/or the number of branches of about 5% to about 100% (e.g., about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% or more or any range or value therein; e.g., about 5% to about 10%, about 5% to about 15%, about 5% to about 20%, about 10% to about 50%, about 10% to about 80%, about 10% to about 90%, about 10% to about 100%, about 20% to about 50%, about 20% to about 80%, about 20% to about 90%, about 20% to about 100%, about 30% to about 50%, about 30% to about 80%, about 30% to about 90%, about 30% to about 100%, about 50% to about 100%, about 75% to about 100% or more, and any range or value therein) in the number of nodes and/or the number of branches as compared to a plant or part thereof that is devoid of the mutated endogenous MAX1 gene.

A "reduced internode length" as used herein refers to a reduction in length of the internodes of a plant comprising at least one mutation in an endogenous MAX1 gene as described herein from about 5% to about 50% (e.g., about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 45, 46, 47, 48, 49, or 50% shorter, and any range or value therein, when compared to a control plant (e.g., a plant devoid of the mutation in the endogenous MAX1 gene).

In some embodiments, a plant may be regenerated from a plant part and/or plant cell of the invention comprising a mutation in one or more than one endogenous MAX1 gene (an endogenous MAX1a gene, an endogenous MAX1b gene, an endogenous MAX1c gene, and/or an endogenous MAX1d gene) as described herein, wherein the regenerated plant comprises the mutation in the one or more than one endogenous MAX1 gene and a phenotype of improvement in plant architecture and/or in one or more yield traits as compared to a plant devoid of the same mutation in the one or more than one MAX1 gene. In some embodiments, the regenerated plant may comprise a mutated MAX1 gene having at least 90% sequence identity to any one of SEQ ID NOs:173, 175, 177, 179, 181, and/or 183.

In some embodiments, a plant cell is provided, the plant cell comprising at least one (e.g., one or more) mutation within an endogenous More Axillary Growth 1 (MAX1) gene, wherein the at least one mutation is a substitution, insertion, or deletion that is introduced using an editing system that comprises a nucleic acid binding domain that binds to a target site in the endogenous MAX1 gene. In some embodiments, the substitution, insertion, or deletion results in, for example, an amino acid substitution. In some embodiments, the substitution, insertion, or deletion results in, for example, a premature stop codon. In some embodiments, the substitution, insertion, or deletion results in, for example, a truncated MAX1 protein and/or the absence of the MAX1 protein (e.g., the truncation results in no or little detectable protein). In some embodiments, the at least one mutation is a point mutation, optionally resulting in a premature stop codon, optionally a truncated MAX1 protein, optionally no or little or no detectable MAX1 protein. In some embodiments, the at least one mutation within the MAX1 gene is an insertion and/or a deletion, optionally the at least one mutation is an out-of-frame insertion or out-of-frame deletion. In some embodiments, the endogenous MAX1 gene is an endogenous MAX1a gene, an endogenous MAX1b gene, an endogenous MAX1c gene, or an endogenous MAX1d gene, optionally wherein one or more than one endogenous MAX1 gene may comprise at least one mutation. In some embodiments, the at least one mutation may be a non-natural mutation. In some embodiments, the plant cell may comprise a mutated MAX1 gene having at least 90% sequence identity to any one of SEQ ID NOs:173, 175, 177, 179, 181, and/or 183.

In some embodiments, a target site in a MAX1 gene of a plant cell may be within a region or portion of the endogenous MAX1 gene, the region having at least 90% sequence identity to any one of the nucleotide sequences of SEQ ID NOs:72-91, 96-113, 118-138, or 143-164, optionally at least 90% sequence identity to any one of SEQ ID NOs:77-79, 81-83, 88, 90, 91, 101-103, 105-107, 113, 121, 124, 125, 127-129, 132-138, 148-150, 152-154, or 160-164. In some embodiments, the target site in the MAX1 gene is within a region of the endogenous MAX1 gene that encodes an amino acid sequence having at least 90% sequence identity to any one of SEQ ID NOs:92, 114, 139 or 165.

In some embodiments, a mutation may be made following cleavage by an editing system that comprises a nuclease and a nucleic acid binding domain that binds to a target site within a sequence having least 80% sequence identity to a sequence encoding of any one of SEQ ID NOs:69, 70, 93, 94, 115, 116, 140 or 141, optionally within the 5' region of a sequence having least 80% sequence identity to any one of SEQ ID NOs:69, 70, 93, 94, 115, 116, 140 or 141, optionally in or adjacent to the first exon of a MAX1 genomic sequence, or a sequence having at least 90% sequence identity to a sequence encoding any one of SEQ ID NOs: 72-91, 96-113, 118-138, or 143-164, optionally at least 90% sequence identity to any one of SEQ ID NOs:77-79, 81-83, 88, 90, 91, 101-103, 105-107, 113, 121, 124, 125, 127-129, 132-138, 148-150, 152-154, or 160-164, and the at least one mutation within a MAX1 gene is made following cleavage by the nuclease. In some embodiments, the at least one mutation may be a non-natural mutation. In some embodiments, the at least one mutation may result in a recessive allele, and/or a null allele. In some embodiments, the cleavage results in a mutated endogenous MAX1 gene comprising a sequence having at least 90% sequence identity to any one of SEQ ID NOs:173, 175, 177, 179, 181, and/or 183.

In some embodiments, the plant cell is regenerated into a plant that comprises the at least one mutation, optionally wherein the plant regenerated from the plant cell exhibits a phenotype of improved plant architecture and/or at least one (one or more) improved yield trait when compared to a wild-type plant not comprising/devoid of the allele (e.g., an isogenic wild type plant), optionally wherein the improved plant architecture includes, but is not limited to, increased branching, increased number of nodes, reduced internode length, and/or a reduced or semi-dwarf stature and/or the one or more improved yield traits includes, but is not limited to, increased yield (bu/acre), increased biomass, increased flower number, altered flowering time (earlier or later), increased kernel number, increased kernel size, increased number of pods, including an increased number of pods per node and/or an increased number of pods per plant, increased number of seeds per pod, increased number of seeds, increased seed size, and/or increased seed weight (e.g., increase in 100-seed weight) as compared to a control plant devoid of the at least one mutation. In some embodiments, the one or more improved yield traits resulting from a mutation as described herein includes, but is not limited to, an increased flower number, increased seed size, increased seed weight, increased number of pods, and/or increased number of seeds per pod as compared to a control plant devoid of the at least one mutation. In some embodiments, the at least one mutation may be a non-natural mutation. In some embodiments, the plant cell may comprise a mutated MAX1 gene having at least 90% sequence identity to any one of SEQ ID NOs:173, 175, 177, 179, 181, and/or 183.

In some embodiments, a method of producing/breeding a transgene-free edited plant (e.g., a soybean plant) is provided, the method comprising: crossing a plant of the present invention (e.g., a plant comprising one or more mutations (e.g., non-natural mutations) in one or more MAX1 genes and having improved plant architecture and/or one or more improved yield traits) with a transgene free plant, thereby introducing the mutation into the plant that is transgene-free; and selecting a progeny plant that comprises the mutation and is transgene-free, thereby producing a transgene free edited plant.

Also provided herein is a method of providing a plurality of plants (e.g., soybean plants) having one or more improved yield traits, the method comprising planting two or more plants of the invention (e.g., 2, 3, 4, 5, 6, 7, 8, 9, 10, 20, 30, 40, 50, 100, 200, 300, 400, 500, 1000, 2000, 3000, 400, 5000, or 10,000 or more plants comprising one or more mutations (e.g., non-natural mutations) in one or more MAX1 genes and having improved plant architecture and/or one or more improved yield traits) in a growing area (e.g., a field (e.g., a cultivated field, an agricultural field), a growth chamber, a greenhouse, a recreational area, a lawn, and/or a roadside and the like), thereby providing a plurality of plants having improved plant architecture and/or one or more improved yield traits as compared to a plurality of control plants devoid of the mutation.

In some embodiments, a method of generating variation in a region of a MAX1 gene is provided, comprising introducing an editing system into a plant cell, wherein the editing system is targeted to a region of a MAX1 gene that encodes a MAX1 polypeptide, and contacting the region of the MAX1 gene with the editing system, thereby introducing a mutation into the MAX1 gene and generating variation in the MAX1 gene of the plant cell. In some embodiments, the MAX1 gene: (a) comprises a nucleotide sequence having at least 80% sequence identity to SEQ ID NOs:69, 70, 93, 94, 115, 116, 140 or 141, (b) comprises a region having at least 80% sequence identity to any one of the nucleotide sequences of SEQ ID NOs:72-91, 96-113, 118-138, or 143-164, (c) encodes an amino acid sequence having at least 80% sequence identity to any one of SEQ ID NOs:71, 95, 117, or 142 and/or encodes a region of a MAX1 polypeptide having at least 90% sequence identity to any one of SEQ ID NOs:92, 114, 139 or 165. In some embodiments, the region of the MAX1 gene that is targeted comprises at least 90% sequence identity to any one of the nucleotide sequences of SEQ ID NOs:72-91, 96-113, 118-138, or 143-164. In some embodiments, contacting a region of the endogenous MAX1 gene in the plant cell with the editing system produces a plant cell comprising in its genome an edited endogenous MAX1 gene, the method further comprising (a) regenerating a plant from the plant cell; (b) selfing the plant to produce progeny plants (E1); (c) assaying the progeny plants of (b) for increased flower number, increased size of floral structures, increased kernel row number, and/or increased ear length; and (d) selecting the progeny plants exhibiting increased flower number, increased size of floral structures and/or increased ear length to produce selected progeny plants exhibiting increased flower number, increased size of floral structures, increased kernel row number, and/or increased ear length as compared to a control plant. In some embodiments, the method may further comprise (e) selfing the selected progeny plants of (d) to produce progeny plants (E2); (f) assaying the progeny plants of (e) for increased flower number, increased size of floral structures, increased kernel row number, and/or increased ear length; and (g) selecting the progeny plants exhibiting increased flower number, increased size of floral structures, increased kernel row number, and/or increased ear length to produce selected progeny plants exhibiting increased flower number, increased size of floral structures, increased kernel row number, and/or increased ear length as compared to a control plant, optionally repeating (e) through (g) one or more additional times.

In some embodiments, a method for editing a specific site in the genome of a plant cell is provided, the method comprising: cleaving, in a site-specific manner, a target site within an endogenous More Axillary Growth 1 (MAX1) gene (e.g., MAX1a, MAX1b, MAX1c, MAX1d,) in the plant cell, the endogenous MAX1 gene: (a) comprising a nucleotide sequence having at least 80% sequence identity to any one of SEQ ID NOs:69, 70, 93, 94, 115, 116, 140 or 141, (b) comprising a region having at least 90% sequence identity to any one of SEQ ID NOs:72-91, 96-113, 118-138, or 143-164, (c) encoding an amino acid sequence having at least 80% sequence identity to any one of SEQ ID NOs:71, 95, 117, or 142, (d) encoding a region having at least 90% sequence identity to an amino acid sequence of any one of SEQ ID NOs:92, 114, 139 or 165, thereby generating an edit in the endogenous MAX1 gene of the plant cell and producing a plant cell comprising the edit in the endogenous MAX1 gene. In some embodiments, the endogenous MAX1 gene is an endogenous MAX1a gene, an endogenous MAX1b gene, an endogenous MAX1c gene, or an endogenous MAX1d gene, optionally wherein an edit is generated in two or more endogenous MAX1 genes (e.g., two or more of MAX1a, MAX1b, MAX1c, and/or MAX1d). In some embodiments, editing a specific site in the genome of a plant cell may result in a mutated MAX1 gene having at least 90% sequence identity to any one of SEQ ID NOs:173, 175, 177, 179, 181, and/or 183. In some embodiments, the plant cell may be from a soybean plant.

In some embodiments, the edit in the endogenous MAX1 gene results in a mutation including, but not limited to, a base deletion, a base substitution, or a base insertion. In some embodiments, the edit may result in a non-natural mutation. In some embodiments, the at least one mutation may be in the 5' region of a MAX1 gene, for example, in the first exon of a MAX1 genomic sequence. In some embodiments, the edit may result in at least one mutation that is an insertion of at least one base pair (e.g., 1, 2, 3, 4, 5, 6, 7, 8, 9, 10, 11, 12, 13, 14, 15 or 16 base pairs, e.g., about 1-16 base pairs, e.g., 1 base pair to about 16 consecutive base pairs; e.g., 1, 2, 4, 5, 7, 8, 10, 11, 13, or 14 consecutive base pairs). In some embodiments, the edit may result in at least one mutation that is a deletion, optionally wherein the deletion is about 1 to about 100 consecutive base pairs in length, e.g., about 1-50 consecutive base pairs, about 1-30 consecutive base pairs or about 1-15 consecutive base pairs in length. A deletion or insertion useful with this invention may be an out-of-frame insertion or an out-of-frame deletion. In some embodiments, an out-of-frame insertion or out-of-frame deletion may result in a premature stop codon and truncated protein, optionally wherein the out-of-frame insertion or out-of-frame deletion results in no or little detectable protein (e.g., a knock-out or null mutation, optionally wherein the mutation is recessive). In some embodiments, the edit in a MAX1 gene results in a truncated MAX1 polypeptide, optionally a C-terminal truncation of the MAX1 polypeptide, optionally wherein the C-terminal truncation results in a deletion of about 100 amino acid residues to about 600 amino acid residues (e.g., about 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, or 600, and any range or value therein) from the C-terminus of the MAX1 polypeptide In some embodiments, a method of editing may further comprise regenerating a plant from the plant cell comprising the edit in the endogenous MAX11 gene, thereby producing a plant comprising the edit in its endogenous MAX1 gene (optionally in the 5' end of the MAX1 gene, optionally in the first exon) and having a phenotype of one or more improved yield traits when compared to a control plant that is devoid of the edit.

In some embodiments, a method for making a plant is provided, the method comprising (a) contacting a population of plant cells comprising an endogenous More Axillary Growth 1 (MAX1) gene (e.g., one or more endogenous MAX1 genes) with a nuclease linked to a nucleic acid binding domain (e.g., editing system) that binds to a sequence (i) having at least 80% sequence identity to a nucleotide sequence of any one of SEQ ID NOs:69, 70, 93, 94, 115, 116, 140 or 141, (ii) comprising a region having at least 90% identity to any one of SEQ ID NOs:72-91, 96-113, 118-138, or 143-164; (iii) encoding an amino acid sequence having at least 80% sequence identity to any one of SEQ ID NOs:71, 95, 117, or 142, and/or (iv) encoding a region having at least 90% sequence identity to any one of SEQ ID NOs:92, 114, 139 or 165, and/or; (b) selecting a plant cell from the population of plant cells in which an endogenous MAX1 gene (e.g., one or more endogenous MAX1 gene) has been mutated, thereby producing a plant cell comprising a mutation in the endogenous MAX1 gene (e.g., in the one or more endogenous MAX1 gene); and (c) growing the selected plant cell into a plant. In some embodiments, the plant that is made comprises a mutated MAX1 gene having at least 90% sequence identity to any one of SEQ ID NOs:173, 175, 177, 179, 181, and/or 183.

In some embodiments, a method of improving one or more yield traits in a plant is provided, the method comprising (a) contacting a plant cell comprising an endogenous More Axillary Growth 1 (MAX1) gene (e.g., one or more endogenous MAX1 genes) with a nuclease targeting the endogenous MAX1 gene, wherein the nuclease is linked to a nucleic acid binding domain (e.g., editing system) that binds to a target site in the endogenous MAX1 gene, wherein the endogenous MAX1 gene: (i) comprises a sequence having at least 80% sequence identity to the nucleotide sequence of any one of SEQ ID NOs:69, 70, 93, 94, 115, 116, 140 or 141; (ii) comprises a region having at least 90% identity to any one of SEQ ID NOs:72-91, 96-113, 118-138, or 143-164; (iii) encodes an amino acid sequence having at least 80% sequence identity to any one of SEQ ID NOs:71, 95, 117, or 142; and/or (iv) encodes an amino acid sequence comprising a region having at least 90% sequence identity to any one of SEQ ID NOs:92, 114, 139 or 165 to produce a plant cell comprising a mutation in the endogenous MAX1 gene (e.g., in the one or more endogenous MAX1 genes); and (b) growing the plant cell into a plant comprising the mutation in the endogenous MAX1 gene thereby producing a plant having a mutated endogenous MAX1 gene (e.g., one or more mutated endogenous MAX1 genes) and improved plant architecture and/or one or more improved yield traits. In some embodiments, the plant having improved plant architecture and/or one or more improved yield traits comprises a mutated MAX1 gene having at least 90% sequence identity to any one of SEQ ID NOs:173, 175, 177, 179, 181, and/or 183.

In some embodiments, a method for producing a plant or part thereof comprising at least one cell having a mutated endogenous More Axillary Growth 1 (MAX1) gene (e.g., one or more mutated endogenous MAX1 genes), the method comprising contacting a target site in an endogenous MAX1 gene (in one or more endogenous MAX1 genes) in the plant or plant part with a nuclease comprising a cleavage domain and a nucleic acid binding domain, wherein the nucleic acid binding domain binds to a target site in the endogenous MAX1 gene, wherein the endogenous MAX1 gene (e.g., one or more mutated endogenous MAX1 genes) (a) comprises a sequence having at least 80% sequence identity to a nucleotide sequence of any one of SEQ ID NOs:69, 70, 93, 94, 115, 116, 140 or 141; (b) comprises a region having at least 90% identity to any one of SEQ ID NOs:72-91, 96-113, 118-138, or 143-164; (c) encodes an amino acid sequence having at least 80% sequence identity to any one of SEQ ID NOs:71, 95, 117, or 142; and/or (d) encodes an amino acid sequence comprising a region having at least 90% identity to any one of SEQ ID NOs:92, 114, 139 or 165, thereby producing the plant or part thereof comprising at least one cell having a mutation in the endogenous MAX1 gene (e.g., one or more mutated endogenous MAX1 genes). In some embodiments, the mutation in an endogenous MAX1 gene results in a nucleic acid having at least 90% sequence identity to any one of SEQ ID NOs:173, 175, 177, 179, 181, and/or 183.

Also provided herein is a method for producing a plant or part thereof comprising a mutated endogenous More Axillary Growth 1 (MAX1) gene (e.g., one or more mutated endogenous MAX1 genes) and exhibiting improved plant architecture and/or one or more improved yield traits, the method comprising contacting a target site in an endogenous MAX1 gene in the plant or plant part with a nuclease comprising a cleavage domain and a nucleic acid binding domain, wherein the nucleic acid binding domain binds to a target site in the endogenous MAX1 gene, wherein the endogenous MAX1 gene: (a) comprises a sequence having at least 80% sequence identity to a nucleotide sequence of any one of SEQ ID NOs:69, 70, 93, 94, 115, 116, 140 or 141; (b) comprises a region having at least 90% identity to any one of SEQ ID NOs:72-91, 96-113, 118-138, or 143-164; (c) encodes an amino acid sequence having at least 80% sequence identity to any one of SEQ ID NOs:71, 95, 117, or 142; and/or (d) encodes an amino acid sequence comprising a region having at least 90% identity to any one of SEQ ID NOs:92, 114, 139 or 165, thereby producing the plant or part thereof comprising an endogenous MAX1 gene having a mutation (e.g., one or more mutated endogenous MAX1 genes) and exhibiting improved plant architecture and/or one or more improved yield traits. In some embodiments, the plant that is produced comprises a mutated endogenous MAX1 gene having at least 90% sequence identity to any one of SEQ ID NOs:173, 175, 177, 179, 181, and/or 183.

In some embodiments, improved plant architecture can include, but is not limited to, increased branching, increased number of nodes, reduced internode length, and/or a reduced or semi-dwarf stature. In some embodiments, the one or more improved yield traits includes, but is not limited to, increased yield (bu/acre), increased biomass, increased flower number, altered flowering time (earlier or later), increased kernel number, increased kernel size, increased number of pods, including an increased number of pods per node and/or an increased number of pods per plant, increased number of seeds per pod, increased number of seeds, increased seed size, and/or increased seed weight (e.g., increase in 100-seed weight), optionally wherein the one or more improved yield traits may be, for example, an increased flower number, increased seed size, increased seed weight, increased number of pods, and/or increased number of seeds per pod, as compared to a control plant devoid of the at least one mutation.

In some embodiments, a nuclease may cleave an endogenous MAX1 gene, thereby introducing the mutation into the endogenous MAX1 gene. A nuclease useful with the invention may be any nuclease that can be utilized to edit/modify a target nucleic acid. Such nucleases include, but are not limited to a zinc finger nuclease, transcription activator-like effector nucleases (TALEN), endonuclease (e.g., Fok1) and/or a CRISPR-Cas effector protein. Likewise, any nucleic acid binding domain useful with the invention may be any DNA binding domain or RNA binding domain that can be utilized to edit/modify a target nucleic acid. Such nucleic acid binding domains include, but are not limited to, a zinc finger, transcription activator-like DNA binding domain (TAL), an argonaute and/or a CRISPR-Cas effector DNA binding domain.

In some embodiments, a nucleic acid binding domain (e.g., DNA binding domain) is comprised in a nucleic acid binding polypeptide. A "nucleic acid binding protein" or "nucleic acid binding polypeptide" as used herein refers to a polypeptide that binds and/or is capable of binding a nucleic acid in a site- and/or sequence-specific manner. In some embodiments, a nucleic acid binding polypeptide may be a sequence-specific nucleic acid binding polypeptide (e.g., a sequence-specific DNA binding domain) such as, but not limited to, a sequence-specific binding polypeptide and/or domain from, for example, a polynucleotide-guided endonuclease, a CRISPR-Cas effector protein (e.g., a CRISPR-Cas endonuclease), a zinc finger nuclease, a transcription activator-like effector nuclease (TALEN) and/or an Argonaute protein. In some embodiments, a nucleic acid binding polypeptide comprises a cleavage polypeptide (e.g., a nuclease polypeptide and/or domain) such as, but not limited to, an endonuclease (e.g., Fok1), a polynucleotide-guided endonuclease, a CRISPR-Cas endonuclease, a zinc finger nuclease, and/or a transcription activator-like effector nuclease (TALEN). In some embodiments, the nucleic acid binding polypeptide associates with and/or is capable of associating with (e.g., forms a complex with) one or more nucleic acid molecule(s) (e.g., forms a complex with a guide nucleic acid as described herein) that can direct or guide the nucleic acid binding polypeptide to a specific target nucleotide sequence (e.g., a gene locus of a genome) that is complementary to the one or more nucleic acid molecule(s) (or a portion or region thereof), thereby causing the nucleic acid binding polypeptide to bind to the nucleotide sequence at the specific target site. In some embodiments, the nucleic acid binding polypeptide is a CRISPR-Cas effector protein as described herein. In some embodiments, reference is made to specifically to a CRISPR-Cas effector protein for simplicity, but a nucleic acid binding polypeptide as described herein may be used. In some embodiments, a polynucleotide and/or a nucleic acid construct of the invention can be an "expression cassette" or can be comprised within an expression cassette.

In some embodiments, a method of editing an endogenous More Axillary Growth 1 (MAX1) gene (e.g., MAX1a, MAX1b, MAX1c, and/or MAX1d) in a plant or plant part is provided, the method comprising contacting a target site in an endogenous MAX1 gene in the plant or plant part with a cytosine base editing system comprising a cytosine deaminase and a nucleic acid binding domain that binds to a target site in the endogenous MAX1 gene, wherein the endogenous MAX1 gene: (a) comprises a sequence having at least 80% sequence identity to a nucleotide sequence of any one of SEQ ID NOs:69, 70, 93, 94, 115, 116, 140 or 141; (b) comprises a region having at least 90% identity to any one of SEQ ID NOs:72-91, 96-113, 118-138, or 143-164; (c) encodes an amino acid sequence having at least 80% sequence identity to any one of SEQ ID NOs:71, 95, 117, or 142; and/or (d) encodes an amino acid sequence comprising a region having at least 90% identity to any one of SEQ ID NOs:92, 114, 139 or 165, thereby editing the endogenous MAX11 gene in the plant or part thereof and producing a plant or part thereof comprising at least one cell having a mutation in the endogenous MAX1 gene.

In some embodiments, a method of editing an endogenous More Axillary Growth 1 (MAX1) gene (e.g., MAX1a, MAX1b, MAX1c, and/or MAX1d) in a plant or plant part is provided, the method comprising contacting a target site in an MAX1 gene in the plant or plant part with an adenosine base editing system comprising an adenosine deaminase and a nucleic acid binding domain that binds to a target site in the MAX1 gene, wherein the MAX1 gene ((a) comprises a sequence having at least 80% sequence identity to a nucleotide sequence of any one of SEQ ID NOs:69, 70, 93, 94, 115, 116, 140 or 141; (b) comprises a region having at least 90% identity to any one of SEQ ID NOs:72-91, 96-113, 118-138, or 143-164; (c) encodes an amino acid sequence having at least 80% sequence identity to any one of SEQ ID NOs:71, 95, 117, or 142; and/or (d) encodes an amino acid sequence comprising a region having at least 90% identity to any one of SEQ ID NOs:92, 114, 139 or 165, thereby editing the endogenous MAX1 gene in the plant or part thereof and producing a plant or part thereof comprising at least one cell having a mutation in the endogenous MAX1 gene.

In some embodiments, a method of creating a mutation in a More Axillary Growth 1 (MAX1) gene (e.g., MAX1a, MAX1b, MAX1c, and/or MAX1d) in a plant is provided, comprising: (a) targeting a gene editing system to a portion of the MAX1 gene that (i) comprises a sequence having at least 90% sequence identity to any one of SEQ ID NOs:72-91, 96-113, 118-138, or 143-164; and/or (ii) encodes a sequence having at least 90% identity to any one of SEQ ID NOs:92, 114, 139 or 165, and (b) selecting a plant that comprises a modified nucleic acid sequence in a region having at least 90% sequence identity to any one of the sequences of SEQ ID NOs:72-91, 96-113, 118-138, or 143-164, optionally SEQ ID NOs:77-79, 81-83, 88, 90, 91, 101-103, 105-107, 113, 121, 124, 125, 127-129, 132-138, 148-150, 152-154, or 160-164. In some embodiments, the modification is an out-of-frame deletion or out-of-frame insertion, optionally resulting in a truncated cytochrome P450 monooxygenase (MAX1) polypeptide, optionally resulting in no or little detectable MAX1 polypeptide.

A mutation provided by methods of the invention is a mutation. In some embodiments, a mutation provided by the method of the invention is a non-natural mutation. In some embodiments, the mutation may be a substitution, an insertion and/or a deletion, optionally wherein the insertion or deletion is an out-of-frame insertion or an out-of-frame deletion. In some embodiments, a mutation may comprise a base substitution to an A, a T, a G, or a C. In some embodiments, the mutation may be a deletion (e.g., out-of-frame deletion) of about 1 base pair to about 100 consecutive base pairs, optionally, 1 to about 50 consecutive base pairs, 1 to about 30 consecutive base pairs, 1 to about 15 consecutive base pairs. In some embodiments, the mutation may be an insertion (e.g., an out-of-frame insertion) of at least one base pair (e.g., 1 base pair to about 16 base pairs; e.g., 1, 2, 3, 4, 5, 6, 7, 8, 9, 10, 11, 12, 13, 14, 15 or 16 consecutive base pairs, optionally 1, 2, 4, 5, 7, 8, 10, 11, 13, or 14 consecutive base pairs). A mutation in a MAX1 gene may be located in the 5' region of the MAX1 gene, optionally wherein the mutation may be within a portion or region of the endogenous MAX1 gene that encodes the MAX1 polypeptide (e.g., the coding regions (exons)). In some embodiments, the mutation in a MAX1 gene may be located in or adjacent to Exon 1 of the MAX1 gene. As used herein, "in or adjacent to Exon 1" means within 1 to about 50 consecutive nucleotides of the 5' or 3' region of Exon 1 of the MAX1 gene (e.g., within about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 30, 31, 32, 33, 34, 35, 36, 37, 38, 39, 40, 41, 42, 43, 44, 45, 46, 47, 48, 49, or 50 consecutive nucleotides 5' or 3' adjacent to Exon 1). In some embodiments, a mutation of a MAX1 gene that is an out-of-frame deletion or an out-of-frame insertion may result in a truncated polypeptide and/or may result in little or no detectible polypeptide. In some embodiments, the out-of-frame deletion or out-of-frame insertion may be a null mutation, optionally a recessive mutation. In some embodiments, a out-of-frame deletion or an out-of-frame insertion may be located in the 5' region of the MAX1 gene (e.g., in or adjacent to Exon 1) that results in a premature stop codon (e.g., an out-of-frame base insertion or an out-of-frame base deletion) and a truncated MAX1 polypeptide, optionally resulting in little or no detectable MAX1 polypeptide.

In some embodiments, a method of detecting a mutant More Axillary Growth 1 (MAX1) gene (e.g., MAX1a, MAX1b, MAX1c, and/or MAX1d) is provided, the method comprising detecting in the genome of a plant an endogenous MAX1 gene encoding a truncated polypeptide, optionally wherein the mutation is located in the 5' region (optionally, within or adjacent to Exon 1) of the MAX1 gene having at least 90% sequence identity to any one of the nucleotide sequences of SEQ ID NOs:72-91, 96-113, 118-138, or 143-164, optionally in a region having at least 90% sequence identity to any one of SEQ ID NOs:77-79, 81-83, 88, 90, 91, 101-103, 105-107, 113, 121, 124, 125, 127-129, 132-138, 148-150, 152-154, or 160-164. In some embodiments, the mutation that is detected is an out-of-frame deletion or an out-of-frame insertion. In some embodiments, the mutant MAX1 gene that is detected may comprise a mutated nucleotide sequence as described herein (see e.g., SEQ ID NOs:173, 175, 177, 179, 181, and/or 183 or a sequence having at least 90% sequence identity to the same), optionally wherein the mutation that is detected is a non-natural mutation.

In some embodiments, the present invention provides a method of producing a plant comprising a mutation in an endogenous More Axillary Growth 1 (MAX1) gene (e.g., MAX1a, MAX1b, MAX1c, and/or MAX1d) and at least one polynucleotide of interest, the method comprising crossing a plant of the invention comprising at least one mutation in an endogenous MAX11 gene (a first plant) with a second plant that comprises the at least one polynucleotide of interest to produce progeny plants; and selecting progeny plants comprising at least one mutation in the MAX1 gene and the at least one polynucleotide of interest, thereby producing the plant comprising a mutation in an endogenous MAX1 gene and at least one polynucleotide of interest.

The present invention further provides a method of producing a plant comprising a mutation in an endogenous MAX1 gene (e.g., MAX1a, MAX1b, MAX1c, and/or MAX1d) and at least one polynucleotide of interest, the method comprising introducing at least one polynucleotide of interest into a plant of the present invention comprising at least one mutation in a MAX1 gene, thereby producing a plant comprising at least one mutation in a MAX1 gene and at least one polynucleotide of interest. In some embodiments, the plant is a corn plant. In some embodiments, the plant is a soybean plant.

In some embodiments, also provided is a method of producing a plant comprising a mutation in an endogenous MAX1 gene (e.g., MAX1a, MAX1b, MAX1c, and/or MAX1d) and exhibiting a phenotype of improved yield traits, improved plant architecture and/or improved defense traits, the method comprising crossing a first plant, which is a plant of the present invention comprising at least one mutation in a MAX1 gene, with a second plant that exhibits a phenotype of improved yield traits, improved plant architecture and/or improved defense traits; and selecting progeny plants comprising the mutation in the MAX1 gene and a phenotype of improved yield traits, improved plant architecture and/or improved defense traits, thereby producing the plant comprising a mutation in an endogenous MAX1 gene and exhibiting a phenotype of improved yield traits, improved plant architecture and/or improved defense traits as compared to a control plant.

Further provided is a method of controlling weeds in a container (e.g., pot, or seed tray and the like), a growth chamber, a greenhouse, a field, a recreational area, a lawn, or on a roadside, the method comprising applying an herbicide to one or more (a plurality) plants of the invention (e.g., a plant comprising at least one mutation in a MAX1 gene (e.g., MAX1a, MAX1b, MAX1c, and/or MAX1d) as described herein), optionally a non-natural mutation, growing in a container, a growth chamber, a greenhouse, a field, a recreational area, a lawn, or on a roadside, thereby controlling the weeds in the container, the growth chamber, the greenhouse, the field, the recreational area, the lawn, or on the roadside in which the one or more plants are growing.

In some embodiments, a method of reducing insect predation on a plant is provided, the method comprising applying an insecticide to one or more plants of the invention, optionally, wherein the one or more plants are growing in a container, a growth chamber, a greenhouse, a field, a recreational area, a lawn, or on a roadside, thereby reducing insect predation on the one or more plants.

In some embodiments, a method of reducing fungal disease on a plant is provided, the method comprising applying a fungicide to one or more plants of the invention, optionally, wherein the one or more plants are growing in a container, a growth chamber, a greenhouse, a field, a recreational area, a lawn, or on a roadside, thereby reducing fungal disease on the one or more plants.

A polynucleotide of interest may be any polynucleotide that can confer a desirable phenotype or otherwise modify the phenotype or genotype of a plant. In some embodiments, a polynucleotide of interest may be polynucleotide that confers herbicide tolerance, insect resistance, nematode resistance, disease resistance, increased yield, increased nutrient use efficiency or abiotic stress resistance.

Thus, plants or plant cultivars which are to be treated with preference in accordance with the invention include all plants which, through genetic modification, received genetic material which imparts particular advantageous useful properties ("traits") to these plants. Examples of such properties are better plant growth, vigor, stress tolerance, standability, lodging resistance, nutrient uptake, plant nutrition, and/or yield, in particular improved growth, increased tolerance to high or low temperatures, increased tolerance to drought or to levels of water or soil salinity, enhanced flowering performance, easier harvesting, accelerated ripening, higher yields, higher quality and/or a higher nutritional value of the harvested products, better storage life and/or processability of the harvested products.

Further examples of such properties are an increased resistance against animal and microbial pests, such as against insects, arachnids, nematodes, mites, slugs and snails owing, for example, to toxins formed in the plants. Among DNA sequences encoding proteins which confer properties of tolerance to such animal and microbial pests, in particular insects, mention will particularly be made of the genetic material from *Bacillus thuringiensis* encoding the Bt proteins widely described in the literature and well known to those skilled in the art. Mention will also be made of proteins extracted from bacteria such as *Photorhabdus* (WO97/17432 and WO98/08932). In particular, mention will be made of the Bt Cry or VIP proteins which include the CrylA, CryIAb, CryIAc, CryIIA, CryIIIA, CryIIIB2, Cry9c Cry2Ab, Cry3Bb and CryIF proteins or toxic fragments thereof and also hybrids or combinations thereof, especially the CrylF protein or hybrids derived from a CrylF protein (e.g. hybrid CrylA-CrylF proteins or toxic fragments thereof), the CrylA-type proteins or toxic fragments thereof, preferably the CrylAc protein or hybrids derived from the CrylAc protein (e.g. hybrid CrylAb-CrylAc proteins) or the CrylAb or Bt2 protein or toxic fragments thereof, the Cry2Ae, Cry2Af or Cry2Ag proteins or toxic fragments thereof, the CrylA.105 protein or a toxic fragment thereof, the VIP3Aa19 protein, the VIP3Aa20 protein, the VIP3A proteins produced in the COT202 or COT203 cotton events, the VIP3Aa protein or a toxic fragment thereof as described in Estruch et al. (1996), Proc Natl Acad Sci USA. 28; 93(11):5389-94, the Cry proteins as described in WO2001/47952, the insecticidal proteins from *Xenorhabdus* (as described in WO98/50427), *Serratia* (particularly from *S. entomophila*) or *Photorhabdus* species strains, such as Tc-proteins from *Photorhabdus* as described in WO98/08932. Also any variants or mutants of any one of these proteins differing in some amino acids (1-10, preferably 1-5) from any of the above named sequences, particularly the sequence of their toxic fragment, or which are fused to a transit peptide, such as a plastid transit peptide, or another protein or peptide, is included herein.

Another and particularly emphasized example of such properties is conferred tolerance to one or more herbicides, for example imidazolinones, sulphonylureas, glyphosate or phosphinothricin. Among DNA sequences encoding proteins (i.e., polynucleotides of interest) which confer properties of tolerance to certain herbicides on the transformed plant cells and plants, mention will be particularly be made to the bar or PAT gene or the *Streptomyces coelicolor* gene described in WO2009/152359 which confers tolerance to glufosinate herbicides, a gene encoding a suitable EPSPS (5-Enolpyruvylshikimat-3-phosphat-Synthase) which confers tolerance to herbicides having EPSPS as a target, especially herbicides such as glyphosate and its salts, a gene encoding glyphosate-n-acetyltransferase, or a gene encoding glyphosate oxidoreductase. Further suitable herbicide tolerance traits include at least one ALS (acetolactate synthase) inhibitor (e.g., WO2007/024782), a mutated *Arabidopsis* ALS/AHAS gene (e.g., U.S. Pat. No. 6,855,533), genes encoding 2,4-D-monooxygenases conferring tolerance to 2,4-D (2,4-dichlorophenoxyacetic acid) and genes encoding Dicamba monooxygenases conferring tolerance to dicamba (3,6-dichloro-2-methoxybenzoic acid).

Further examples of such properties are increased resistance against phytopathogenic fungi, bacteria and/or viruses owing, for example, to systemic acquired resistance (SAR), systemin, phytoalexins, elicitors and also resistance genes and correspondingly expressed proteins and toxins.

Particularly useful transgenic events in transgenic plants or plant cultivars which can be treated with preference in accordance with the invention include Event 531/PV-GHBK04 (cotton, insect control, described in WO2002/040677), Event 1143-14A (cotton, insect control, not deposited, described in WO2006/128569); Event 1143-51B (cotton, insect control, not deposited, described in WO2006/128570); Event 1445 (cotton, herbicide tolerance, not deposited, described in US-A 2002-120964 or WO2002/034946); Event 17053 (rice, herbicide tolerance, deposited as PTA-9843, described in WO2010/117737); Event 17314 (rice, herbicide tolerance, deposited as PTA-9844, described in WO2010/117735); Event 281-24-236 (cotton, insect control-herbicide tolerance, deposited as PTA-6233, described in WO2005/103266 or US-A 2005-216969); Event 3006-210-23 (cotton, insect control-herbicide tolerance, deposited as PTA-6233, described in US-A 2007-143876 or WO2005/103266); Event 3272 (corn, quality trait, deposited as PTA-9972, described in WO2006/098952 or US-A 2006-230473); Event 33391 (wheat, herbicide tolerance, deposited as PTA-2347, described in WO2002/027004), Event 40416 (corn, insect control-herbicide tolerance, deposited as ATCC PTA-11508, described in WO 11/075593); Event 43A47 (corn, insect control-herbicide tolerance, deposited as ATCC PTA-11509, described in WO2011/075595); Event 5307 (corn, insect control, deposited as ATCC PTA-9561, described in WO2010/077816); Event ASR-368 (bent grass, herbicide tolerance, deposited as ATCC PTA-4816, described in US-A 2006-162007 or WO2004/053062); Event B16 (corn, herbicide tolerance, not deposited, described in US-A 2003-126634); Event BPS-CV127-9 (soybean, herbicide tolerance, deposited as NCIMB No. 41603, described in WO2010/080829); Event BLRl (oilseed rape, restoration of male sterility, deposited as NCIMB 41193, described in WO2005/074671), Event CE43-67B (cotton, insect control, deposited as DSM ACC2724, described in US-A 2009-217423 or WO2006/128573); Event CE44-69D (cotton, insect control, not deposited, described in US-A 2010-0024077); Event CE44-69D (cotton, insect control, not deposited, described in WO2006/128571); Event CE46-02A (cotton, insect control, not deposited, described in WO2006/128572); Event COT102 (cotton, insect control, not deposited, described in US-A 2006-130175 or WO2004/039986); Event COT202 (cotton, insect control, not deposited, described in US-A 2007-067868 or WO2005/054479); Event COT203 (cotton, insect control, not deposited, described in WO2005/054480););  Event DAS21606-3/1606 (soybean, herbicide tolerance, deposited as PTA-11028, described in WO2012/033794), Event DAS40278 (corn, herbicide tolerance, deposited as ATCC PTA-10244, described in WO2011/022469); Event DAS-44406-6/pDAB8264.44.06.1 (soybean, herbicide tolerance, deposited as PTA-11336, described in WO2012/075426), Event DAS-14536-7/pDAB8291.45.36.2 (soybean, herbicide tolerance, deposited as PTA-11335, described in WO2012/075429), Event DAS-59122-7 (corn, insect control-herbicide tolerance, deposited as ATCC PTA 11384, described in US-A 2006-070139); Event DAS-59132 (corn, insect control-herbicide tolerance, not deposited, described in WO2009/100188); Event DAS68416 (soybean, herbicide tolerance, deposited as ATCC PTA-10442, described in WO2011/066384 or WO2011/066360); Event DP-098140-6 (corn, herbicide tolerance, deposited as ATCC PTA-8296, described in US-A 2009-137395 or WO 08/112019); Event DP-305423-1 (soybean, quality trait, not deposited, described in US-A 2008-312082 or WO2008/054747); Event DP-32138-1 (corn, hybridization system, deposited as ATCC PTA-9158, described in US-A 2009-0210970 or WO2009/103049); Event DP-356043-5 (soybean, herbicide tolerance, deposited as ATCC PTA-8287, described in US-A 2010-0184079 or WO2008/002872); Event EE-I (brinjal, insect control, not deposited, described in WO 07/091277); Event Fil 17 (corn, herbicide tolerance, deposited as ATCC 209031, described in US-A 2006-059581 or WO 98/044140); Event FG72 (soybean, herbicide tolerance, deposited as PTA-11041, described in WO2011/063413), Event GA21 (corn, herbicide tolerance, deposited as ATCC 209033, described in US-A 2005-086719 or WO 98/044140); Event GG25 (corn, herbicide tolerance, deposited as ATCC 209032, described in US-A 2005-188434 or WO98/044140); Event GHB119 (cotton, insect control-herbicide tolerance, deposited as ATCC PTA-8398, described in WO2008/151780); Event GHB614 (cotton, herbicide tolerance, deposited as ATCC PTA-6878, described in US-A 2010-050282 or WO2007/017186); Event GJ11 (corn, herbicide tolerance, deposited as ATCC 209030, described in US-A 2005-188434 or WO98/044140); Event GM RZ13 (sugar beet, virus resistance, deposited as NCIMB-41601, described in WO2010/076212); Event H7-1 (sugar beet, herbicide tolerance, deposited as NCIMB 41158 or NCIMB 41159, described in US-A 2004-172669 or WO 2004/074492); Event JOPLINl (wheat, disease tolerance, not deposited, described in US-A 2008-064032); Event LL27 (soybean, herbicide tolerance, deposited as NCIMB41658, described in WO2006/108674 or US-A 2008-320616); Event LL55 (soybean, herbicide tolerance, deposited as NCIMB 41660, described in WO 2006/108675 or US-A 2008-196127); Event LLcotton25

(cotton, herbicide tolerance, deposited as ATCC PTA-3343, described in WO2003/013224 or US-A 2003-097687); Event LLRICE06 (rice, herbicide tolerance, deposited as ATCC 203353, described in U.S. Pat. No. 6,468,747 or WO2000/026345); Event LLRice62 (rice, herbicide tolerance, deposited as ATCC 203352, described in WO2000/026345), Event LLRICE601 (rice, herbicide tolerance, deposited as ATCC PTA-2600, described in US-A 2008-2289060 or WO2000/026356); Event LY038 (corn, quality trait, deposited as ATCC PTA-5623, described in US-A 2007-028322 or WO2005/061720); Event MIR162 (corn, insect control, deposited as PTA-8166, described in US-A 2009-300784 or WO2007/142840); Event MIR604 (corn, insect control, not deposited, described in US-A 2008-167456 or WO2005/103301); Event MON15985 (cotton, insect control, deposited as ATCC PTA-2516, described in US-A 2004-250317 or WO2002/100163); Event MON810 (corn, insect control, not deposited, described in US-A 2002-102582); Event MON863 (corn, insect control, deposited as ATCC PTA-2605, described in WO2004/011601 or US-A 2006-095986); Event MON87427 (corn, pollination control, deposited as ATCC PTA-7899, described in WO2011/062904); Event MON87460 (corn, stress tolerance, deposited as ATCC PTA-8910, described in WO2009/111263 or US-A 2011-0138504); Event MON87701 (soybean, insect control, deposited as ATCC PTA-8194, described in US-A 2009-130071 or WO2009/064652); Event MON87705 (soybean, quality trait-herbicide tolerance, deposited as ATCC PTA-9241, described in US-A 2010-0080887 or WO2010/037016); Event MON87708 (soybean, herbicide tolerance, deposited as ATCC PTA-9670, described in WO2011/034704); Event MON87712 (soybean, yield, deposited as PTA-10296, described in WO2012/051199), Event MON87754 (soybean, quality trait, deposited as ATCC PTA-9385, described in WO2010/024976); Event MON87769 (soybean, quality trait, deposited as ATCC PTA-8911, described in US-A 2011-0067141 or WO2009/102873); Event MON88017 (corn, insect control-herbicide tolerance, deposited as ATCC PTA-5582, described in US-A 2008-028482 or WO2005/059103); Event MON88913 (cotton, herbicide tolerance, deposited as ATCC PTA-4854, described in WO2004/072235 or US-A 2006-059590); Event MON88302 (oilseed rape, herbicide tolerance, deposited as PTA-10955, described in WO2011/153186), Event MON88701 (cotton, herbicide tolerance, deposited as PTA-11754, described in WO2012/134808), Event MON89034 (corn, insect control, deposited as ATCC PTA-7455, described in WO 07/140256 or US-A 2008-260932); Event MON89788 (soybean, herbicide tolerance, deposited as ATCC PTA-6708, described in US-A 2006-282915 or WO2006/130436); Event MS1 1 (oilseed rape, pollination control-herbicide tolerance, deposited as ATCC PTA-850 or PTA-2485, described in WO2001/031042); Event MS8 (oilseed rape, pollination control-herbicide tolerance, deposited as ATCC PTA-730, described in WO2001/041558 or US-A 2003-188347); Event NK603 (corn, herbicide tolerance, deposited as ATCC PTA-2478, described in US-A 2007-292854); Event PE-7 (rice, insect control, not deposited, described in WO2008/114282); Event RF3 (oilseed rape, pollination control-herbicide tolerance, deposited as ATCC PTA-730, described in WO2001/041558 or US-A 2003-188347); Event RT73 (oilseed rape, herbicide tolerance, not deposited, described in WO2002/036831 or US-A 2008-070260); Event SYHTOH2/SYN-000H2-5 (soybean, herbicide tolerance, deposited as PTA-11226, described in WO2012/082548), Event T227-1 (sugar beet, herbicide tolerance, not deposited, described in WO2002/44407 or US-A 2009-265817); Event T25 (corn, herbicide tolerance, not deposited, described in US-A 2001-029014 or WO2001/051654); Event T304-40 (cotton, insect control-herbicide tolerance, deposited as ATCC PTA-8171, described in US-A 2010-077501 or WO2008/122406); Event T342-142 (cotton, insect control, not deposited, described in WO2006/128568); Event TC1507 (corn, insect control-herbicide tolerance, not deposited, described in US-A 2005-039226 or WO2004/099447); Event VIP1034 (corn, insect control-herbicide tolerance, deposited as ATCC PTA-3925, described in WO2003/052073), Event 32316 (corn, insect control-herbicide tolerance, deposited as PTA-11507, described in WO2011/084632), Event 4114 (corn, insect control-herbicide tolerance, deposited as PTA-11506, described in WO2011/084621), event EE-GM3/FG72 (soybean, herbicide tolerance, ATCC Accession No. PTA-11041) optionally stacked with event EE-GM1/LL27 or event EE-GM2/LL55 (WO2011/063413A2), event DAS-68416-4 (soybean, herbicide tolerance, ATCC Accession No. PTA-10442, WO2011/066360A1), event DAS-68416-4 (soybean, herbicide tolerance, ATCC Accession No. PTA-10442, WO2011/066384A1), event DP-040416-8 (corn, insect control, ATCC Accession No. PTA-11508, WO2011/075593A1), event DP-043A47-3 (corn, insect control, ATCC Accession No. PTA-11509, WO2011/075595A1), event DP-004114-3 (corn, insect control, ATCC Accession No. PTA-11506, WO2011/084621A1), event DP-032316-8 (corn, insect control, ATCC Accession No. PTA-11507, WO2011/084632A1), event MON-88302-9 (oilseed rape, herbicide tolerance, ATCC Accession No. PTA-10955, WO2011/153186A1), event DAS-21606-3 (soybean, herbicide tolerance, ATCC Accession No. PTA-11028, WO2012/033794A2), event MON-87712-4 (soybean, quality trait, ATCC Accession No. PTA-10296, WO2012/051199A2), event DAS-44406-6 (soybean, stacked herbicide tolerance, ATCC Accession No. PTA-11336, WO2012/075426A1), event DAS-14536-7 (soybean, stacked herbicide tolerance, ATCC Accession No. PTA-11335, WO2012/075429A1), event SYN-000H2-5 (soybean, herbicide tolerance, ATCC Accession No. PTA-11226, WO2012/082548A2), event DP-061061-7 (oilseed rape, herbicide tolerance, no deposit No. available, WO2012071039A1), event DP-073496-4 (oilseed rape, herbicide tolerance, no deposit No. available, US2012131692), event 8264.44.06.1 (soybean, stacked herbicide tolerance, Accession No. PTA-11336, WO2012075426A2), event 8291.45.36.2 (soybean, stacked herbicide tolerance, Accession No. PTA-11335, WO2012075429A2), event SYHT0H2 (soybean, ATCC Accession No. PTA-11226, WO2012/082548A2), event MON88701 (cotton, ATCC Accession No. PTA-11754, WO2012/134808A1), event KK179-2 (alfalfa, ATCC Accession No. PTA-11833, WO2013/003558A1), event pDAB8264.42.32.1 (soybean, stacked herbicide tolerance, ATCC Accession No. PTA-11993, WO2013/010094A1), event MZDT09Y (corn, ATCC Accession No. PTA-13025, WO2013/012775A1).

The genes/events (e.g., polynucleotides of interest), which impart the desired traits in question, may also be present in combinations with one another in the transgenic plants. Examples of transgenic plants which may be mentioned are the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (with the fruits apples, pears, citrus fruits and grapes), with particular emphasis being given to maize, soya beans, wheat, rice, potatoes, cotton, sugar cane, tobacco and oilseed rape. Traits which are particularly emphasized are the increased resistance of the plants to insects, arachnids, nematodes and slugs and snails, as well as the increased resistance of the plants to one or more herbicides.

Commercially available examples of such plants, plant parts or plant seeds that may be treated with preference in accordance with the invention include commercial products, such as plant seeds, sold or distributed under the GENUITY®, DROUGHTGARD®, SMARTSTAX®, RIB COMPLETE®, ROUNDUP READY®, VT DOUBLE PRO®, VT TRIPLE PRO®, BOLLGARD II®, ROUNDUP READY 2 YIELD®, YIELDGARD®, ROUNDUP READY® 2 XTEND™, INTACTA RR2 PRO®, VISTIVE GOLD®, and/or XTENDFLEX™ trade names.

A More Axillary Growth 1 (MAX1) gene (e.g., MAX1a, MAX1b, MAX1c, and/or MAX1d) useful with this invention includes any MAX1 gene in which a mutation as described herein can confer improvement in plant architecture and/or in one or more yield traits in a plant or part thereof comprising the mutation. In some embodiments, an endogenous MAX1 gene (a) comprises a sequence having at least 80% sequence identity to a nucleotide sequence of any one of SEQ ID NOs:69, 70, 93, 94, 115, 116, 140 or 141; (b) comprises a region having at least 90% identity to any one of SEQ ID NOs:72-91, 96-113, 118-138, or 143-164; (c) encodes an amino acid sequence having at least 80% sequence identity to any one of SEQ ID NOs:71, 95, 117, or 142; and/or (d) encodes an amino acid sequence comprising a region having at least 90% identity to any one of SEQ ID NOs:92, 114, 139 or 165.

In some embodiments, the at least one mutation in an endogenous MAX1 gene in a plant may be a base substitution, a base deletion and/or a base insertion. In some embodiments, the at least one mutation may be a non-natural mutation. In some embodiments, the at least one mutation in an endogenous MAX1 gene in a plant may result in a plant having the phenotype of improved architecture and/or one or more improved yield traits as compared to a control plant devoid of the edit/mutation, optionally wherein improved plant architecture can include but is not limited to, increased branching, increased number of nodes, reduced internode length, and/or a reduced or semi-dwarf stature and the improved yield trait can include, but is not limited to, increased yield (bu/acre), increased biomass, increased flower number, altered timing of flowering (earlier or later), increased kernel number, increased kernel size, increased number of pods, including an increased number of pods per node and/or an increased number of pods per plant, increased number of seeds per pod, increased number of seeds, increased seed size, and/or increased seed weight (e.g., increase in 100-seed weight). In some embodiments, the one or more improved yield traits includes, but not limited to, an increased flower number, increased seed size, increased seed weight, increased number of pods, and/or increased number of seeds per pod.

In some embodiments, a mutation in an endogenous MAX1 gene may be a base substitution, a base deletion and/or a base insertion of at least 1 base pair. In some embodiments, the at least one mutation may be a non-natural mutation. In some embodiments, a base deletion may be 1 nucleotide to about 100 nucleotides (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 consecutive base pairs, or any range or value therein, e.g., 1 to about 50 base pairs, 1 to about 30 base pairs, 1 to about 15 base pairs, or any range or value therein), optionally where the mutation is at about 2 to about 100 consecutive nucleotides (e.g., 1 to about 50 consecutive base pairs, 1 to about 30 consecutive base pairs, 1 to about 15 consecutive base pairs)). In some embodiments, a mutation in an endogenous MAX1 gene may be a base insertion of 1 to about 16 nucleotides, optionally 1-16 consecutive nucleotides (e.g., 1, 2, 3, 4, 5, 6, 7, 8, 9, 10, 11, 12, 13, 14, 15 or 16 nucleotides, optionally consecutive nucleotides) of the MAX1 nucleic acid. In some embodiments, a mutation in an endogenous MAX1 gene may be an out-of-frame insertion or an out-of-frame deletion that results in a truncated MAX1 protein (e.g., a truncated cytochrome P450 monooxygenase) or little or no detectable MAX1 protein. In some embodiments, the at least one mutation may be a base substitution, optionally a substitution to an A, a T, a G, or a C. A mutation useful with this invention may be a point mutation.

In some embodiments, a mutation in an endogenous MAX1 gene may be made following cleavage by an editing system that comprises a nuclease and a nucleic acid binding domain that binds to a target site within a target nucleic acid (e.g., a MAX1 gene, e.g., MAX1a, MAX1b, MAX1c, and/or MAX1d), the target nucleic acid comprising a sequence having at least 80% sequence identity to any one of the nucleotide sequences of SEQ ID NOs:69, 70, 93, 94, 115, 116, 140 or 141, and/or encoding an amino acid sequence having at least 80% sequence identity to any one of SEQ ID NOs:71, 95, 117, or 142, optionally wherein the target site is located in a region of the MAX1 gene: the region comprising a sequence having at least 90% identity to any one of SEQ ID NOs:72-91, 96-113, 118-138, or 143-164 and/or encoding a sequence having at least 90% sequence identity to an amino acid sequence of any one of SEQ ID NOs:92, 114, 139 or 165. In some embodiments, the editing system generates a non-natural mutation. In some embodiments, the editing system may generate a mutated MAX1 gene having at least 90% sequence identity to any one of SEQ ID NOs:173, 175, 177, 179, 181, and/or 183.

Further provided are guide nucleic acids (e.g., gRNA, gDNA, crRNA, crDNA) that bind to a target site in a More Axillary Growth 1 (MAX1) gene (e.g., MAX1a, MAX1b, MAX1c, and/or MAX1d)), wherein the target site is in a region of the MAX1 gene having at least 90% sequence identity to any one of the nucleotide sequences of SEQ ID NOs:72-91, 96-113, 118-138, or 143-164, optionally any one of SEQ ID NOs:77-79, 81-83, 88, 90, 91, 101-103, 105-107, 113, 121, 124, 125, 127-129, 132-138, 148-150, 152-154, or 160-164. In some embodiments, the guide nucleic acid comprises a spacer comprising any one of the nucleotide sequences of SEQ ID NOs:166-168 or SEQ ID NOs:169-172.

In some embodiments, a soybean plant or plant part thereof is provided that comprises at least one mutation in at least one endogenous More Axillary Growth 1 (MAX1) gene having the gene identification number (gene ID) of Glyma.04g052100 (MAX1a), Glyma.06g052700 (MAX1b), Glyma.14g096900 (MAX1c) and/or Glyma.17g227500 (MAX1d), optionally where the at least one mutation is a non-natural mutation.

In some embodiments, a guide nucleic acid is provided that binds to a target nucleic acid in a More Axillary Growth 1 (MAX1) gene having the gene identification number (gene ID) of Glyma.04g052100 (MAX1a), Glyma.06g052700 (MAX1b), Glyma.14g096900 (MAX1c) and/or Glyma.17g227500 (MAX1d).

In some embodiments, a system is provided comprising a guide nucleic acid comprising a spacer (e.g., one or more spacers) having the nucleotide sequence of any one of SEQ ID NOs:166-168 or 169-172, and a CRISPR-Cas effector protein that associates with the guide nucleic acid. In some embodiments, the system may further comprise a tracr nucleic acid that associates with the guide nucleic acid and a CRISPR-Cas effector protein, optionally wherein the tracr nucleic acid and the guide nucleic acid are covalently linked.

As used herein, "a CRISPR-Cas effector protein in association with a guide nucleic acid" refers to the complex that is formed between a CRISPR-Cas effector protein and a guide nucleic acid in order to direct the CRISPR-Cas effector protein to a target site in a gene.

The invention further provides a gene editing system comprising a CRISPR-Cas effector protein in association with a guide nucleic acid and the guide nucleic acid comprises a spacer sequence that binds to a More Axillary Growth 1 (MAX1) gene, optionally wherein the MAX1 (a) comprises a sequence having at least 80% sequence identity to a nucleotide sequence of any one of SEQ ID NOs:69, 70, 93, 94, 115, 116, 140 or 141; (b) comprises a region having at least 90% identity to any one of SEQ ID NOs:72-91, 96-113, 118-138, or 143-164 optionally a region having at least 90% sequence identity to any one of SEQ ID NOs:77-79, 81-83, 88, 90, 91, 101-103, 105-107, 113, 121, 124, 125, 127-129, 132-138, 148-150, 152-154, or 160-164; (c) encodes an amino acid sequence having at least 80% sequence identity to any one of SEQ ID NOs:71, 95, 117, or 142; and/or (d) encodes an amino acid sequence comprising a region having at least 90% identity to any one of SEQ ID NOs:92, 114, 139 or 165. In some embodiments, a spacer sequence of the guide nucleic acid may comprise the nucleotide sequence of any of SEQ ID NOs:166-172. In some embodiments, the gene editing system may further comprise a tracr nucleic acid that associates with the guide nucleic acid and a CRISPR-Cas effector protein, optionally wherein the tracr nucleic acid and the guide nucleic acid are covalently linked.

The present invention further provides a complex comprising a CRISPR-Cas effector protein comprising a cleavage domain and a guide nucleic acid, wherein the guide nucleic acid binds to a target site in an endogenous More Axillary Growth 1 (MAX1) gene, wherein the endogenous MAX1 gene: (a) comprises a sequence having at least 80% sequence identity to a nucleotide sequence of any one of SEQ ID NOs:69, 70, 93, 94, 115, 116, 140 or 141; (b) comprises a region having at least 90% identity to any one of SEQ ID NOs:72-91, 96-113, 118-138, or 143-164; (c) encodes an amino acid sequence having at least 80% sequence identity to any one of SEQ ID NOs:71, 95, 117, or 142; and/or (d) encodes an amino acid sequence comprising a region having at least 90% identity to any one of SEQ ID NOs:92, 114, 139 or 165, and the cleavage domain cleaves a target strand in the MAX1 gene. In some embodiments, the cleavage domain cleaves a target strand in the MAX1 gene resulting in a mutation in an endogenous MAX1 gene comprising a sequence having at least 90% sequence identity to any one of SEQ ID NOs:173, 175, 177, 179, 181, and/or 183. In some embodiments, the mutation in the endogenous MAX1 gene is a non-natural mutation.

In some embodiments, an expression cassette(s) is/are provided that comprise (a) a polynucleotide encoding CRISPR-Cas effector protein comprising a cleavage domain and (b) a guide nucleic acid that binds to a target site in an endogenous More Axillary Growth 1 (MAX1) gene, wherein the guide nucleic acid comprises a spacer sequence that is complementary to and binds to (i) a portion of a nucleic acid having at least 80% sequence identity to any one of SEQ ID NOs:69, 70, 93, 94, 115, 116, 140 or 141; (ii) a portion of a nucleic acid having at least 90% sequence identity to any one of SEQ ID NOs:72-91, 96-113, 118-138, or 143-164, optionally SEQ ID NOs:77-79, 81-83, 88, 90, 91, 101-103, 105-107, 113, 121, 124, 125, 127-129, 132-138, 148-150, 152-154, or 160-164; (iii) a portion of a nucleic acid encoding an amino acid sequence having at least 80% sequence identity to any one of SEQ ID NOs:71, 95, 117, or 142; and/or (iv) a portion of a nucleic acid encoding an amino acid sequence having at least 90% identity to any one of SEQ ID NOs:92, 114, 139 or 165.

Also provided are nucleic acids encoding a cytochrome P450 monooxygenase (MAX1) polypeptide (e.g., MAX1a, MAX1b, MAX1c, MAX1d), optionally wherein when present in a plant or plant part the mutated MAX1 polypeptide/mutated MAX1 gene results in the plant comprising a phenotype of improved plant architecture and/or one or more improved yield traits as compared to a plant or plant part devoid of the mutation. In some embodiments, a mutated MAX1 gene may comprise a sequence having at least 90% sequence identity to any one of SEQ ID NOs:173, 175, 177, 179, 181, and/or 183.

Nucleic acid constructs of the invention (e.g., a construct comprising a sequence specific nucleic acid binding domain (e.g., sequence specific DNA binding domain), a CRISPR-Cas effector domain, a deaminase domain, reverse transcriptase (RT), RT template and/or a guide nucleic acid, etc.) and expression cassettes/vectors comprising the same may be used as an editing system of this invention for modifying target nucleic acids (e.g., endogenous MAX1 genes, e.g., endogenous MAX1a gene, endogenous MAX1b gene, endogenous MAX1c gene, endogenous MAX1d gene) and/or their expression.

Any plant comprising an endogenous MAX1 gene that is capable of conferring at least one improved yield trait and/or improved plant architecture, when modified as described herein, may be modified (e.g., mutated, e.g., base edited, cleaved, nicked, etc.) as described herein (e.g., using the polypeptides, polynucleotides, RNPs, nucleic acid constructs, expression cassettes, and/or vectors of the invention) to improve one or more yield traits in the plant. A plant exhibiting an improved yield trait may show an improvement of about 5% to about 100% (e.g., about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% or more or any range or value therein; e.g., about 5% to about 10%, about 5% to about 15%, about 5% to about 20%, about 10% to about 50%, about 10% to about 80%, about 10% to about 90%, about 10% to about 100%, about 20% to about 50%, about 20% to about 80%, about 20% to about 90%, about 20% to about 100%, about 30% to about 50%, about 30% to about 80%, about 30% to about 90%, about 30% to about 100%, about 50% to about 100%, about 75% to about 100% or more, and any range or value therein) in the yield trait as compared to a plant or part thereof that is devoid of the mutated endogenous MAX1 gene.

An editing system useful with this invention can be any site-specific (sequence-specific) genome editing system now known or later developed, which system can introduce mutations in a target specific manner. For example, an editing system (e.g., site- or sequence-specific editing system) can include, but is not limited to, a CRISPR-Cas editing system, a meganuclease editing system, a zinc finger nuclease (ZFN) editing system, a transcription activator-like effector nuclease (TALEN) editing system, a base editing system and/or a prime editing system, each of which can comprise one or more polypeptides and/or one or more polynucleotides that when expressed as a system in a cell can modify (mutate) a target nucleic acid in a sequence specific manner. In some embodiments, an editing system (e.g., site- or sequence-specific editing system) can comprise one or more polynucleotides and/or one or more polypeptides, including but not limited to a nucleic acid binding domain (DNA binding domain), a nuclease, and/or other polypeptide, and/or a polynucleotide.

In some embodiments, an editing system can comprise one or more sequence-specific nucleic acid binding domains (DNA binding domains) that can be from, for example, a polynucleotide-guided endonuclease, a CRISPR-Cas endonuclease (e.g., CRISPR-Cas effector protein), a zinc finger nuclease, a transcription activator-like effector nuclease (TALEN) and/or an Argonaute protein. In some embodiments, an editing system can comprise one or more cleavage domains (e.g., nucleases) including, but not limited to, an endonuclease (e.g., Fok1), a polynucleotide-guided endonuclease, a CRISPR-Cas endonuclease (e.g., CRISPR-Cas effector protein), a zinc finger nuclease, and/or a transcription activator-like effector nuclease (TALEN). In some embodiments, an editing system can comprise one or more polypeptides that include, but are not limited to, a deaminase (e.g., a cytosine deaminase, an adenine deaminase), a reverse transcriptase, a Dna2 polypeptide, and/or a 5' flap endonuclease (FEN). In some embodiments, an editing system can comprise one or more polynucleotides, including, but is not limited to, a CRISPR array (CRISPR guide) nucleic acid, extended guide nucleic acid, and/or a reverse transcriptase template.

In some embodiments, a method of modifying or editing More Axillary Growth 1 (MAX1) gene may comprise contacting a target nucleic acid (e.g., a nucleic acid encoding a cytochrome P450 monooxygenase (MAX1) polypeptide, e.g., a MAX1a polypeptide, a MAX1b polypeptide, a MAX1c polypeptide, a MAX1d polypeptide) with a base-editing fusion protein (e.g., a sequence specific DNA binding protein (e.g., a CRISPR-Cas effector protein or domain) fused to a deaminase domain (e.g., an adenine deaminase and/or a cytosine deaminase) and a guide nucleic acid, wherein the guide nucleic acid is capable of guiding/targeting the base editing fusion protein to the target nucleic acid, thereby editing a locus within the target nucleic acid. In some embodiments, a base editing fusion protein and guide nucleic acid may be comprised in one or more expression cassettes. In some embodiments, the target nucleic acid may be contacted with a base editing fusion protein and an expression cassette comprising a guide nucleic acid. In some embodiments, the sequence-specific nucleic acid binding fusion proteins and guides may be provided as ribonucleoproteins (RNPs). In some embodiments, a cell may be contacted with more than one base-editing fusion protein and/or one or more guide nucleic acids that may target one or more target nucleic acids in the cell.

In some embodiments, a method of modifying or editing a More Axillary Growth 1 (MAX1) gene may comprise contacting a target nucleic acid (e.g., a nucleic acid encoding a MAX1 polypeptide) with a sequence-specific nucleic acid binding fusion protein (e.g., a sequence-specific DNA binding protein (e.g., a CRISPR-Cas effector protein or domain) fused to a peptide tag, a deaminase fusion protein comprising a deaminase domain (e.g., an adenine deaminase and/or a cytosine deaminase) fused to an affinity polypeptide that is capable of binding to the peptide tag, and a guide nucleic acid, wherein the guide nucleic acid is capable of guiding/targeting the sequence-specific nucleic acid binding fusion protein to the target nucleic acid and the sequence-specific nucleic acid binding fusion protein is capable of recruiting the deaminase fusion protein to the target nucleic acid via the peptide tag-affinity polypeptide interaction, thereby editing a locus within the target nucleic acid. In some embodiments, the sequence-specific nucleic acid binding fusion protein may be fused to the affinity polypeptide that binds the peptide tag and the deaminase may be fused to the peptide tag, thereby recruiting the deaminase to the sequence-specific nucleic acid binding fusion protein and to the target nucleic acid. In some embodiments, the sequence-specific binding fusion protein, deaminase fusion protein, and guide nucleic acid may be comprised in one or more expression cassettes. In some embodiments, the target nucleic acid may be contacted with a sequence-specific binding fusion protein, deaminase fusion protein, and an expression cassette comprising a guide nucleic acid. In some embodiments, the sequence-specific nucleic acid binding fusion proteins, deaminase fusion proteins and guides may be provided as ribonucleoproteins (RNPs).

In some embodiments, methods such as prime editing may be used to generate a mutation in an endogenous MAX1 gene. In prime editing, RNA-dependent DNA polymerase (reverse transcriptase, RT) and reverse transcriptase templates (RT template) are used in combination with sequence specific nucleic acid binding domains that confer the ability to recognize and bind the target in a sequence-specific manner, and which can also cause a nick of the PAM-containing strand within the target. The nucleic acid binding domain may be a CRISPR-Cas effector protein and in this case, the CRISPR array or guide RNA may be an extended guide that comprises an extended portion comprising a primer binding site (PSB) and the edit to be incorporated into the genome (the template). Similar to base editing, prime editing can take advantages of the various methods of recruiting proteins for use in the editing to the target site, such methods including both non-covalent and covalent interactions between the proteins and nucleic acids used in the selected process of genome editing.

As used herein, a "CRISPR-Cas effector protein" is a protein or polypeptide or domain thereof that cleaves or cuts a nucleic acid, binds a nucleic acid (e.g., a target nucleic acid and/or a guide nucleic acid), and/or that identifies, recognizes, or binds a guide nucleic acid as defined herein. In some embodiments, a CRISPR-Cas effector protein may be an enzyme (e.g., a nuclease, endonuclease, nickase, etc.) or portion thereof and/or may function as an enzyme. In some embodiments, a CRISPR-Cas effector protein refers to a CRISPR-Cas nuclease polypeptide or domain thereof that comprises nuclease activity or in which the nuclease activity has been reduced or eliminated, and/or comprises nickase activity or in which the nickase has been reduced or eliminated, and/or comprises single stranded DNA cleavage activity (ss DNAse activity) or in which the ss DNAse activity has been reduced or eliminated, and/or comprises self-processing RNAse activity or in which the self-processing RNAse activity has been reduced or eliminated. A CRISPR-Cas effector protein may bind to a target nucleic acid.

In some embodiments, a sequence-specific nucleic acid binding domain may be a CRISPR-Cas effector protein. In some embodiments, a CRISPR-Cas effector protein may be from a Type I CRISPR-Cas system, a Type II CRISPR-Cas system, a Type III CRISPR-Cas system, a Type IV CRISPR-Cas system, Type V CRISPR-Cas system, or a Type VI CRISPR-Cas system. In some embodiments, a CRISPR-Cas effector protein of the invention may be from a Type II CRISPR-Cas system or a Type V CRISPR-Cas system. In some embodiments, a CRISPR-Cas effector protein may be Type II CRISPR-Cas effector protein, for example, a Cas9 effector protein. In some embodiments, a CRISPR-Cas effector protein may be Type V CRISPR-Cas effector protein, for example, a Cas12 effector protein.

In some embodiments, a CRISPR-Cas effector protein may include, but is not limited to, a Cas9, C2c1, C2c3, Cas12a (also referred to as Cpf1), Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmrl, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5 nuclease, optionally wherein the CRISPR-Cas effector protein may be a Cas9, Cas12a (Cpf1), Cas12b, Cas12c (C2c3), Cas12d (CasY), Cas12e (CasX), Cas12g, Cas12h, Cas12i, C2c4, C2c5, C2c8, C2c9, C2c10, Cas14a, Cas14b, and/or Cas14c effector protein.

In some embodiments, a CRISPR-Cas effector protein useful with the invention may comprise a mutation in its nuclease active site (e.g., RuvC, HNH, e.g., RuvC site of a Cas12a nuclease domain; e.g., RuvC site and/or HNH site of a Cas9 nuclease domain). A CRISPR-Cas effector protein having a mutation in its nuclease active site, and therefore, no longer comprising nuclease activity, is commonly referred to as "dead," e.g., dCas. In some embodiments, a CRISPR-Cas effector protein domain or polypeptide having a mutation in its nuclease active site may have impaired activity or reduced activity as compared to the same CRISPR-Cas effector protein without the mutation, e.g., a nickase, e.g., Cas9 nickase, Cas12a nickase.

A CRISPR Cas9 effector protein or CRISPR Cas9 effector domain useful with this invention may be any known or later identified Cas9 nuclease. In some embodiments, a CRISPR Cas9 polypeptide can be a Cas9 polypeptide from, for example, *Streptococcus* spp. (e.g., *S. pyogenes, S. thermophiles*), *Lactobacillus* spp., *Bifidobacterium* spp., *Kandleria* spp., *Leuconostoc* spp., *Oenococcus* spp., *Pediococcus* spp., *Weissella* spp., and/or *Olsenella* spp. Example Cas9 sequences include, but are not limited to, the amino acid sequences of SEQ ID NO:56 and SEQ ID NO:57 or the nucleotide sequences of SEQ ID NOs:58-68.

In some embodiments, the CRISPR-Cas effector protein may be a Cas9 polypeptide derived from *Streptococcus pyogenes* and recognizes the PAM sequence motif NGG, NAG, NGA (Mali et al, Science 2013; 339(6121): 823-826). In some embodiments, the CRISPR-Cas effector protein may be a Cas9 polypeptide derived from *Streptococcus thermophiles* and recognizes the PAM sequence motif NGGNG and/or NNAGAAW (W=A or T) (See, e.g., Horvath et al, Science, 2010; 327(5962): 167-170, and Deveau et al, J Bacteriol 2008; 190(4): 1390-1400). In some embodiments, the CRISPR-Cas effector protein may be a Cas9 polypeptide derived from *Streptococcus mutans* and recognizes the PAM sequence motif NGG and/or NAAR (R=A or G) (See, e.g., Deveau et al, J BACTERIOL 2008; 190(4): 1390-1400). In some embodiments, the CRISPR-Cas effector protein may be a Cas9 polypeptide derived from *Streptococcus aureus* and recognizes the PAM sequence motif NNGRR (R=A or G). In some embodiments, the CRISPR-Cas effector protein may be a Cas9 protein derived from *S. aureus*, which recognizes the PAM sequence motif N GRRT (R=A or G). In some embodiments, the CRISPR-Cas effector protein may be a Cas9 polypeptide derived from *S. aureus*, which recognizes the PAM sequence motif N GRRV (R=A or G). In some embodiments, the CRISPR-Cas effector protein may be a Cas9 polypeptide that is derived from *Neisseria meningitidis* and recognizes the PAM sequence motif N GATT or N GCTT (R=A or G, V=A, G or C) (See, e.g., Hou et ah, PNAS 2013, 1-6). In the aforementioned embodiments, N can be any nucleotide residue, e.g., any of A, G, C or T. In some embodiments, the CRISPR-Cas effector protein may be a Cas13a protein derived from *Leptotrichia shahii*, which recognizes a protospacer flanking sequence (PFS) (or RNA PAM (rPAM)) sequence motif of a single 3' A, U, or C, which may be located within the target nucleic acid.

In some embodiments, the CRISPR-Cas effector protein may be derived from Cas12a, which is a Type V Clustered Regularly Interspaced Short Palindromic Repeats (CRISPR)-Cas nuclease see, e.g., SEQ ID NOs:1-20). Cas12a differs in several respects from the more well-known Type II CRISPR Cas9 nuclease. For example, Cas9 recognizes a G-rich protospacer-adjacent motif (PAM) that is 3' to its guide RNA (gRNA, sgRNA, crRNA, crDNA, CRISPR array) binding site (protospacer, target nucleic acid, target DNA) (3'-NGG), while Cas12a recognizes a T-rich PAM that is located 5' to the target nucleic acid (5'-TTN, 5'-TTTN. In fact, the orientations in which Cas9 and Cas12a bind their guide RNAs are very nearly reversed in relation to their N and C termini. Furthermore, Cas12a enzymes use a single guide RNA (gRNA, CRISPR array, crRNA) rather than the dual guide RNA (sgRNA (e.g., crRNA and tracrRNA)) found in natural Cas9 systems, and Cas12a processes its own gRNAs. Additionally, Cas12a nuclease activity produces staggered DNA double stranded breaks instead of blunt ends produced by Cas9 nuclease activity, and Cas12a relies on a single RuvC domain to cleave both DNA strands, whereas Cas9 utilizes an HNH domain and a RuvC domain for cleavage.

A CRISPR Cas12a effector protein/domain useful with this invention may be any known or later identified Cas12a polypeptide (previously known as Cpf1) (see, e.g., U.S. Pat. No. 9,790,490, which is incorporated by reference for its disclosures of Cpf1 (Cas12a) sequences). The term "Cas12a", "Cas12a polypeptide" or "Cas12a domain" refers to an RNA-guided nuclease comprising a Cas12a polypeptide, or a fragment thereof, which comprises the guide nucleic acid binding domain of Cas12a and/or an active, inactive, or partially active DNA cleavage domain of Cas12a. In some embodiments, a Cas12a useful with the invention may comprise a mutation in the nuclease active site (e.g., RuvC site of the Cas12a domain). A Cas12a domain or Cas12a polypeptide having a mutation in its nuclease active site, and therefore, no longer comprising nuclease activity, is commonly referred to as deadCas12a (e.g., dCas12a). In some embodiments, a Cas12a domain or Cas12a polypeptide having a mutation in its nuclease active site may have impaired activity, e.g., may have nickase activity.

Any deaminase domain/polypeptide useful for base editing may be used with this invention. In some embodiments, the deaminase domain may be a cytosine deaminase domain or an adenine deaminase domain. A cytosine deaminase (or cytidine deaminase) useful with this invention may be any known or later identified cytosine deaminase from any organism (see, e.g., U.S. Pat. No. 10,167,457 and Thuronyi et al. *Nat. Biotechnol.* 37:1070-1079 (2019), each of which is incorporated by reference herein for its disclosure of cytosine deaminases). Cytosine deaminases can catalyze the hydrolytic deamination of cytidine or deoxycytidine to uridine or deoxyuridine, respectively. Thus, in some embodiments, a deaminase or deaminase domain useful with this invention may be a cytidine deaminase domain, catalyzing the hydrolytic deamination of cytosine to uracil. In some embodiments, a cytosine deaminase may be a variant of a naturally occurring cytosine deaminase, including but not limited to a primate (e.g., a human, monkey, chimpanzee, gorilla), a dog, a cow, a rat or a mouse. Thus, in some embodiments, a cytosine deaminase useful with the invention may be about 70% to about 100% identical to a wild type cytosine deaminase (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical, and any range or value therein, to a naturally occurring cytosine deaminase).

In some embodiments, a cytosine deaminase useful with the invention may be an apolipoprotein B mRNA-editing complex (APOBEC) family deaminase. In some embodiments, the cytosine deaminase may be an APOBEC1 deaminase, an APOBEC2 deaminase, an APOBEC3A deaminase, an APOBEC3B deaminase, an APOBEC3C deaminase, an APOBEC3D deaminase, an APOBEC3F deaminase, an APOBEC3G deaminase, an APOBEC3H deaminase, an APOBEC4 deaminase, a human activation induced deaminase (hAID), an rAPOBEC1, FERNY, and/or a CDA1, optionally a pmCDA1, an atCDA1 (e.g., At2g19570), and evolved versions of the same (e.g., SEQ ID NO:27, SEQ ID NO:28 or SEQ ID NO:29). In some embodiments, the cytosine deaminase may be an APOBEC1 deaminase having the amino acid sequence of SEQ ID NO:23. In some embodiments, the cytosine deaminase may be an APOBEC3A deaminase having the amino acid sequence of SEQ ID NO:24. In some embodiments, the cytosine deaminase may be an CDA1 deaminase, optionally a CDA1 having the amino acid sequence of SEQ ID NO:25. In some embodiments, the cytosine deaminase may be a FERNY deaminase, optionally a FERNY having the amino acid sequence of SEQ ID NO:26. In some embodiments, a cytosine deaminase useful with the invention may be about 70% to about 100% identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identical) to the amino acid sequence of a naturally occurring cytosine deaminase (e.g., an evolved deaminase). In some embodiments, a cytosine deaminase useful with the invention may be about 70% to about 99.5% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical) to the amino acid sequence of SEQ ID NO:23, SEQ ID NO:24, SEQ ID NO:25 or SEQ ID NO:26 (e.g., at least 80%, at least 85%, at least 90%, at least 92%, at least 95%, at least 96%, at least 97%, at least 98%, at least 99%, or at least 99.5% identical to the amino acid sequence of SEQ ID NO:23, SEQ ID NO:24, SEQ ID NO:25, SEQ ID NO:26, SEQ ID NO:27, SEQ ID NO:28 or SEQ ID NO:29). In some embodiments, a polynucleotide encoding a cytosine deaminase may be codon optimized for expression in a plant and the codon optimized polypeptide may be about 70% to 99.5% identical to the reference polynucleotide.

In some embodiments, a nucleic acid construct of this invention may further encode a uracil glycosylase inhibitor (UGI) (e.g., uracil-DNA glycosylase inhibitor) polypeptide/domain. Thus, in some embodiments, a nucleic acid construct encoding a CRISPR-Cas effector protein and a cytosine deaminase domain (e.g., encoding a fusion protein comprising a CRISPR-Cas effector protein domain fused to a cytosine deaminase domain, and/or a CRISPR-Cas effector protein domain fused to a peptide tag or to an affinity polypeptide capable of binding a peptide tag and/or a deaminase protein domain fused to a peptide tag or to an affinity polypeptide capable of binding a peptide tag) may further encode a uracil-DNA glycosylase inhibitor (UGI), optionally wherein the UGI may be codon optimized for expression in a plant. In some embodiments, the invention provides fusion proteins comprising a CRISPR-Cas effector polypeptide, a deaminase domain, and a UGI and/or one or more polynucleotides encoding the same, optionally wherein the one or more polynucleotides may be codon optimized for expression in a plant. In some embodiments, the invention provides fusion proteins, wherein a CRISPR-Cas effector polypeptide, a deaminase domain, and a UGI may be fused to any combination of peptide tags and affinity polypeptides as described herein, thereby recruiting the deaminase domain and UGI to the CRISPR-Cas effector polypeptide and a target nucleic acid. In some embodiments, a guide nucleic acid may be linked to a recruiting RNA motif and one or more of the deaminase domain and/or UGI may be fused to an affinity polypeptide that is capable of interacting with the recruiting RNA motif, thereby recruiting the deaminase domain and UGI to a target nucleic acid.

A "uracil glycosylase inhibitor" useful with the invention may be any protein that is capable of inhibiting a uracil-DNA glycosylase base-excision repair enzyme. In some embodiments, a UGI domain comprises a wild type UGI or a fragment thereof. In some embodiments, a UGI domain useful with the invention may be about 70% to about 100% identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identical and any range or value therein) to the amino acid sequence of a naturally occurring UGI domain. In some embodiments, a UGI domain may comprise the amino acid sequence of SEQ ID NO:41 or a polypeptide having about 70% to about 99.5% sequence identity to the amino acid sequence of SEQ ID NO:41 (e.g., at least 80%, at least 85%, at least 90%, at least 92%, at least 95%, at least 96%, at least 97%, at least 98%, at least 99%, or at least 99.5% identical to the amino acid sequence of SEQ ID NO:41). For example, in some embodiments, a UGI domain may comprise a fragment of the amino acid sequence of SEQ ID NO:41 that is 100% identical to a portion of consecutive nucleotides (e.g., 10, 15, 20, 25, 30, 35, 40, 45, 50, 55, 60, 65, 70, 75, 80 consecutive nucleotides; e.g., about 10, 15, 20, 25, 30, 35, 40, 45, to about 50, 55, 60, 65, 70, 75, 80 consecutive nucleotides) of the amino acid sequence of SEQ ID NO:41. In some embodiments, a UGI domain may be a variant of a known UGI (e.g., SEQ ID NO:41) having about 70% to about 99.5% sequence identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% sequence identity, and any range or value therein) to the known UGI. In some embodiments, a polynucleotide encoding a UGI may be codon optimized for expression in a plant (e.g., a plant) and the codon optimized polypeptide may be about 70% to about 99.5% identical to the reference polynucleotide.

An adenine deaminase (or adenosine deaminase) useful with this invention may be any known or later identified adenine deaminase from any organism (see, e.g., U.S. Pat. No. 10,113,163, which is incorporated by reference herein for its disclosure of adenine deaminases). An adenine deaminase can catalyze the hydrolytic deamination of adenine or adenosine. In some embodiments, the adenine deaminase may catalyze the hydrolytic deamination of adenosine or deoxyadenosine to inosine or deoxyinosine, respectively. In some embodiments, the adenosine deaminase may catalyze the hydrolytic deamination of adenine or adenosine in DNA. In some embodiments, an adenine deaminase encoded by a nucleic acid construct of the invention may generate an A→G conversion in the sense (e.g., "+"; template) strand of the target nucleic acid or a T→C conversion in the antisense (e.g., "−", complementary) strand of the target nucleic acid.

In some embodiments, an adenosine deaminase may be a variant of a naturally occurring adenine deaminase. Thus, in some embodiments, an adenosine deaminase may be about 70% to 100% identical to a wild type adenine deaminase (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical, and any range or value therein, to a naturally occurring adenine deaminase). In some embodiments, the deaminase or deaminase does not occur in nature and may be referred to as an engineered, mutated or evolved adenosine deaminase. Thus, for example, an engineered, mutated or evolved adenine deaminase polypeptide or an adenine deaminase domain may be about 70% to 99.9% identical to a naturally occurring adenine deaminase polypeptide/domain (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8% or 99.9% identical, and any range or value therein, to a naturally occurring adenine deaminase polypeptide or adenine deaminase domain). In some embodiments, the adenosine deaminase may be from a bacterium, (e.g., *Escherichia coli, Staphylococcus aureus, Haemophilus influenzae, Caulobacter crescentus*, and the like). In some embodiments, a polynucleotide encoding an adenine deaminase polypeptide/domain may be codon optimized for expression in a plant.

In some embodiments, an adenine deaminase domain may be a wild type tRNA-specific adenosine deaminase domain, e.g., a tRNA-specific adenosine deaminase (TadA) and/or a mutated/evolved adenosine deaminase domain, e.g., mutated/evolved tRNA-specific adenosine deaminase domain (TadA*). In some embodiments, a TadA domain may be from *E. coli*. In some embodiments, the TadA may be modified, e.g., truncated, missing one or more N-terminal and/or C-terminal amino acids relative to a full-length TadA (e.g., 1, 2, 3, 4, 5, 6, 7, 8, 9, 10, 11, 12, 13, 14, 15, 6, 17, 18, 19, or 20 N-terminal and/or C terminal amino acid residues may be missing relative to a full length TadA. In some embodiments, a TadA polypeptide or TadA domain does not comprise an N-terminal methionine. In some embodiments, a wild type *E. coli* TadA comprises the amino acid sequence of SEQ ID NO:30. In some embodiments, a mutated/evolved *E. coli* TadA* comprises the amino acid sequence of SEQ ID NOs:31-40 (e.g., SEQ ID NOs: 31, 32, 33, 34, 35, 36, 37, 38, 39 or 40). In some embodiments, a polynucleotide encoding a TadA/TadA* may be codon optimized for expression in a plant.

A cytosine deaminase catalyzes cytosine deamination and results in a thymidine (through a uracil intermediate), causing a C to T conversion, or a G to A conversion in the complementary strand in the genome. Thus, in some embodiments, the cytosine deaminase encoded by the polynucleotide of the invention generates a C→T conversion in the sense (e.g., "+"; template) strand of the target nucleic acid or a G→A conversion in antisense (e.g., "−", complementary) strand of the target nucleic acid.

In some embodiments, the adenine deaminase encoded by the nucleic acid construct of the invention generates an A→G conversion in the sense (e.g., "+"; template) strand of the target nucleic acid or a T→C conversion in the antisense (e.g., "−", complementary) strand of the target nucleic acid.

The nucleic acid constructs of the invention encoding a base editor comprising a sequence-specific nucleic acid binding protein and a cytosine deaminase polypeptide, and nucleic acid constructs/expression cassettes/vectors encoding the same, may be used in combination with guide nucleic acids for modifying target nucleic acid including, but not limited to, generation of C→T or G→A mutations in a target nucleic acid including, but not limited to, a plasmid sequence; generation of C→T or G→A mutations in a coding sequence to alter an amino acid identity; generation of C→T or G→A mutations in a coding sequence to generate a stop codon; generation of C→T or G→A mutations in a coding sequence to disrupt a start codon; generation of point mutations in genomic DNA to disrupt function; and/or generation of point mutations in genomic DNA to disrupt splice junctions.

The nucleic acid constructs of the invention encoding a base editor comprising a sequence-specific nucleic acid binding protein and an adenine deaminase polypeptide, and expression cassettes and/or vectors encoding the same may be used in combination with guide nucleic acids for modifying a target nucleic acid including, but not limited to, generation of A→G or T→C mutations in a target nucleic acid including, but not limited to, a plasmid sequence; generation of A→G or T→C mutations in a coding sequence to alter an amino acid identity; generation of A→G or T→C mutations in a coding sequence to generate a stop codon; generation of A→G or T→C mutations in a coding sequence to disrupt a start codon; generation of point mutations in genomic DNA to disrupt function; and/or generation of point mutations in genomic DNA to disrupt splice junctions.

The nucleic acid constructs of the invention comprising a CRISPR-Cas effector protein or a fusion protein thereof may be used in combination with a guide RNA (gRNA, CRISPR array, CRISPR RNA, crRNA), designed to function with the encoded CRISPR-Cas effector protein or domain, to modify a target nucleic acid. A guide nucleic acid useful with this invention comprises at least one spacer sequence and at least one repeat sequence. The guide nucleic acid is capable of forming a complex with the CRISPR-Cas nuclease domain encoded and expressed by a nucleic acid construct of the invention and the spacer sequence is capable of hybridizing to a target nucleic acid, thereby guiding the complex (e.g., a CRISPR-Cas effector fusion protein (e.g., CRISPR-Cas effector domain fused to a deaminase domain and/or a CRISPR-Cas effector domain fused to a peptide tag or an affinity polypeptide to recruit a deaminase domain and optionally, a UGI) to the target nucleic acid, wherein the target nucleic acid may be modified (e.g., cleaved or edited) or modulated (e.g., modulating transcription) by the deaminase domain.

As an example, a nucleic acid construct encoding a Cas9 domain linked to a cytosine deaminase domain (e.g., fusion protein) may be used in combination with a Cas9 guide nucleic acid to modify a target nucleic acid, wherein the cytosine deaminase domain of the fusion protein deaminates a cytosine base in the target nucleic acid, thereby editing the target nucleic acid. In a further example, a nucleic acid construct encoding a Cas9 domain linked to an adenine deaminase domain (e.g., fusion protein) may be used in combination with a Cas9 guide nucleic acid to modify a target nucleic acid, wherein the adenine deaminase domain of the fusion protein deaminates an adenosine base in the target nucleic acid, thereby editing the target nucleic acid.

Likewise, a nucleic acid construct encoding a Cas12a domain (or other selected CRISPR-Cas nuclease, e.g., C2c1, C2c3, Cas12b, Cas12c, Cas12d, Cas12e, Cas13a, Cas13b, Cas13c, Cas13d, Cas1, CaslB, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmrl, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5) linked to a cytosine deaminase domain or adenine deaminase domain (e.g., fusion protein) may be used in combination with a Cas12a guide nucleic acid (or the guide nucleic acid for the other selected CRISPR-Cas nuclease) to modify a target nucleic acid, wherein the cytosine deaminase domain or adenine deaminase domain of the fusion protein deaminates a cytosine base in the target nucleic acid, thereby editing the target nucleic acid.

A "guide nucleic acid," "guide RNA," "gRNA," "CRISPR RNA/DNA" "crRNA" or "crDNA" as used herein means a nucleic acid that comprises at least one spacer sequence, which is complementary to (and hybridizes to) a target DNA (e.g., protospacer), and at least one repeat sequence (e.g., a repeat of a Type V Cas12a CRISPR-Cas system, or a fragment or portion thereof; a repeat of a Type II Cas9 CRISPR-Cas system, or fragment thereof; a repeat of a Type V C2c1 CRISPR Cas system, or a fragment thereof; a repeat of a CRISPR-Cas system of, for example, C2c3, Cas12a (also referred to as Cpf1), Cas12b, Cas12c, Cas12d, Cas12e, Cas13a, Cas13b, Cas13c, Cas13d, Cas1, CaslB, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmrl, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5, or a fragment thereof), wherein the repeat sequence may be linked to the 5' end and/or the 3' end of the spacer sequence. The design of a gRNA of this invention may be based on a Type I, Type II, Type III, Type IV, Type V, or Type VI CRISPR-Cas system.

In some embodiments, a Cas12a gRNA may comprise, from 5' to 3', a repeat sequence (full length or portion thereof ("handle"); e.g., pseudoknot-like structure) and a spacer sequence.

In some embodiments, a guide nucleic acid may comprise more than one repeat sequence-spacer sequence (e.g., 2, 3, 4, 5, 6, 7, 8, 9, 10, or more repeat-spacer sequences) (e.g., repeat-spacer-repeat, e.g., repeat-spacer-repeat-spacer-repeat-spacer-repeat-spacer-repeat-spacer, and the like). The guide nucleic acids of this invention are synthetic, human-made, and not found in nature. A gRNA can be quite long and may be used as an aptamer (like in the MS2 recruitment strategy) or other RNA structures hanging off the spacer.

A "repeat sequence" as used herein, refers to, for example, any repeat sequence of a wild-type CRISPR Cas locus (e.g., a Cas9 locus, a Cas12a locus, a C2c1 locus, etc.) or a repeat sequence of a synthetic crRNA that is functional with the CRISPR-Cas effector protein encoded by the nucleic acid constructs of the invention. A repeat sequence useful with this invention can be any known or later identified repeat sequence of a CRISPR-Cas locus (e.g., Type I, Type II, Type III, Type IV, Type V or Type VI) or it can be a synthetic repeat designed to function in a Type I, II, III, IV, V or VI CRISPR-Cas system. A repeat sequence may comprise a hairpin structure and/or a stem loop structure. In some embodiments, a repeat sequence may form a pseudoknot-like structure at its 5' end (i.e., "handle"). Thus, in some embodiments, a repeat sequence can be identical to or substantially identical to a repeat sequence from wild-type Type I CRISPR-Cas loci, Type II, CRISPR-Cas loci, Type III, CRISPR-Cas loci, Type IV CRISPR-Cas loci, Type V CRISPR-Cas loci and/or Type VI CRISPR-Cas loci. A repeat sequence from a wild-type CRISPR-Cas locus may be determined through established algorithms, such as using the CRISPRfinder offered through CRISPRdb (see, Grissa et al. *Nucleic Acids Res.* 35 (Web Server issue):W52-7). In some embodiments, a repeat sequence or portion thereof is linked at its 3' end to the 5' end of a spacer sequence, thereby forming a repeat-spacer sequence (e.g., guide nucleic acid, guide RNA/DNA, crRNA, crDNA).

In some embodiments, a repeat sequence comprises, consists essentially of, or consists of at least 10 nucleotides depending on the particular repeat and whether the guide nucleic acid comprising the repeat is processed or unprocessed (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 to 100 or more nucleotides, or any range or value therein). In some embodiments, a repeat sequence comprises, consists essentially of, or consists of about 10 to about 20, about 10 to about 30, about 10 to about 45, about 10 to about 50, about 15 to about 30, about 15 to about 40, about 15 to about 45, about 15 to about 50, about 20 to about 30, about 20 to about 40, about 20 to about 50, about 30 to about 40, about 40 to about 80, about 50 to about 100 or more nucleotides.

A repeat sequence linked to the 5' end of a spacer sequence can comprise a portion of a repeat sequence (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more contiguous nucleotides of a wild type repeat sequence). In some embodiments, a portion of a repeat sequence linked to the 5' end of a spacer sequence can be about five to about ten consecutive nucleotides in length (e.g., about 5, 6, 7, 8, 9, 10 nucleotides) and have at least 90% sequence identity (e.g., at least about 90%, 91%, 92%, 93%, 94%, 95%, 96%, 97%, 98%, 99%, or more (e.g., 99.1, 99.2, 99.3, 99.4, 99.5, 99.6, 99.7, 99.8, 99.9, or 100%)) to the same region (e.g., 5' end) of a wild type CRISPR Cas repeat nucleotide sequence. In some embodiments, a portion of a repeat sequence may comprise a pseudoknot-like structure at its 5' end (e.g., "handle").

A "spacer sequence" as used herein is a nucleotide sequence that is complementary to a target nucleic acid (e.g., target DNA) (e.g., protospacer) (e.g., a portion of consecutive nucleotides of a sequence that (a) comprises a sequence having at least 80% sequence identity to a nucleotide sequence of any one of SEQ ID NOs:69, 70, 93, 94, 115, 116, 140 or 141; (b) comprises a region having at least 90% identity to any one of SEQ ID NOs:72-91, 96-113, 118-138, or 143-164, optionally SEQ ID NOs:77-79, 81-83, 88, 90, 91, 101-103, 105-107, 113, 121, 124, 125, 127-129, 132-138, 148-150, 152-154, or 160-164; (c) encodes an amino acid sequence having at least 80% sequence identity to any one of SEQ ID NOs:71, 95, 117, or 142; and/or (d) encodes an amino acid sequence comprising a region having at least 90% identity to any one of SEQ ID NOs:92, 114, 139 or 165. In some embodiments, a spacer sequence (e.g., one or more spacers) may include, but is not limited to, the nucleotide sequences of any one of SEQ ID NOs:166-168 and/or 169-172. The spacer sequence can be fully complementary or substantially complementary (e.g., at least about 70% complementary (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more (e.g., 99.1, 99.2, 99.3, 99.4, 99.5, 99.6, 99.7, 99.8, 99.9, or 100%)) to a target nucleic acid. Thus, in some embodiments, the spacer sequence can have one, two, three, four, or five mismatches as compared to the target nucleic acid, which mismatches can be contiguous or noncontiguous. In some embodiments, the spacer sequence can have 70% complementarity to a target nucleic acid. In other embodiments, the spacer nucleotide sequence can have 80% complementarity to a target nucleic acid. In still other embodiments, the spacer nucleotide sequence can have 85%, 90%, 95%, 96%, 97%, 98%, 99% or 99.5% complementarity, and the like, to the target nucleic acid (protospacer). In some embodiments, the spacer sequence is 100% complementary to the target nucleic acid. A spacer sequence may have a length from about 15 nucleotides to about 30 nucleotides (e.g., 15, 16, 17, 18, 19, 20, 21, 22, 23, 24, 25, 26, 27, 28, 29, or 30 nucleotides, or any range or value therein). Thus, in some embodiments, a spacer sequence may have complete complementarity or substantial complementarity over a region of a target nucleic acid (e.g., protospacer) that is at least about 15 nucleotides to about 30 nucleotides in length. In some embodiments, the spacer is about 20 nucleotides in length. In some embodiments, the spacer is about 21, 22, or 23 nucleotides in length.

In some embodiments, the 5' region of a spacer sequence of a guide nucleic acid may be identical to a target DNA, while the 3' region of the spacer may be substantially complementary to the target DNA (e.g., Type V CRISPR-Cas), or the 3' region of a spacer sequence of a guide nucleic acid may be identical to a target DNA, while the 5' region of the spacer may be substantially complementary to the target DNA (e.g., Type II CRISPR-Cas), and therefore, the overall complementarity of the spacer sequence to the target DNA may be less than 100%. Thus, for example, in a guide for a Type V CRISPR-Cas system, the first 1, 2, 3, 4, 5, 6, 7, 8, 9, 10 nucleotides in the 5' region (i.e., seed region) of, for example, a 20 nucleotide spacer sequence may be 100% complementary to the target DNA, while the remaining nucleotides in the 3' region of the spacer sequence are substantially complementary (e.g., at least about 70% complementary) to the target DNA. In some embodiments, the first 1 to 8 nucleotides (e.g., the first 1, 2, 3, 4, 5, 6, 7, 8, nucleotides, and any range therein) of the 5' end of the spacer sequence may be 100% complementary to the target DNA, while the remaining nucleotides in the 3' region of the spacer sequence are substantially complementary (e.g., at least about 50% complementary (e.g., 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to the target DNA.

As a further example, in a guide for a Type II CRISPR-Cas system, the first 1, 2, 3, 4, 5, 6, 7, 8, 9, 10 nucleotides in the 3' region (i.e., seed region) of, for example, a 20 nucleotide spacer sequence may be 100% complementary to the target DNA, while the remaining nucleotides in the 5' region of the spacer sequence are substantially complementary (e.g., at least about 70% complementary) to the target DNA. In some embodiments, the first 1 to 10 nucleotides (e.g., the first 1, 2, 3, 4, 5, 6, 7, 8, 9, 10 nucleotides, and any range therein) of the 3' end of the spacer sequence may be 100% complementary to the target DNA, while the remaining nucleotides in the 5' region of the spacer sequence are substantially complementary (e.g., at least about 50% complementary (e.g., at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more or any range or value therein)) to the target DNA.

In some embodiments, a seed region of a spacer may be about 8 to about 10 nucleotides in length, about 5 to about 6 nucleotides in length, or about 6 nucleotides in length.

As used herein, a "target nucleic acid", "target DNA," "target nucleotide sequence," "target region," or a "target region in the genome" refers to a region of a plant's genome that is fully complementary (100% complementary) or substantially complementary (e.g., at least 70% complementary (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a spacer sequence in a guide nucleic acid of this invention. A target region useful for a CRISPR-Cas system may be located immediately 3' (e.g., Type V CRISPR-Cas system) or immediately 5' (e.g., Type II CRISPR-Cas system) to a PAM sequence in the genome of the organism (e.g., a plant genome). A target region may be selected from any region of at least 15 consecutive nucleotides (e.g., 16, 17, 18, 19, 20, 21, 22, 23, 24, 25, 26, 27, 28, 29, 30 nucleotides, and the like) located immediately adjacent to a PAM sequence.

A "protospacer sequence" refers to the target double stranded DNA and specifically to the portion of the target DNA (e.g., or target region in the genome) that is fully or substantially complementary (and hybridizes) to the spacer sequence of the CRISPR repeat-spacer sequences (e.g., guide nucleic acids, CRISPR arrays, crRNAs).

In the case of Type V CRISPR-Cas (e.g., Cas12a) systems and Type II CRISPR-Cas (Cas9) systems, the protospacer sequence is flanked by (e.g., immediately adjacent to) a protospacer adjacent motif (PAM). For Type IV CRISPR-Cas systems, the PAM is located at the 5' end on the non-target strand and at the 3' end of the target strand (see below, as an example).

```
  5'-NNNNNNNNNNNNNNNNNNN-3' RNA Spacer
     |||||||||||||||||||
3'AAANNNNNNNNNNNNNNNNNNN-5' Target strand
  ||||
5'TTTNNNNNNNNNNNNNNNNNNN-3' Non-target strand
```

In the case of Type II CRISPR-Cas (e.g., Cas9) systems, the PAM is located immediately 3' of the target region. The PAM for Type I CRISPR-Cas systems is located 5' of the target strand. There is no known PAM for Type III CRISPR-Cas systems. Makarova et al. describes the nomenclature for all the classes, types and subtypes of CRISPR systems (*Nature Reviews Microbiology* 13:722-736 (2015)). Guide structures and PAMs are described in by R. Barrangou (*Genome Biol.* 16:247 (2015)).

Canonical Cas12a PAMs are T rich. In some embodiments, a canonical Cas12a PAM sequence may be 5'-TTN, 5'-TTTN, or 5'-TTTV. In some embodiments, canonical Cas9 (e.g., *S. pyogenes*) PAMs may be 5'-NGG-3'. In some embodiments, non-canonical PAMs may be used but may be less efficient.

Additional PAM sequences may be determined by those skilled in the art through established experimental and computational approaches. Thus, for example, experimental approaches include targeting a sequence flanked by all possible nucleotide sequences and identifying sequence members that do not undergo targeting, such as through the transformation of target plasmid DNA (Esvelt et al. 2013. *Nat. Methods* 10:1116-1121; Jiang et al. 2013. *Nat. Biotechnol.* 31:233-239). In some aspects, a computational approach can include performing BLAST searches of natural spacers to identify the original target DNA sequences in bacteriophages or plasmids and aligning these sequences to determine conserved sequences adjacent to the target sequence (Briner and Barrangou. 2014. *Appl. Environ. Microbiol.* 80:994-1001; Mojica et al. 2009. *Microbiology* 155:733-740).

In some embodiments, the present invention provides expression cassettes and/or vectors comprising the nucleic acid constructs of the invention (e.g., one or more components of an editing system of the invention). In some embodiments, expression cassettes and/or vectors comprising the nucleic acid constructs of the invention and/or one or more guide nucleic acids may be provided. In some embodiments, a nucleic acid construct of the invention encoding a base editor (e.g., a construct comprising a CRISPR-Cas effector protein and a deaminase domain (e.g., a fusion protein)) or the components for base editing (e.g., a CRISPR-Cas effector protein fused to a peptide tag or an affinity polypeptide, a deaminase domain fused to a peptide tag or an affinity polypeptide, and/or a UGI fused to a peptide tag or an affinity polypeptide), may be comprised on the same or on a separate expression cassette or vector from that comprising the one or more guide nucleic acids. When the nucleic acid construct encoding a base editor or the components for base editing is/are comprised on separate expression cassette(s) or vector(s) from that comprising the guide nucleic acid, a target nucleic acid may be contacted with (e.g., provided with) the expression cassette(s) or vector(s) encoding the base editor or components for base editing in any order from one another and the guide nucleic acid, e.g., prior to, concurrently with, or after the expression cassette comprising the guide nucleic acid is provided (e.g., contacted with the target nucleic acid).

Fusion proteins of the invention may comprise sequence-specific nucleic acid binding domains (e.g., sequence-specific DNA binding domains), CRISPR-Cas polypeptides, and/or deaminase domains fused to peptide tags or affinity polypeptides that interact with the peptide tags, as known in the art, for use in recruiting the deaminase to the target nucleic acid. Methods of recruiting may also comprise guide nucleic acids linked to RNA recruiting motifs and deaminases fused to affinity polypeptides capable of interacting with RNA recruiting motifs, thereby recruiting the deaminase to the target nucleic acid. Alternatively, chemical interactions may be used to recruit polypeptides (e.g., deaminases) to a target nucleic acid.

A peptide tag (e.g., epitope) useful with this invention may include, but is not limited to, a GCN4 peptide tag (e.g., Sun-Tag), a c-Myc affinity tag, an HA affinity tag, a His affinity tag, an S affinity tag, a methionine-His affinity tag, an RGD-His affinity tag, a FLAG octapeptide, a strep tag or strep tag II, a V5 tag, and/or a VSV-G epitope. Any epitope that may be linked to a polypeptide and for which there is a corresponding affinity polypeptide that may be linked to another polypeptide may be used with this invention as a peptide tag. In some embodiments, a peptide tag may comprise 1 or 2 or more copies of a peptide tag (e.g., repeat unit, multimerized epitope (e.g., tandem repeats)) (e.g., 1, 2, 3, 4, 5, 6, 7, 8, 9, 10, 11, 12, 13, 14, 15, 16, 17, 18, 19, 20, 21, 22, 23, 24, 25 or more repeat units. In some embodiments, an affinity polypeptide that interacts with/binds to a peptide tag may be an antibody. In some embodiments, the antibody may be a scFv antibody. In some embodiments, an affinity polypeptide that binds to a peptide tag may be synthetic (e.g., evolved for affinity interaction) including, but not limited to, an affibody, an anticalin, a monobody and/or a DARPin (see, e.g., Sha et al., *Protein Sci.* 26(5): 910-924 (2017)); Gilbreth (*Curr Opin Struc Biol* 22(4):413-420 (2013)), U.S. Pat. No. 9,982,053, each of which are incorporated by reference in their entireties for the teachings relevant to affibodies, anticalins, monobodies and/or DARPins. Example peptide tag sequences and their affinity polypeptides include, but are not limited to, the amino acid sequences of SEQ ID NOs:42-44.

In some embodiments, a guide nucleic acid may be linked to an RNA recruiting motif, and a polypeptide to be recruited (e.g., a deaminase) may be fused to an affinity polypeptide that binds to the RNA recruiting motif, wherein the guide binds to the target nucleic acid and the RNA recruiting motif binds to the affinity polypeptide, thereby recruiting the polypeptide to the guide and contacting the target nucleic acid with the polypeptide (e.g., deaminase). In some embodiments, two or more polypeptides may be recruited to a guide nucleic acid, thereby contacting the target nucleic acid with two or more polypeptides (e.g., deaminases). Example RNA recruiting motifs and their affinity polypeptides include, but are not limited to, the sequences of SEQ ID NOs:45-55.

In some embodiments, a polypeptide fused to an affinity polypeptide may be a reverse transcriptase and the guide nucleic acid may be an extended guide nucleic acid linked to an RNA recruiting motif. In some embodiments, an RNA recruiting motif may be located on the 3' end of the extended portion of an extended guide nucleic acid (e.g., 5'-3', repeat-spacer-extended portion (RT template-primer binding site)-RNA recruiting motif). In some embodiments, an RNA recruiting motif may be embedded in the extended portion.

In some embodiments of the invention, an extended guide RNA and/or guide RNA may be linked to one or to two or more RNA recruiting motifs (e.g., 1, 2, 3, 4, 5, 6, 7, 8, 9, 10 or more motifs; e.g., at least 10 to about 25 motifs), optionally wherein the two or more RNA recruiting motifs may be the same RNA recruiting motif or different RNA recruiting motifs. In some embodiments, an RNA recruiting motif and corresponding affinity polypeptide may include, but is not limited, to a telomerase Ku binding motif (e.g., Ku binding hairpin) and the corresponding affinity polypeptide Ku (e.g., Ku heterodimer), a telomerase Sm7 binding motif and the corresponding affinity polypeptide Sm7, an MS2 phage operator stem-loop and the corresponding affinity polypeptide MS2 Coat Protein (MCP), a PP7 phage operator stem-loop and the corresponding affinity polypeptide PP7 Coat Protein (PCP), an SfMu phage Com stem-loop and the corresponding affinity polypeptide Com RNA binding protein, a PUF binding site (PBS) and the affinity polypeptide Pumilio/fem-3 mRNA binding factor (PUF), and/or a synthetic RNA-aptamer and the aptamer ligand as the corresponding affinity polypeptide. In some embodiments, the RNA recruiting motif and corresponding affinity polypeptide may be an MS2 phage operator stem-loop and the affinity polypeptide MS2 Coat Protein (MCP). In some embodiments, the RNA recruiting motif and corresponding affinity polypeptide may be a PUF binding site (PBS) and the affinity polypeptide Pumilio/fem-3 mRNA binding factor (PUF).

In some embodiments, the components for recruiting polypeptides and nucleic acids may those that function through chemical interactions that may include, but are not limited to, rapamycin-inducible dimerization of FRB-FKBP; Biotin-streptavidin; SNAP tag; Halo tag; CLIP tag; DmrA-DmrC heterodimer induced by a compound; bifunctional ligand (e.g., fusion of two protein-binding chemicals together, e.g., dihyrofolate reductase (DHFR).

In some embodiments, the nucleic acid constructs, expression cassettes or vectors of the invention that are optimized for expression in a plant may be about 70% to 100% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to the nucleic acid constructs, expression cassettes or vectors comprising the same polynucleotide(s) but which have not been codon optimized for expression in a plant.

Further provided herein are cells comprising one or more polynucleotides, guide nucleic acids, nucleic acid constructs, expression cassettes or vectors of the invention.

The nucleic acid constructs of the invention (e.g., a construct comprising a sequence specific DNA binding domain, a CRISPR-Cas effector domain, a deaminase domain, reverse transcriptase (RT), RT template and/or a guide nucleic acid, etc.) and expression cassettes/vectors comprising the same may be used as an editing system of this invention for modifying target nucleic acids and/or their expression.

A target nucleic acid of any plant or plant part (or groupings of plants, for example, into a genus or higher order classification) may be modified (e.g., mutated, e.g., base edited, cleaved, nicked, etc.) using the polypeptides, polynucleotides, ribonucleoproteins (RNPs), nucleic acid constructs, expression cassettes, and/or vectors of the invention including an angiosperm, a gymnosperm, a monocot, a dicot, a C3, C4, CAM plant, a bryophyte, a fern and/or fern ally, a microalgae, and/or a macroalgae. A plant and/or plant part that may be modified as described herein may be a plant and/or plant part of any plant species/variety/cultivar. In some embodiments, a plant that may be modified as described herein is a monocot. In some embodiments, a plant that may be modified as described herein is a dicot.

The term "plant part," as used herein, includes but is not limited to reproductive tissues (e.g., petals, sepals, stamens, pistils, receptacles, anthers, pollen, flowers, fruits, flower bud, ovules, seeds, embryos, nuts, kernels, ears, cobs and husks); vegetative tissues (e.g., petioles, stems, roots, root hairs, root tips, pith, coleoptiles, stalks, shoots, branches, bark, apical meristem, axillary bud, cotyledon, hypocotyls, and leaves); vascular tissues (e.g., phloem and xylem); specialized cells such as epidermal cells, parenchyma cells, chollenchyma cells, schlerenchyma cells, stomates, guard cells, cuticle, mesophyll cells; callus tissue; and cuttings. The term "plant part" also includes plant cells, including plant cells that are intact in plants and/or parts of plants, plant protoplasts, plant tissues, plant organs, plant cell tissue cultures, plant calli, plant clumps, and the like. As used herein, "shoot" refers to the above ground parts including the leaves and stems. As used herein, the term "tissue culture" encompasses cultures of tissue, cells, protoplasts and callus.

As used herein, "plant cell" refers to a structural and physiological unit of the plant, which typically comprise a cell wall but also includes protoplasts. A plant cell of the present invention can be in the form of an isolated single cell or can be a cultured cell or can be a part of a higher-organized unit such as, for example, a plant tissue (including callus) or a plant organ. In some embodiments, a plant cell can be an algal cell. A "protoplast" is an isolated plant cell without a cell wall or with only parts of the cell wall. Thus, in some embodiments of the invention, a transgenic cell comprising a nucleic acid molecule and/or nucleotide sequence of the invention is a cell of any plant or plant part including, but not limited to, a root cell, a leaf cell, a tissue culture cell, a seed cell, a flower cell, a fruit cell, a pollen cell, and the like. In some aspects of the invention, the plant part can be a plant germplasm. In some aspects, a plant cell can be non-propagating plant cell that does not regenerate into a plant.

"Plant cell culture" means cultures of plant units such as, for example, protoplasts, cell culture cells, cells in plant tissues, pollen, pollen tubes, ovules, embryo sacs, zygotes and embryos at various stages of development.

As used herein, a "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

In some embodiments of the invention, a transgenic tissue culture or transgenic plant cell culture is provided, wherein the transgenic tissue or cell culture comprises a nucleic acid molecule/nucleotide sequence of the invention. In some embodiments, transgenes may be eliminated from a plant developed from the transgenic tissue or cell by breeding of the transgenic plant with a non-transgenic plant and selecting among the progeny for the plants comprising the desired gene edit and not the transgenes used in producing the edit.

Any plant comprising an endogenous More Axillary Growth 1 (MAX1) gene may be modified as described herein to improve one or more yield traits. Non-limiting examples of plants that may be modified as described herein may include, but are not limited to, turf grasses (e.g., bluegrass, bentgrass, ryegrass, fescue), feather reed grass, tufted hair grass, miscanthus, arundo, switchgrass, vegetable crops, including artichokes, kohlrabi, arugula, leeks, asparagus, lettuce (e.g., head, leaf, romaine), malanga, melons (e.g., muskmelon, watermelon, crenshaw, honeydew, cantaloupe), cole crops (e.g., brussels sprouts, cabbage, cauliflower, broccoli, collards, kale, chinese cabbage, bok choy), cardoni, carrots, napa, okra, onions, celery, parsley, chick peas, parsnips, chicory, peppers, potatoes, cucurbits (e.g., marrow, cucumber, zucchini, squash, pumpkin, honeydew melon, watermelon, cantaloupe), radishes, dry bulb onions, rutabaga, eggplant, salsify, escarole, shallots, endive, garlic, spinach, green onions, squash, greens, beet (sugar beet and fodder beet), sweet potatoes, chard, horseradish, tomatoes, turnips, and spices; a fruit crop such as apples, apricots, cherries, nectarines, peaches, pears, plums, prunes, cherry, quince, fig, nuts (e.g., chestnuts, pecans, pistachios, hazelnuts, pistachios, peanuts, walnuts, macadamia nuts, almonds, and the like), citrus (e.g., clementine, kumquat, orange, grapefruit, tangerine, mandarin, lemon, lime, and the like), blueberries, black raspberries, boysenberries, cranberries, currants, gooseberries, loganberries, raspberries, strawberries, blackberries, grapes (wine and table), avocados, bananas, kiwi, persimmons, pomegranate, pineapple, tropical fruits, pomes, melon, mango, papaya, and lychee, a field crop plant such as clover, alfalfa, timothy, evening primrose, meadow foam, corn/maize (field, sweet, popcorn), hops, jojoba, buckwheat, safflower, quinoa, wheat, rice, barley, rye, millet, sorghum, oats, triticale, sorghum, tobacco, kapok, a leguminous plant (beans (e.g., green and dried), lentils, peas, soybeans), an oil plant (rape, canola, mustard, poppy, olive, sunflower, coconut, castor oil plant, cocoa bean, groundnut, oil palm), duckweed, *Arabidopsis*, a fiber plant (cotton, flax, hemp, jute), *Cannabis* (e.g., *Cannabis sativa, Cannabis indica*, and *Cannabis ruderalis*), lauraceae (cinnamon, camphor), or a plant such as coffee, sugar cane, tea, and natural rubber plants; and/or a bedding plant such as a flowering plant, a cactus, a succulent and/or an ornamental plant (e.g., roses, tulips, violets), as well as trees such as forest trees (broad-leaved trees and evergreens, such as conifers; e.g., elm, ash, oak, maple, fir, spruce, cedar, pine, birch, cypress, eucalyptus, willow), as well as shrubs and other nursery stock. In some embodiments, the nucleic acid constructs of the invention and/or expression cassettes and/or vectors encoding the same may be used to modify, for example, soybean.

In some embodiments, a plant that may be modified as described herein may include, but is not limited to, corn, soybean, canola, wheat, rice, cotton, sugarcane, sugar beet, barley, oats, alfalfa, sunflower, safflower, oil palm, sesame, coconut, tobacco, potato, sweet potato, cassava, coffee, apple, plum, apricot, peach, cherry, pear, fig, banana, citrus, cocoa, avocado, olive, almond, walnut, strawberry, watermelon, pepper, grape, tomato, cucumber, or a *Brassica* spp (e.g., *B. napus, B. oleracea, B. rapa, B. juncea*, and/or *B. nigra*). In some embodiments, a plant that may be modified as described herein is a dicot. In some embodiments, a plant that may be modified as described herein is a monocot. In some embodiments, a plant that may be modified as described herein is canola (e.g., *Brassica napus, Brassica rapa, Brassica juncea*). In some embodiments, a plant that may be modified as described herein is soybean (i.e., *Glycine max*).

The invention will now be described with reference to the following examples. It should be appreciated that these examples are not intended to limit the scope of the claims to the invention but are rather intended to be exemplary of certain embodiments. Any variations in the exemplified methods that occur to the skilled artisan are intended to fall within the scope of the invention.

EXAMPLES

Example 1. Modification of More Axillary Growth 1 (MAX1) Genes in Soybean

A strategy to generate knock-down edits or knock-out edits in endogenous More Axillary Growth 1 (MAX1) genes (e.g., MAX1a, MAX1b, MAX1c, MAX1d) genes in soybean was developed. Specifically, the MAX1 genes from soybean having the gene identification number (gene ID) of Glyma.04g052100 (MAX1a) (SEQ ID NO:69 (genomic), SEQ ID NO:70 (coding), Glyma.06g052700 (MAX1b) (SEQ ID NO:93 (genomic), SEQ ID NO:94 (coding), Glyma.14g096900 (MAX1c) (SEQ ID NO:115 (genomic), SEQ ID NO:116 (coding), and/or Glyma.17g227500 (MAX1d) (SEQ ID NO:140 (genomic), SEQ ID NO:141 (coding) to alter biosynthesis of strigolactone and subsequently generate soybean plants with improved plant architecture (e.g., decreased stature (e.g., semi-dwarf), reduced internode length, and/or increased number of internodes and/or one or more improved yield traits (e.g., increased seed size and/or number; increased yield (e.g., increased seed yield; e.g., increased number of seeds produced per hectare).

To generate a range of alleles, multiple editing constructs comprising one or more spacers having complementarity to targets within the MAX1 genes were generated as outlined in Table 1:

| Editing vector | Gene targets | spacer |
|---|---|---|
| pWISE4325 | Glyma.04g052100 (SEQ ID NO: 69) Glyma.06g052700 (SEQ ID NO: 93) | PWsp1482 (SEQ ID NO: 166); PWsp1484 (SEQ ID NO: 168); PWsp1483 (SEQ ID NO: 167) |
| pWISE4326 | Glyma.14g096900 (SEQ ID NO: 115); Glyma.17g.227500 (SEQ ID NO: 140); | PWsp1486 (SEQ ID NO: 170); PWsp1487 (SEQ ID NO: 171); PWsp1488 (SEQ ID NO: 172); PWsp1485 (SEQ ID NO: 169) |

Lines carrying edits in the MAX1 genes were screened and those showing sequencing reads having edits in the targeted gene were advanced to the next generation. The edited alleles of the soybean MAX1 genes recovered are further described in Tables 2-4 below.

TABLE 2

Edited alleles Glyma.04g052100 MAX1a

| Glyma.04g052100 allele | Allele description | Notes |
|---|---|---|
| Allele A (SEQ ID NO: 173) | 10 bp deletion (ATGGTCCTGA SEQ ID NO: 185) at position 414 of SEQ ID NO: 69 | Out of frame edit leading to an early stop codon (SEQ ID NO: 174) |

TABLE 3

Edited alleles Glyma.06g052700 MAX1b

| Glyma.06g052700 allele | Allele description | Notes |
|---|---|---|
| Allele B (SEQ ID NO: 175) | 8 bp deletion (GTTCACCC) at position 156 of SEQ ID NO: 93 | Out of frame edit leading to an early stop codon (SEQ ID NO: 176) |

TABLE 4

| Edited alleles Glyma.17g227500 MAX1d | | |
|---|---|---|
| Allele name | Allele description | Notes |
| Allele C (SEQ ID NO: 177) | 22 bp deletion (TTCTGATGTTAA TAGGAGGATT SEQ ID NO: 186) at position 145 of SEQ ID NO: 140 | Out of frame edit leading to an early stop codon (SEQ ID NO: 178) |
| Allele D (SEQ ID NO: 179) | 8 bp deletion (TAATAGGA) at position 154 of SEQ ID NO: 140 | Out of frame edit leading to an early stop codon (SEQ ID NO: 180) |
| Allele E (SEQ ID NO: 181) | 1 bp deletion of the "C" at position 266 of SEQ ID NO: 140 | Out of frame edit leading to an early stop codon (SEQ ID NO: 182) |
| Allele F (SEQ ID NO: 183) | 10 bp (TGTTAATAGG SEQ ID NO: 187) deletion at position 151 of SEQ ID NO: 140; 21 bp insertion at position 256 of SEQ ID NO: 140 | Out of frame edit leading to an early stop codon prior to the 21 bp insertion (SEQ ID NO: 184) |

Example 3. Phenotype Analysis

Soybean plants with a range of edited alleles of the MAX1 genes were grown in a greenhouse and evaluated at the R6 growth stage for plant architectural features that may be indicative of an increase in yield, as well as seed counts which are a direct indication of plant yield. The plant phenotypes measured included plant height, number of nodes on the mainstem, number of branches, pods on branches, pods on mainstem, pod per node on the mainstem, pods per plant, seeds per pod and seeds per plant. Results are summarized in Table 5 and Table 6, which demonstrate that editing the alleles of the MAX1 genes can alter architectural features of plants that may lead to an increase in yield.

TABLE 5

Phenotype analysis

| MAX1 gene alleles (number of plants) | Nodes on Mainstem | Number of branches | Pods on branches | Pods on Mainstem | Pods per node on mainstem | Pods per plant | Seeds per plant | Seeds per pod |
|---|---|---|---|---|---|---|---|---|
| Allele A homozygous (1) | 20 | 13 | 95 | 67 | 3.35 | 162 | 190 | 1.2 |
| Allele A heterozygous (1) | 21 | 14 | 129 | 62 | 2.9 | 191 | 219 | 1.1 |
| Allele A (heterozygous) Allele B (heterozygous) (1) | 22 | 12 | 104 | 75 | 3.4 | 179 | 391 | 2.2 |
| Transformation control* (9) | 20.2 | 14 | 106.8 | 58.9 | 2.9 | 165.7 | 429.4 | 2.6 |

*A plant that has gone through the transformation process to express the β-glucuronidase (GUS) reporter gene, but which is not edited.

TABLE 6

Phenotype analysis

| MAX1 gene alleles (number of plants) | Nodes on Mainstem | Number of branches | Pods on branches | Pods on Mainstem | Pods per node on mainstem | Pods per plant | Seeds per plant | Seeds per pod |
|---|---|---|---|---|---|---|---|---|
| Allele D (Heterozygous) Allele C (heterozygous) (6) | 21.17 | 10.33 | 101.3 | 64.33 | 3.04 | 165.7 | 335.0 | 2.02 |
| Allele C (homozygous) (6) | 21.00 | 10.50 | 95.5 | 64.33 | 3.07 | 159.8 | 319.2 | 1.99 |
| Allele D (homozygous) (3) | 19.67 | 8.67 | 101.3 | 61.67 | 3.12 | 163.0 | 336.3 | 2.04 |
| Allele E (heterozygous) (1) | 20.00 | 7.00 | 116.0 | 68.00 | 3.40 | 184.0 | 351.0 | 1.91 |
| Allele F (homozygous) (2) | 22.00 | 9.50 | 98.5 | 67.50 | 3.07 | 166.0 | 369.5 | 2.23 |
| Null segregant (10) | 21.50 | 9.20 | 76.0 | 66.20 | 3.08 | 142.2 | 340.2 | 2.38 |
| Unedited control (10) | 21.40 | 10.10 | 105.8 | 61.70 | 2.88 | 167.5 | 397.9 | 2.37 |

The foregoing is illustrative of the present invention and is not to be construed as limiting thereof. The invention is defined by the following claims, with equivalents of the claims to be included therein.

---

That which is claimed is:

1. A plant or plant part thereof comprising at least one mutation in an endogenous More Axillary Growth 1 (MAX1) gene encoding a cytochrome P450 monooxygenase (MAX1) polypeptide, wherein the at least one mutation is an out-of-frame mutation in a region of the endogenous MAX1 gene having at least 90% sequence identity to a nucleotide sequence of any one of SEQ ID NOs: 72-91, 96-113, 118-138, or 143-164, wherein the plant comprising the at least one mutation has a phenotype of improved plant architecture as compared to a plant devoid of the at least one mutation.

2. The plant or part thereof of claim 1, wherein the at least one mutation is a base deletion and/or a base insertion.

3. The plant or part thereof of claim 2, wherein the base insertion or base deletion is an out-of-frame insertion or an out-of-frame deletion, optionally wherein the out-of-frame insertion or out-of-frame deletion produces/results in a premature stop codon.

4. The plant or part thereof of claim 3, wherein the at least one mutation in the MAX1 gene results in a C-terminal truncation of the encoded polypeptide.

5. The plant or part thereof of claim 1, wherein the at least one mutation in the endogenous MAX1 gene results in a C-terminal truncation of the encoded polypeptide.

6. The plant or part thereof of claim 1, wherein the endogenous MAX1 gene comprises a nucleotide sequence having at least 80% sequence identity to any one of SEQ ID NOs: 69, 70, 93, 94, 115, 116, 140, 141 or comprises a region having at least 90% sequence identity to a nucleotide sequence of any one of SEQ ID NOs: 72-91, 96-113, 118-138, or 143-164; encodes a cytochrome P450 monooxygenase (MAX1) polypeptide having at least 80% sequence identity to any one of SEQ ID NOs: 71, 95, 117, or 142 and/or encodes a region of a cytochrome P450 monooxygenase (MAX1) polypeptide having at least 90% sequence identity to any one of SEQ ID NOs: 92, 114, 139 or 165, optionally wherein the at least one mutation results in a deletion or insertion of one or more base pairs located in a region having at least 90% sequence identity to any one of the nucleotide sequences of SEQ ID NOs: 72-91, 96-113, 118-138, or 143-164.

7. The plant or part thereof of claim 1, wherein the improved plant architecture results in one or more improved yield traits comprising increased number of pods per plant, number of pods on branches, and/or number of pods on the main stem.

8. The plant or part thereof of claim 1, wherein at least one mutation results in a mutated MAX1 gene having at least 90% sequence identity to any one of SEQ ID NOs: 173, 175, 177, 179, 181, and/or 183.

9. A plant cell comprising at least one mutation within an endogenous More Axillary Growth 1 (MAX1) gene, wherein the at least one mutation is a base insertion and/or base deletion that is introduced using an editing system that comprises a nucleic acid binding domain that binds to a target site in the endogenous MAX1 gene, wherein the at least one mutation is an out-of-frame mutation in a region of the endogenous MAX1 gene having at least 90% sequence identity to a nucleotide sequence of any one of SEQ ID NOs: 72-91, 96-113, 118-138, or 143-164.

10. The plant cell of claim 9, wherein the target site is within a region of the endogenous MAX1 gene that encodes an amino acid sequence having at least 90% sequence identity to any one of SEQ ID NOs: 92, 114, 139 or 165.

11. The plant cell of claim 9, wherein the editing system further comprises a nuclease, the nucleic acid binding domain binds to a target site in a sequence having least 80% sequence identity to any one of SEQ ID NOs: 69, 70, 93, 94, 115, 116, 140 or 141 and/or in a sequence having at least 90% sequence identity to a sequence of any one of SEQ ID NOs: 72-91, 96-113, 118-138, or 143-164, and the at least one mutation within a MAX1 gene is made following cleavage by the nuclease.

12. The plant cell of claim 9, wherein the at least one mutation within the MAX1 gene is an out-of-frame insertion or an out-of-frame deletion.

13. The plant cell of claim 9, wherein the at least one mutation results in a mutated MAX1 gene comprising a nucleotide sequence having at least 90% sequence identity to any one of SEQ ID NOs: 173, 175, 177, 179, 181, and/or 183.

14. A method for producing a plant or plant part thereof comprising at least one cell having a mutated endogenous More Axillary Growth 1 (MAX1) gene, the method comprising contacting a target site in an endogenous MAX1 gene in the plant or plant part thereof with a nuclease comprising a cleavage domain and a nucleic acid binding domain, wherein the nucleic acid binding domain binds to a target site in the endogenous MAX1 gene, wherein the endogenous MAX1 gene (a) comprises a sequence having at least 80% sequence identity to a nucleotide sequence of any one of SEQ ID NOs: 69, 70, 93, 94, 115, 116, 140 or 141;

(b) comprises a region having at least 90% identity to any one of SEQ ID NOs: 72-91, 96-113, 118-138, or 143-164;

(c) encodes an amino acid sequence having at least 80% sequence identity to any one of SEQ ID NOs: 71, 95, 117, or 142; and/or (d) encodes an amino acid sequence comprising a region having at least 90% identity to any one of SEQ ID NOs: 92, 114, 139 or 165, thereby producing the plant or plant part thereof comprising at least one cell having a mutation in the endogenous MAX1 gene, wherein the mutation is an out-of-frame mutation in a region of the endogenous MAX1 gene having at least 90% sequence identity to a nucleotide sequence of any one of SEQ ID NOs: 72-91, 96-113, 118-138, or 143-164.

15. The method of claim 14, wherein the mutation is an insertion and/or a deletion, optionally wherein the mutation is an out-of-frame insertion or an out-of-frame deletion.

16. The method of claim 14, wherein the mutation is an insertion and/or a deletion that results in a premature stop codon, optionally resulting in a truncated protein.

17. A plant regenerated from the plant cell of claim 9, wherein the plant exhibits a phenotype of improved plant architecture as compared to a plant devoid of the at least one mutation.

18. The plant of claim 17, wherein the improved plant architecture results in one or more improved yield traits comprising increased number of pods per plant, number of pods on branches, and/or number of pods on the main stem.

19. The method of claim 14, wherein the plant comprising at least one cell having the mutation in the endogenous MAX1 gene exhibits a phenotype of improved plant architecture as compared to a plant devoid of the mutation.

20. The method of claim 19, wherein the improved plant architecture results in one or more improved yield traits comprising increased number of pods per plant, number of pods on branches, and/or number of pods on the main stem.

* * * * *